United States Patent

Hayashi et al.

[11] Patent Number: 5,866,592
[45] Date of Patent: Feb. 2, 1999

[54] FIBRINOGEN RECEPTOR ANTAGONIST AND PHARMACEUTICAL COMPOSITIONS COMPRISING THE SAME

[75] Inventors: Yoshio Hayashi; Takeo Harada; Jun Katada; Akira Tachiki; Takeo Okazaki; Yoshimi Satoh; Hiroshi Miyazaki; Tohru Asari, all of Kanagawa, Japan

[73] Assignees: Nippon Steel Corporation, Chiyoda-ku; Nippon Steel Chemical Co., Ltd., Chuo-Ku, both of Japan

[21] Appl. No.: 882,356

[22] Filed: Jun. 25, 1997

Related U.S. Application Data

[63] Continuation-in-part of PCT/JP95/02763, Dec. 28, 1995, published as WO96/20172, Jul. 4, 1996.

[30]  Foreign Application Priority Data

Dec. 28, 1994 [JP] Japan ................................. 6-328980
Sep. 29, 1995 [JP] Japan ................................. 7-252841
Dec. 27, 1995 [JP] Japan ................................. 7-341746
Jun. 27, 1996 [JP] Japan ................................. 8-167982

[51] Int. Cl.⁶ ............... A61K 31/445; A61K 31/395; A61K 31/535; C07D 211/32
[52] U.S. Cl. ............ 514/330; 514/227.8; 514/235.5; 514/252; 514/316; 514/326; 514/330; 540/597; 544/100; 544/130; 544/360; 544/391; 546/188; 546/189; 546/205; 546/208; 546/209; 546/214; 546/226

[58] Field of Search ................... 546/226, 214, 546/189, 209, 208, 205, 188; 544/130, 60, 360, 391; 540/597; 514/316, 326, 330, 235.5, 227.8, 252, 212

[56]  References Cited

U.S. PATENT DOCUMENTS 5,430,024  7/1995  Alig et al. ................................. 514/18

OTHER PUBLICATIONS

PCT International Preliminary Examination Report, PCT/JP 95/02763, 1997.

Primary Examiner—Evelyn Huang
Attorney, Agent, or Firm—Kenyon & Kenyon

[57]  ABSTRACT

Compounds of the following general formula (I) and pharmaceutically acceptable salts thereof.

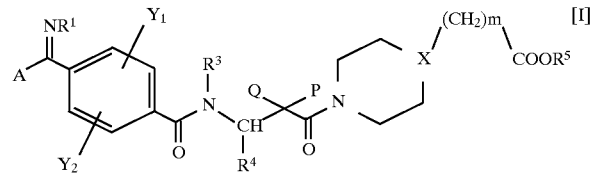

14 Claims, 1 Drawing Sheet

FIBRINOGEN RECEPTOR ANTAGONIST AND PHARMACEUTICAL COMPOSITIONS COMPRISING THE SAME

CROSS-REFERENCES

This is a continuation-in-part of International Application No. PCT/JP95/02763, with an international filing date of 28 Dec., 1995, published as WO96/20172 on Jul. 4, 1996.

SPECIFICATION

BACKGROUND OF THE INVENTION

The present invention relates to novel compounds having a platelet aggregation-inhibiting action, pharmaceutical compositions comprising the compounds as an active ingredient which can be used for inhibiting platelet aggregation, blood coagulation in extracorporeal circulation, the occlusion of arteries or reocclusion of coronary artery after PTCA and methods for inhibiting platelet aggregation, blood coagulation in extracorporeal circulation or the occlusion of coronary arteries.

Platelets play an important role in hemostasis by adhering to the surface of a damaged blood vessel. However, under diseased conditions, platelet aggregation is known to be primarily responsible for the formation of thrombi, which can obstruct blood vessels. This obstruction prevents the adequate supply of oxygen and nutrients to tissues and organs and thereby causes ischemic diseases in circulatory organs as represented by myocardial infarction and cerebral infarction. At present, the high mortality of these ischemic diseases has become a great social problem.

When medical treatments involving the extracorporeal circulation of blood, as exemplified by the use of artificial hearts and lungs during surgical operations and renal dialysis for patients with renal failure, are conducted, blood coagulation may be caused in the extracorporeal circulation of blood by the activation and aggregation of platelets, which is a great obstacle to the performance of such medical treatments.

It is suggested that platelet aggregation partakes in acute reocclusion after pericutaneous transluminal coronary angioplasty (PTCA) as applied to thrombi in coronary arteries in patients with cardiac infarction.

Hence, preventing thrombus formation, blood coagulation and reocclusion after the operation of coronary arteries by inhibiting platelet aggregation is very important for the purpose of preventing or treating ischemic diseases or performing medical treatments through extracorporeal circulation in a safe manner. It has become known in recent year that platelet aggregation also plays an important role in the progress of arterial sclerosis.

The process of platelet aggregation consists of two stages, i.e., the activation of platelets and a subsequent aggregation mediated by cross-linking protein "fibrinogen" in plasma. Almost all platelet aggregation-inhibiting agents heretofore in use target the first activation process. These agents include cyclooxygenase inhibitor aspirin, adenylate cyclase activator ticlopidine, phosphodiesterase inhibitor dipyridamole and the like. These compounds are not satisfactory in the specificity of action and the aggregation-inhibiting activity. Therefore, there is a need for the development of pharmaceutical agents having a more specific and potent action.

As regards the aggregation process mediated by fibrinogen, it is known that fibrinogen is associated with platelets by a very highly specific binding to glycoprotein "gpIIbIIIa" which is a fibrinogen receptor on the surface of platelet membranes. Inhibition of such platelet-specific binding will lead to the development of a highly specific drug. Inhibiting the binding of fibrinogen to platelets will also contribute to the creation of a potent and highly specific platelet aggregation-inhibiting agent because even activated platelets cannot aggregate if the fibrinogen-mediated aggregation process is inhibited.

In a study from the viewpoint of molecular biology, Andrieux et al. found that the binding of fibrinogen to a fibrinogen receptor is primarily dependent on an amino acid sequence in the fibrinogen molecule, that is, arginine-glycine-aspartic acid-phenylalanine (RGDF) (Andrieux et al., J. Biol. Chem., vol. 264, pp. 9258–9265, 1989).

An attempt was made to synthesize this partial peptide and its analogues and use them as fibrinogen receptor antagonists. Japanese Unexamined Patent Publication (hereinafter referred to as "KOKAI") Nos. Hei 1-190699 and Hei 2-62892, EPO 422937 A1 and U.S. Pat. (hereinafter referred to as "USP") No. 4,952,562 disclose tetrapeptide derivatives containing the RGD peptide. KOKAI No. Sho 63-215696 discloses derivatives consisting of peptides. KOKAI Nos. Hei 3-118331 and Hei 2-62892 and WO91/01331 disclose derivatives having the cyclic structure of the RGD peptide.

The RGD peptide is characterized in that it is digested in vivo by protease to amino acids which are safe and useful to the organism. Based on the finding of such a characteristic property, the inventors thought that for uses which did not require the sustained action of drugs, such as extracorporeal circulation and surgical operation, the creation of highly active peptide compounds having structures as similar to native peptides as possible was important for the development of platelet aggregation-inhibiting agents having few or no side effects. As a result of the various studies the inventors conducted, they developed novel peptides as described in KOKAI Nos. Hei 4-23864, Hei 5-203962, Hei 6-139107 and Hei 6-235745.

There are also reports on so-called peptidomimetics in which peptide structures containing more or less native amino acids were further derivatized and/or modified as described in KOKAI No. Hei 3-248808, WO93/16697, EP0503548, EP0502536, WO93/08181, WO93/08174, WO93/07867, WO94/08577, EP0445796 and EP0505868.

In general, compounds having chemical structures stable in vivo are required by drugs that need a sustained action. In the case of oral drugs, the stability and absorption of compounds in digestive tracts must also be taken into consideration. Peptides are generally unsuitable for such drugs of long lasting action because of their low stability.

EP445796 discloses acetic acid derivatives having β-alanine residues which have a platelet thrombus formation-inhibiting action. The inventors have been developed independently acetic acid derivatives having a β-alanine residue or mono-substituted β-alanine residues, these compounds do not have a sufficiently high biological activity to be used for practical purposes and the development of compounds having a higher biological activity has therefore been desired.

An object of the present invention is to provide novel compounds that antagonize the action of fibrinogen receptors and which have a high platelet aggregation-inhibiting activity, in vivo stability and high bioavailability, as well as novel pharmaceutical compositions comprising the compounds as an active ingredient and therapeutic methods using the compounds.

SUMMARY OF THE INVENTION

As a result of the various studies made to solve the aforementioned problems, the inventors found that β-amino acid derivatives having two lower alkyl groups at the α position had a high platelet aggregation-inhibiting activity and a high blood coagulation-inhibiting activity and that these biological activities were increased by modification of these derivatives at the β position, and they have accomplished the present invention.

The present invention provides compounds of the following general formula (I) and pharmaceutically acceptable salts thereof

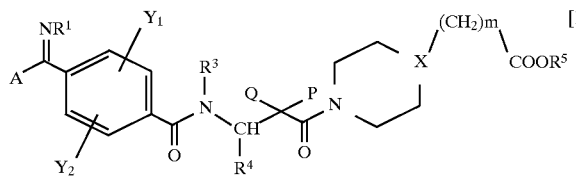

wherein A is an amine, $R^1$ is hydrogen, a lower alkyl or a physiologically cleavable amino-protecting group;

$R^3$ is hydrogen, a lower alkyl, lower alkenyl, lower alkynyl, ar(lower) alkyl or aryl;

$R^4$ is hydrogen, a lower alkyl, lower alkenyl, lower alkynyl, hydroxy(lower)alkyl, nitrooxy(lower)alkyl, nitrosooxy(lower)alkyl, amino(lower)alkyl or heterocycle-substituted lower alkyl; ar(lower) alkyl, ar(lower)alkenyl or ar(lower)alkynyl the aryl portion of which may have a lower alkyl, halogen, nitro, amino, carboxyl, hydroxy(lower) alkyl, hydroxyl or protected hydroxyl; aryl or a heterocyclic group which may have a lower alkyl, halogen, nitro, amino, carboxyl, hydroxy (lower)alkyl, hydroxyl or protected hydroxyl; a cycloalkyl with a 3–8 membered ring the ring portion of which may have a lower alkyl, halogen, nitro, amino, carboxyl, hydroxy(lower)alkyl, hydroxyl or protected hydroxyl, or a lower alkyl, a lower alkynyl or a lower alkenyl which are substituted with the cycloalkyl; or a lower alkyloxy, P and Q are each independently a lower alkyl, or when combined together, form a cycloalkyl with the adjacent carbon atom;

$R^5$ is hydrogen or a physiologically cleavable carboxyl-protecting group;

X is nitrogen or CH;

$Y_1$ and $Y_2$ are each independently hydrogen, a lower alkyl, halogen, hydroxy, a lower alkoxy, a lower acyloxy, an acyl, caboxyl, a lower alkoxycarbonyl, nitro or trifluoromethyl; and m is an integer of 0 to 2.

The present invention further provides pharmaceutical compositions comprising the aforementioned compounds or salts thereof and pharmaceutically acceptable carriers which can be used for inhibiting platelet aggregation, blood coagulation in extracorporeal circulation or the reocclusion of coronary arteries.

The present invention also provides methods for inhibiting platelet aggregation, blood coagulation in extracorporeal circulation or the reocclusion of coronary arteries, which comprise administering an effective amount of the aforementioned compounds or salts thereof to a patient.

According to the present invention, novel compounds which antagonize a fibrinogen receptor so that they have a high platelet-aggregation inhibiting activity, as well as pharmaceutical compositions comprising these compounds which are superior in platelet-aggregation inhibiting activity, stability against proteolytic enzymes in the body and bioavailability are provided. These pharmaceutical compositions can be used for inhibiting platelet aggregation, blood coagulation in extracorporeal circulation and the occlusion of arteries. They are very effective in preventing and treating platelet thrombosis, thromboembolism and reocclusion of coronary arteries during and after the treatment of thrombolysis, after the angioplasty of coronary arteries and other arteries and after the treatment of coronary artery bypass; preventing and treating unstable angina; preventing and treating myocardial infarction; improving the peripheral circular bloodstream; and inhibiting blood coagulation in extracorporeal circulation.

DESCRIPTION OF THE PREFERRED EMBODIMENT

Figure 1:
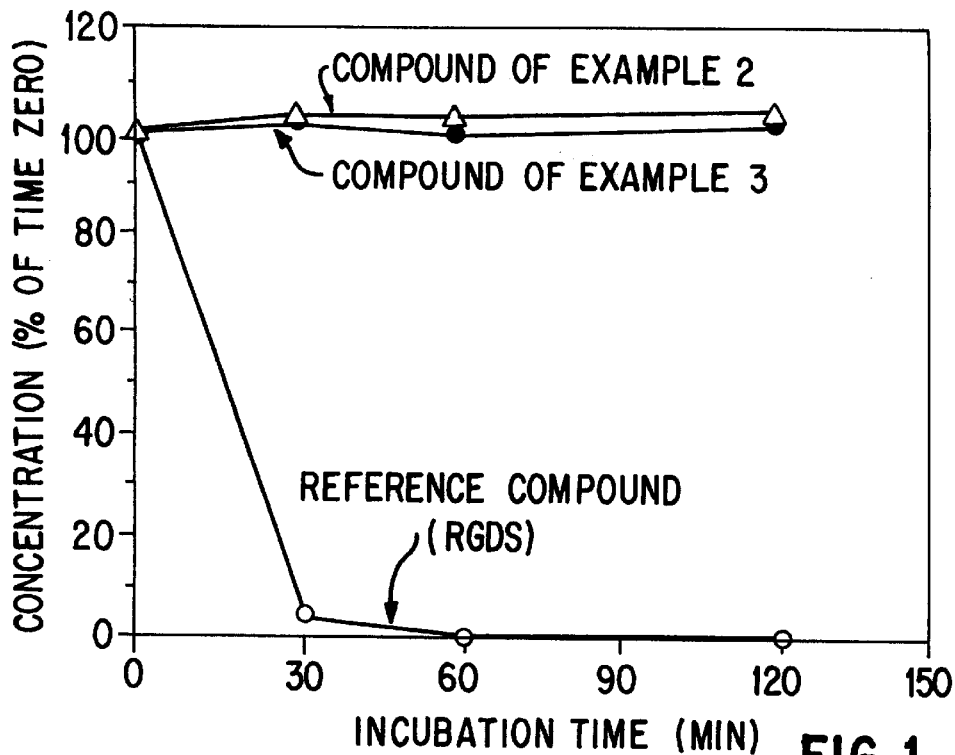
FIG. 1 shows the stability of the compounds of the present invention in mouse liver homogenate.

In the compounds of the present invention, the α and β positions mean the 2 and 3 positions, respectively, of a β-alanine residue, that is, 3-aminopropionic acid residue.

Suitable examples and explanation of various definitions contained in the scope of the present invention will be described below.

Unless otherwise indicated, the term "lower" means groups having 1–10 carbon atoms, preferably 1–6 carbon atoms, more preferably 1–3 carbon atoms.

When A is a primary or secondary amine in general formula (I), it is represented by $NHR^2$ wherein $R^2$ may be hydrogen, a lower alkyl or a physiologically cleavable amino-protecting group.

When A is a tertiary amine in general formula (I), this tertiary amine may include a cyclic or non-cyclic tertiary amine, for example, tertiary amines represented by the following general formula (IIa), (III) or (IV).

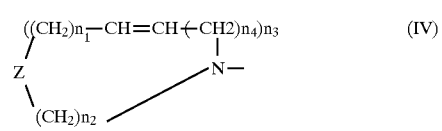

wherein $R^{11}$ and $R^{12}$ are each independently a lower alkyl, lower alkenyl, lower alkynyl, ar(lower) alkyl or aryl which may have a hydroxyl, amino, nitro, nitrooxy, nitrosooxy, halogen or alkoxy such as methoxy on its side chain;

Z is oxygen, sulfur,

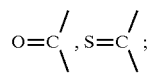

carbon having hydrogen, a lower alkyl, lower alkenyl, lower alkynyl, ar(lower)alkyl, hydroxyl or substituted hydroxyl, amino or substituted amino, nitro, nitrooxy, nitrosooxy, halogen, thiol or substituted thiol, or aryl on its side chain; or nitrogen having hydrogen, a lower alkyl, lower alkenyl, lower alkynyl, ar(lower) alkyl, hydroxyl or substituted hydroxyl, amino or substituted amino, nitro, nitroso or aryl on its side chain;

$n_1$, $n_2$ and $n_4$ are each independently an integer of 0 to 6 and $n_3$ is an integer of 0 to 3.

Preferred examples of the "lower alkyl" represented by $R^{11}$ and $R^{12}$ may include $C_{1-10}$ straight-chain, branched-chain or cyclic alkyls such as methyl, ethyl, propyl, isopropyl, cyclopropyl, butyl, isobutyl, tert-butyl, pentyl, isopentyl, cyclopentyl, isohexyl, cyclohexyl, heptyl, 5-methylhexyl, cycloheptyl, octyl, 6-methylheptyl, nonyl, 7-methyloctyl, decyl and 8-methylnonyl. Considering steric hindrance, $C_{1-4}$ alkyls are preferred.

Preferred examples of the "lower alkenyl" represented by $R^{11}$ and $R^{12}$ may include $C_{2-10}$ straight- or branched-chain alkenyls such as vinyl and propenyl. Considering steric hindrance, $C_{2-4}$ alkenyls are preferred.

Preferred examples of the "lower alkynyl" represented by $R^{11}$ and $R^{12}$ may include $C_{2-10}$ straight- or branched-chain alkynyls such as ethynyl, propynyl and butynyl. Considering steric hindrance, $C_{2-4}$ alkynyls are preferred.

Preferred examples of the "ar(lower) alkyl" represented by $R^{11}$ and $R^{12}$ may include phenylalkyls such as benzyl and phenethyl; and those alkyls having an aromatic heterocycle such as pyridyl and furyl. In these cases, the aryl portion such as phenyl may have a lower alkyl, hydroxy(lower)alkyl or hydroxyl, where the hydroxyl includes a protected hydroxyl. The lower alkyl in the ar(lower)alkyl and hydroxy(lower)alkyl is preferably a $C_{1-3}$ alkyl having small steric hindrance. Preferred examples of the protective groups in the "protected hydroxyl" may include ar(lower)alkyls such as benzyl, phenethyl and trityl; lower alkyls such as methyl, ethyl, propyl, isopropyl and tert-butyl; acyls such as acetyl and benzoyl; nitro, nitroso, tetrahydropyranyl and methoxymethyl. Preferred examples of the ar(lower)alkyl include phenyl, benzyl, 4-hydroxybenzyl and 4-hydroxymethylbenzyl.

Preferred examples of the "aryl" represented by $R^{11}$ and $R^{12}$ may include phenyl; aromatic heterocycles such as pyridyl, furyl, thiophene, oxazolyl and thiazolyl; or condensed polycyclic hydrocarbons such as naphthyl and anthranyl. In these cases, the aromatic ring may be substituted with a lower alkyl, hydroxy(lower) alkyl, hydroxyl and/or protected hydroxyl. In general, the aromatic ring is suitable for the present invention because it takes on a planar structure and thereby has small steric hindrance and high hydrophobic property. Phenyl or pyridyl is a preferred aromatic ring. The lower alkyl per se or the lower alkyl in the hydroxy(lower)alkyl as a substituent on the aromatic ring is preferably a $C_{1-3}$ alkyl having small steric hindrance, such as methyl, ethyl or propyl.

Preferred examples of the "lower alkyl" when Z is carbon or nitrogen may include $C_{1-10}$ straight-chain, branched-chain or cyclic alkyls such as methyl, ethyl, propyl, isopropyl, cyclopropyl, butyl, isobutyl, tert-butyl, pentyl, isopentyl, cyclopentyl, isohexyl, cyclohexyl, heptyl, 5-methylhexyl, cycloheptyl, octyl, 6-methylheptyl, nonyl, 7-methyloctyl, decyl and 8-methylnonyl. Considering steric hindrance, $C_{1-6}$ alkyls are preferred.

Preferred examples of the "lower alkenyl" when Z is carbon or nitrogen may include $C_{2-10}$ straight- or branched-chain alkenyls such as vinyl and propenyl. Considering steric hindrance, $C_{2-6}$ alkenyls are preferred.

Preferred examples of the "lower alkynyl" when Z is carbon or nitrogen may include $C_{2-10}$ straight- or branched-chain alkynyls such as ethynyl, propynyl and butynyl. Considering steric hindrance, $C_{2-6}$ alkynyls are preferred.

Preferred examples of the "ar(lower) alkyl" when Z is carbon or nitrogen may include phenylalkyls such as benzyl and phenethyl; and those alkyls having an aromatic heterocycle such as pyridyl and furyl. In these cases, the aryl portion such as phenyl may have a lower alkyl, halogen, hydroxy(lower)alkyl or hydroxyl, where the hydroxyl includes a protected hydroxyl. The lower alkyl in the ar(lower)alkyl and hydroxy(lower)alkyl is preferably a $C_{1-3}$ alkyl having small steric hindrance. Preferred examples of the protective groups in the "protected hydroxyl" may include ar(lower)alkyls such as behzyl, phenethyl and trityl; lower alkyls such as methyl, ethyl, propyl, isopropyl and tert-butyl; acyls such as acetyl and benzoyl; nitro, nitroso, tetrahydropyranyl and methoxymethyl. Preferred examples of the ar(lower)alkyl include phenyl, benzyl, 4-hydroxybenzyl and 4-hydroxymethylbenzyl.

Preferred examples of the "aryl" when Z is carbon or nitrogen may include phenyl; aromatic heterocycles such as pyridyl, furyl, thiophene, oxazolyl and thiazolyl; or condensed polycyclic hydrocarbons such as naphthyl and anthranyl. In these cases, the aromatic ring may be substituted with a lower alkyl, halogen, hydroxy(lower)alkyl, hydroxyl and/or protected hydroxyl. In general, the aromatic ring is suitable for the present invention because it takes on a planar structure and thereby has small steric hindrance and high hydrophobic property. Phenyl or pyridyl is a preferred aromatic ring. The lower alkyl per se or the lower alkyl in the hydroxy(lower)alkyl as a substituent on the aromatic ring is preferably a $C_{1-3}$ alkyl having small steric hindrance, such as methyl, ethyl or propyl.

Preferred examples of the substituent of the "substituted hydroxyl" when Z is carbon or nitrogen may include an ar(lower)alkyl such as benzyl, phenethyl and trityl; a lower alkyl such as methyl, ethyl, propyl, isopropyl and tert-butyl; an acyl such as acetyl and benzoyl; nitro, nitroso, tatrahydropyranyl and methoxymethyl.

Preferred examples of the substituent of the "substituted amino" when Z is carbon or nitrogen may include an ar(lower)alkyl such as benzyl, phenethyl and trityl; a lower alkyl such as methyl, ethyl, propyl, isopropyl and tert-butyl; an acyl such as acetyl and benzoyl; a carbamate such as benzyloxycarbonyl and methoxycarbonyl; and nitroso.

Preferred examples of the substituent of the "substituted thiol" when Z is carbon may include an ar(lower)alkyl such as benzyl, phenethyl and trityl; a lower alkyl such as methyl, ethyl, propyl, isopropyl and tert-butyl; and nitroso.

Preferred examples of the "halogen" when Z is carbon may include chlorine, fluorine and bromine.

$n_1$, $n_2$ and $n_4$ are each independently an integer of 0 to 6, preferably 1 to 3. $n_3$ is an integer of 1 to 3, most preferably 1.

The "lower alkyl" represented by $R^1$ in general formula (I) or $R^2$ includes $C_{1-10}$ straight- and branched-chain alkyls, and cyclic alkyls such as methyl, ethyl, propyl, isopropyl, cyclopropyl, butyl, isobutyl, tert-butyl, pentyl, isopentyl, cyclopentyl, hexyl, isohexyl, cyclohexyl, heptyl, 5-methylhexyl, cycloheptyl, octyl, 6-methylheptyl, nonyl, 7-methyloctyl, decyl and 8-methylnonyl. Considering steric hindrance, $C_{1-6}$ alkyls are preferred. Straight-chain alkyls are preferred to branched-chain and cyclic ones.

The "physiologically cleavable amino-protecting group" as represented by $R^1$ or $R^2$ includes any amino-protecting groups which are known to be physiologically cleavable. Specific examples include protective groups which protect the amino group in binding modes as described in "Development of Medicines", vol. 13, "Drug Delivery", p. 116, Table 2.29, Jin Sezaki ed., Hirokawa Shoten, 1989, July. Examples of the protective groups are fatty acid residues such as acetyl, amino acid residues having a free carboxylic acid and protected amino acid residues thereof, carbamates such as benzyloxycarbonyl ethoxycarbonyl, methoxycarbonyl, and 1-acyloxyalkyloxycarbonyl. In particular, ethoxycarbonyl, acetoxymethyloxycarbonyl and 1-acetoxyethyloxycarbonyl are preferred.

The "lower alkyl" represented by $R^3$ includes $C_{1-10}$ straight- and branched-chain alkyls, and cyclic alkyls such as methyl, ethyl, propyl, isopropyl, cyclopropyl, butyl, isobutyl, tert-butyl, pentyl, isopentyl, cyclopentyl, hexyl, isohexyl, cyclohexyl, heptyl, 5-methylhexyl, cycloheptyl, octyl, 6-methylheptyl, nonyl, 7-methyloctyl, decyl and 8-methylnonyl. Considering steric hindrance, $C_{1-6}$ alkyls are preferred. Straight-chain alkyls are preferred to branched-chain and cyclic ones.

The "lower alkenyl" represented by $R^3$ includes $C_{2-10}$ straight- and branched-chain alkenyls such as vinyl and propenyl. Considering steric hindrance, $C_{2-6}$ alkenyls are preferred.

The "lower alkynyl" represented by $R^3$ includes $C_{2-10}$ straight- and branched-chain alkynyls such as ethynyl, propynyl and butynyl. Considering steric hindrance, $C_{2-6}$ alkynyls are preferred.

The "ar(lower)alkyl" represented by $R^3$ includes phenylalkyl such as benzyl and phenethyl. In this case, the aryl portion such as phenyl may have a lower alkyl, hydroxy (lower)alkyl or hydroxyl, where the hydroxyl includes a protected hydroxyl. The lower alkyl in the ar(lower)alkyl and hydroxy(lower)alkyl is preferably a $C_{1-3}$ alkyl having small steric hindrance. The protective groups in the "protected hydroxyl" include ar(lower)alkyls such as benzyl, phenethyl and trityl, lower alkyls such as methyl, ethyl, propyl, isopropyl and tert-butyl, acyls such as acetyl and benzoyl, nitro, nitroso, as well as tetrahydropyranyl and methoxymethyl. Preferred examples of the ar(lower)alkyl include phenyl, benzyl, 4-hydroxybenzyl and 4-hydroxymethylbenzyl. This is also the case in the following description.

The "aryl" represented by $R^3$ includes phenyl and condensed polycyclic hydrocarbons such as naphthyl and anthranyl. In this case, the aromatic ring may be substituted with a lower alkyl, hydroxy(lower) alkyl, hydroxyl and/or protected hydroxyl. In general, the aromatic ring is suitable for the present invention because it takes on a planar structure and thereby has small steric hindrance and high hydrophobic property. Phenyl is a preferred aromatic ring. The lower alkyl per se or the lower alkyl in the hydroxy (lower)alkyl as a substituent on the aromatic ring is preferably a $C_{1-3}$ alkyl having small steric hindrance such as methyl, ethyl or propyl.

In general formula (I), the total number of carbon atoms of the substituents represented by $R^4$, P and Q is preferably 2–20 for the purpose of improved molecular stability and hydrophobic property.

The "lower alkyl" represented by $R^4$, P or Q includes $C_{1-10}$ straight- and branched-chain alkyls, and cyclic alkyls such as methyl, ethyl, propyl, isopropyl, cyclopropyl, butyl, isobutyl, tert-butyl, pentyl, isopentyl, cyclopentyl, hexyl, isohexyl, cyclohexyl, heptyl, 5-methylhexyl, cycloheptyl, octyl, 6-methylheptyl, nonyl, 7-methyloctyl, decyl and 8-methylnonyl. Considering steric hindrance, $C_{1-6}$ alkyls are preferred. Straight-chain alkyls are preferred to branched chain and cyclic ones. In particular, both P and Q are preferably methyl.

P and Q may be combined together to form a cycloalkyl with the adjacent carbon atom. Examples of the cycloalkyl include cycloalkyls with a 3–8 membered ring. Considering steric hindrance, a cycloalkyl with a 3–6 membered ring is preferred.

The "lower alkenyl" represented by $R^4$ includes $C_{2-10}$ straight- and branched-chain alkenyls such as vinyl and propenyl. Considering steric hindrance, $C_{2-6}$ alkenyls are preferred.

The "lower alkynyl" represented by $R^4$ includes $C_{2-10}$ straight- and branched-chain alkynyls such as ethynyl, propynyl and butynyl. Considering steric hindrance, $C_{2-6}$ alkynyls are preferred.

The lower alkyl portion of the hydroxy(lower)alkyl, nitrooxy (lower)alkyl or nitrosooxy(lower)alkyl represented by $R^4$ includes $C_{1-10}$ lower alkyls. Preferred are $C_{1-6}$ alkyls. Examples of the hydroxy(lower)alkyl include hydroxymethyl, 1-hydroxyethyl, 2-hydroxyethyl and 3-hydroxypropyl. Preferred examples of the nitrooxy(lower) alkyl include 1-nitrooxyethyl. Preferred examples of the nitrosooxy(lower)alkyl include 1-nitrosooxyethyl.

The lower alkyl portion of the "amino(lower)alkyl" represented by $R^4$ includes $C_{1-10}$ lower alkyls. Preferred are $C_{1-6}$ alkyls. Examples of the amino(lower)alkyl include aminomethyl, 1-aminoethyl, 2-aminoethyl, 3-aminopropyl and piperidine. The amino group in the amino(lower)alkyl may be modified with an alkyl. Preferred examples of the modified case include 1-N,N-dimethylaminomethyl, 2-N,N-dimethylaminoethyl, 3-N,N-dimethylaminopropyl, 1-N,N-diethylamino-methyl, 2-N,N-diethylaminoethyl and 3-N,N-diethylaminopropyl.

The "heterocycle-substituted lower alkyl" represented by $R^4$ includes lower alkyls substituted with a 5–6 membered heterocycle containing at least one hetero atom such as nitrogen. Preferred examples include piperidine(lower) alkyls such as piperidinemethyl and piperidineethyl, and piperazine(lower)alkyls such as piperazinemethyl and piperazineethyl. The heterocycle-substituted lower alkyl also includes lower alkyls substituted with an unsaturated condensed heterocycle containing at least one hetero atom such as nitrogen. Preferred examples include pyridine(lower) alkyls such as pyridinemethyl and pyridineethyl, and indole (lower)alkyls such as indolemethyl and indoleethyl.

The "ar(lower)alkyl" represented by $R^4$ includes phenylalkyls such as benzyl and phenethyl. In this case, the aryl portion such as phenyl may have lower alkyl, halogen, nitro, amino, carboxyl, hydroxy(lower)alkyl, hydroxyl or protected hydroxyl. The lower alkyl per se or the lower alkyl in the hydroxy(lower)alkyl is preferably a $C_{1-3}$ alkyl having small steric hindrance such as methyl, ethyl or propyl. Specific examples include benzyl, phenethyl and phenylpropyl which may have methyl, ethyl, propyl, isopropyl, butyl, chloro, fluoro, methoxy, ethyoxy, hydroxy, hydroxymethyl, amino, carboxyl, nitro or dimethylamino independently as substituents at the o, p and/or m positions. Preferred are benzyl, phenethyl, phenylpropyl, 4-hydroxybenzyl, 3-hydroxybenzyl, 4-methoxybenzyl, 4-fluorobenzyl, 4-chlorobenzyl, 4-hydroxyphenethyl, 3-hydroxyphenethyl, 4-methoxyphenethyl, 4-fluorophenethyl and 4-chlorophenethyl.

The "ar(lower)alkenyl" represented by R⁴ includes phenylalkenyls such as cinnamyl and styryl. In this case, the aryl portion such as phenyl may have a lower alkyl, halogen, nitro, amino, carboxyl, hydroxy(lower)alkyl, hydroxyl or protected hydroxyl. The lower alkyl per se or the lower alkyl in the hydroxy(lower)alkyl is preferably a $C_{1-3}$ alkyl having small steric hindrance such as methyl, ethyl or propyl. Specific examples include cinnamyl and styryl which may have methyl, ethyl, propyl, isopropyl, butyl, chloro, fluoro, methoxy, ethyoxy, hydroxy, hydroxymethyl, amino, carboxyl, nitro or dimethylamino independently as substituents at the o, p and/or m positions. Preferred are cinnamyl, styryl, 4-hydroxycinnamyl, 3-hydroxycinnamyl, 4-methoxycinnamyl, 4-fluorocinnamyl, 4-chlorocinnamyl, 4-hydroxystyryl, 3-hydroxystyryl, 4-methoxystyryl, 4-fluorostyryl and 4-chlorostyryl.

The "ar(lower)alkynyl" represented by R⁴ includes phenylalkynyls such as phenylethynyl and phenylpropynyl. In this case, the aryl portion such as phenyl may have a lower alkyl, halogen, nitro, amino, carboxyl, hydroxy(lower)alkyl, hydroxyl or protected hydroxyl. The lower alkyl per se or the lower alkyl in the hydroxy(lower)alkyl is preferably a $C_{1-3}$ alkyl having small steric hindrance such as methyl, ethyl or propyl. Specific examples include phenylethynyl and phenylpropynyl which may have methyl, ethyl, propyl, isopropyl, butyl, chloro, fluoro, methoxy, ethyoxy, hydroxy, hydroxymethyl, amino, carboxyl, nitro or dimethylamino independently as substituents at the o, p and/or m positions. Preferred are phenylethynyl, phenylpropynyl, 4-hydroxyethynyl, 3-hydroxyethynyl, 4-methoxyethynyl, 4-fluoroethynyl, 4-chloroethynyl, 4-hydroxypropynyl, 3-hydroxypropynyl, 4-methoxypropynyl, 4-fluoropropynyl and 4-chloropropynyl.

The "aryl" represented by R⁴ includes phenyl and condensed polycyclic hydrocarbons such as naphthyl and anthranyl. In this case, the aromatic ring may be substituted with a lower alkyl, halogen, nitro, amino, carboxyl, hydroxy (lower)alkyl, hydroxyl or protected hydroxyl. In general, the aromatic ring is suitable for the present invention because it takes on a planar structure and thereby has small steric hindrance and high hydrophobic property. Phenyl is a preferred aromatic ring. The lower alkyl per se or the lower alkyl in the hydroxy(lower) alkyl as a substituent on the aromatic ring is preferably a $C_{1-3}$ alkyl having small steric hindrance such as methyl, ethyl or propyl.

The "heterocycle" represented by R⁴ includes any heterocyclic functional groups. Specific examples include pyridyl, furyl, pyrrolyl, thiophene, oxazolyl, thiazolyl, imidazolyl, pyrazolyl, tetrazolyl, triazolyl, indolyl, benzothiazolyl, benzimidazolyl, benzoxazolyl, coumaryl, carbazolyl, pyranyl, pyronyl, quinolyl, isoquinolyl, pyrimidyl, pyrazinyl, piperidyl, piperazyl and tetrahydrofuryl. In this case, the heterocycle may be substituted with a lower alkyl, halogen, nitro, amino, carboxyl, hydroxy (lower)alkyl, hydroxyl or protected hydroxyl. The lower alkyl per se or the lower alkyl in the hydroxy(lower)alkyl is preferably a $C_{1-3}$ alkyl having small steric hindrance such as methyl, ethyl or propyl. Preferred examples of the heterocycle include pyridyl, piperidyl and furyl.

The lower alkyl portion of the "lower alkyl substituted with a cycloalkyl having a 3–8 membered ring" represented by R⁴ includes $C_{1-10}$ alkyls. Preferred are $C_{1-3}$ alkyls. The lower alkyl substituted with a suitable cycloalkyl includes cyclohexylmethyl, cyclopentylmethyl, cyclohexylethyl, cyclopentylethyl, cyclohexylpropyl and cyclopentylpropyl. The ring portion of the lower alkyl substituted with a cycloalkyl having a 3–8 membered ring may have a lower alkyl, halogen, nitro, amino, carboxyl, hydroxy(lower)alkyl, hydroxyl or protected hydroxyl. The lower alkyl per se or the lower alkyl in the hydroxy(lower)alkyl is preferably a $C_{1-3}$ alkyl having small steric hindrance such as methyl, ethyl or propyl. More specifically, preferred are 4-hydroxycyclohexylmethyl, 3-hydroxycyclohexylmethyl, 4-methoxycyclohexylmethyl, 4-fluorocyclohexylmethyl, 4-chlorocyclohexylmethyl, 3-hydroxycyclopentylmethyl, 3-methoxycyclopentylmethyl, 3-fluorocyclopentylmethyl, 3-chlorocyclopentylmethyl, 4-hydroxycyclohexylethyl, 3-hydroxycyclohexylethyl, 4-methoxycyclohexylethyl, 4-fluorocyclohexylethyl, 4-chlorocyclohexylethyl, 3-hydroxycyclopentylethyl, 3-methoxycyclopentylethyl, 3-fluorocyclopentylethyl, 3-chlorocyclopentylethyl, 4-hydroxycyclohexylpropyl, 3-hydroxycyclohexylpropyl, 4-methoxycyclohexylpropyl, 4-fluorocyclohexylpropyl, 4-chlorocyclohexylpropyl, 3-hydroxycyclopentylpropyl, 3-methoxycyclopentylpropyl, 3-fluorocyclopentylpropyl and 3-chlorocyclopentylpropyl.

The lower alkynyl portion of the "lower alkynyl substituted with a cycloalkyl having a 3–8 membered ring" represented by R⁴ includes $C_{1-10}$ alkynyls. Preferred are $C_{2-3}$ alkynyls. The cycloalkyl(lower)alkynyl includes cyclohexylethynyl and cyclohexylpropynyl. The ring portion of the lower alkynyl substituted with a cycloalkyl having a 3–8 membered ring may have a lower alkyl, halogen, nitro, amino, carboxyl, hydroxy(lower)alkyl, hydroxyl or protected hydroxyl. The lower alkyl per se or the lower alkyl in the hydroxy(lower)alkyl is preferably a $C_{1-3}$ alkyl having small steric hindrance such as methyl, ethyl or propyl. More specifically, preferred are 4-hydroxycyclohexylethynyl, 3-hydroxycyclohexylethynyl, 4-methoxycyclohexylethynyl, 4-fluorocyclohexylethynyl, 4-chlorocyclohexylethynyl, 3-hydroxycyclopentylethynyl, 3-methoxycyclopentylethynyl, 3-fluorocyclopentylethynyl, 3-chlorocyclopentylethynyl, 4-hydroxycyclohexylpropynyl, 3-hydroxycyclohexylpropynyl, 4-methoxycyclohexylpropynyl, 4-fluorocyclohexylpropynyl, 4-chlorocyclohexylpropynyl, 3-hydroxycyclopentylpropynyl, 3-methoxycyclopentylpropynyl, 3-fluorocyclopentylpropynyl and 3-chlorocyclopentylpropynyl.

The lower alkenyl portion of the "lower alkenyl substituted with a cycloalkyl having a 3–8 membered ring" represented by R⁴ includes $C_{1-10}$ alkenyls. Preferred are $C_{2-3}$ alkenyls. The cycloalkyl(lower)alkenyl includes 2-cyclohexylvinyl, 2-cyclopentylvinyl, 3-cyclohexyl-2-propenyl and 3-cyclopentyl-2-propenyl. The ring portion of the lower alkenyl substituted with a cycloalkyl having a 3–8 membered ring may have a lower alkyl, halogen, nitro, amino, carboxyl, hydroxy(lower)alkyl, hydroxyl or protected hydroxyl. The lower alkyl per se or the lower alkyl in the hydroxy(lower)alkyl is preferably a $C_{1-3}$ alkyl having small steric hindrance such as methyl, ethyl or propyl. More specifically, preferred are 2-(4-hydroxy)-cyclohexylvinyl, 2-(3-hydroxy)-cyclohexylvinyl, 2-(4-methoxy)-cyclohexylvinyl, 2-(4-fluoro)-cyclohexylvinyl, 2-(4-chloro)-cyclohexylvinyl, 2-(3-hydroxy)-cyclopentylvinyl, 2-(3-methoxy)-cyclopentylvinyl, 2-(3-fluoro)-cyclopentylvinyl, 2-(3-chloro)-cyclopentylvinyl, 3-(4-hydroxy)-cyclohexyl-2-propenyl, 3-(3-hydroxy)-cyclohexyl-2-propenyl, 3-(4-methoxy)-cyclohexyl-2-propenyl, 3-(4-fluoro)-cyclohexyl-2-propenyl, 3-(4-chloro)-cyclohexyl-2-propenyl, 3-(3-hydroxy)-cyclopentyl-2-propenyl, 3-(3-methoxy)-cyclopentyl-2-propenyl, 3-(3-fluoro)-cyclopentyl-2-propenyl and 3-(3-chloro)-cyclopentyl-2-propenyl.

The lower alkyl portion of the "lower alkyloxy" represented by $R^4$ includes $C_{1-10}$ lower alkyls. Preferred are $C_{1-6}$ alkyls. The lower alkyloxy includes methoxy, ethoxy, propoxy, isopropoxy, butoxy and isobutoxy.

The "physiologically cleavable carboxyl-protecting group" represented by $R^5$ includes any carboxyl-protecting groups which are known to be physiologically cleavable. Specific examples include protective groups which protect the carboxyl group in binding modes as described in "Development of Medicines", vol. 13, "Drug Delivery", p. 116, Table 2.29, Jin Sezaki ed., Hirokawa Shoten, 1989, July. Examples of the protective groups are alkoxy groups capable of forming esters such as methyl esters, ethyl esters, propyl esters, isopropyl esters and butyl esters, amino acid residues having a free amino group, protected amino acid residues thereof and 1-acyloxyalkoxides. In particular, ethoxy, propoxy, isopropoxy, butoxy and acyloxymethoxy are preferred.

X is nitrogen or CH and preferably CH.

$Y_1$ and $Y_2$ are each independently the atom or group, as defined above, preferably H or halogen. The "lower alkyl" represented by $Y_1$ and $Y_2$ is preferably a $C_{1-3}$ alkyl having small steric hindrance, i.e., methyl, ethyl or propyl. The "halogen" represented by $Y_1$ and $Y_2$ is preferably fluorine or chlorine. The "lower alkoxy" represented by $Y_1$ and $Y_2$ includes methoxy and ethoxy. Preferred is methoxy having small steric hindrance. The "lower acyloxy" represented by $Y_1$ and $Y_2$ includes acetoxy, propionyloxy and benzoyloxy. Preferred is acetoxy having small steric hindrance. The "acyl" represented by $Y_1$ and $Y_2$ includes formyl, acetyl, propionyl and benzoyl. Preferred is acetyl. The "lower alkoxycarbonyl" represented by $Y_1$ and $Y_2$ includes methoxycarbonyl, ethoxycarbonyl, propoxycarbonyl and butoxycarbonyl. Preferred are methoxycarbonyl and ethoxycarbonyl. Preferred examples are 2-methyl, 3-methyl, 2-chloro, 2,6-dichloro, 2-fluoro, 2,6-difluoro, 2-hydroxy, 2-methoxy, 2-acetoxy, 2-acetyl, 2-benzoyl, 2-carboxyl, 2-methoxycarbonyl, 2-nitro, 3-nitro and 2-trifluoromethyl.

m is an integer of 0 to 2 and most preferably 1.

Among the compounds of general formula (I), compounds of the following general formula (II) wherein P and Q are both methyl, m is 1 and X is CH are preferred.

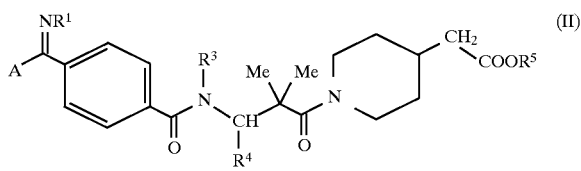

wherein $R^1$, A, $R^3$, $R^4$ and $R^5$ are as defined above.

When A is a primary or secondary amine, $R^1$ may be any one of hydrogen, a lower alkyl or a physiologically cleavable amino-protecting group. When A is a tertiary amine, $R^1$ is preferably hydrogen.

In the case where A is a primary or secondary amine, preferred examples of the compounds of general formula (I) are N-(N-4-Amidinobenzoyl-α,α-dimethyl-β-alanyl)-4-piperidineacetic acid, N-(N-4-Amidinobenzoyl-β-phenyl-α,α-dimethyl-β-alanyl)-4-piperidineacetic acid, N-(N-4-Amidinobenzoyl-β-ethyl-α,α-dimethyl-β-alanyl)-4-piperidineacetic acid, N-(N- 4-Amidinobenzoyl-β-n-propyl-α,α-dimethyl-β-alanyl)-4-piperidineacetic acid, N-(N-4-Amidinobenzoyl-β-isopropyl-α,α-dimethyl-β-alanyl)-4-piperidineacetic acid, N-(N-4-Amidinobenzoyl-β-n-butyl-α,α-dimethyl-β-alanyl)-4-piperidineacetic acid, N-(N-4-Amidinobenzoyl-β-n-pentyl-α,α-dimethyl-β-alanyl)-4-piperidineacetic acid, N-(N-4-Amidinobenzoyl-β-p-methoxyphenyl-α,α-dimethyl-β-alanyl)-4-piperidineacetic acid, N-(N-4-Amidinobenzoyl-β-m-chlorophenyl-α,α-dimethyl-β-alanyl)-4-piperidineacetic acid, N-(N-4-Amidinobenzoyl-β-p-fluorophenyl-α,α-dimethyl-β-alanyl)-4-piperidineacetic acid, N-(N-4-Amidinobenzoyl-β-phenyl-α,α-dimethyl-β-alanyl)-4-piperidineacetic acid, N-(N-4-Amidinobenzoyl-β-cyclohexylmethyl-α,α-dimethyl-β-alanyl)-4-piperidineacetic acid, N-(N-4-Amidinobenzoyl-β-(3-furyl)-α,α-dimethyl-β-alanyl)-4-piperidineacetic acid, N-(N-4-Amidinobenzoyl-β-styryl-α,α-dimethyl-β-alanyl)-4-piperidineacetic acid, N-(N-4-Amidinobenzoyl-β-(4-piperidyl)-α,α-dimethyl-β-alanyl)-4-piperidineacetic acid, N-(N-4-Amidinobenzoyl-β-(2-naphthyl)-α,α-dimethyl-β-alanyl)-4-piperidineacetic acid, N-(N-4-Amidinobenzoyl-β-cyclopropyl-α,α-dimethyl-β-alanyl)-4-piperidineacetic acid, N-(N-4-n-Butyl-amidinobenzoyl)-β-m-chlorophenyl-α,α-dimethyl-β-alanyl)-4-piperidineacetic acid, N-(N-4-Amidinobenzoyl-β-phenyl-α,α-dimethyl-β-alanyl)-4-piperidineacetic acid ethyl ester, N-(N-4-Amidinobenzoyl-β-phenyl-α,α-dimethyl-β-alanyl)-4-piperidineacetic acid t-butyl ester, N-(N-4-Amidinobenzoyl-N-methyl-β-phenyl-α,α-dimethyl-β-alanyl)-4-piperidineacetic acid, N-(N-4-Amidinobenzoyl-β-methyl-α,α-dimethyl-β-alanyl)-4-piperidineacetic acid, N-(N-4-Amidinobenzoyl-β-phenyl-α,α-dimethyl-β-alanyl)-4-piperadineacetic acid N-(N-4-Amidinobenzoyl-β-i-butyl-α,α-dimethyl-β-alanyl)-4-piperidineacetic acid, N-(N-4-Amidinobenzoyl-β-p-chlorophenyl-α,α-dimethyl-β-alanyl)- 4-piperidineacetic acid, N-(N-4-Amidinobenzoyl-β-o-methoxyphenyl-α,α-dimethyl-β-alanyl)-4-piperidineacetic acid, N-(N-4-Amidinobenzoyl-β-p-hydroxyphenyl-α,α-dimethyl-β-alanyl)-4-piperidineacetic acid, N-(N-4-Amidinobenzoyl-β-m-hydroxyphenyl-α,α-dimethyl-β-alanyl)-4-piperidineacetic acid, N-(N-4-Amidinobenzoyl-β-1-propenyl-α,α-dimethyl-β-alanyl)-4-piperidineacetic acid, N-(N-4-Amidinobenzoyl-β-3,3,3-trifluoropropyl-α,α-dimethyl-β-alanyl)-4-piperidineacetic acid, N-(((N-4-Amidinobenzoyl)-1-amino)-1-pentyl-1-cyclohexane-carbonyl)-4-piperidineacetic acid, N-(N-4-Amidinobenzoyl-β-p-N, N-dimethylaminophenyl-α,α-dimethyl-β-alanyl)-4-piperidineacetic acid, N-(N-4-Amidinobenzoyl-β-m-trifluoromethylphenyl-α,α-dimethyl-β-alanyl)-4-piperidineacetic acid, N-(N-4-Amidinobenzoyl-β-p-n-butylphenyl-α,α-dimethyl-β-alanyl)-4-piperidineacetic acid, N-(N-4-Amidino-2-fluorobenzoyl-β-n-butyl-α,α-dimethyl-β-alanyl)-4-piperidineacetic acid, N-(N-4-Amidino-2-chlorobenzoyl-β-phenyl-α,α-dimethyl-β-alanyl)-4-piperidineacetic acid, N-((N-4-(N-1-Acetoxyethyloxycarbonyl)amidinobenzoyl)-β-n-butyl-α,α-dimethyl-β-alanyl)-4-piperidineacetic acid and N-((N-4-(N-1-Acetoxyethyloxycarbonyl)amidinobenzoyl)-β-n-butyl-α, α-dimethyl-β-alanyl)-4-piperidineacetic acid ethyl ester N-(N-4-Amidinobenzoyl-β-m-hydroxyphenethyl-α,α-dimethyl-β-alanyl)-4-piperidineacetic acid, N-(N-4-Amidinobenzoyl-β-ethynyl-α,α-dimethyl-β-alanyl)-4-piperidineacetic acid, N-(N-4-Amidino-2-fluorobenzoyl-β-ethyl-α,α-dimethyl-β-alanyl)-4-piperidineacetic acid and N-(N-4-Amidino-2-fluorobenzoyl-β-methyl-α,α-dimethyl-β-alanyl)-4-piperidineacetic acid.

In the case where A is a tertiary amine, preferred examples of the compounds are Ethyl N-(N-(4-(4-morpholinoimidoyl) benzoyl)-β-ethyl-α,α-dimethyl-β-alanyl)-4-piperidineacetate, N-(N-(4-(4-Morpholinoimidoyl) benzoyl)-β-ethyl-α,α-dimethyl-β-alanyl)-4-piperidineacetic acid, Ethyl-N-(N-(4-(4-morpholinoimidoyl)-2-fluorobenzoyl)-β-ethyl-α,α-dimethyl-β-alanyl)-4-piperidineacetate, N-(N-(4-(4-morpholinoimidoyl)-2-fluorobenzoyl)-β-ethyl-α,α-dimethyl-β-alanyl)-4- piperidineacetic acid, Ethyl-N-(N-(4-(N,N-diethylaminoimidoyl)-2-fluorobenzoyl)-β-ethyl-α,α-dimethyl-β-alanyl)-4-piperidineacetate, N-(N-(4-(N,N-diethylaminoimidoyl)-2-fluorobenzoyl)-β-ethyl-α,α-dimethyl-β-alanyl)-4-piperidineacetic acid, Ethyl-N-(N-(4-(1-piperidinoimidoyl)-2-fluorobenzoyl)-β-ethyl-α,α-dimethyl-β-alanyl)-4-piperidineacetate, N-(N-(4-(1-piperidinoimidoyl)-2-fluorobenzoyl)-β-ethyl-α,α-dimethyl-β-alanyl)-4-piperidineacetic acid, Ethyl-N-(N-(4-(1-pyrrolidinoimidoyl)-2-fluorobenzoyl)-β-ethyl-α,α-dimethyl-β-alanyl)-4-piperidineacetate, N-(N-(4-(1-pyrrolidinoimidoyl)-2-fluorobenzoyl)-β-ethyl-α,α-dimethyl-β-alanyl)-4-piperidineacetic acid, Ethyl-N-(N-(4-(1-4-piperidinoimidoyl)-2-fluorobenzoyl)-β-ethyl-α,α-dimethyl-β-alanyl)-4-piperidineacetate, N-(N-(4-(1–4-piperidinoimidoyl)-2-fluorobenzoyl)-β-ethyl-α,α-dimethyl-β-alanyl)-4-piperidineacetic acid, Ethyl-N-(N-(4-(4-hydroxy-1-piperidinoimidoyl)-2-fluorobenzoyl)-β-ethyl-α,α-dimethyl-β-alanyl)-4-piperidineacetate, N-(N-(4-(4-hydroxy-1-piperidinoimidoyl)-2-fluorobenzoyl)-β-ethyl-α,α-dimethyl-β-alanyl)-4-piperidineacetic acid, Ethyl-N-(N-(4-(3-thiazolidinoimidoyl)-2-fluorobenzoyl)-β-ethyl-α,α-dimethyl-β-alanyl)-4-piperidineacetate, N-(N-(4-(3-thiazolidinoimidoyl)-2-fluorobenzoyl)-β-ethyl-α,α-dimethyl-β-alanyl)-4-piperidineacetic acid, Ethyl-N-(N-(4-(1-hexamethyleneiminoimidoyl)-2-fluorobenzoyl)-β-ethyl-α,α-dimethyl-β-alanyl)-4-piperidineacetate, N-(N-(4-(1-hexamethyleneiminoimidoyl)- 2-fluorobenzoyl)-β-ethyl-α,α-dimethyl-β-alanyl)-4-piperidineacetic acid, Ethyl-N-(N-(4-(N-thiomorpholinoimidoyl)-2-fluorobenzoyl)-β-ethyl-α,α-dimethyl-β-alanyl)-4-piperidineacetate, N-(N-(4-(N-thiomorpholinoimidoyl)-2-fluorobenzoyl)-β-ethyl-α,α-dimethyl-β-alanyl)-4-piperidineacetic acid, Ethyl-N-(N-(4-(4-methyl-1-piperazinoimidoyl)-2-fluorobenzoyl)-β-ethyl-α,α-dimethyl-β-alanyl)-4-piperidineacetate, N-(N-(4-(4-methyl-1-piperazinoimidoyl)-2-fluorobenzoyl)-β-ethyl-α,α-dimethyl-β-alanyl)-4-piperidineacetic acid, Ethyl-N-(N-(4-(4-phenyl-1-piperazino)imidoyl)-2-fluorobenzoyl)-β-ethyl-α,α-dimethyl-β-alanyl)-4-piperidineacetate, N-(N-(4-(4-phenyl-1-piperazinoimidoyl)-2-fluorobenzoyl)-β-ethyl-α,α-dimethyl-β-alanyl)-4-piperidineacetic acid, Ethyl-N-(N-(4-(4-(4-fluorophenyl)-1-piperazinoimidoyl)-2-fluorobenzoyl)-β-ethyl-α,α-dimethyl-β-alanyl)-4-piperidineacetate, N-(N-(4-(4-(4-fluorophenyl)-1-piperazinoimidoyl)-2-fluorobenzoyl)-β-ethyl-α,α-dimethyl-β-alanyl)-4-piperidineacetic acid, Benzyl-N-(N-(4-(4-morpholinoimidoyl)benzoyl-β-phenyl-α,α-dimethyl-β-alanyl)-4-piperidineacetate, N-(N-(4-(4-morpholinoimidoyl)benzoyl-β-phenyl-α,α-dimethyl-β-alanyl)-4-piperidineacetic acid, Methyl-N-(N-(4-(1-pyrrolidinoimidoyl)-2-fluorobenzoyl)-β-ethyl-α,α-dimethyl-β-alanyl)-4-piperidineacetate, N-(N-(4-(N-Tetrahydroisoquinolinoimidoyl)-2-fluorobenzoyl)-β-ethyl-α,α-dimethyl-β-alanyl)-4-piperidineacetic acid, N-(N-(4-(4-Phenyl-1-piperazinoimidoyl)-2-fluorobenzoyl)-β-(m-hydroxyphenyl)-α,α-dimethyl-β-alanyl)-4-piperidineacetic acid, N-(N-(4-(4-Fluoro-1-piperidinoimidoyl)-2-fluorobenzoyl)-β-(3,5-difluorophenyl)-α,α-dimethyl-β-alanyl)-4-piperidineacetic acid, N-(N-(4-(Diphenylaminoimidoyl)-2-fluorobenzoyl)-β-methyl-α,α-dimethyl-β-alanyl)- 4-piperidineacetic acid, N-(N-(4-(N-Indolylimidoyl)-2-fluorobenzoyl)-β-n-butyl-α,α-dimethyl-β-alanyl)-4-piperidineacetic acid, N-(N-(4-(4-Phenyl-1-piperazinoimidoyl)-2-fluorobenzoyl)-β-ethyl-α,α-dimethyl-β-alanyl)-4-piperazineacetic acid, N-(N-(4-(4-(2-Pyrimidyl)-1-piperazinoimidoyl)-2-fluorobenzoyl)-β-cyclopropyl-α,α-dimethyl-β-alanyl)-4-piperidineacetic acid, N-(N-(4-(4-Methyl-1-homopiperazinoimidoyl)-2-chlorobenzoyl)-β-n-butyl-α,α-dimethyl-β-alanyl)-4-piperidineacetic acid, N-(N-(4-(N-(4,4'-Dipiperidino)imidoyl)-benzoyl)-β-ethyl-α,α-dimethyl-β-alanyl)-4-piperidineacetic acid, N-(N-(4-(4-(3-Trifluorophenyl)-1-piperazinoimidoyl)-2-fluorobenzoyl)-β-ethyl-α,α-dimethyl-β-alanyl)-4-piperidineacetic acid, N-(N-(4-(4-(2-Quinolyl)-1-piperazinoimidoyl)-2-methoxybenzoyl)-β-phenyl-α,α-dimethyl-β-alanyl)-4-piperidineacetic acid, N-(N-(4-(N-(3-Hydroxypyrrolidinoimidoyl)-2-fluorobenzoyl)-β-ethyl-α,α-dimethyl-β-alanyl)-4-piperidineacetic acid, N-(N-(4-(N-cis-3,4-Dihydroxypyrrolidinoimidoyl)-2-fluorobenzoyl)-β-phenyl-α,α-dimethyl-β-alanyl)-4-piperidineacetic acid, N-(N-(4-(N-3-Hydroxypiperidinoimidoyl)-2-fluorobenzoyl)-β-ethyl-α,α-dimethyl-β-alanyl)-4-piperidineacetic acid, N-(N-(4-(N-cis-3,4-Dihydroxypiperidino-imidoyl)-2-fluorobenzoyl)-β-ethyl-α,α-dimethyl-β-alanyl)-4-piperidineacetic acid, N-(N-(4-(N-(4-Methylamino)piperidinoimidoyl)-2-fluorobenzoyl)-β-ethyl-α,α-dimethyl-β-alanyl)-4-piperidineacetic acid, N-(N-(4-(N-Methylpipeconylimidoyl)-2-fluorobenzoyl)-β-ethyl-α,α-dimethyl-β-alanyl)-4-piperidineacetic acid, N-(N-(4-(N-Methylnipecotinylimidoyl)-2-fluorobenzoyl)-β-methyl-α,α-dimethyl-β-alanyl)-4-piperidineacetic acid, N-(N-(4-(N-(2,2,6,6-Pentamethylpiperidino)imidoyl)benzoyl)-β-ethyl-α,α-dimethyl-β-alanyl)- 4-piperidineacetic acid, N-(N-(4-(1-(1,4,8,11-Tetraazacyclotetradecanyl)imidoyl)-2-fluorobenzoyl)-β-(4-hydroxyphenyl)-α,α-dimethyl-β-alanyl)-4-piperidineacetic acid, N-(N-(4-(N-Tetrahydroisoquinolinylimidoyl)-2-fluorobenzoyl)-β-2-morpholinyl-α,α-dimethyl-β-alanyl)-4-piperidineacetic acid, N-(N-(4-(N-Oxazolidinoylimidoyl)-2-fluorobenzoyl)-β-3-hydroxyphenyl-α,α-dimethyl-β-alanyl)-4-piperidineacetic acid, N-(N-(4-(N-4, 5-Dihydro-oxazolidinoylimidoyl)-2-fluorobenzoyl)-β-ethyl-α,α-dimethyl-β-alanyl)-4-piperidineacetic acid, N-(N-(4-(N-Thiazolidinoylimidoyl)-2-fluorobenzoyl)-β-ethyl-α,α-dimethyl-β-alanyl)-4-piperidineacetic acid, N-(N-(4-(N-4,5-Dihydro-thiazolidinoylimidoyl)-2-fluorobenzoyl)-β-methyl-α,α-dimethyl-β-alanyl)-4-piperidineacetic acid, N-(N-(4-(N-3-Methoxy-piperidinylimidoyl)-2-fluorobenzoyl)-β-ethyl-α,α-dimethyl-β-alanyl)-4-piperidineacetic acid, N-(N-(4-(1,2-Dihydro-triazinylimidoyl)-2-fluorobenzoyl)-β-ethyl-α,α-dimethyl-β-alanyl)-4-piperidineacetic acid, N-(N-(4-(18-crown-6-Morpholinoimidoyl)-2-fluorobenzoyl)-β-ethyl-α,α-dimethyl-β-alanyl)-4-piperidineacetic acid, N-(N-(4-(Azetidinylimidoyl)-2-fluorobenzoyl)-β-ethyl-α,α-dimethyl-β-alanyl)-4-piperidineacetic acid, N-(N-(4-(Azetidinylimidoyl)-2-fluorobenzoyl)-β-ethyl-α,α-dimethyl-β-alanyl)-4-piperazineacetic acid, N-(N-(4-(2-Hydroxy-piperidinylimidoyl)benzoyl)-β-ethyl-α,α-dimethyl-β-alanyl)-4-piperidineacetic acid, N-(N-(4-(N-Imidazolylimidoyl)-2-fluorobenzoyl)-β-ethyl-α,α-dimethyl-β-alanyl)-4-piperidineacetic acid, N-(N-(4-(1-(4-Hydroxypiperazinyl)imidoyl)-2-fluorobenzoyl)-β-ethyl-α,α-dimethyl-β-alanyl)-4-piperidineacetic acid, N-(N-(4-(1-cis-3, 4-Dihydroxypyrrolidinyl-imidoyl)-2-fluorobenzoyl)-β-ethyl-α,α-dimethyl-β-alanyl)-4-piperidineacetic acid, N-(N-( 4-(N-Pyrrolidinylimidoyl)-2-fluorobenzoyl)-β-ethyl-α,α-dimethyl-β-alanyl)-4-piperidineacetic acid, and N-(N-(4-(N-3,4-Dehydro-pyrrolidinylimidoyl)-2-fluorobenzoyl)-β-ethyl-α,α-dimethyl-β-alanyl)-4-piperidineacetic acid.

The pharmaceutically acceptable salts of the compounds of the present invention are generally non-toxic salts. Exemplary salts are salts with bases and acid addition salts including salts with inorganic bases such as alkaline metal salts (e.g., sodium salt and potassium salt), alkaline earth metal salts (e.g., calcium salt and magnesium salt) and ammonium salts; salts with organic bases such as organic amine salts (e.g, triethylamine salt, pyridine salt, picoline salt, ethanolamine salt, triethanolamine salt, dicyclohexylamine salt and N,N'-dibenzylethylenediamine salt); inorganic acid addition salts (e.g., hydrochloride, hydrobromide, sulfate and phosphate); organic carboxylic acid or sulfonic acid addition salts (e.g., formate, acetate, propionate, trifluoroacetate, maleate, malate, tartrate, succinate, citrate, methanesulfonate, benzenesulfonate, p-toluenesulfonate and glycolate); and salts with basic or acidic amino acids (e.g., salts with arginine, aspartic acid and glutamic acid salts).

The compounds of the present invention can be prepared by synthesis. A method for preparing the compounds of the present invention will now be described in detail.

Three structual parts of the compounds are synthesized and combined to prepare the compounds. The three parts are (a) a substituted-4-amidinobenzoic part which is located on the left side of general formula (I), (b) a substituted β-amino acid residue part which is located in the middle, and (c) a piperidine or piperazine part having a carboxyl or carboxyalkyl group at the 4-position which is located on the right side. If these units are commercially available, they are used with or without protecting functional groups which do not take part in the reaction to prepare the compounds of the present invention. If these units are not commercially available, they are synthesized by an appropriate method and then used to prepare the compounds of the present invention by a conventional method which is used in peptide chemistry as described below.

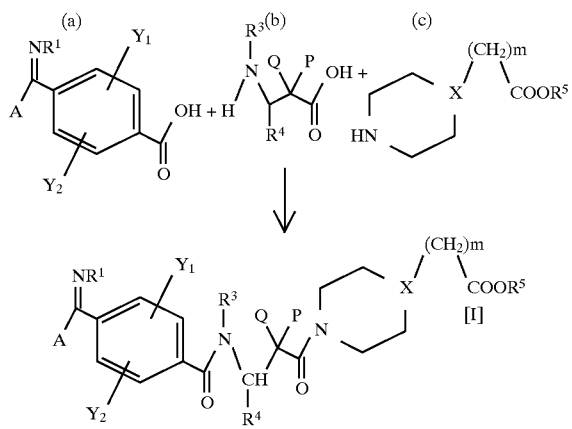

The compounds of the present invention can be also obtained by condensing synthetic precursors of the respective units and then derivatizing the obtained compounds to ones having desired functional groups.

Since the compounds of the present invention have two peptide bonds in the molecule, each amino acid-like unit can be synthesized either in a liquid or solid phase by any conventional methods used in peptide chemistry such as those described in Schroder and Luhke, "The Peptides" vol.1, Academic Press, New York, U.S.A. (1966), Nobuo Izumiya et al., "The Fundamentals and Experiments of Peptide Synthesis", Maruzen (1985), and other references. These preparation methods may be a column or batch method.

The condensation methods for forming peptide bonds include, for example, the azide method, acid chloride method, acid anhydride method, carbodiimide method, carbodiimide-additive method, active ester method, carbonyl imidazole method, redox method, enzymatic method and the method using Woodward's reagent K, HATU reagent or Bop reagent. In the case of performing a condensation reaction by a solid phase method, the acid anhydride method, carbodiimide method and active ester method may predominantly be used.

When a peptide chain is to be extended by the solid phase method, the C-terminal amino acid is coupled to a support such as a resin that is insoluble in organic solvents to be used. In this case, resin may be modified depending on the purpose by introducing a functional group for the purpose of bonding amino acids to the resin, by inserting a spacer between the resin and a functional group or by introducing a chain called "handle" which can be cleaved in various positions depending on the conditions. Exemplary resins include halomethyl resins (such as chloromethyl resin), oxymethyl resin, 4-(oxymethyl)-phenylacetamide methyl resin, 4-(oxymethyl)-phenoxymethyl resin, resin for C-terminal amidation, and the like.

Prior to the condensation reaction, carboxyl, amino, hydroxyl and amidino groups that do not take part in the condensation reaction may be protected by conventional and known techniques. In contrast with this, carboxyl and amino groups that directly take part in the condensation reaction may be activated.

As protective groups for use in the protection of functional groups that do not take part in the condensation reaction of each unit, those which are commonly used in the field of organic chemistry, as described in Greene, "Protective Groups in Organic Synthesis", John Wiley & Sons, Inc. (1981), can be used.

Exemplary protective groups for carboxyl group include commonly used and known protective groups such as various kinds of methyl ester, ethyl ester, benzyl ester, p-nitrobenzyl ester, t-butyl ester, cyclohexyl ester, and the like.

Exemplary protective groups for amino group include benzyloxycarbonyl, t-butoxycarbonyl, isobornyloxycarbonyl and 9-fluorenylmethoxycarbonyl groups.

Exemplary protective groups for hydroxyl group in the substituted β-amino acid residue containing a hydroxyl group include t-butyl, benzyl, trimethylsilyl and tetrahydropyranyl groups.

Exemplary protective groups for amidino group include benzyloxycarbonyl group.

Exemplary compounds with an activated carboxyl group include an acid anhydride corresponding to the carboxyl group; azide; active esters with pentafluorophenol, 2,4-dinitrophenol, cyanomethyl alcohol, p-nitrophenol, N-hydroxysuccinimide, N-hydroxy-5-norbornene-2,3-dicarboximide, N-hydroxyphthalimide and 1-hydroxybenzotriazole.

Exemplary compounds with an activated amino group include an amide phosphate corresponding to the amino group.

The condensation reaction for peptide synthesis is usually carried out in a solvent. Exemplary solvents include chloroform, dichloromethane, ethyl acetate, N,N-dimethylformamide, dimethyl sulfoxide, pyridine, dioxane, tetrahydrofuran, N-methylpyrrolidone, water, methanol and the like, and mixtures thereof. The condensation reaction can be carried out at a temperature of from −30° to 50° C. as in the usual case.

The kind of the deprotection reaction to be carried out in the peptide preparation process can be selected depending on the kind of protective groups provided that they can be eliminated without affecting the peptide bonds. Exemplary deprotection reactions include a treatment with an acid such as hydrogen chloride, hydrogen bromide, anhydrous hydrogen fluoride, methanesulfonic acid, trifluoromethanesulfonic acid, trifluoroacetic acid, or a mixture thereof; a treatment with an alkali such as sodium hydroxide, potassium hydroxide, hydrazine, diethylamine, piperidine or the like; a treatment with sodium in liquid ammonia; reduction with palladium on carbon; a silylation treatment with trimethylsilyl triflate, trimethylsilyl bromide or the like. In the above deblocking reaction with an acid or silylation agent, cation-trapping agents such as anisole, phenol, cresol, thioanisole and ethanedithiol are preferably added to carry out the deblocking reaction effectively.

The compounds synthesized by the solid phase method can be cleaved from the solid phase by conventional methods. Exemplary methods for cleaving the compounds include treatments with the acid or silylation agents described above.

The compounds of the present invention thus prepared can be separated and purified in a conventional and known manner after the end of the series of reactions described above. For example, extraction, partition, reprecipitation, recrystallization, column chromatography and the like can be used to obtain the compounds in a more purified form.

The method of synthesizing each unit will now be described. A substituted-4-amidinobenzoic acid of Unit (a) can be used as such in the condensation of the unit. Alternatively, it can be converted to 4-cyanobenzoic acid and then condensed, followed by the conversion of the cyano group to a substituted amidino group (see the following formula).

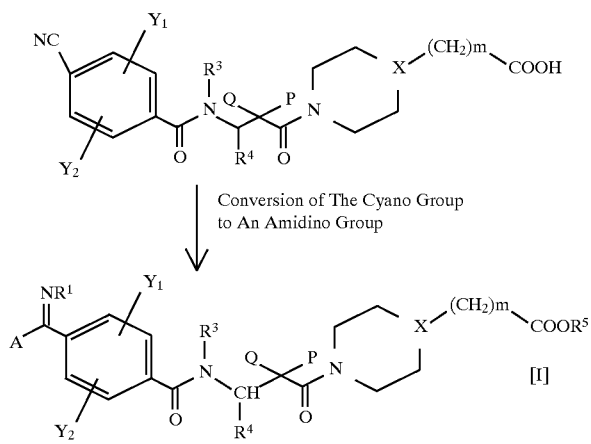

Unit (b) can be obtained by general methods of synthesizing substituted β-amino acids, for example, the method described in "Enantioselective Synthesis of β-amino acids", Eusebio Juaristi, et al., Aldrichimica Acta, Vol.27, No.1, pp.3–11, 1994 and the references cited therein. Alternatively, since β-lactam derivatives provide substituted β-amino acids upon cleavage of the lactam rings by hydrolysis, Unit (b) can be obtained easily at low cost by the preparation of β-lactam and subsequent hydrolysis as described in "A Synthetic Chemistry Review of Recent Advances in the Reaction of β-lactam Ring Formation", Koichi Imai, Vol.50 of "Organic Synthetic Chemistry", No.2, pp.112–130, 1992, "The Ester Enolate-Imine Condensation Route to beta-Lactams", David J. Hart and Deok-Chan Ha, Chemical Reviews, Vol.89, No.7, pp.1447–1465, 1989 and the references cited therein. Unit (c) can be obtained easily by reducing the corresponding 4-carboxyalkylpyridine or by oxidizing the hydroxyl group of a 4-hydroxyalkylpyridine having the same number of side chain carbon atoms including the carbon atoms of the carboxyl group and reducing the pyridine ring.

The compounds of the present invention can be used effectively as platelet aggregation-inhibiting agents in treating and preventing various diseases caused primarily or secondarily by platelet aggregation. In particular, they are useful as agents for inhibiting or preventing the arterial occlusion caused by thrombus formation as in cardiac infarction and cerebral infarction. Furthermore, they are useful as agents for inhibiting: i) acute reocclusion after pericutaneous transluminal coronary angioplasty (PTCA) is applied to stenosed coronary arteries in patients with angina or myocardial infarction; ii) reocclusion caused by reactivated platelets released from thrombus at the time of applying thrombolytic therapy using a fibrinolytic agent such as urokinase to the arterial thrombus, and iii) blood coagulation and platelet aggregation in medical treatments involving the extracorporeal circulation of blood.

The compounds of the present invention can also be used as cell adhesion-inhibiting agents, anti-inflammatory agents, anti-rheumatic agents, anti-osteoporosis agents and cancer metastasis-inhibiting agents.

When the compounds of the present invention thus prepared are used as active ingredients of platelet aggregation-inhibiting agents, they or their salts are formulated together with a solid or liquid pharmaceutically acceptable carrier or diluent, that is, an excipient, stabilizer, etc. In the pharmaceutical preparation, the ratio of the active ingredient to the carrier can be varied in the range of 1 to 90% by weight. The preparation may be in the form of granules, fine granules, powders, tablets, capsules, pills, liquids and solutions. The preparations may be orally administered in the form of bulk powders or they can be administered intravenously, intramuscularly or subcutaneously as injections. The injections may be prepared from powders of the compounds of the present invention or salts thereof just before use.

An organic or inorganic, solid or liquid pharmaceutically acceptable carrier or diluent suitable for oral, enteral or parenteral administration can be used to prepare the platelet aggregation-inhibiting agents of the present invention. Water, gelatin, lactose, starch, magnesium stearate, talc, animal fats and oils, vegetable fats and oils, benzyl alcohol, gums, polyalkylene glycol, petroleum resins, coconut oil, lanolin, and all other carriers for medicines can be used as carriers or diluents for the platelet aggregation-inhibiting agents of the present invention. Stabilizers, wetting agents, emulsifying agents, and salts for adjusting the osmolarity or pH of the preparation can appropriately be used as adjuvants.

If necessary, the platelet aggregation-inhibiting agents of the present invention may contain other pharmaceutically active ingredients such as other kinds of platelet aggregation-inhibiting agents.

In the case where the platelet aggregation-inhibiting agents are used in the form of granules, fine granules, powders, tablets or capsules, the content of the active ingredient is preferably in the range from 5 to 80% by weight. In the case where the platelet aggregation-inhibiting agents are used in the form of liquids and solutions, the content of the active ingredient is preferably in the range from 1 to 30% by weight. Furthermore, in the case where the platelet aggregation-inhibiting agents are used in the form of injections, the content of the active ingredient is preferably in the range from 1 to 10% by weight.

When the platelet aggregation-inhibiting agents are to be administered orally, the clinical dose of the active ingredient is preferably in the range from 100 to 1000 mg per day for adult patients, which can be varied depending on the age of the patients, severity of the diseases to be treated and the like. The platelet aggregation-inhibiting agents can be administered in the aforementioned daily dose either once a day, or twice or three times a day at suitable intervals. In the case of injections, the dose of the active ingredient is preferably in the range from one to several hundreds milligrams per injection for adult patients. The administration can be conducted stepwise by means of injection or continued over time by means of drip infusion and the like. When the compounds or salts of the present invention are used for extracorporeal circulation, they can be used in the form of injections. The dose thereof is the same as in the case of the platelet aggregation-inhibiting agents.

As shown in the Comparative Examples described below, β-amino acid derivatives which are mono-substituted at the α positions do not generally have high biological activity. If substituents are introduced at the β positions of these derivatives, their biological activity greatly decreases. In contrast, the β-amino acid derivatives of the present invention which are substituted at the α positions with two lower alkyls are generally about 10 times more biologically active than unsubstituted β-amino acid derivatives. Moreover, the introduction of substituents at the β positions causes a great increase in the biological activity. This would be because the β-amino acid derivative of the present invention has the spatial position of a substituent at the β position fixed at the site where it can interact with a receptor by inserting the substituent at the β position between two substituents at the α position and the amide group.

The β-amino acid residues of the compounds of the present invention are formed by converting the portion of peptide-bond forming amino acid residues from α-amino acid residues, which generally constitute proteins in the body, to nearly non-native β-amino acid residues. Such a conversion can greatly increase the in vivo stability of peptide bonds against proteolytic enzymes, thereby inhibits the degradation of the compounds of the present invention in the body and prolongs the working time of drugs. The introduction of substituents in the β-amino acid residues further increases the stability against proteolytic enzymes and enhances the hydrophobic nature of the molecules, whereby the poor bioavailability of peptide-bond-containing compounds like those of the present invention which results from the hydrophilic nature of peptide bonds is modified such as to increase the bioavailability in oral administration.

In order to antagonize the action of fibrinogen receptors, compounds should have both a basic and an acidic site, keeping at a certain spatial distance in the molecule, and these sites should bind to the fibrinogen receptors. In the compounds of the present invention, the basic site is a substituted amidino group and the acidic site is a fatty acid residue at the 4 position of the piperidine ring. Basically, any substituents that are not bulky enough to inhibit the binding of the two aforementioned receptor-recognizing sites to the receptor and which improve the oral bioavailability due to increased in vivo stability and hydrophobicity can be employed as substituents of the β-amino acid residues. In order to have high platelet aggregation-inhibiting activity, the substituents described herein are preferred for the following reasons. The substituents described herein have a hydrophobic nature and thereby provide new sites of interaction with the receptor. As a result, the receptor-binding force of the compounds of the present invention is further increased. In addition, the introduction of the substituents described herein regulates the motility of the compounds having straight-chain structures with a great degree of freedom and fixes the steric molecular structures so that the steric structures required for the development of high biological acivity can be held stable and the receptor-binding force is increased. Hence, the introduction of those substituents is very important for improving the usefulness of the compounds.

The bioavailability of a compound is influenced by the nature of the functional groups in its molecule. An amidino group is generally a negative factor with respect to bioavailability. The compounds of the invention include those having an amidino group of which the free amino group has been replaced with a tertiary amine. These compounds have enhanced hydrophobic nature than those compounds having an unsubstituted amidino group, and thus they acquire still higher bioavailability.

As regards the preparation, the β-amino acid residues of the compounds of the present invention can be synthesized by directly applying the methods for synthesizing β-lactams which are used as antiboitics. Since a wide variety of methods for synthesizing β-lactams have been developed, the compounds of the present invention can be synthesized easily and at low cost.

As is clear from the description, the novel compounds of the present invention having substituted β-amino acid residues are useful as fibrinogen receptor antagonists.

The present invention will now be explained in greater detail with reference to the following examples. It should, however, be noted that the scope of the present invention is not limited by these examples.

SYNTHESIS OF COMPOUNDS

EXAMPLE 1

Synthesis of N-(N-4-amidinobenzoyl-α,α-dimethyl-β-alanyl)-4-piperidineacetic acid

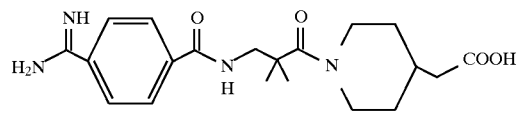

(1) Methyl 2,2-dimethyl-cyanoacetate

Methyl cyanoacetate (15 ml) and methyl iodide (200 g) were stirred and refluxed under the presence of potassium carbonate in acetone for 4 days and the potassuim carbonate was then removed by filtration. Acetone was distilled off from the filtrate and the residue was distilled in vacuo (16 mmHg, 76° C.) to yield methyl 2,2-dimethyl-cyanoacetate (19.5 g, 73%).

NMR: $^1$H (270 MHz, CDCl$_3$) 1.62, s, 6H: 3.83, s, 3H: $^{13}$C(67.5 MHz, CDCl$_3$) 24.6, 38.4, 121.0, 170.0

(2) N-(N-t-Butoxycarbonyl-α,α-dimethyl-β-alanyl)-4-piperidineacetic acid benzyl ester Methyl 2,2-dimethyl-cyanoacetate (2.0 g) was stirred under a hydrogen atmosphere in a 1N ammonium-containing methanol/ethanol (1:1) mixed solution under the presence of rhodium-alumina catalyst at a room temperature for 6 hours. The catalyst was removed from the reaction solution by filtration and the solvents were distilled off. To the residue were added 4N caustic soda (3 ml) and dioxane (3 ml) and the mixture was stirred at a room temperature for 6 hours. To the resulting mixture were added a 2N aqueous solution of sodium carbonate (25 ml) and di-t-butyl carbonate (2.9 g) dissolved in dioxane (20 ml) and the mixture was stirred for 12 hours. After the solvents were distilled off from the reaction solution, the residue was dissolved in water, washed with ether and adjusted to pH 3 with citric acid under cooling with ice, followed by extraction three times with ethyl acetate. The organic layer was washed with saturated NaCl three times and dried over sodium sulfate. The solvents were distilled off to yield N-t-butoxycarbonyl-α,α-dimethyl-β-alanine (2.5 g). The obtained N-t-butoxycarbonyl-α,α-dimethyl-β-alanine (1.1 g), 4-piperidineacetic acid benzyl ester tosylate (1.52 g), bromo-tris-pyrrolidinophosphoniumhexafluorophosphate (PyBrop, 2.20 g) and triethylamine (1.7 ml) were dissolved in methylene chloride (15 ml) and the mixture was stirred at room temperature for 1 hour. After the solvent was distilled off, the residue was applied to a silica gel column (φ 2.5×40 cm, Si-60, eluent: 30% ethyl acetate/hexane) for purification to yield N-(N-t-butoxycarbonyl-α,α-dimethyl-β-alanyl)-4-piperidineacetic acid benzyl ester (1.55 g, 96.0%).

NMR: $^1$H (270 MHz, CDCl$_3$) 1.08–1.28, m, 1H: 1.25, s, 6H: 1.42, s, 9H: 1.77, br-d, J=11 Hz, 2H: 1.92–2.10, m, 1H: 2.31, d, J=7.3 Hz, 2H: 2.77, t, J=13 Hz, 2H: 3.21, d, J=6.8 Hz, 2H: 4.35, d, J=12 Hz, 2H: 5.45, t, J=6.4 Hz, 1H: 7.33–7.40, m, 5H: $^{13}$C(67.5 MHz, CDCl$_3$) 14.2, 22.2, 27.5, 32.1, 33.3, 40.9, 43.5, 45.0, 51.5, 66.3, 77.3, 78.7, 128.3, 128.4, 135.9, 156.7, 172.0, 175.2; MS: [M+H]$^+$ calculated: 433.568, found: 433.3; [M+Na]$^+$ calculated: 455.550, found: 455.3

(3) N-(N-4-cyanobenzoyl-α,α-dimethyl-β-alanyl)-4-piperidineacetic acid benzyl ester N-(N-t-Butoxycarbonyl-α,α-dimethyl-β-alanyl)-4-piperidineacetic acid benzyl ester (1.6 g) was dissolved in trifluoroacetic acid (15 ml) and the mixture was stirred at room temperature for 2 hours. After trifluoroacetic acid was distilled off from the reaction solution, the residue was washed three times with hexane and volatile products were removed by toluene azeotropy in vacuo. The resulting residue, 4-cyanobenzoic acid (0.83 g), WSDC (2.16 g), HOBT (0.76 g) and triethylamine (3.2 ml) were dissolved in methylene chloride (50 ml) and the mixture was stirred at room temperature for 6 hours. After the solvent was distilled off, the residue was applied to a silica gel column (φ 2.5×40 cm, Si-60, eluent: 50% ethyl acetate/hexane) for purification to yield N-(N-4-cyanobenzoyl-α,α-dimethyl-β-alanyl)-4-piperidineacetic acid benzyl ester (1.26 g, 76.0%).

NMR: $^1$H (270 MHz, CDCl$_3$) 1.15–1.41, m, 2H: 1.36, mp, 6H: 1.81, d, J=12 Hz, 2H: 1.91–2.18, m, 1H: 2.37, d, J=6.8 Hz, 2H: 2.82–3.01, m, 2H: 3.62, s, 2H: 4.34–4.46, m, 2H: 4.83, s, 2H: 7.33–7.40, m, 5H: 7.85, d, J=8.8 Hz, 2H: 7.96, d, J=8.8 Hz, 2H; MS: [M+H]$^+$ calculated: 462.239, found: 462.3; [M+Na]$^+$ calculated: 484.221, found: 484.2

(4) N-(N-4-Amidinobenzoyl-α,α-dimethyl-β-alanyl)-4-piperidineacetic acid benzyl ester N-(N-4-Cyanobenzoyl-α,α-dimethyl-β-alanyl)-4-piperidineacetic acid benzyl ester (0.6 g) was dissolved in pyridine (15 ml) and hydrogen sulfide gas was introduced for 1 hour. The reaction container was sealed and the reaction mixture was stirred at a room temperature for 12 hours. The solvent was distilled off and methyl iodide (2 g) was added, followed by refluxing in acetone for 3 hours. After the solvent and excess methyl iodide were distilled off from the reaction solution, ammonium acetate (0.2 g) was added and the mixture was refluxed in methanol for 6 hours. After the solvent was distilled off, the residue was dissolved in a small amount of methylene chloride and reprecipitated from hexane to yield N-(N-4-amidinobenzoyl-α,α-dimethyl-β-alanyl)-4-piperidineacetic acid benzyl ester (0.25 g, 40.0%).

MS: [M+H]$^+$ calculated: 479.599, found: 479.3; [M+Na]$^+$ calculated: 501.581, found: 501.3

(5) Synthesis of the titled compound

N-(N-4-Amidinobenzoyl-α,α-dimethyl-β-alanyl)-4-piperidineacetic acid benzyl ester (0.10 g) was stirred under a hydrogen atmosphere in a 50% water/methanol mixed solution under the presence of palladium hydroxide catalyst at a room temperature for 6 hours. The catalyst was removed by filtration and the solvents were distilled off. The residue was dissolved in a 1N aqueous solution of acetic acid and the resulting solution was purified with a high performance liquid chromatography (HPLC) [column: ODS 5C$_{18}$ (μ bondasphere, φ 19×150 mm), mobile phase: (A) 0.1% TFA, (B) 100% CH$_3$CN/0.1% TFA, gradient: (A):(B)= 80:20–70:30, 20 minutes, flow rate: 17 ml/min]. The desired fractions were collected and lyophilized to yield N-(N-4-amidinobenzoyl-α,α-dimethyl-β-alanyl)-4-piperidineacetic acid (15 ml).

NMR: $^1$H (270 MHz, CDCl$_3$) 0.62–0.92, m, 8H: 1.32–1.74, m, 4H: 1.68, d, J=6.8, 1H: 2.4, br-tt, J=2.8, 12 Hz, 1H: 2.65, m, 1H: 2.91–3.10, m, 2H: 3.74, br-d, J=13 Hz, 1H: 4.17, br-d, J=13 Hz, 1H: 7.50–7.70, m, 4H; MS: [M+H]$^+$ calculated: 389.468, found: 389.2

EXAMPLE 2

Synthesis of N-(N-4-amidinobenzoyl-β-phenyl-α,α-dimethyl-β-alanyl)-4-piperidineacetic acid

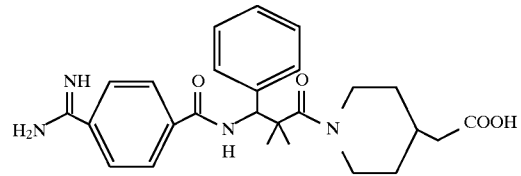

(1) Fmoc[N-9-fluorenylmethoxycarbonyl]-4-piperidineacetic acid

4-Pyridineacetic acid hydrochloride (10 g) was dissolved in 6N HCl (300 ml). To the resulting solution was added platinum oxide (1 g) and the mixture was stirred in a hydrogen stream at room temperature for 3 days. HCl was removed from the reaction solution and the residue was completely dried with a high-vacuum pump to yield a white crystal (9.5 g). The obtained crystal was dissolved in a 10% aqueous solution of sodium carbonate (187 ml). To the resulting solution, a solution of Fmoc-Cl (13.6 g) in dioxane (100 ml) was added dropwise under cooling with ice and the mixture was stirred at room temperature overnight. The solvents were distilled off and the residue was dissolved in water and washed with ether. The aqueous layer was adjusted to pH 3 with concentrated HCl under cooling with ice and extracted with ethyl acetate. The ethyl acetate layer was washed with a saturated aqueous solution of NaCl and dried-over anhydrous sodium sulfate. Ethyl acetate was distilled off and a crystal was obtained upon recrystallization from hexane (14.5 g, 79.2%).

NMR: $^1$H (270 MHz: CDCl$_3$: 45° C.) 1.02–1.28, m, 2H: 1.73, d, 2H (J=12.7 Hz): 1.86–2.03, m, 1H: 2.28, d, 2H (J=7.3 Hz): 2.79, t, 2H (J=11.7 Hz): 4.10, m, 2H: 4.23, t, 1H (J=6.8 Hz): 4.45, d, 2H (J=6.8 Hz): 7.30, t, 2H (J=7.3 Hz): 7.38, t, 2H (J=7.3 Hz): 7.56, d, 2H (J=7.3 Hz): 7.75, d, 2H (J=7.3 Hz): $^{13}$C(67.5 MHz: CDCl$_3$) 31.7, 32.9, 40.7, 44.1, 47.7, 67.3, 120.1, 125.1, 127.1, 127.8, 141.6, 144.3, 155.4, 177.2; MS: [M+Na]$^+$ calculated: 388.16, found: 388.2

(2) 4-Phenyl-3,3-dimethyl-2-azetidinone

A solution of n-butyl lithium in n-hexane (14.4 ml, 24 mmol) was added to a solution of diisopropylamine (3.4 ml) in tetrahydrofuran (15 ml) at −78° C. and reaction was performed at −78° C. for 20 minutes. To the reaction solution, a solution of ethyl iso-butyrate (2.68 ml, 20 mmol) in tetrahydrofuran (10 ml) was added dropwise and reaction was performed at −78° C. for 1 hour. To the resulting reaction solution, N-(trimethylsilyl)benzaldimine was added dropwise and reaction was performed for 1 hour. N-(Trimethylsilyl)benzaldimine had been prepared by reacting a solution of 1,1,1,3,3,3-hexamethyldisilazane (4.8 ml) in tetrahydrofuran (10 ml) with a solution of n-butyl lithium in n-hexane (13.2 ml, 22 mmol) at 0° C. for 20 minutes, distilling off the solvents in vacuo, adding dropwise a solution of benzaldehyde (2.25 ml, 20 mmol) in tetrahydrofuran (10 ml) and performing reaction for 30 minutes.

The reaction was stopped by adding a saturated aqueous solution of ammonium chloride to the reaction solution and the reaction mixture was extracted 3 times with diethyl ether. The collected organic layer was washed 3 times with a saturated aqueous solution of NaCl and the organic layer was dried over anhydrous sodium sulfate. The solvent was distilled off and the obtained oil was applied to a silica gel column (2.5×40 cm) and eluted with a mixed solution (hexane:ethyl acetate=4:1). The desired fractions were collected and the solvents were distilled off to yield a crystal of 4-phenyl-3,3-dimethyl-2-azetidinone (2.18 g, 62.2%).

NMR: $^1$H (270 MHz: CDCl$_3$: 25° C.) 0.78, S, 3H: 1.47, S, 3H: 4.51, S, 1H: 6.27, br-s, 1H: 7.24–7.40, m, 5H; MS: [M+H]$^+$ calculated: 176.108, found: 176.0

(3) N-Fmoc-β-phenyl-α,α-dimethyl-β-alanine

To 4-phenyl-3,3-dimethyl-2-azetidinone (2.18 g, 12.4 mmol) was added 6N HCl (100 ml) and the mixture was stirred at room temperature for 24 hours. The reaction solution was washed with chloroform and the solvent was distilled off to yield a powder of β-phenyl-α,α-dimethyl-β-alanine hydrochloride (2.81 g, quant.).

NMR: $^1$H (270 MHz: D$_2$O: 25° C.) 1.06, s, 3H: 1.20, s, 3H: 4.41, s, 1H: 7.24–7.29, m, 2H: 7.32–7.36, m, 3H MS: [M+H]$^+$ calculated: 194.118, found: 194.0

The obtained β-phenyl-α,α-dimethyl-β-alanine hydrochloride (2.0 g, 10.8 mmol) was dissolved in a 10% aqueous solution of sodium carbonate (46 ml). To the resulting solution, a solution of Fmoc-Cl (3.35 g, 12.96 mmol) in dioxane (20 ml) was added dropwise under cooling with ice and the mixture was stirred at room temperature overnight. The solvents were distilled off and the residue was dissolved in water and washed with ether. The aqueous layer was adjusted to pH 3 with concentrated HCl under cooling with ice and extracted with ethyl acetate. The collected ethyl acetate layer was washed with a saturated solution of NaCl and dried over anhydrous sodium sulfate. The solvent was distilled off and the obtained oil was applied to a silica gel column (2.5×40 cm) and eluted with a mixed solution (chloroform:methanol=50:1). The desired fractions were collected and the solvents were distilled off to yield a crystal of N-Fmoc-β-phenyl-α,α-dimethyl-β-alanine (1.21 g, 26.6%).

NMR: $^1$H (270 MHz: CDCl$_3$: 25° C.) 1.03–1.42, m, 6H: 4.02–4.24, m, 1H: 4.24–4.48, m, 2H: 4.52–4.86, m, 1H: 7.12–7.78, m, 13H; MS: [M+Na]$^+$ calculated: 438.186, found: 438.2

(4) 4-Amidinobenzoic acid hydrochloride

4-Amidinobenzamide hydrochloride (10 g) was dissolved in a mixed solution of 6N HCl (300 ml) and acetic acid (50 ml) and the solution was refluxed at 110° C. for 6 hours. The reaction solution was cooled with ice and the resulting precipitate was filtered to yield a crystal of 4-amidinobenzoic acid hydrochloride (10.4 g).

NMR: $^1$H (270 MHz: DMSO: 27° C.) 7.95, d, 2H (J=7.8 Hz): 8.10, d, 2H (J=7.8 Hz): 9.45, s, 2H: 9.62, s, 2H: $^{13}$C(67.5 MHz: DMSO) 128.6, 129.5, 131.9, 135.2, 165.3, 166.3; MS: [M+H]$^+$ calculated: 165.07, found: 165.0

(5) Synthesis of the titled compound by a solid phase method p-Alkoxybenzyl alcohol resin [hydroxyl group content: 0.92 meq/g] (HOCH$_2$-Ph(1,4)-OCH$_2$-Ph(1,4)-Polymer) (0.272 g, 0.25 mmol) was placed in a reaction vessel and suspended in dimethylformamide (DMF). To the resulting suspension were added N-Fmoc-4-piperidineacetic acid (366 mg, 1 mmol) and diisopropylcarbodiimide (0.167 ml, 1 mmol) and the mixture was stirred in the presence of 4-dimethylaminopyridine (DMAP) (31 mg, 0.25 mmol) at room temperature for 4 hours. The resin was washed with dimethylformamide to give N-Fmoc-4-piperidineacetic acid-resin. By repeating the steps of shaking and filtering as shown in Table 1, N-Fmoc-β-phenyl-α,α-dimethyl-β-alanine and 4-amidinobenzoic acid hydrochloride was sequentially introduced in the N-Fmoc-4-piperidineacetic acid-resin to yield N-(N-4-amidinobenzoyl-β-phenyl-α,α-dimethyl-β-alanyl)-piperidineacetyl resin. The obtained resin was suspended in trifluoroacetic acid (20 ml) containing m-cresol (1 ml), thioanisole (1 ml) and ethanedithiol (0.2 ml) and the suspension was stirred at room temperature for 4 hours. The resulting resin was filtered through a glass filter and the filtrate was concentrated at room temperature. To the concentrate was added diethyl ether under cooling with ice to yield a crude powder of the desired compound as cleaved from the resin. The powder was washed again with diethyl ether and then dissolved in a 1N aqueous solution of acetic acid. The resulting solution was purified with a high performance liquid chromatography (HPLC) [column: ODS 5C$_{18}$ ($\mu$ bondasphere, $\phi$ 19×150 mm), mobile phase: (A) 0.1% TFA, (B) 100% CH$_3$CN/0.1% TFA, gradient: (A):(B) =80:20–70:30, 20 minutes, flow rate: 17 ml/min]. The desired fractions were collected and lyophilized to yield a powder of N-(N-4-amidinobenzoyl-β-phenyl-α,α-dimethyl-β-alanyl)-4-piperidineacetic acid (8.0 mg).

NMR: $^1$H (270 MHz, DMSO-d6, 30° C.) 0.78–1.27, m, 10H: 1.56–1.78, m, 1H: 2.03–2.16, m, 2H: 2.56–2.94, m, 2H: 3.36–3.52, m, 1H: 3.72–4.01, p, 1H: 4.42, br-d, J=12 Hz, 1H: 5.71, br-d, J=9.6 Hz, 1H: 7.12–7.37, m, 4H: 7.46, d, J=9.6 Hz, 2H: 7.91, d, J=9.6 Hz, 2H; MS: [M+H]$^+$ calculated: 465.250, found: 465.1; HPLC analysis A spectrum of analytical HPLC using CrestPak C18T-5 ($\phi$ 4.6×250 mm) column at a flow rate of 1.0 ml/min at room temperature by elution in a gradient of 10–40% acetonitrile (60 min) in 0.1% TFA had a single peak at a retention time of 38.04 minutes.

A spectrum of analytical HPLC using Wakosil-II 5C18HG ($\phi$ 4.6×250 mm) column at a flow rate of 1.0 ml/min at room temperature by elution in a gradient of 10–40% acetonitrile (60 min) in 0.1% TFA had a single peak at a retention time of 42.17 minutes.

TABLE 1

| Steps | Reagent or Solvent | Amount of use (ml/step) | Time (minute) | Cycle number |
|---|---|---|---|---|
| 1. | Dimethylformamide (DMF) | 30 | 1 | 6 |
| 2. | 20% Piperidine/DMF | 6 | 2 | 1 |
| 3. | 20% Piperidine/DMF | 6 | 20 | 1 |
| 4. | DMF | 50 | 1 | 10 |
| 5. | Fmoc-amino-acid & HOBT/DMF (3 eq each) | 6 | 2* | 1 |
| 6. | Diisopropylcarbodiimide (DIPCD) (3 eq) | 6 | 120 | 1 |

* Shaking was immediately followed by the next step without removal of the reagent or solvent.

(6) Synthesis of the titled compound by a liquid phase method (6-1) N-4-Cyanobenzoyl-β-phenyl-α,α-dimethyl-β-alanine β-Phenyl-α,α-dimethyl-β-alanine hydrochloride (1.88 g, 8.19 mmol) was dissolved in DMF (100 ml). To the resulting solution, triethylamine (Et₃N) (3.5 ml, 25.11 mmol) and 4-cyanobenzoyl-N-hydroxysuccinimide ester (4-cyanobenzoyl-OSu) (2.2 g, 9.01 mmol) were added under cooling with ice and the mixture was stirred at room temperature overnight. The solvent was distilled off and the residue was dissolved in a 5% aqueous ammonia and washed with ether. The aqueous layer was adjusted to pH 3 with citric acid under cooling with ice and extracted with ethyl acetate. The collected ethyl acetate layer was washed with a saturated aqueous solution of NaCl and dried over anhydrous sodium sulfate. The solvent was distilled off and a crystal of N-4-cyanobenzoyl-β-phenyl-α,α-dimethyl-β-alanine was obtained upon recrystallization from an ether-hexane mixed solution (2.54 g, 96.2%).

NMR: ¹H (270 MHz: CDCl₃: 25° C.)1.14, s, 3H: 1.44, s, 3H: 5.04, d, J=9.3 Hz, 1H: 7.15–7.40, m, 5H: 7.71, d, J=8.8 Hz, 2H: 7.93, d, J=8.8 Hz, 2H: 8.65, d, J=9.3 Hz, 1H; MS: [M+H]⁺ calculated: 345.129, found: 345.4

(6-2) N-4-Cyanobenzoyl-β-phenyl-α,α-dimethyl-β-alanyl-4-piperidineacetic acid benzyl ester N-4-Cyanobenzoyl-β-phenyl-α,α-dimethyl-β-alanine (0.5 g, 1.55 mmol) was dissolved in methylene chloride (30 ml). To the resulting solution, BOP reagent (0.89 g, 4.03 mmol) and diisopropylethyl-amine (DIEA) (1.67 ml, 9.3 mmol) were added under cooling with ice and the mixture was stirred for 30 minutes. To the reaction mixture was added 4-piperidineacetic acid benzyl ester (1.08 g, 4.65 mmol) and the resulting mixture was stirred overnight. After the solvent was distilled off, the residue was dissolved in ethyl acetate, washed sequentially with a 5% aqueous solution of citric acid, a 5% aqueous solution of sodium bicarbonate and a saturated aqueous solution of NaCl 3 times each and dried over anhydrous sodium sulfate. The solvent was distilled off and the residue was applied to a silica gel column (2.2×20 cm) and eluted with a mixed solution (hexane:ethyl acetate=3:1). The desired fractions were collected and the solvents were distilled off to yield an oil of N-4-cyanobenzoyl-β-phenyl-α,α-dimethyl-β-alanyl-4-piperidineacetic acid benzyl ester (0.58 g, 69.6%).

NMR: ¹H (270 MHz: CDCl₃: 25° C.) 0.91–1.12, m, 2H: 1.23, s, 3H: 1.41, s, 3H: 1.66, br-t, J=13.2 Hz, 2H: 1.91–2.02, m, 1H: 2.19, d, J=6.8 Hz, 2H: 2.61, br-t, J=12.4 Hz, 1H: 2.69, br-t, J=18.8 Hz, 1H: 3.69, s, 2H: 4.08–4.32, br, 2H: 4.92, d, J=8.8 Hz, 1H: 6.74, dt, J=8.4 Hz, 3.2 Hz, 2H: 7.22–7.30, m, 8H: 7.62, d, J=8.0 Hz, 2H: 7.83, d, J=8.0 Hz, 2H ¹³C(100 MHz: CDCl₃: 25° C.) 25.23, 26.43, 31.74, 32.09, 32.96, 40.59, 45.36, 46.86, 55.15, 56.30, 63.12, 66.25, 113.50, 127.69, 128.17, 128.28, 130.07, 131.59, 132.29, 135.74, 138.54, 158.89, 164.22, 171.84, 175.76; MS: [M+Na]⁺ calculated: 560.252, found: 560.2

(6-3) N-4-Amidinobenzoyl-β-phenyl-α,α-dimethyl-β-alanyl-4-piperidineacetic acid benzyl ester N-4-Cyanobenzoyl-β-phenyl-α,α-dimethyl-β-alanyl-4-piperidineacetic acid benzyl ester (150 mg, 0.279 mmol) was dissolved in pyridine (10 ml). To the resulting solution was added triethylamine (1 ml) and the mixture was saturated with hydrogen sulfide gas. The reaction vessel was sealed and the reaction mixture was stirred at room temperature overnight. The pyridine was distilled off and the volatile products were removed by two cycles of toluene azeotropy. The residue was dissolved n acetone (15 ml) and methyl iodide (1 ml) was added thereto, followed by refluxing for 30 minutes. The solvent was distilled off and the residue was dissolved in methanol (10 ml). To the obtained solution was added ammonium acetate (100 mg) and the mixture was refluxed for 2 hours. After the solvent was distilled off, the residue was dissolved in chloroform, washed with a saturated aqueous solution of NaCl and dried over an hydrous sodium sulfate. The solvent was distilled off and the residue was applied to a silica gel column (1.5×14 cm) and eluted with a mixed solution (chloroform:methanol=5:1). The desired fractions were collected and the solvents were distilled off to yield an oil of N-4-amidinobenzoyl-β-phenyl-α,α-dimethyl-β-alanyl-4-piperidineacetic acid benzyl ester (72 mg, 46.5%).

NMR: ¹H (400 MHz: CDCl₃: 25° C.) 1.00, dd, J=12.4 Hz, 11.0 Hz, 1H: 1.10, dd, J=11.2 Hz, 11.0 Hz, 1H: 1.26, s, 3H: 1.31, s, 3H: 1.67, d, J=10.8 Hz, 2H: 1.97, br-s, 1H: 2.22, d, J=6.8 Hz, 2H: 2.6, br-s, 1H: 2.78, br-s, 1H: 4.17–4.33, 2H: 5.07, s, 2H: 5.23, d, J=7.1 Hz, 1H: 7.15–7.43, m, 10H: 7.65, d, J=8.0 Hz, 2H: 7.79, d, J=8.0 Hz, 2H: 8.98–9.11, m, 3H; MS: [M+H]⁺ calculated: 555.297, found: 555.4

(6-4) Synthesis of the titled compound

N-4-Amidinobenzoyl-β-phenyl-α,α-dimethyl-β-alanyl-4-piperidineacetic acid benzyl ester (63 mg, 0.114 mmol) was dissolved in an 80% aqueous methanol solution (10 ml) containing 2% acetic acid. To the reulting solution was added palladium hydroxide (50 mg) and the mixture was stirred in a hydrogen atmosphere for 15 minutes. The solvents were distilled off and the res idue was dissolved in a 1N aqueous solution of acetic acid. The resulting solution was purified with a high performance liquid chromatography (HPLC) under the same conditions as described in (3) to yield a powder of N-(N-4-amidinobenzoyl-β-phenyl-α,α-dimethyl-β-alanyl-4-piperidineacetic acid (47.5 mg, 89.9%). The obtained product was identified by NMR, MS and HPLC analyses to be the same compound as prepared by the solid phase method.

EXAMPLE 3

Synthesis of N-(N-4-Amidinobenzoyl-β-ethyl-α,α-dimethyl-β-alanyl)-4-piperidineacetic acid

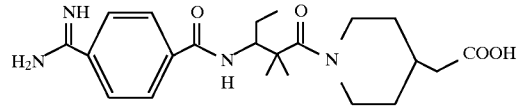

(1) 4-Ethyl-3,3-dimethyl-2-azetidinone

The same procedure as in Example 2-(2) was performed with ethyl isobutyrate (6.68 ml, 50 mmol) and propionaldehyde (4.0 ml, 55 mmol) to yield 4-ethyl-3,3-dimethyl-2-azetidinone (3.33 g, 52.5%).

NMR: ¹H (270 MHz: CDCl₃: 25° C.) 0.95, t, J=8.0 Hz, 3H: 1.18, s, 3H: 1.32, s, 3H: 1.56, m, 2H: 3.22, dd, J=6.0 Hz, 9.0 Hz, 1H: 6.01, br-s, 1H; MS: [M+H]⁺ calculated: 128.108, found: 128.1

(2) N-4-Cyanobenzoyl-β-ethyl-α,α-dimethyl-β-alanine

The same procedure as in Example 2-(3) was performed with 4-ethyl-3,3-dimethyl-2-azetidinone (2.0 g, 15.7 mmol) to yield a powder of β-ethyl-α,α-dimethyl-β-alanine hydrochloride (2.31 g, 81.3%).

NMR: ¹H (270 MHz: D₂O: 25° C.) 0.84, t, J=7.0 Hz, 3H: 1.06, s, 3H: 1.10, s, 3H: 1.38, m, 1H: 1.63, m, 1H: 3.16, dd, J=3.0 Hz, 10.0 Hz, 1H; MS: [M+H]⁺ calculated: 146.118, found: 146.0

The same procedure as in Example 2-(6-1) was performed with the obtained β-ethyl-α,α-dimethyl-β-alanine hydrochloride (1.0 g, 5.5 mmol) to yield a crystal of N-4-cyanobenzoyl-β-ethyl-α,α-dimethyl-β-alanine (1.32 g, 87.4%).

NMR: ¹H (270 MHz: CDCl₃: 25° C.) 0.94, t, J=7.3 Hz, 3H: 1.27, s, 3H: 1.29, s, 3H: 1.14, ddq, J=10.7 Hz, 14.0 Hz, 7.3 Hz, 1H: 1.83, ddq, J=2.0 Hz, 14.0 Hz, 7.3 Hz, 1H: 4.06, dt, J=2.0 Hz, 10.7 Hz, 1H: 7.44, d, J=10.7 Hz, 1H: 7.75, d, J=8.8 Hz, 2H: 7.94, d, J=8.8 Hz, 2H ¹³C(67.5 MHz: CDCl₃: 25° C.) 10.8, 23.0, 23.6, 24.1, 45.3, 57.7, 114.3, 117.8, 127.4, 132.0, 138.5, 165.2, 178.9; MS: [M+Na]⁺ calculated: 297.129, found: 297.0

(3) N-4-Cyanobenzoyl-β-ethyl-α,α-dimethyl-β-alanyl-4-piperidineacetic acid benzyl ester The same procedure as in Example 2-(6-2) was performed with N-4-cyanobenzoyl-β-ethyl-α,α-dimethyl-β-alanine (0.5 g, 1.82 mmol) to yield an oil of N-4-cyanobenzoyl-β-ethyl-α,α-dimethyl-β-alanyl-4-piperidineacetic acid benzyl ester (0.6 g, 67.2%).

NMR: ¹H (270 MHz: CDCl₃: 25° C.) 0.94, t, J=7.8 Hz, 3H: 1.07–1.30, m, 2H: 1.33, s, 3H: 1.41, s, 3H: 1.63–1.86, m, 4H: 1.98–2.17, m, 1H: 2.31, d, J=6.8 Hz, 2H: 2.69–2.92, m, 2H: 3.95, dt, J=3.9 Hz, 9.8 Hz, 1H: 4.36, br-d, J=12.7, 2H: 5.12, s, 2H: 7.35, m, 5H: 7.67–7.76, m, 1H: 7.72, d, J=8.3 Hz, 2H: 7.90, d, J=8.3 Hz, 2H ¹³C(67.5 MHz: CDCl₃: 25° C.) 11.7, 23.9, 24.5, 24.6, 31.9, 32.2, 33.1, 40.7, 46.2, 62.1, 66.3, 114.7, 118.1, 127.6, 128.2, 128.3, 128.6, 132.3, 135.8, 138.8, 165.5, 171.9, 175.4; MS: [M+Na]⁺ calculated: 512.271, found: 512.3

(4) N-4-Amidinobenzoyl-β-ethyl-α,α-dimethyl-β-alanyl-4-piperidineacetic acid benzyl ester The same procedure as in Example 2-(6-3) was performed with N-4-cyanobenzoyl-β-ethyl-α,α-dimethyl-β-alanyl-4-piperidineacetic acid benzyl ester (245 mg, 0.5 mmol) to yield an oil of N-4-amidinobenzoyl-β-ethyl-α,α-dimethyl-β-alanyl-4-piperidineacetic acid benzyl ester (81 mg, 31.9%).

NMR: ¹H (400 MHz: CDCl₃: 25° C.) 0.84, t, J=7.0 Hz, 3H: 1.07–1.22, m, 2H: 1.28 s, 3H: 1.24, s, 3H: 1.53–2.07, m, 5H: 2.28, d, J=7.2 Hz, 2H: 2.58–2.96, m, 2H: 4.09, t, J=6.8 Hz, 1H: 4.34, d, J=12.0 Hz, 2H: 5.10, s, 2H: 7.28–7.37, m, 5H: 7.83, d, J=8.4 Hz, 2H: 7.92, d, J=8.4 Hz, 2H: 8.18, br-s, 3H; MS: [M+H]⁺ calculated: 507.297, found: 507.3

(5) Synthesis of the titled compound

The same procedure as in Example 2-(6-4) was performed with N-4-amidinobenzoyl-β-ethyl-α,α-dimethyl-β-alanyl-4-piperidineacetic acid benzyl ester (40 mg, 0.096 mmol) to yield N-(N-4-amidinobenzoyl-β-ethyl-α,α-dimethyl-β-alanyl)-4-piperidineacetic acid (21 mg, 63.9%).

NMR: ¹H (400 MHz: CD₃OD: 25° C.) 0.89–0.99, m, 3H: 1.12–1.26, m, 2H: 1.27, s, 3H: 1.30, s, 3H: 1.53–1.70, m, 2H: 1.84, br-t, J=14.8 Hz, 2H: 2.00–2.14, m, 1H: 2.21–2.30, m, 2H: 2.75–3.10, br, 2H: 4.47, m, 1H: 4.55, br-d, J=13.6 Hz, 2H: 7.89, d, J=8.4 Hz, 2H: 7.99, d, J=8.4 Hz, 2H ¹³C(100 MHz: CD₃OD: 25° C.) 12.71, 27.09, 24.58, 25.02, 34.00, 34.14, 35.13, 42.32, 47–49, 130.07, 133.08, 144.90, 168.78, 170.51, 176.79, 177.10; MS: [M+H]⁺ calculated: 417.266, found: 417.2

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 26.73 minutes.

EXAMPLE 4

Synthesis of N-(N-4-amidinobenzoyl-β-n-propyl-α,α-dimethyl-β-alanyl)-4-piperidineacetic acid

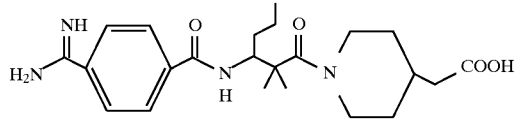

(1) 4-n-Propyl-3,3-dimethyl-2-azetidinone

The same procedure as in Example 2-(2) was performed with ethyl isobutyrate (6.68 ml, 50 mmol) and n-butylaldehyde (4.51 ml, 50 mmol) to yield a crystal of 4-n-propyl-3,3-dimethyl-2-azetidinone (2.95 g, 41.8%).

NMR: ¹H (270 MHz: CDCl₃: 25° C.) 0.92, t, J=7.0 Hz, 3H: 1.17, s, 3H: 1.31, s, 3H: 1.25–1.64, m, 4H: 3.27, dd, J=6.0 Hz, 8.0 Hz, 1H: 5.92, br-s, 1H; MS: [M+H]⁺ calculated: 142.123, found: 142.1

(2) N-4-Cyanobenzoyl-β-n-propyl-α,α-dimethyl-β-alanine

The same procedure as in Example 2-(3) was performed with 4-n-propyl-3,3-dimethyl-2-azetidinone (2.95 g, 20.9 mmol) to yield a powder of β-n-propyl-α,α-dimethyl-β-alanine hydrochloride (3.33 g, quant.).

NMR: ¹H (270 MHz: D₂O: 25° C.) 0.74, t, J=7.0 Hz, 3H: 1.07, s, 3H: 1.10, s, 3H: 1.04–1.57, m, 4H: 3.23, dd, J=2.0 Hz, 10.0 Hz, 1H; MS: [M+H]⁺ calculated: 160.114, found: 160.1

The same procedure as in Example 2-(6-1) was performed with the obtained β-n-propyl-α,α-dimethyl-β-alanine hydrochloride (1.0 g, 5.11 mmol) to yield a crystal of N-4-cyanobenzoyl-β-n-propyl-α,α-dimethyl-β-alanine (0.99 g, 67.2%).

NMR: ¹H (270 MHz: CDCl₃: 25° C.) 0.91, t, J=7.3 Hz, 3H: 1.28, s, 3H: 1.29, s, 3H: 1.26–1.46, m, 3H: 1.69, m, 1H: 4.12, m, 1H: 7.41, d, J=9.8 Hz, 1H: 7.74, d, J=8.8 Hz, 2H: 7.93, d, J=8.8 Hz, 2H ¹³C(67.5 MHz: CDCl₃: 25° C.) 13.6, 19.5, 23.1, 24.2, 32.9, 45.4, 55.9, 114.3, 117.8, 127.4, 132.0, 138.5, 165.0, 179.0; MS: [M+H]⁺ calculated: 289.155, found: 289.1

(3) N-4-Cyanobenzoyl-β-n-propyl-α,α-dimethyl-β-alanyl-4-piperidineacetic acid benzyl ester The same procedure as in Example 2-(6-2) was performed with N-4-cyanobenzoyl-β-n-propyl-α,α-dimethyl-β-alanine (400 mg, 1.39 mmol) to yield an oil of N-4-cyanobenzoyl-β-n-propyl-α,α-dimethyl-β-alanyl-4-piperidineacetic acid benzyl ester (175 mg, 25.1%).

NMR: ¹H (270 MHz: CDCl₃: 25° C.) 0.19, t, J=7.3 Hz, 3H: 1.08–1.46, m, 4H: 1.33, s, 3H: 1.41, s, 3H: 1.55–1.85, m, 4H: 1.98–2.16, m, 1H: 2.31, d, J=7.3 Hz, 2H: 2.68–2.89, m, 2H: 4.03, dt, J=3.0 Hz, 10.3 Hz, 1H: 4.36, br-d, J=13.2 Hz, 2H: 5.12, s, 2H: 7.35, m, 5H: 7.67–7.76, m, 1H(NH): 7.72, d, J=8.3 Hz, 2H: 7.89, d, J=8.3 Hz, 2H ¹³C(67.5 MHz: CDCl₃: 25° C.) 14.0, 20.4, 24.5, 24.7, 31.9, 32.2, 33.1, 33.3, 40.7, 46.2, 60.3, 66.3, 114.7, 118.1, 127.6, 128.2, 128.3, 128.6, 132.3, 135.8, 138.8, 165.3, 171.9, 175.5; MS: [M+H]⁺ calculated: 526.280, found: 526.3

(4) N-4-Amidinobenzoyl-β-n-propyl-α,α-dimethyl-β-alanyl-4-piperidineacetic acid benzyl ester The same procedure as in Example 2-(6-3) was performed with N-4-cyanobenzoyl-β-n-propyl-α,α-dimethyl-β-alanyl-4-piperidineacetic acid benzyl ester (175 mg, 0.35 mmol) to yield an oil of N-4-amidinobenzoyl-β-n-propyl-α,α-dimethyl-β-alanyl-4-piperidineacetic acid benzyl ester (69.1 mg, 38.2%).

NMR: ¹H (270 MHz: CDCl₃: 25° C.) 0.84, t, J=6.8 Hz, 3H: 0.99–1.49, m, 5H: 1.22, s, 3H: 1.27, s, 3H: 1.59–1.82, m, 3H: 2.03, m, 1H: 2.28, d, J=5.9 Hz, 2H: 2.60–2.87, m, 2H: 4.12–4.45, m, 3H: 5.10, s, 2H: 7.33, m, 5H; 7.77–7.98, m, 1H: 7.82, br-d, J=7.3 Hz, 2H: 7.94, br-d, J=7.3 Hz, 2H: 9.01, br-s, 1.5H: 9.31, br-s, 1.5H; MS: [M+H]+ calculated: 521.313, found: 521.4

(5) Synthesis of the titled compound

The same procedure as in Example 2-(6-4) was performed with N-4-amidinobenzoyl-β-n-propyl-α,α-dimethyl-β-alanyl-4-piperidineacetic acid benzyl ester (35 mg, 0.067 mmol) to yield N-(N-4-amidinobenzoyl-β-n-propyl-α,α-dimethyl-β-alanyl)-4-piperidineacetic acid (24.3 mg, 84.0%).

NMR: $^1$H (400 MHz: CD$_3$OD: 25° C.) 0.90–0.97, m, 3H: 1.15–1.36, m, 3H: 1.27, s, 3H: 1.31, m, 3H: 1.36–1.47, m 2H: 1.58–1.71, m, 1H: 1.76–1.89, m, 2H: 1.97–2.13, m, 1H: 2.19–2.08, m, 2H: 4.48–4.63, m, 3H: 7.83–7.92, m, 2H: 7.94–8.02, m, 2H $^{13}$C(100 MHz: CD$_3$OD: 25° C.) 15.00, 22.01, 24.13, 24.58, 24.09, 35.15, 42.35, 56.82, 130.81, 133.07, 141.89, 168.70, 170.24, 176.80, 177.12; MS: [M+H]+ calculated: 431.266, found: 431.3

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 32.51 minutes.

EXAMPLE 5

Synthesis of N-(N-4-amidinobenzoyl-β-isopropyl-α, α-dimethyl-β-alanyl)-4-piperidineacetic acid

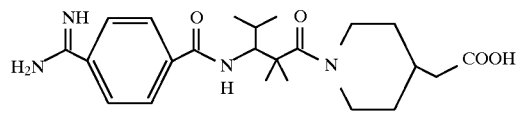

(1) 4-Isopropyl-3,3-dimethyl-2-azetidinone

The same procedure as in Example 2-(2) was performed with ethyl isobutyrate (6.68 ml, 50 mmol) and isobutylaldehyde (4.93 ml, 50 mmol) to yield 4-isopropyl-3,3-dimethyl-2-azetidinone (3.87 g, 54.9%).

NMR: $^1$H (270 MHz: CDCl$_3$: 25° C.) 0.89, d, J=6.0 Hz, 3H: 0.93, d, J=6.0 Hz, 3H: 1.23, s, 3H: 1.31, s, 3H: 1.75, m, 1H: 2.90, d, J=10.0 Hz, 1H: 5.85, br-s, 1H; MS: [M+H]+ calculated: 142.123, found: 142.0

(2) N-4-Cyanobenzoyl-β-isopropyl-α,α-dimethyl-β-alanine

The same procedure as in Example 2-(3) was performed with 4-isopropyl-3,3-dimethyl-2-azetidinone (2.0 g, 14.2 mmol) to yield a powder of β-isopropyl-α,α-dimethyl-β-alanine hydrochloride (2.68 g, 97.2%).

NMR: $^1$H (270 MHz: D$_2$O: 25° C.) 0.75, d, J=7.0 Hz, 3H: 0.86, d, J=7.0 Hz, 3H: 1.09, s, 3H: 1.14, s, 3H: 2.02, m, 1H: 3.12, d, J=3.0 Hz, 1H; MS: [M+H]+ calculated: 160.134, found: 160.4

The same procedure as in Example 2-(6-1) was performed with the obtained β-isopropyl-α,α-dimethyl-β-alanine hydrochloride (1.0 g, 5.11 mmol) to yield a crystal of N-4-cyanobenzoyl-β-isopropyl-α,α-dimethyl-β-alanine (1.26 g, 85.3%).

NMR: $^1$H (270 MHz: CDCl$_3$: 25° C.) 0.86, d, J=6.8 Hz, 3H: 1.00, d, J=6.8 Hz, 3H: 1.33, s, 3H: 1.36, s, 3H: 2.21, d-sep, J=3.4 Hz, 6.8 Hz, 1H: 4.19, dd, J=3.4 Hz, 10.3 Hz, 1H: 7.57, d, J=10.3 Hz, 1H: 7.77, d, J=8.8 Hz, 2H: 7.95, d, J=8.8 Hz, 2H $^{13}$C(67.5 MHz: CDCl$_3$: 25° C.) 16.6, 22.0, 23.0, 26.0, 29.2, 44.6, 60.8, 115.1, 117.9, 127.6, 132.5, 138.4, 166.1, 182.8; MS: [M+Na]+ calculated: 311.145, found: 311.0

(3) N-4-Cyanobenzoyl-β-isopropyl-α,α-dimethyl-β-alanyl-4-piperidineacetic acid benzyl ester The same procedure as in Example 2-(6-2) was performed with N-4-cyanobenzoyl-β-isopropyl-α,α-dimethyl-β-alanine (0.4 g, 1.34 mmol) to yield an oil of N-4-cyanobenzoyl-β-isopropyl-α,α-dimethyl-β-alanyl-4-piperidineacetic acid benzyl ester (105 mg, 15.0%).

NMR: $^1$H (270 MHz: CDCl$_3$: 25° C.) 0.93, d, J=6.4 Hz, 3H: 1.02, d, J=6.4 Hz, 3H: 1.08–1.27, m, 2H: 1.30, s, 3H: 1.40, s, 3H: 1.75–1.88, m, 2H: 1.97–2.18, m, 2H: 2.33, d, J=6.8 Hz, 2H: 2.69–2.95, m, 2H: 4.11, dd, J=5.4 Hz, 9.8 Hz, 1H: 4.45, br-d, J=13.2 Hz, 2H: 5.12, s, 2H: 7.35, m, 5H: 7.75, d, J=8.3 Hz, 2H: 7.84–7.93, m, 1H: 7.92, d, J=8.3 Hz, 2H $^{13}$C (67.5 MHz: CDCl$_3$: 25° C.) 19.3, 22.7, 24.3, 24.6, 29.9, 31.7, 32.0, 33.0, 40.6, 46.6, 62.5, 66.3, 114.6, 118.0, 127.6, 128.1, 128.2, 128.4, 132.3, 135.6, 138.6, 166.1, 172.1, 175.9; MS: [M+H]+ calculated: 504.286, found: 504.1

(4) N-4-Amidinobenzoyl-β-isopropyl-α,α-dimethyl-β-alanyl-4-piperidineacetic acid benzyl ester The same procedure as in Example 2-(6-3) was performed with N-4-cyanobenzoyl-β-isopropyl-α,α-dimethyl-β-alanyl-4-piperidineacetic acid benzyl ester (160 mg, 0.318 mmol) to yield an oil of N-4-amidinobenzoyl-β-isopropyl-α,α-dimethyl-β-alanyl-4-piperidineacetic acid benzyl ester (99 mg, 60.0%).

NMR: $^1$H (400 MHz: CDCl$_3$: 25° C.) 0.92, dd, J=5.6 Hz, 12.4 Hz, 3H: 1.00, d, J=6.4 Hz, 3H: 1.19, br-t, J=12.4 Hz, 1H: 1.13–1.43, m, 2H: 1.32, s, 3H: 1.39, s, 3H: 1.54, t, J=3.4 Hz, 1H: 1.79, d, J=11.2 Hz, 2H: 2.03–2.18, m, 2H: 2.31, d, J=7.2 Hz, 2H: 4.07, dd, J=5.2 Hz, 9.6 Hz, 1H: 4.36, br-s, 2H: 5.12, s, 2H: 7.31–7.38, m, 5H: 7.86, d, J=8.4 Hz, 2H: 7.94, d, J=8.4 Hz, 2H; MS: [M+H]+ calculated: 521.329, found: 521.3

(5) Synthesis of the titled compound

The same procedure as in Example 2-(6-4) was performed with N-4-amidinobenzoyl-β-isopropyl-α,α-dimethyl-β-alanyl-4-piperidineacetic acid benzyl ester (45 mg, 0.086 mmol) to yield N-(N-4-amidinobenzoyl-β-isopropyl-α,α-dimethyl-β-alanyl)-4-piperidineacetic acid (23.8 mg, 64.0%).

NMR: $^1$H (400 MHz: CD$_3$OD: 25° C.) 0.97, d, J=5.6 Hz, 6H: 1.17–1.32, m, 6H: 1.28, m, 6H: 1.83–1.92, m, 2H: 1.96–2.13, m, 2H: 2.27, d, J=6.8 Hz, 2H: 2.73–3.09, br-s, 2H: 4.45, J=8.8 Hz, 1H: 4.48–4.73, m, 2H: 7.90, d, J=7.2 Hz, 2H: 8.01, d, J=7.2 Hz, 2H; MS: [M+H]+ calculated: 431.282, found: 431.2

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 29.80 minutes.

EXAMPLE 6

Synthesis of N-(N-4-amidinobenzoyl-β-normal-butyl-α,α-dimethyl-β-alanyl)-4-piperidineacetic acid

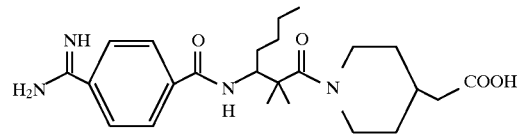

(1) 4-n-Butyl-3,3-dimethyl-2-azetidinone

The same procedure as in Example 2-(2) was performed with ethyl isobutyrate (6.68 ml, 50 mmol) and n-valeroaldehyde (5.13 ml, 50 mmol) to yield a crystal of 4-n-butyl-3,3-dimethyl-2-azetidinone (4.07 g, 52.4%).

NMR: $^1$H (270 MHz: CDCl$_3$: 25° C.) 0.93, t, J=6.0 Hz, 3H: 1.17, s, 3H: 1.31, s, 3H: 1.21–1.64, m, 6H: 3.28, dd, J=6.0 Hz, 8.0 Hz, 1H: 5.87, br-s, 1H; MS: [M+H]$^+$ calculated: 156.139, found: 156.0

(2) N-4-Cyanobenzoyl-β-n-butyl-α,α-dimethyl-β-alanine

The same procedure as in Example 2-(3) was performed with 4-n-butyl-3,3-dimethyl-2-azetidinone (2.0 g, 12.89 mmol) to yield a powder of β-n-butyl-α,α-dimethyl-β-alanine hydrochloride (2.65 g, 98.8%).

NMR: $^1$H (270 MHz: D2O: 25° C.) 0.69, t, J=7.0 Hz, 3H: 1.07, s, 3H: 1.10, s, 3H: 1.12–1.32, m, 4H: 1.37, m, 1H: 1.55, m, 1H: 3.22, dd, J=10.0 Hz, 2.0 Hz, 1H; MS: [M+H]$^+$ calculated: 174.149, found: 174.4

The same procedure as in Example 2-(6-1) was performed with the obtained β-n-butyl-α,α-dimethyl-β-alanine hydrochloride (1.0 g, 4.8 mmol) to yield a crystal of N-4-cyanobenzoyl-β-n-butyl-α,α-dimethyl-β-alanine (0.61 g, 41.4%).

NMR: $^1$H (270 MHz: CDCl$_3$: 25° C.) 0.88, t, J=6.8 Hz, 3H: 1.14–1.48, m, 4H: 1.19, s, 3H: 1.22, s, 3H: 1.48–1.65, m 2H: 4.40, m, 1H: 7.83, d, J=10.0 Hz, 2H: 7.96, d, J=10.0 Hz, 2H; MS: [M+H]$^+$ calculated: 303.171, found: 303.0

(3) N-4-Cyanobenzoyl-β-n-butyl-α,α-dimethyl-β-alanyl-4-piperidineacetic acid benzyl ester The same procedure as in Example 2-(6-2) was performed with N-4-cyanobenzoyl-β-n-butyl-α,α-dimethyl-β-alanine (200 mg, 0.66 mmol) to yield an oil of N-4-cyanobenzoyl-β-n-butyl-α,α-dimethyl-β-alanyl-4-piperidineacetic acid benzyl ester (207 mg, 58.0%).

NMR: $^1$H (400 MHz: CDCl$_3$: 25° C.) 0.86, t, J=6.0 Hz, 3H: 1.15–1.45, m, 6H: 1.33, s, 3H: 1.41, s, 3H: 1.70, br-s, 2H: 1.79, d, J=12.8 Hz: 2.04–2.13, m, 1H: 2.31, d, J=7.6 Hz, 2H: 2.80, br-s, 2H: 4.04, dt, J=2.8 Hz, 6.8 Hz, 1H: 4.38, br-d, J=11.6 Hz, 2H: 5.12, s, 2H: 7.30–7.38, m, 5H: 7.71, d, J=8.0 Hz, 2H: 7.90, d, J=8.0 Hz, 2H; MS: [M+Na]$^+$ calculated: 540.284, found: 540.4

(4) Synthesis of the titled compound

N-4-Cyanobenzoyl-β-n-butyl-α,α-dimethyl-β-alanyl-4-piperidineacetic acid benzyl ester (106 mg, 0.20 mmol) was dissolved in pyridine (10 ml). To the resulting solution was added triethylamine (1 ml) and the mixture was saturated with hydrogen sulfide gas. The reaction vessel was sealed and the reaction mixture was stirred at room temperature overnight. The pyridine was distilled off and the volatile products were removed by two cycles of toluene azeotropy. The residue was dissolved in acetone (15 ml) and methyl iodide (1 ml) was added thereto, followed by refluxing for 30 minutes. The solvent was distilled off and the residue was dissolved in methanol (10 ml). To the obtained solution was added ammonium acetate (100 mg) and the mixture was refluxed for 2 hours. After the solvent was distilled off, the residue was dissolved in chloroform, washed with a saturated aqueous solution of NaCl and dried over anhydrous sodium sulfate. The obtained crude N-4-amidinobenzoyl-β-n-butyl-α,α-dimethyl-β-alanyl-4-piperidineacetic acid benzyl ester (32 mg, 0.06 mmol) was dissolved in an 50% aqueous methanol solution (10 ml) containing 5% acetic acid. To the resulting solution was added palladium hydroxide (50 mg) and the mixture was stirred in a hydrogen atmosphere for 15 minutes. The solvents were distilled off and the residue was dissolved in a 1N aqueous solution of acetic acid. The resulting solution was purified with a HPLC to yield N-(N-4-amidinobenzoyl-β-n-butyl-α,α-dimethyl-β-alanyl)-4-piperidineacetic acid (6.5 mg, 24.3%).

NMR: $^1$H (400 MHz: CD3OD: 25° C.) 0.89, t, J=6.8 Hz, 3H: 1.13–1.43. m, 6H: 1.27, s, 3H: 1.30, s, 3H: 1.49, br-dd, J=6.9 Hz, 13.8 Hz: 1H: 1.64, br-dd, J=11.1 Hz, 22.0 Hz, 1H: 1.86, br-t, J=12.8 Hz, 2H: 2.01–2.12, m, 1H: 2.25, d, J=6.8 Hz, 2H: 2.77–3.08, br, 2H: 4.52–4.61, m, 3H: 7.89, d, J=8.0 Hz, 2H: 7.99, d, J=8.0 Hz, 2H; MS: [M+H]$^+$ calculated: 445.281, found: 445.3

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 39.77 minutes.

EXAMPLE 7

Synthesis of N-(N-4-amidinobenzoyl-β-normal-pentyl-α,α-dimethyl-β-alanyl)-4-piperidineacetic acid

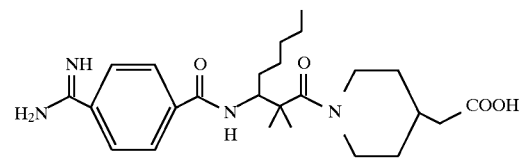

(1) 4-n-Pentyl-3,3-dimethyl-2-azetidinone

The same procedure as in Example 2-(2) was performed with ethyl isobutyrate (6.68 ml, 50 mmol) and 1-hexanal (5.27 ml, 50 mmol) to yield an oil of 4-n-pentyl-3,3-dimethyl-2-azetidinone (4.41 g, 52.1%).

NMR: $^1$H (270 MHz: CDCl$_3$: 25° C.) 0.90, m, 3H: 1.17, s, 3H: 1.31, s, 3H: 1.22–1.40, m, 6H: 1.43–1.62, m, 2H: 3.29, dd, J=5.8 Hz, 3.0 Hz, 1H: 5.96, br-s, 1H; MS: [M+H]$^+$ calculated: 170.154, found: 170.0

(2) N-4-Cyanobenzoyl-β-n-pentyl-α,α-dimethyl-β-alanine

The same procedure as in Example 2-(3) was performed with 4-n-pentyl-3,3-dimethyl-2-azetidinone (2.0 g, 11.8 mmol) to yield a powder of β-n-pentyl-α,α-dimethyl-β-alanine hydrochloride (2.37 g, 90.2%).

NMR: $^1$H (270 MHz: D2O: 25° C.) 0.70–0.76, m, 3H: 1.12, s, 3H: 1.14, s, 3H: 1.08–1.29, m, 5H: 1.33–1.49, m, 2H: 1.52–1.66, m, 1H: 3.26, dd, J=3.8 Hz, 14.0 Hz, 1H; MS: [M+H]$^+$ calculated: 188.165, found: 188.0

The same procedure as in Example 2-(6-1) was performed with the obtained β-n-pentyl-α,α-dimethyl-β-alanine hydrochloride (2.37 g, 12.7 mmol) to yield a crystal of N-4-cyanobenzoyl-β-n-pentyl-α,α-dimethyl-β-alanine (820 mg, 20.4%).

NMR: $^1$H (270 MHz: CDCl$_3$: 25° C.) 0.87, t, J=6.35 Hz, 3H: 1.15–1.38, m, 6H: 1.18, s, 3H: 1.22, s, 3H: 1.47–1.60, m 2H: 4.39, dd, J=4.3 Hz, 9.18 Hz, 1H: 7.84, d, J=8.4 Hz, 2H: 7.93, d, J=8.4 Hz, 2H; MS: [M+Na]$^+$ calculated: 339.169, found: 339.1

(3) N-4-Cyanobenzoyl-β-n-pentyl-α,α-dimethyl-β-alanyl-4-piperidineacetic acid benzyl ester The same procedure as in Example 2-(6-2) was performed with N-4-cyanobenzoyl-β-n-pentyl-α,α-dimethyl-β-alanine (360 mg, 1.14 mmol) to yield an oil of N-4-cyanobenzoyl-β-n-pentyl-α,α-dimethyl-β-alanyl-4-piperidineacetic acid benzyl ester (461 mg, 76.4%).

NMR: $^1$H (400 MHz: CDCl$_3$: 25° C.) 0.75, t, J=7.0 Hz, 3H: 1.03–1.35, m, 8H: 1.24, s, 3H: 1.32, s, 3H: 1.52–1.66, m, 2H: 1.70, br-d, J=13.2 Hz, 2H: 1.94–2.03, m, 1H: 2.22, d, J=8.4 Hz, 2H: 2.71, br-s, 2H: 3.96, dt, J=2.8 Hz, 10.4 Hz, 1H: 4.29, d, J=12.4 Hz, 2H: 5.03, s, 2H: 7.21–7.29, m, 5H: 7.62, d, J=8.4 Hz, 2H: 7.81, J=8.4 Hz, 2H; MS: [M+H]$^+$ calculated: 532.317, found: 532.4

(4) Synthesis of the titled compound

The same procedure as in Example 2-(6-3) was performed with N-4-cyanobenzoyl-β-n-pentyl-α,α-dimethyl-β-alanyl- 4-piperidineacetic acid benzyl ester (231 mg, 0.434 mmol) to yield an oil of N-4-amidinobenzoyl-β-n-pentyl-α,α-dimethyl-β-alanyl-4-piperidineacetic acid benzyl ester (102 mg, 42.8%).

MS: [M+H]$^+$ calculated: 549.344, found: 549.5

The same procedure as in Example 2-(6-4) was performed with the obtained N-4-amidinobenzoyl-β-n-pentyl-α,α-dimethyl-β-alanyl-4-piperidineacetic acid benzyl ester (52 mg, 0.095 mmol) to yield N-(N-4-amidinobenzoyl-β-n-pentyl-α,α-dimethyl-β-alanyl)-4-piperidineacetic acid (40 mg, 92.0%).

NMR: $^1$H (400 MHz: CD$_3$OD: 25° C.) 0.88, t, J=7.0 Hz, 3H: 1.15–1.52, m, 9H: 1.26, s, 3H: 1.30, s, 3H: 1.57–1.69, m, 1H: 1.85, br-t, J=12.4 Hz, 2H: 2.02–2.13, m, 1H: 2.25, d, J=6.8 Hz, 2H: 2.70–3.09, br-m, 2H: 4.52–4.61, m, 3H: 7.89, dt, J=6.8 Hz, 2.0 Hz, 2H: 7.99, dt, J=6.8 Hz, 2.0 Hz, 2H; MS: [M+H]$^+$ calculated: 459.297, found: 459.3

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 45.94 minutes.

EXAMPLE 8

Synthesis of N-(N-4-amidinobenzoyl-β-p-methoxyphenyl-α,α-dimethyl-β-alanyl)-4-piperidineacetic acid

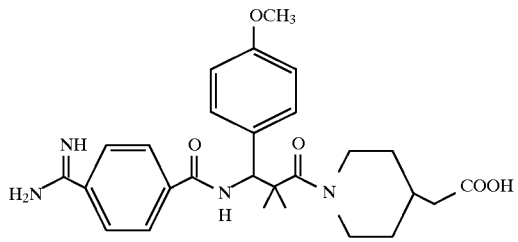

(1) 4-p-Methoxyphenyl-3,3-dimethyl-2-azetidinone

The same procedure as in Example 2-(2) was performed with ethyl isobutyrate (6.68 ml, 50 mmol) and p-methoxybenzaldehyde (6.08 ml, 50 mmol) to yield a crystal of 4-p-methoxyphenyl-3,3-dimethyl-2-azetidinone (3.39 g, 33.0%).

NMR: $^1$H (270 MHz: CDCl$_3$: 25° C.) 0.77, s, 3H: 1.49, s, 3H: 3.81, s, 3H: 4.45, s, 1H: 6.10, br-s, 1H: 6.90, d, J=8.5 Hz, 2H: 7.17, d, J=8.5 Hz, 2H; MS: [M+H]$^+$ calculated: 206.118, found: 206.0

(2) N-4-Cyanobenzoyl-β-p-methoxyphenyl-α,α-dimethyl-β-alanine

The same procedure as in Example 2-(3) was performed with 4-p-methoxyphenyl-3,3-dimethyl-2-azetidinone (1.54 g, 7.5 mmol) to yield a powder of β-p-methoxyphenyl-α,α-dimethyl-β-alanine hydrochloride (2.01 g, 77.3%).

NMR: $^1$H (270 MHz: D$_2$O: 25° C.) 1.10, s, 3H: 1.23, s, 3H: 3.75, s, 3H: 4.42, s, 1H: 6.95, d, J=8.7 Hz, 2H: 7.25, d, J=8.7 Hz, 2H; MS: [M+Na-H20]$^+$ calculated: 228.100, found: 227.9

The same procedure as in Example 2-(6-1) was performed with the obtained β-p-methoxyphenyl-α,α-dimethyl-β-alanine hydrochloride (1.0 g, 3.86 mmol) to yield a crystal of N-4-cyanobenzoyl-β-p-methoxyphenyl-α,α-dimethyl-β-alanine (860 mg, 63.0%).

NMR: $^1$H (270 MHz: CDCl$_3$: 25° C.) 1.17, s, 3H: 1.27, s. 3H: 3.77, s, 3H: 5.28, s, 1H: 6.86, d, J=8.4 Hz, 2H: 7.30, d, J=8.4 Hz, 2H: 7.83, d, J=8.0 Hz, 2H: 7.90, d, J=8.0 Hz, 2H; MS: [M+Na]$^+$ calculated: 375.132, found: 375.0

(3) N-4-Cyanobenzoyl-β-p-methoxyphenyl-α,α-dimethyl-β-alanyl-4-piperidineacetic acid benzyl ester The same procedure as in Example 2-(6-2) was performed with N-4-cyanobenzoyl-β-p-methoxyphenyl-α,α-dimethyl-β-alanine (200 mg, 0.57 mmol) to yield an oil of N-4-cyanobenzoyl-β-p-methoxyphenyl-α,α-dimethyl-β-alanyl-4-piperidineacetic acid benzyl ester (230 mg, 72.0%).

NMR: $^1$H (400 MHz: CDCl$_3$: 25° C.) 0.87–0.97, m, 1H: 0.97–1.03, m, 1H: 1.25, s, 3H: 1.42, s, 3H: 1.65, br-t: J=14.0 Hz, 2H: 1.94, m, 1H: 2.18, d, J=7.2 Hz, 2H: 2.58, br-t, J=12.0 Hz, 1H: 2.69, br-t, J=11.0 Hz, 1H: 4.11–4.37, m, 2H: 4.98, d, J=8.8 Hz, 1H: 5.04, m, 2H: 7.15–7.38, m, 10H: 7.62, d, J=8.4 Hz, 2H: 7.84, d, J=8.4 Hz, 2H $^{13}$C(100 MHz: CDCl$_3$: 25° C.) 25.23, 26.58, 31.72, 32.05, 40.57, 45.36, 46.81, 63.47, 66.25, 114.78, 118.11, 127.60, 127.71, 127.95, 128.17, 128.28, 128.54, 128.92, 132.30, 135.74, 138.45, 139.36, 164.31, 171.84, 175.63; MS: [M+Na]$^+$ calculated: 590.263, found: 590.4

(4) Synthesis of the titled compound

The same procedure as in Example 6-(4) was performed with N-4-cyanobenzoyl-β-p-methoxyphenyl-α,α-dimethyl-β-alanyl-4-piperidineacetic acid benzyl ester (100 mg, 0.18 mmol) to yield N-(N-4-amidinobenzoyl-β-p-methoxyphenyl-α,α-dimethyl-β-alanyl)-4-piperidineacetic acid (16.1 mg, 18.1%).

NMR: $^1$H (400 MHz: CD$_3$OD: 25° C.) 1.03–1.14, m, 2H: 1.14–1.37, m, 2H: 1.29, s, 3H: 1.33, s, 3H: 1.78, m, 2H: 1.97–2.03, m, 1H: 2.19, dd, J=2.4 Hz, 6.8 Hz, 2H: 2.79–3.97, br-s, 2H: 3.77, s, 3H: 4.44–4.53, m, 2H: 5.53, m, 1H: 6.88, d, J=8.8 Hz, 2H: 7.35, d, J=8.8 Hz, 2H: 7.88, d, J=8.4 Hz, 2H: 7.95, d, J=8.4 Hz, 2H $^{13}$C(100 MHz: CD$_3$OD: 25° C.) 25.28, 25.92, 33.93, 33.96, 35.06, 42.28, 47.66, 56.51, 61.43, 115.31, 125.11, 130.10, 130.14, 130.18, 130.19, 130.23, 131.66, 131.71, 132.59, 133.14, 141.90, 146.93, 161.49, 168.78, 168.93, 176.79, 177.01; MS: [M+H]$^+$ calculated: 495.216, found: 495.3

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 42.64 minutes.

EXAMPLE 9

Synthesis of N-(N-4-amidinobenzoyl-β-m-chlorophenyl-α,α-dimethyl-β-alanyl)-4-piperidineacetic acid

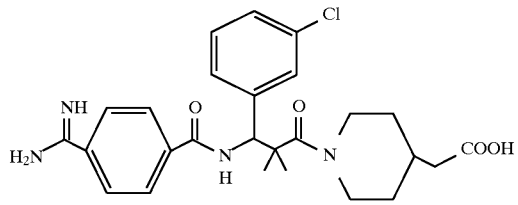

(1) 4-m-Chlorophenyl-3,3-dimethyl-2-azetidinone

The same procedure as in Example 2-(2) was performed with ethyl isobutyrate (6.68 ml, 50 mmol) and m-chlorobenzaldehyde (6.80 ml, 60 mmol) to yield a crystal of 4-m-chlorophenyl-3,3-dimethyl-2-azetidinone (9.1 g, 86.9%).

NMR: $^1$H (270 MHz: CDCl$_3$: 25° C.) 0.80, s, 3H: 1.47, s, 3H: 4.48, s, 1H: 6.41, br-s, 1H: 7.14, dt, J=7.0 Hz, 2.0 Hz, 1H: 7.30, s, 1H: 7.22–7.35, m, 2H; MS: [M+H]$^+$ calculated: 210.069, found: 209.9

(2) N-4-Cyanobenzoyl-β-m-chlorophenyl-α,α-dimethyl-β-alanine

The same procedure as in Example 2-(3) was performed with 4-m-chlorophenyl-3,3-dimethyl-2-azetidinone (2.0 g, 9.55 mmol) to yield a powder of β-m-chlorophenyl-α,α-dimethyl-β-alanine hydrochloride (2.47 g, 98.4%).

NMR: $^1$H (270 MHz: D$_2$O: 25° C.) 1.12, s, 3H: 1.31, s, 3H: 4.50, s, 1H: 7.33, dt, J=7.0 Hz, 2.0 Hz, 1H: 7.41–7.52, m, 3H; MS: [M+H]$^+$ calculated: 228.079, found: 227.8

The same procedure as in Example 2-(6-1) was performed with the obtained β-m-chlorophenyl-α,α-dimethyl-β-alanine hydrochloride (1.3 g, 4.9 mmol) to yield a crystal of N-4-cyanobenzoyl-β-m-chlorophenyl-α,α-dimethyl-β-alanine (1.6 g, 92.0%).

NMR: $^1$H (400 MHz: CDCl$_3$: 25° C.) 1.19, s, 3H: 1.28, s, 3H: 5.34, s, 1H: 7.27–7.34, m, 3H: 7.44, s, 1H: 7.83, d, J=8.4 Hz, 2H: 7.90, dt, J=8.4 Hz, 1.6 Hz, 2H; MS: [M+H]$^+$ calculated: 379.083, found: 378.9

(3) N-4-Cyanobenzoyl-β-m-chlorophenyl-α,α-dimethyl-β-alanyl-4-piperidineacetic acid methyl ester N-4-Cyanobenzoyl-β-m-chlorophenyl-α,α-dimethyl-β-alanine (300 mg, 0.84 mmol) was dissolved in methylene chloride (30 ml). To the resulting solution, BOP reagent (409 mg, 0.92 mmol) and triethylamine (1 ml) were added under cooling with ice and the mixture was stirred for 30 minutes. To the reaction mixture was added 4-piperidineacetic acid methyl ester (572 mg, 3.36 mmol) and the resulting mixture was stirred overnight. After the solvent was distilled off, the residue was applied to a silica gel column (2.2×20 cm) and eluted with a mixed solution (hexane:ethyl acetate=3:1). The desired fractions were collected and the solvents were distilled off to yield an oil of N-4-cyanobenzoyl-β-m-chlorophenyl-α,α-dimethyl-β-alanyl-4-piperidineacetic acid methyl ester (270 mg, 65.0%).

NMR: $^1$H (400 MHz: CDCl$_3$: 25° C.) 1.01, br-dd, J=11.1 Hz, 25.2 Hz, 1H: 1.16, ddd, J=4.0 Hz, 12.4 Hz, 25.2 Hz, 1H: 1.33, s, 3H: 1.51, s, 3H: 1.70, br-d, J=16.0 Hz, 1H: 1.79, br-d, J=16.4 Hz, 1H: 1.96–2.10, m, 1H: 2.23, d, J=6.8 Hz, 2H: 2.71, dd, J=10.8 Hz, 1.2 Hz: 1H: 2.67–2.86, m, 1H: 3.67, s, 3H: 4.33, br-s, 2H: 4.99, d, J=9.2 Hz, 1H: 7.23–7.25, m, 2H: 7.30–7.36, m, 1H: 7.46, s, 1H: 7.72, d, J=8.4 Hz, 2H: 7.92, d, J=8.4 Hz, 2H $^{13}$C (100 MHz: CDCl$_3$: 25° C.) 25.30, 26.54, 31.81, 32.12, 32.89, 40.35, 45.44, 46.73, 51.54, 63.50, 114.93, 118.09, 127.59, 127.75, 127.82, 128.98, 129.40, 132.36, 134.11, 138.17, 141.58, 164.36, 172.48, 175.35; MS: [M+Na]$^+$ calculated: 518.182, found: 518.2

(4) Synthesis of the titled compound

N-4-Cyanobenzoyl-β-m-chlorophenyl-α,α-dimethyl-β-alanyl-4-piperidineacetic acid methyl ester (80 mg, 0.16 mmol) was dissolved in pyridine (10 ml). To the resulting solution was added triethylamine (1 ml) and the mixture was saturated with hydrogen sulfide gas. The reaction vessel was sealed and the reaction mixture was stirred at room temperature overnight. The pyridine was distilled off and the volatile products were removed by two cycles of toluene azeotropy. The residue was dissolved in acetone (15 ml) and methyl iodide (1 ml) was added thereto, followed by refluxing for 30 minutes. The solvent was distilled off and the residue was dissolved in methanol (10 ml). To the obtained solution was added ammonium acetate (100 mg) and the mixture was refluxed for 2 hours. After the solvent was distilled off, the residue was dissolved in chloroform, washed with a saturated aqueous solution of NaCl and dried over anhydrous sodium sulfate. The obtained crude N-4-amidinobenzoyl-β-m-chlorophenyl-α,α-dimethyl-β-alanyl-4-piperidineacetic acid methyl ester (18 mg) was dissolved in an 50% aqueous methanol solution (10 ml). To the resulting solution was added a 2N aqueous solution of lithium hydroxide (3 ml) at room temperature and the mixture was stirred for 15 minutes. After the reaction solution was neutralized with 3N HCl to pH 7, the solvents were distilled off and the residue was dissolved in a 1N aqueous solution of acetic acid. The resulting solution was purified with a HPLC to yield N-(N-4-amidinobenzoyl-β-m-chlorophenyl-α,α-dimethyl-β-alanyl)-4-piperidineacetic acid (3.5 mg, 20.0%).

NMR: $^1$H (400 MHz: CD$_3$OD: 25° C.) 1.08, br-dd, J=22.0 Hz, 8.0 Hz, 1H: 1.22, ddd. J=2.8 Hz, 12.4 Hz, 24.4 Hz, 1H: 1.30, s, 3H: 1.36, s, 3H: 1.81, br-s, 2H: 1.97–2.10, m, 1H: 2.14–2.25, m, 2H: 2.80–3.03, br-m, 2H: 4.51, br-d, J=13.2 Hz, 2H: 5.56, s, 1H: 7.29–7.34, m, 2H: 7.39, dt, J=6.8 Hz, 1.6 Hz, 1H: 7.52, s, 1H: 7.89, dt, J=8.4 Hz, 2.0 Hz, 2H: 7.96, dt, J=8.4 Hz, 2.0 Hz, 2H; MS: [M+H]$^+$ calculated: 499.211, found: 499.1

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 50.10 minutes.

EXAMPLE 10

Synthesis of N-(N-4-amidinobenzoyl-β-p-fluorophenyl-α,α-dimethyl-β-alanyl)-4-piperidineacetic acid

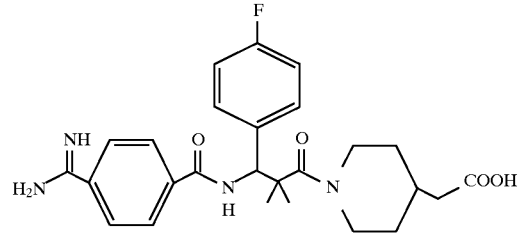

(1) 4-p-Fluorophenyl-3,3-dimethyl-2-azetidinone

The same procedure as in Example 2-(2) was performed with ethyl isobutyrate (6.68 ml, 50 mmol) and p-fluorobenzaldehyde (5.30 ml, 50 mmol) to yield a crystal of 4-p-fluorophenyl-3,3-dimethyl-2-azetidinone (2.64 g, 27.3%).

NMR: $^1$H (270 MHz: CDCl$_3$: 25° C.) 0.77, s, 3H: 1.46, s, 3H: 4.49, s, 1H: 6.34, br-s, 1H: 7.04–7.11, m, 2H: 7.19–7.25, m, 2H; MS: [M+H]$^+$ calculated: 194.098, found: 194.0

(2) N-4-Cyanobenzoyl-β-p-fluorophenyl-α,α-dimethyl-β-alanine

The same procedure as in Example 2-(3) was performed with 4-p-fluorophenyl-3,3-dimethyl-2-azetidinone (0.97 g, 5.0 mmol) to yield a powder of β-p-fluorophenyl-α,α-dimethyl-β-alanine hydrochloride (1.13 g, 91.3%).

NMR: $^1$H (270 MHz: D$_2$O: 25° C.) 1.07, s, 3H: 1.21, s, 3H: 4.44, s, 1H: 7.06–7.12, m, 2H: 7.27–7.32, m, 2H; MS: [M+H]$^+$ calculated: 212.108, found: 212.0

The same procedure as in Example 2-(6-1) was performed with the obtained β-p-fluorophenyl-α,α-dimethyl-β-alanine hydrochloride (0.50 g, 2.02 mmol) to yield a crystal of N-4-cyanobenzoyl-β-p-fluorophenyl-α,α-dimethyl-β-alanine (0.64 g, 93.8%).

NMR: $^1$H (270 MHz: CDCl$_3$: 25° C.) 1.12, s, 3H: 1.44, s, 3H: 5.01, d, J=8.8 Hz, 1H: 6.93–7.02, m, 2H: 7.30–7.39, m, 2H: 7.74, d, J=8.8 Hz, 2H: 7.94, d, J=8.8 Hz, 2H: 8.75, d, J=8.8 Hz, 1H $^{13}$C(67.5 MHz: CDCl$_3$: 25° C.) 22.9, 25.8, 45.3, 60.3, 114.6, 114.7, 115.0, 117.8, 127.5, 129.3, 129.4, 132.1, 135.0, 135.1, 138.0, 164.1, 179.1; MS: [M+H]$^+$ calculated: 341.138, found: 341.2

(3) N-4-Cyanobenzoyl-β-p-fluorophenyl-α,α-dimethyl-β-alanyl-4-piperidineacetic acid benzyl ester The same procedure as in Example 2-(6-2) was performed with N-4-cyanobenzoyl-β-p-fluorophenyl-α,α-dimethyl-β-alanine (200 mg, 0.59 mmol) to yield an oil of N-4-cyanobenzoyl-β-p-fluorophenyl-α,α-dimethyl-β-alanyl-4-piperidineacetic acid benzyl ester (169 mg, 51.8%).

NMR: $^1$H (270 MHz: CDCl$_3$: 25° C.) 0.98–1.22, m, 2H: 1.30, s, 3H: 1.50, s, 3H: 1.69–1.83, m 2H: 1.95–2.14, m, 1H: 2.28, d, J=7.3 Hz, 2H: 2.65–2.85, m 2H: 4.22–4.42, m, 2H: 5.02, d, J=8.8 Hz, 1H: 5.11, s, 2H: 6.93–7.03, m, 2H: 7.31–7.37, m, 5H: 7.39–7.48, m, 2H: 7.71, d, J=8.8 Hz, 2H: 7.91, d, J=8.8 Hz, 2H: 9.04, d, J=9.3 Hz, 1H $^{13}$C(67.5 MHz: CDCl$_3$: 25° C.) 25.2, 26.3, 31.8, 32.2, 33.0, 40.6, 46.7, 63.4, 66.3, 114.9, 115.2, 118.1, 127.7, 128.2, 128.3, 128.6, 130.7, 130.9, 132.3, 135.37, 135.42, 135.7, 138.3, 164.3, 171.8, 175.6; MS: [M+H]$^+$ calculated: 556.273, found: 556.3

(4) N-4-Amidinobenzoyl-β-p-fluorophenyl-α,α-dimethyl-β-alanyl-4-piperidineacetic acid benzyl ester The same procedure as in Example 2-(6-3) was performed with N-4-cyanobenzoyl-β-p-fluorophenyl-α,α-dimethyl-β-alanyl-4-piperidineacetic acid benzyl ester (142 mg, 0.256 mmol) to yield an oil of N-4-amidinobenzoyl-β-p-fluorophenyl-α,α-dimethyl-β-alanyl-4-piperidineacetic acid benzyl ester (66.2 mg, 45.2%).

NMR: $^1$H (400 MHz: CDCl$_3$: 25° C.) 0.90–1.10, m, 2H: 1.12, s, 3H: 1.24, s, 3H: 1.62, br-d, J=10.8 Hz, 2H: 1.85–1.98, br-s, 1H: 2.16, d, J=6.8 Hz, 2H: 2.51–2.64, br-s, 1H: 2.64–2.80, br-s, 1H: 4.14–4.30, br-m, 2H: 5.01, s, 2H: 5.10, d, J=8.8Hz, 1H: 6.87, t, J=8.0 Hz, 2H: 7.19–7.29, m, 5H: 7.35, t, J=6.6 Hz, 2H: 7.61, d, J=8.8 Hz, 2H: 7.74, d, J=8.8 Hz, 2H $^{13}$C (100 MHz: CDCl$_3$: 25° C.) 24.53, 25.43, 31.74, 31.99, 32.91, 40.59, 46.97, 61.51, 66.25, 114.87, 115.09, 128.19, 128.26, 128.43, 128.50, 128.55, 129.92, 130.73, 130.80, 134.85, 135.80, 138.98, 160.81, 165.57, 171.97, 174.86; MS: [M+H]$^+$ calculated: 573.303, found: 573.4

(5) Synthesis of the titled compound

The same procedure as in Example 2-(6-4) was performed with N-4-amidinobenzoyl-β-p-fluorophenyl-α,α-dimethyl-β-alanyl-4-piperidineacetic acid benzyl ester (30 mg, 0.0524 mmol) to yield N-(N-4-amidinobenzoyl-β-p-fluorophenyl-α,α-dimethyl-β-alanyl)-4-piperidineacetic acid (23 mg, 91.0%).

NMR: $^1$H (400 MHz: CD$_3$OD: 25° C.) 1.08–1.38, m, 2H: 1.29, s, 3H: 1.34, s, 3H: 1.80, br-d, J=13.2 Hz, 2H: 2.02, m, 1H: 2.19, m, 2H: 2.91, br, 2H: 4.50, m, 2H: 5.59, s, 1H: 7.06, m, 2H: 7.48, m, 2H: 7.88, m, 2H: 7.97, m, 2H $^{13}$C(100 MHz: CD$_3$OD: 25° C.) 25.15, 25.73, 33.91, 33.96, 35.02, 42.25, 47.68, 61.40, 116.46, 116.68, 130.12, 132.44, 132.52, 133.23, 136.46, 141.66, 163.24, 165.67, 168.75, 169.00, 176.76; MS: [M+H]$^+$ calculated: 483.257, found: 483.3

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 42.77 minutes.

EXAMPLE 11

Synthesis of N-(N-4-amidinobenzoyl-β-phenethyl-α,α-dimethyl-β-alanyl)-4-piperidineacetic acid

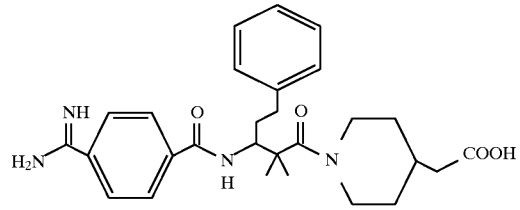

(1) 4-Phenethyl-3,3-dimethyl-2-azetidinone

The same procedure as in Example 2-(2) was performed with ethyl isobutyrate (6.68 ml, 50 mmol) and 3-phenylpropionaldehyde (6.57 ml, 50 mmol) to yield an oil of 4-phenethyl-3,3-dimethyl-2-azetidinone (3.50 g, 34.5%).

NMR: $^1$H (270 MHz: CDCl$_3$: 25° C.) 1.17, s, 3H: 1.30, s, 3H: 1.71–1.98, m, 2H: 2.53–2.75, m, 2H: 3.29, dd, J=4.0 Hz, 8.0 Hz, 1H: 5.52, br-s, 1H: 7.09–7.31, m, 5H; MS: [M+H]$^+$ calculated: 204.139, found: 203.9

(2) N-4-Cyanobenzoyl-β-phenethyl-α,α-dimethyl-β-alanyl-4-piperidineacetic acid benzyl ester The same procedure as in Example 2-(3) was performed with 4-phenethyl-3,3-dimethyl-2-azetidinone (3.50 g, 17.2 mmol) to yield a powder of β-phenethyl-α,α-dimethyl-β-alanine hydrochloride (4.42 g, quant.).

NMR: $^1$H (270 MHz: D$_2$O: 25° C.) 1.02, s, 3H: 1.06, s, 3H: 1.69, m, 1H: 1.82, m, 1H: 2.47, m, 1H: 2.68, m, 1H: 3.22, br-d, J=9.0 Hz, 1H: 7.02–7.23, m, 5H; MS: [M+H]$^+$ calculated: 222.149, found: 221.9

β-Phenethyl-α,α-dimethyl-β-alanine hydrochloride (600 mg, 2.33 mmol) was dissolved in DMF (100 ml). To the resulting solution, triethylamine (Et$_3$N) (0.98 ml, 6.99 mmol) and 4-cyanobenzoyl-OSu (630 mg, 2.56 mmol) were added under cooling with ice and the mixture was stirred at room temperature overnight. After the solvent was distilled off, the residue was dissolved in a 2N aqueous solution of sodium carbonate and washed with hexane. The aqueous layer was adjusted to pH 3 with citric acid and extracted with ethyl acetate. The collected ethyl acetate layer was washed with a saturated aqueous solution of NaCl and dried over anhydrous sodium sulfate. After the solvent was distilled off, the obtained crude N-4-cyanobenzoyl-β-phenethyl-α,α-dimethyl-β-alanine (200 mg, 0.57 mmol) was derivatized to N-4-cyanobenzoyl-β-phenethyl-α,α-dimethyl-β-alanyl-4-piperidineacetic acid benzyl ester (212 mg, 65.8%) by the same procedure as in Example 2-(6-2).

NMR: $^1$H (400 MHz: CDCl$_3$: 25° C.) 0.76–0.89, m, 1H: 1.05, br-dd, J=12.0 Hz, 11.0 Hz, 2H: 1.24, s, 3H: 1.27, s, 3H: 1.64–1.72, m, 2H: 1.83–2.11, m, 3H: 2.21, d, J=6.8 Hz, 1H: 2.47–2.57, m, 1H: 2.57–2.69, m, 2H: 4.03, dt, J=9.6 Hz, 0.3 Hz: 4.18–4.29, m, 2H: 5.04, s, 2H: 7.05–7.12, m 3H: 7.15–7.19, m, 2H: 7.25–7.29, m, 5H: 7.64, d, J=8.0 Hz, 2H: 7.80, d, J=8.0 Hz, 2H $^{13}$C(100 MHz: CDCl$_3$: 25° C.) 24.33, 24.51, 24.57, 31.79, 32.16, 33.04, 33.20, 33.48, 40.64, 44.85, 46.29, 60.03, 65.24, 66.34, 125.81, 126.96, 127.66, 128.21, 128.32, 128.48, 128.55, 132.34, 135.76, 138.61, 141.83; MS: [M+Na]$^+$ calculated: 588.284, found: 588.4

(3) Synthesis of the titled compound

The same procedure as in Example 6-(4) was performed with N-4-cyanobenzoyl-β-phenethyl-α,α-dimethyl-β-alanyl-4-piperidineacetic acid benzyl ester (100 mg, 0.17 mmol) to yield N-(N-4-amidinobenzoyl-β-p-phenethyl-α,α-dimethyl-β-alanyl)-4-piperidineacetic acid (14.1 mg, 16.8%).

NMR: $^1$H (400 MHz: CD$_3$OD: 25° C.) 0.77–0.97, br-s, 1H: 0.97–1.13, m, 1H: 1.13–1.28, m, 6H: 1.62–1.78, m, 2H: 1.83–1.96, m, 1H: 1.96–2.11, m, 1H: 2.18, d, J=6.8 Hz, 2H: 2.41–2.57, m, 2H: 2.68–2.87, m, 2H: 4.38, br-t, J=14.4 Hz, 2H: 4.58, br-t, J=11.2 Hz, 1H: 7.15–7.21, m, 3H: 7.27, t, J=7.2 Hz, 2H: 7.92, d, J=7.2 Hz, 2H: 8.04, d, J=7.2 Hz, 2H $^{13}$C(100 MHz: CD$_3$OD: 25° C.) 23.85, 24.36, 33.74, 33.89, 34.27, 34.58, 35.02, 42.17, 54.98, 128.06, 130.14, 130.36, 130.87, 133.14, 141.86, 143.55, 168.80, 170.48, 176.79; MS: [M+H]$^+$ calculated: 493.281, found: 493.3

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 43.67 minutes.

EXAMPLE 12

Synthesis of N-(N-4-amidinobenzoyl-β-cyclohexylmethyl-α,α-dimethyl-β-alanyl)-4-piperidineacetic acid

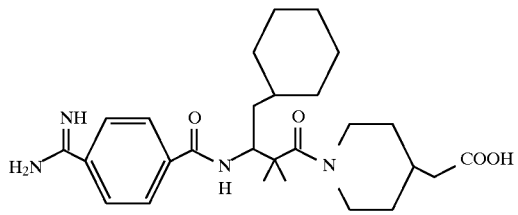

(1) 4-Cyclohexylmethyl-3,3-dimethyl-2-azetidinone

Dimethyl sulfoxide (DMSO) (3.3 ml, 58.5 mmol) was added dropwise at −78° C. to a solution of oxazolyl dichloride (3.6 ml, 46.8 mmol) in methylene chloride and the mixture was stirred for 15 minutes. To the resulting mixture, a solution of 2-cyclohexylethanol (5.5 ml, 39.0 mmol) in methylene chloride was added dropwise and the mixture was stirred at −78° C. for 1 hour. The reaction was stopped by adding triethylamine (20 ml) and water (100 ml). The reaction mixture was extracted 3 times with diethyl ether. The organic layer was washed 3 times each with saturated aqueous solutions of ammonium chloride and NaCl and dried over anhydrous sodium sulfate. After the solvent was distilled off, the obtained oil was applied to a silica gel column (2.5×40 cm) and eluted with a mixed solution (chloroform:methanol=10:1). The desired fractions were collected and the solvents were distilled off to yield cyclohexylacetaldehyde (2.88 g, 58.4%) as an oil. The same procedure as in Example 2-(2) was performed with ethyl isobutyrate (2.14 ml, 17.8 mmol) and the obtained cyclohexylacetaldehyde (2.25 g, 17.8 mmol) to yield a crystal of 4-cyclohexylmethyl-3,3-dimethyl-2-azetidinone (0.46 g, 13.3%).

NMR: $^1$H (270 MHz: CDCl$_3$: 25° C.) 0.87–1.08, m, 2H: 1.15, s, 3H: 1.30, s, 3H: 1.13–1.55, m, 5H: 1.67–1.77, m, 4H: 3.41, dd, J=4.0 Hz, 9.0 Hz, 1H: 5.81, br-s, 1H; MS: [M+H]$^+$ calculated: 196.170, found: 196.2

(2) N-4-Cyanobenzoyl-β-cyclohexylmethyl-α,α-dimethyl-β-alanine

The same procedure as in Example 2-(3) was performed with 4-cyclohexylmethyl-3,3-dimethyl-2-azetidinone (0.46 g, 2.36 mmol) to yield a powder of β-cyclohexylmethyl-α,α-dimethyl-β-alanine hydrochloride (0.51 g, 87.2%).

NMR: $^1$H (270 MHz: D$_2$O: 25° C.) 0.87, m, 1H: 1.06, m, 1H: 1.267, s, 3H: 1.274, s, 3H: 1.18–1.50, m, 6H: 1.63–1.82, m, 4H: 1.90, br-d, J=12.0 Hz, 1H: 3.43, dd, J=4.0 Hz, 9.0 Hz, 1H; MS: [M+H]$^+$ calculated: 214.181, found: 214.1

The same procedure as in Example 2-(6-1) was performed with the obtained β-cyclohexylmethyl-α,α-dimethyl-β-alanine hydrochloride (0.4 g, 1.60 mmol) to yield a crystal of N-4-cyanobenzoyl-β-cyclohexylmethyl-α,α-dimethyl-β-alanine (244 mg, 44.7%).

NMR: $^1$H (270 MHz: CDCl$_3$: 25° C.) 0.74–1.43, m, 7H: 1.32, br-s, 6H: 1.45–1.76, m, 5H: 1.99, br-d, J=12.7 Hz, 1H: 4.32, dt, J=2.4 Hz, 10.4 Hz, 1H: 6.80, d, J=9.8 Hz, 1H: 7.76, d, J=8.3 Hz, 2H: 7.89, d, J=8.3 Hz, 2H $^{13}$C(67.5 MHz: CDCl$_3$: 25° C.) 23.1, 24.1, 26.0, 26.3, 26.4, 32.1, 34.4, 34.7, 39.0, 46.4, 53.8, 115.1, 117.9, 127.6, 132.5, 138.5, 165.6, 182.2; MS: [M+H]$^+$ calculated: 343.202, found: 343.1

(3) N-4-Cyanobenzoyl-β-cyclohexylmethyl-α,α-dimethyl-β-alanyl-4-piperidineacetic acid benzyl ester The same procedure as in Example 2-(6-2) was performed with N-4-cyanobenzoyl-β-cyclohexylmethyl-α,α-dimethyl-β-alanine (100 mg, 0.292 mmol) to yield an oil of N-4-cyanobenzoyl-β-cyclohexylmethyl-α,α-dimethyl-β-alanyl-4-piperidineacetic acid benzyl ester (122 mg, 74.9%).

NMR: $^1$H (270 MHz: CDCl$_3$: 25° C.) 0.72–1.01, m, 2H: 1.06–1.50, m, 7H: 1.32, s, 3H: 1.38, s, 3H: 1.55–1.85, m, 7H: 1.92–2.15, m, 2H: 2.31, d, J=6.8 Hz, 2H: 2.69–2.89, m, 2H: 4.13, br-t, J=9.8 Hz, 1H: 4.36, br-d, J=13.2 Hz, 2H: 5.12, s, 2H: 7.35, m, 5H: 7.61, d, J=9.8 Hz, 1H: 7.72, d, J=8.3 Hz, 2H: 7.89, d, J=8.3 Hz, 2H $^{13}$C(67.5 MHz: CDCl$_3$: 25° C.) 24.4, 24.7, 26.1, 26.3, 26.5, 31.8, 32.2, 32.5, 33.1, 34.4, 35.2, 39.3, 40.7, 46.5, 57.7, 66.3, 114.7, 118.2, 127.6, 128.2, 128.3, 128.6, 132.3, 135.8, 138.9, 165.1, 171.9, 175.4; MS: [M+H]$^+$ calculated: 558.333, found: 558.5

(4) N-4-Amidinobenzoyl-β-cyclohexylmethyl-α,α-dimethyl-β-alanyl-4-piperidineacetic acid benzyl ester The same procedure as in Example 2-(6-3) was performed with N-4-cyanobenzoyl-β-cyclohexylmethyl-α,α-dimethyl-β-alanyl-4-piperidineacetic acid benzyl ester (122 mg, 0.219 mmol) to yield an oil of N-4-amidinobenzoyl-β-cyclohexylmethyl-α,α-dimethyl-β-alanyl-4-piperidineacetic acid benzyl ester (52 mg, 41.4%).

NMR: $^1$H (270 MHz: CDCl$_3$: 25° C.) 0.67–1.36, m, 9H: 1.23, s, 3H: 1.27, s, 3H: 1.48–1.93, m, 8H: 2.03, m, 1H: 2.29, d, J=6.4 Hz, 2H: 2.78, m, 2H: 4.26–4.45, m, 3H: 5.11, s, 2H: 7.34, m, 5H: 7.78, d, J=8.6 Hz, 1H: 7.85, d, J=7.8 Hz, 2H: 7.97, d, J=7.8 Hz, 2H: 9.14, br-s, 1.5H: 9.28, br-s, 1.5H; MS: [M+H]$^+$ calculated: 575.375, found: 575.5

(5) Synthesis of the titled compound

The same procedure as in Example 2-(6-4) was performed with N-4-amidinobenzoyl-β-cyclohexylmethyl-α,α-dimethyl-β-alanyl-4-piperidineacetic acid benzyl ester (28 mg, 0.049 mmol) to yield N-(N-4-amidinobenzoyl-β-cyclohexylmethyl-α,α-dimethyl-β-alanyl)-4-piperidineacetic acid (20.2 mg, 85.6%).

NMR: $^1$H (400 MHz: CD$_3$OD: 25° C.) 0.81–0.93, m, 0.6H: 0.93–1.08, m, 0.6H: 1.10–1.37, m, 9.4H: 1.55–1.77, m, 4.4H: 1.85, br-d, J=13.2 Hz, 1.3H: 1.93, br-d, J=12.8 Hz, 0.7H: 2.05, m, 1H:, 2.25, m, 2H: 2.93, br-s, 2H: 4.56, m, 2H: 4.73, br-t, J=10.0 Hz: 4.89, d, J=4.8 Hz, 2H: 7.99, d, J=8.4 Hz; MS: [M+H]$^+$ calculated: 485.313, found: 485.3

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 51.49 minutes.

EXAMPLE 13

Synthesis of N-(N-4-amidinobenzoyl-β-(3-furyl)-α,α-dimethyl-β-alanyl)-4-piperidineacetic acid

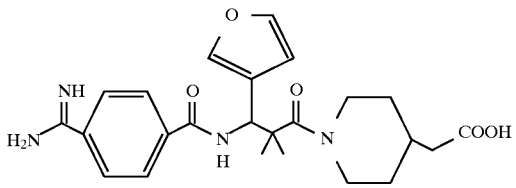

(1) 4-(3-Furyl)-3,3-dimethyl-2-azetidinone

The same procedure as in Example 2-(2) was performed with ethyl isobutyrate (6.68 ml, 50 mmol) and 3-furylaldehyde (4.32 ml, 50 mmol) to yield 4-(3-furyl)-3,3-dimethyl-2-azetidinone (4.83 g, 58.5%).

NMR: $^1$H (270 MHz: CDCl$_3$: 25° C.) 0.96, s, 3H: 1.41, s, 3H: 4.37, s, 1H: 6.17, br-s, 1H: 6.33, d, J=1.0 Hz, 1H: 7.39, s, 1H: 7.43, t, J=1.7 Hz, 1H; MS: [M+H]$^+$ calculated: 166.087, found: 165.9

(2) N-4-Cyanobenzoyl-β-(3-furyl)-α,α-dimethyl-β-alanine

Sodium hydroxide (378 mg, 9.45 mmol) and tetrahydrofuran (10 ml) were added to 4-(3-furyl)-3,3-dimethyl-2-azetidinone (1.2 g, 7.21 mmol) and the mixture was refluxed for 8 hours. After the solvent was distilled off, the residue was washed with ethyl acetate to give a powder of β-(3-furyl)-α,α-dimethyl-β-alanine sodium salt (1.4 g, quant.).

NMR: $^1$H (270 MHz: D$_2$O: 25° C.) 0.85, s, 3H: 0.97, s, 3H: 3.96, s, 1H: 6.33, s, 1H: 7.29, s, 1H: 7.33, s, 1H; MS: [M+H]$^+$ calculated: 206.079, found: 206.0

The same procedure as in Example 2-(6-1) was performed with the obtained β-(3-furyl)-α,α-dimethyl-β-alanine sodium salt (1.4 g, 7.21 mmol) to yield a crystal of N-4-cyanobenzoyl-β-(3-furyl)-α,α-dimethyl-β-alanine (0.98 g, 44.0%).

NMR: $^1$H (400 MHz: CDCl$_3$: 25° C.) 1.29, s, 3H: 1.32, s, 3H: 5.49, s, 1H: 7.48, t, J=1.7 Hz, 1H: 7.55, s, 1H: 7.88, d, J=8.4 Hz, 2H: 7.95, d, J=8.4 Hz, 2H $^{13}$C(100 MHz: CDCl$_3$: 25° C.) 23.96, 24.01, 48.73, 54.35, 111.93, 116.89, 119.81, 125.15, 130.09, 134.25, 134.35, 140.91, 142.92, 145.01, 168.97, 180.85; MS: [M+H]$^+$ calculated: 313.119, found: 313.1

(3) N-4-Cyanobenzoyl-β-(3-furyl)-α,α-dimethyl-β-alanyl-4-piperidineacetic acid methyl ester The same procedure as in Example 9-(3) was performed with N-4-cyanobenzoyl-β-(3-furyl)-α,α-dimethyl-β-alinine (400 mg, 1.28 mmol) to yield an oil of N-4-cyanobenzoyl-β-(3-furyl)-α,α-dimethyl-β-alanyl-4-piperidineacetic acid methyl ester (367 mg, 64.0%)

NMR: $^1$H (400 MHz: CDCl$_3$: 25° C.) 1.02–1.16, m, 2H: 1.74, br-t, J=12.8 Hz, 2H: 1.93–2.06, m, 1H: 2.19, d, J=7.6 Hz, 2H: 2.67–2.82, br-s, 2H: 4.27–4.37, br, 2H: 4.94, d, J=9.6 Hz, 1H: 7.23, t, J=1.6 Hz, 1H: 7.392, s, 1H: 7.63, d, J=8.8 Hz, 2H: 7.82, d, J=8.8 Hz, 2H $^{13}$C(100 MHz: CDCl$_3$: 25° C.) 24.68, 24.92, 31.76, 32.21, 32.94, 40.37, 45.07, 46.29, 51.49, 56.59, 111.29, 114.71, 118.06, 123.80, 127.68, 127.68, 132.21, 138.48, 141.48, 142.29; MS: [M+Na]$^+$ calculated: 474.200, found: 474.2

(4) Synthesis of the titled compound

The same procedure as in Example 9-(4) was performed with N-4-cyanobenzoyl-β-(3-furyl)-α,α-dimethyl-β-alanyl-4-piperidineacetic acid methyl ester (210 mg, 0.46 mmol) to yield N-(N-4-amidinobenzoyl-β-(3-furyl)-α,α-dimethyl-β-alanyl)-4-piperidineacetic acid (24 mg, 10.9%).

NMR: $^1$H (400 MHz: CD$_3$OD: 25° C.) 1.10–1.29, m, 2H: 1.34, s, 3H: 1.37, s, 3H: 1.83, br-d, J=12.4 Hz, 2H: 1.96–2.10, m, 1H: 2.23, d, J=7.2 Hz, 2H: 2.77–3.04, br-m, 2H: 4.50, br-d, J=13.2 Hz, 2H: 5.52, s, 1H: 6.50, s, 1H: 7.43, t, J=1.8 Hz, 7.53, s, 1H: 7.89, dt, J=8.8 Hz, 1.6 Hz, 2H: 7.96, dt, J=8.8 Hz, 2.0 Hz, 2H; MS: [M+H]$^+$ calculated: 455.229, found: 455.3

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 35.23 minutes.

EXAMPLE 14

Synthesis of N-(N-4-amidinobenzoyl-β-styryl-α,α-dimethyl-β-alanyl)-4-piperidineacetic acid

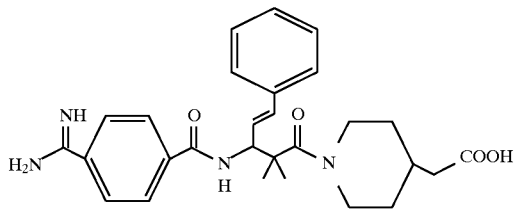

(1) 4-Styryl-3,3-dimethyl-2-azetidinone

The same procedure as in Example 2-(2) was performed with ethyl isobutyrate (6.68 ml, 50 mmol) and cinnamaldehyde (6.3 ml, 50 mmol) to yield 4-styryl-3,3-dimethyl-2-azetidinone (6.94 g, 69.0%).

NMR: $^1$H (270 MHz: CDCl$_3$: 25° C.) 1.32, s, 3H: 1.57, s, 3H: 4.19, dd, J=7.0 Hz, 1.0 Hz, 1H: 6.09, br-s, 1H: 6.60, bd, J=16.0 Hz, 1H: 7.24–7.42, m, 5H; MS: [M+H]$^+$ calculated: 220.134, found: 220.1

(2) N-4-Cyanobenzoyl-β-styryl-α,α-dimethyl-β-alanine

The same procedure as in Example 2-(3) was performed with 4-styryl-3,3-dimethyl-2-azetidinone (2.5 g, 12.0 mmol) to yield a powder of β-styryl-α,α-dimethyl-β-alanine hydrochloride (0.78 g, 30.0%).

NMR: $^1$H (270 MHz: D$_2$O: 25° C.) 0.98, s, 3H: 1.04, s, 3H: 3.71, d, J=8.8 Hz, 1H: 6.06, dd, J=9.0 Hz, 16.0 Hz, 1H: 6.61, d, J=16.0 Hz, 1H: 7.15–7.26, m, 3H: 7.32–7.35, m, 2H; MS: [M+H]$^+$ calculated: 220.134, found: 220.1

The same procedure as in Example 2-(6-1) was performed with the obtained β-styryl-α,α-dimethyl-β-alanine hydrochloride (0.4 g, 1.56 mmol) to yield a crystal of N-4-cyanobenzoyl-β-styryl-α,α-dimethyl-β-alanine (615 mg, 60.2%).

NMR: $^1$H (270 MHz: CDCl$_3$: 25° C.) 1.37, s, 3H: 1.42, s, 3H: 4.85, t, J=8.8 Hz, 1H: 6.20, dd, J=8.3 Hz, 15.6 Hz, 1H: 6.70, d, J=15.6 Hz, 1H: 7.22–7.38, m, 5H: 7.51, d, J=9.3 Hz, 1H: 7.72, d, J=8.3 Hz, 2H: 7.90, d, J=8.3 Hz, 2H $^{13}$C(67.5 MHz: CDCl$_3$: 25° C.) 23.0, 24.5, 45.9, 58.8, 115.2, 117.9, 124.8, 126.5, 127.7, 128.2, 128.6, 132.5, 134.6, 136.0, 138.1, 165.0, 181.6 MS: [M+H]$^+$ calculated: 349.155, found: 349.1

(3) N-4-Cyanobenzoyl-β-styryl-α,α-dimethyl-β-alanyl-4-piperidineacetic acid t-butyl ester The same procedure as in Example 2-(6-2) was performed with N-4-cyanobenzoyl-β-styryl-α,α-dimethyl-β-alanine (100 mg, 0.287 mmol) using 4-piperidineacetic acid t-butyl ester (203 mg, 0.86 mmol) to yield an oil of N-4-cyanobenzoyl-β-styryl-α,α-dimethyl-β-alanyl-4-piperidineacetic acid t-butyl ester (46 mg, 30.3%).

NMR: $^1$H (270 MHz: CDCl$_3$: 25° C.) 1.09–1.35, m, 2H: 1.41, s, 3H: 1.45, br-s, 12H: 1.81, br-d, J=12.7 Hz, 2H: 1.95–2.11, m, 1H: 2.16, d, J=7.3 Hz, 2H: 2.72–2.93, m, 2H: 4.40, br-d, J=12.2 Hz, 2H: 4.63, t, J=8.8 Hz, 1H: 6.49, dd,

J=8.8 Hz, 16.1 Hz, 1H: 6.66, d, J=16.1 Hz, 1H: 7.17–7.33, m, 3H: 7.39, d, J=8.8 Hz, 2H: 7.72, d, J=8.8 Hz, 2H: 7.91, d, J=8.8 Hz, 2H: 8.24, d, J=9.8 Hz, 1H $^{13}$C(67.5 MHz: CDCl$_3$: 25° C.) 24.1, 24.6, 28.1, 31.9, 32.1, 33.2, 41.9, 46.0, 63.6, 80.5, 114.8, 118.1, 126.5, 127.5, 127.65, 127.73, 128.4, 132.3, 134.0, 136.7, 138.7, 164.5, 171.5, 175.0; MS: [M+Na]$^+$ calculated: 552.284, found: 552.4

(4) N-4-Amidinobenzoyl-β-styryl-α,α-dimethyl-β-alanyl-4-piperidineacetic acid t-butyl ester The same procedure as in Example 2-(6-3) was performed with N-4-cyanobenzoyl-β-styryl-α,α-dimethyl-β-alanyl-4-piperidineacetic acid t-butyl ester (118 mg, 0.223 mmol) to yield an oil of N-4-amidinobenzoyl-β-styryl-α,α-dimethyl-β-alanyl-4-piperidineacetic acid t-butyl ester (53.2 mg, 43.7%).

NMR: $^1$H (400 MHz: CDCl$_3$: 25° C.) 1.06–1.20, br-m, 2H: 1.31, s, 3H: 1.34, s, 3H: 1.43, s, 9H: 1.67–1.78, br-m, 2H: 1.92–2.05, m, 1H: 2.11, d, J=8.8 Hz, 2H: 2.25–2.60, br-s, 2H: 4.27–4.38, br-s, 2H: 4.67, t, J=8.8 Hz, 1H: 6.44, dd, J=16 Hz, 8.4 Hz, 1H: 6.59, d, J=16.0, 1H: 7.16, t, J=7.4 Hz, 1H: 7.24, t, J=7.6 Hz, 2H: 7.35, d, J=7.6 Hz, 2H: 7.77, d, J=8.4 Hz, 2H: 7.89, d, J=8.0 Hz, 2H; MS: [M+H]$^+$ calculated: 547.328, found: 547.3

(5) Synthesis of the titled compound

N-4-Amidinobenzoyl-β-styryl-α,α-dimethyl-β-alanyl-4-piperidineacetic acid t-butyl ester (30 mg, 0.055 mmol) was dissolved in a mixed solution of TFA (10 ml) and water (0.5 ml). The resulting solution was stirred at room temperature for 3 hours. After the TFA was distilled off at room temperature, the residue was purified by the same method as in Example 2-(6-4) to yield N-(N-4-amidinobenzoyl-β-styryl-α,α-dimethyl-β-alanyl)-4-piperidineacetic acid (7.2 mg, 26.7%).

NMR: $^1$H (400 MHz: CD$_3$OD: 25° C.) 1.06–1.20, br-m, 2H: 1.31, s, 3H: 1.34, s, 3H: 1.67–1.78, br-m, 2H: 1.92–2.05, m, 1H: 2.11, d, J=8.8 Hz, 2H: 2.25–2.60, br-s, 2H: 4.27–4.38, br-s, 2H: 4.67, t, J=8.8 Hz, 1H: 6.44, dd, J=16 Hz, 8.4 Hz, 1H: 6.59, d, J=16 Hz, 1H: 7.16, t, J=7.4 Hz, 1H: 7.24, t, J=7.6 Hz, 2H: 7.35, d, J=7.6 Hz, 2H: 7.77, d, J=8.4 Hz, 2H: 7.89, d, J=8.0 Hz, 2H; MS: [M+H]$^+$ calculated: 491.266, found: 491.1

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 45.68 minutes.

EXAMPLE 15

Synthesis of N-(N-4-amidinobenzoyl-β-(4-piperidyl)-α,α-dimethyl-β-alanyl)-4-piperidineacetic acid

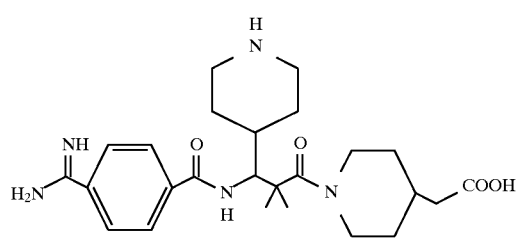

(1) 4-(4-Pyridyl)-3,3-dimethyl-2-azetidinone

The same procedure as in Example 2-(2) was performed with ethyl isobutyrate (6.68 ml, 50 mmol) and pyridine-4-aldehyde (4.77 ml, 50 mmol) to yield 4-(4-pyridyl)-3,3-dimethyl-2-azetidinone (4.05 g, 46.0%).

NMR: $^1$H (270 MHz: CDCl$_3$: 25° C.) 0.80, s, 3H: 1.51, s, 3H: 4.50, s, 1H: 6.73, br-s, 1H: 7.18–7.28, m, 2H: 8.61–8.63, m, 2H; MS: [M+H]$^+$ calculated: 177.103, found: 176.9

(2) N-4-Cyanobenzoyl-β-(4-pyridyl)-α,α-dimethyl-β-alanine

The same procedure as in Example 2-(3) was performed with 4-(4-pyridyl)-3,3-dimethyl-2-azetidinone (1.76 g, 10 mmol) to yield a powder of β-(4-pyridyl)-α,α-dimethyl-β-alanine hydrochloride (2.51 g, 93.9%).

NMR: $^1$H (270 MHz: D$_2$O: 25° C.) 1.13, s, 3H: 1.28, s, 3H: 4.84, s, 1H: 8.04, d, J=6.4 Hz, 2H: 8.80, d, J=6.4 Hz, 2H; MS: [M+H]$^+$ calculated: 195.113, found: 195.2

The same procedure as in Example 2-(6-1) was performed with the obtained β-(4-pyridyl)-α,α-dimethyl-β-alanine hydrochloride (0.4 g, 1.50 mmol) to yield a crystal of N-4-cyanobenzoyl-β-(4-pyridyl)-α,α-dimethyl-β-alanine (0.70 g, quant.).

NMR: $^1$H (270 MHz: CDCl$_3$: 25° C.) 1.15, s, 3H: 1.39, s, 3H: 5.08, d, J=8.8 Hz, 1H: 7.38, d, J=4.1 Hz, 2H: 7.77, d, J=8.8 Hz, 2H: 7.98, d, J=8.8 Hz, 2H: 8.50, d, J=4.1 Hz, 2H: 9.18, d, J=7.8 Hz, 1H $^{13}$C(67.5 MHz: CDCl$_3$: 25° C.) 22.2, 24.6, 44.5, 59.2, 113.9, 117.2, 122.7, 127.2, 131.4, 137.4, 148.0, 148.4, 164.0, 178.3; MS: [M+H]$^+$ calculated: 324.135, found: 324.1

(3) N-4-Cyanobenzoyl-β-(4-pyridyl)-α,α-dimethyl-β-alanyl-4-piperidineacetic acid benzyl ester The same procedure as in Example 2-(6-2) was performed with N-4-cyanobenzoyl-β-(4-pyridyl)-α,α-dimethyl-β-alanine (0.32 g, 1.0 mmol) to yield an oil of N-4-cyanobenzoyl-β-(4-pyridyl)-α,α-dimethyl-β-alanyl-4-piperidineacetic acid benzyl ester (251 mg, 46.6%)

NMR: $^1$H (270 MHz: CDCl$_3$: 25° C.) 1.01–1.24, m, 2H: 1.32, s, 3H: 1.52, s, 3H: 1.70–1.88, m, 2H: 1.97–2.16, m, 1H: 2.29, d, J=6.8 Hz, 2H: 2.68–2.90, m, 2H: 4.25–4.43, m, 2H: 5.01, d, J=9.3 Hz, 1H: 5.11, s, 2H: 7.35, m, 5H: 7.41, d, J=6.3 Hz, 2H: 7.73, d, J=8.3 Hz, 2H: 7.91, d, J=8.3 Hz, 2H: 8.53, d, J=6.3 Hz, 2H: 9.06, d, J=9.3 Hz, 1H $^{13}$C (67.5 MHz: CDCl$_3$: 25° C.) 25.1, 25.9, 31.8, 32.2, 32.9, 40.5, 46.3, 63.6, 66.3, 115.1, 118.0, 124.4, 127.7, 128.2, 128.3, 128.6, 132.4, 135.7, 138.0, 148.2, 149.8, 164.6, 171.8, 175.2; MS: [M+H]$^+$ calculated: 539.266, found: 539.3

(4) Synthesis of the titled compound

The same procedure as in Example 6-(4) was performed with N-4-cyanobenzoyl-β-(4-pyridyl)-α,α-dimethyl-β-alanyl-4-piperidineacetic acid benzyl ester (250 mg, 0.464 mmol) to yield N-(N-4-amidinobenzoyl-β-(4-piperidyl)-α,α-dimethyl-β-alanyl)-4-piperidineacetic acid (23.0 mg, 10.5%).

NMR: $^1$H (400 MHz: CD$_3$OD: 25° C.) 1.19–1.39, m, 2H: 1.41–1.62, m, 2H: 1.32, s, 3H: 1.33, s, 3H: 1.80–1.93, br-m, 2H: 1.97–2.14, m, 4H: 2.27, d, J=6.8 Hz, 2H: 2.80–3.15, br-m, 2H: 2.89–2.98, m, 2H: 2.37, br-t, J=12.0 Hz, 2H: 4.48, d, J=7.6 Hz, 1H: 4.56–4.65, br-m, 2H: 7.91, d, J=8.4 Hz, 2H: 8.02, d, J=8.4 Hz, 2H; MS: [M+H]$^+$ calculated: 472.292, found: 472.3

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 15.74 minutes.

EXAMPLE 16

Synthesis of N-(N-4-amidinobenzoyl-β-(2-naphthyl)-α,α-dimethyl-β-alanyl)-4-piperidineacetic acid

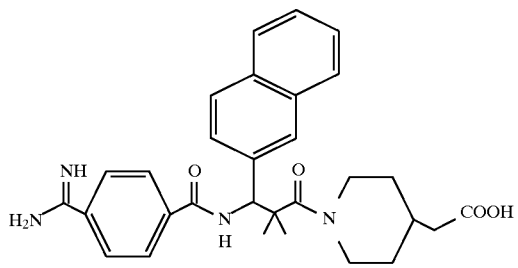

(1) 4-(2-Naphthyl)-3,3-dimethyl-2-azetidinone

The same procedure as in Example 2-(2) was performed with ethyl isobutyrate (6.68 ml, 50 mmol) and 2-naphthaldehyde (7.81 ml, 50 mmol) to yield a crystal of 4-(2-naphthyl)-3,3-dimethyl-2-azetidinone (9.85 g, 87.4%).

NMR: $^1$H (270 MHz: CDCl$_3$: 25° C.) 0.79, s, 3H: 1.53, s, 3H: 4.66, s, 1H: 6.36, br-s, 1H: 7.31–7.34, m, 1H: 7.47–7.53, m, 2H: 7.72, s, 1H: 7.82–7.86, m, 3H; MS: [M+H]$^+$ calculated: 226.123, found: 225.9

(2) N-4-Cyanobenzoyl-β-(2-naphthyl)-α,α-dimethyl-β-alanine

The same procedure as in Example 2-(3) was performed with 4-(2-naphthyl)-3,3-dimethyl-2-azetidinone (2.25 g, 10 mmol) to yield a powder of β-(2-naphthyl)-α,α-dimethyl-β-alanine hydrochloride (2.81 g, quant.).

NMR: $^1$H (270 MHz: D$_2$O: 25° C.) 1.09, s, 3H: 1.22, s, 3H: 4.59, s, 1H: 7.33–7.37, m, 1H: 7.46–7.51, m, 2H: 7.79–7.87, m, 4H; MS: [M+H]$^+$ calculated: 244.133, found: 243.9

The same procedure as in Example 2-(6-1) was performed with the obtained β-(2-naphthyl)-α,α-dimethyl-β-alanine hydrochloride (1.5 g, 5.37 mmol) to yield a crystal of N-4-cyanobenzoyl-β-(2-naphthyl)-α,α-dimethyl-β-alanine (1.65 g, 82.5%).

NMR: $^1$H (400 MHz: CD$_3$OD: 25° C.) 1.23, s, 3H: 1.33, s, 3H: 5.53, s, 1H: 7.41–7.43, m, 7.52, dd, J=8.4 Hz, 1.6 Hz, 1H: 7.74, 1H, t, J=1.8 Hz, 1H: 7.74–7.80, m, 4H: 7.86–7.89, m, 3H; MS: [M+H]$^+$ calculated: 373.155, found: 373.1

(3) N-4-Cyanobenzoyl-β-(2-naphthyl)-α,α-dimethyl-β-alanyl-4-piperidineacetic acid benzyl ester The same procedure as in Example 2-(6-2) was performed with N-4-cyanobenzoyl-β-(2-naphthyl )-α,α-dimethyl-β-alanine (600 mg, 1.61 mmol) to yield an oil of N-4-cyanobenzoyl-β-(2-naphthyl)-α,α-dimethyl-β-alanyl-4-piperidineacetic acid benzyl ester (425 mg, 45.0%)

NMR: $^1$H(400 MHz: CDCl$_3$: 25° C.) 0.67–0.72, m, 0.5H: 0.72–1.35, m, 3.5H 1.35–1.50, m, 3H: 1.50–1.76, m, 1H: 1.83–1.92, m, 1H: 2.02–2.09, m, 1.4H: 2.14–2.24, m, 0.6H: 2.48–2.93, m, 2H: 2.57–2.63, m, 2H: 4.10–4.35, br-s, 2H: 4.97–5.06, m, 1H: 5.06–5.20, m, 2H: 7.15–7.89, m, 16H $^{13}$C (100 MHz: CDCl$_3$: 25° C.) 22.97, 24.84, 25.38, 25.54, 25.92, 26.67, 27.09, 31.66, 31.98, 32.83, 33.16, 33.85, 36.20, 36.25, 38.83, 40.24, 41.01, 45.36, 45.50, 46.28, 46.87, 46.96, 51.74, 61.33, 63.71, 65.97, 66.16, 67.12, 114.74, 118.08, 125.13, 125.98, 126.07, 126.20, 126.71, 127.13, 127.41, 127.55, 127.60, 127.69, 127.76, 127.95, 128.05, 128.11, 128.22, 128.38, 128.48, 128.64, 132.21, 132.26, 132.71, 132.81, 132.95, 134.98, 135.71, 135.95, 136.13, 136.84, 136.89, 138.39, 164.22, 164.32, 171.76, 172.45, 175.61, 176.96; MS: [M+H]$^+$ calculated: 588.286, found: 588.3

(4) Synthesis of the titled compound

The same procedure as in Example 6-(4) was performed with N-4 -cyanobenzoyl-β-(2-naphthyl)-α,α-dimethyl-β-alanyl-4-piperidineacetic acid benzyl ester (180 mg, 0.31 mmol) to yield N-(N-4-amidinobenzoyl-β-(2-naphthyl)-α, α-dimethyl-β-alanyl)-4-piperidineacetic acid (5.3 mg, 3.2%).

NMR: $^1$H (400 MHz: CD$_3$OD: 25° C.) 0.95–1.08, m, 1H: 1.16–1.29, m, 1H: 1.36, s, 3H: 1.41, m, 3H: 1.79, br-t, J=12.8 Hz, 2H: 1.92–2.07, m, 1H: 2.07–2.17, m, 2H: 2.53–3.07, br, 1H: 2.99, br-t, J=13.2 Hz, 1H: 4.55, br-d, J=13.6 Hz, 2H: 5.76, s, 1H: 7.42–7.53, m, 2H: 7.59, d, J=8.4 Hz, 7.81–7.87, m, 3H: 7.87–7.91, m, 3H: 7.99, d, J=6.8 Hz, 2H; MS: [M+H]$^+$ calculated: 515.266, found: 515.2

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 54.39 minutes.

EXAMPLE 17

Synthesis of N-(N-4-amidinobenzoyl-β-cyclopropyl)-α,α-dimethyl-β-alanyl)-4-piperidineacetic acid

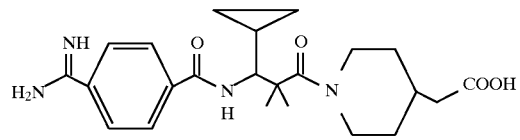

(1) 4-Cyclopropyl-3,3-dimethyl-2-azetidinone

The same procedure as in Example 2-(2) was performed with ethyl isobutyrate (6.68 ml, 50 mmol) and cyclopropanecarboxyaldehyde (3.74 ml, 50 mmol) to yield 4-cyclopropyl-3,3-dimethyl-2-azetidinone (7.02 g, quant.).

NMR: $^1$H (270 MHz: CDCl$_3$: 25° C.) 0.13–0.30, m, 2H: 0.56–0.65, m, 2H: 0.83–0.95, m, 1H: 1.29, s, 6H: 2.66, d, J=8.8 Hz, 1H: 5.87, br-s, 1H; MS: [M+H]$^+$ calculated: 140.108, found: 140.0

(2) N-4-Cyanobenzoyl-β-cyclopropyl-α,α-dimethyl-βalanine

The same procedure as in Example 2-(3) was performed with 4-cyclopropyl-3,3-dimethyl-2-azetidinone (2.0 g, 14.38 mmol) to yield a powder of β-cyclopropyl-α,α-dimethyl-β-alanine hydrochloride (2.16 g, 78.3%).

NMR: $^1$H (270 MHz: D$_2$O: 25° C.) 0.39–0.58, m, 2H: 0.63–0.73, m, 1H: 0.77–0.86, m, 1H: 0.97–1.12, m, 1H: 1.35, s, 3H: 1.37, s, 3H: 2.64, d, J=10.7 Hz, 1H; MS: [M+H]$^+$ calculated: 158.118, found: 158.2

The same procedure as in Example 2-(6-1) was performed with the obtained β-cyclopropyl-α,α-dimethyl-β-alanine hydrochloride (2.1 g, 10.9 mmol) to yield a crystal of N-4-cyanobenzoyl-β-cyclopropyl-α,α-dimethyl-β-alanine (2.2 g, 70.5%).

NMR: $^1$H (400 MHz: CD$_3$OD: 25° C.) 0.23–0.29, m, 1H: 0.39–0.49, m, 2H: 0.61–0.67, m, 2H: 1.28, s, 3H: 1.30, s, 3H: 3.72, d, J=9.6 Hz, 1H: 7.83, dt, J=8.0 Hz, 1.6 Hz, 2H: 7.92, dt, J=8.0 Hz, 1.6 Hz: 2H $^{13}$C(100 MHz: CD$_3$OD: 25° C.) 3.35, 7.79, 14.38, 23.41, 24.62, 62.33, 116.79, 119.84, 130.03, 134.33, 141.08, 169.17, 180.98; MS: [M+H]$^+$ calculated: 287.140, found: 287.1

(3) N-4-Cyanobenzoyl-β-cyclopropyl-α,α-dimethyl-β-alanyl-4-piperidineacetic acid methyl ester The same procedure as in Example 9-(3) was performed with N-4-cyanobenzoyl-β-cyclopropyl-α,α-dimethyl-β- alanine (420 mg, 1.47 mmol) to yield an oil of N-4-cyanobenzoyl-β-cyclopropyl-α,α-dimethyl-β-alanyl-4-piperidineacetic acid methyl ester (590 mg, 95.0%)

NMR: ¹H (400 MHz: CDCl₃: 25° C.) 0.19–0.42, m, 3H: 0.55–0.62, m, 1H: 1.04–1.26, m, 3H: 1.28, s, 3H: 1.45, s, 3H: 1.69–1.77, m, 2H: 1.86–2.03, m, 1H: 2.12–2.24, m, 2H: 2.68–2.71, br-s, 2H: 3.28, t, J=9.8 Hz, 1H: 3.60, m, 3H: 4.29–4.40, br-m, 2H: 7.61–7.68, m, 2H: 7.78–7.87, m, 2H; MS: [M+Na]⁺ calculated: 448.221, found: 448.1

(4) Synthesis of the titled compound

The same procedure as in Example 9-(4) was performed with N-4-cyanobenzoyl-β-cyclopropyl-α,α-dimethyl-β-alanyl-4-piperidineacetic acid methyl ester (340 mg, 0.80 mmol) to yield N-(N-4-amidinobenzoyl-β-cyclopropyl-α,α-dimethyl-β-alanyl)-4-piperdineacetic acid (77.3 mg, 22.0%).

NMR: ¹H (400 MHz: CD₃OD: 25° C.) 0.22–0.27, m, 1H: 0.36–0.48, m, 2H: 0.61–0.67, m, 1H: 1.15–1.26, m, 3H: 1.39, s, 6H: 1.77–1.86, m, 2H: 1.97–2.10, m, 1H: 2.25, d, J=6.8 Hz, 2H: 2.75–3.05, br-s, 2H: 3.81, d, J=9.2 Hz, 1H: 4.50, br-d, J=13.2 Hz, 2H: 7.90, d, J=8.4 Hz, 2H: 7.98, d, J=8.4 Hz, 2H ¹³C(100 MHz: CD₃OD: 25° C.) 3.66, 7.70, 14.38, 24.89, 33.85, 35.07, 42.30, 129.99, 130.09, 133.08, 141.75, 168.75, 169.33, 176.81, 177.03; MS: [M+H]⁺ calculated: 429.250, found: 429.3

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 29.85 minutes.

EXAMPLE 18

Synthesis of N-(N-4-n-butyl-amidinobenzoyl)-β-m-chlorophenyl-α,α-dimethyl-β-alanyl)-4-piperidineacetic acid

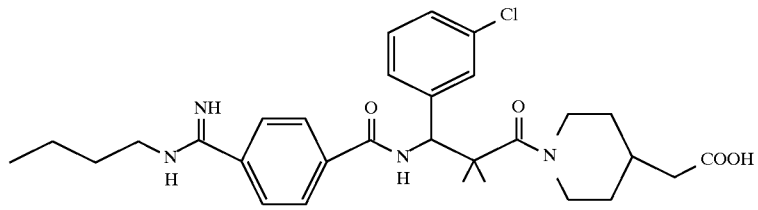

(1) Synthesis of the titled compound

N-4-Cyanobenzoyl-β-m-chlorophenyl-α,α-dimethyl-β-alanyl-4-piperidineacetic acid methyl ester (70 mg, 0.141 mmol) as prepared in Example 9-(3) was dissolved in pyridine (10 ml). To the resulting solution was added triethylamine (1 ml) and the mixture was saturated with hydrogen sulfide gas. The reaction vessel was sealed and the reaction mixture was stirred at room temperature overnight. The pyridine was distilled off and the volatile products were removed by two cycles of toluene azeotropy. The residue was dissolved in acetone (15 ml) and methyl iodide (1 ml) was added thereto, followed by refluxing for 30 minutes. The solvent was distilled off and the residue was dissolved in methanol (10 ml). To the obtained solution was added n-butylamine (1 ml) and the mixture was refluxed for 2 hours. After the solvent was distilled off, the residue was dissolved in chloroform, washed with a saturated aqueous solution of NaCl and dried over anhydrous sodium sulfate. The obtained crude N-4-n-butyl-amidinobenzoyl-β-m-chlorophenyl-α,α-dimethyl-β-alanyl-4-piperidineacetic acid methyl ester was dissolved in a 50% aqueous methanol solution (10 ml). To the resulting solution was added a 2N aqueous solution of lithium hydroxide (3 ml) at room temperature and the mixture was stirred for 15 minutes. After the reaction solution was neutralized with 3N HCl to pH 7, the solvents were distilled off. The residue was dissolved in a 1N aqueous solution of acetic acid. The resulting solution was purified with a HPLC to yield N-(N-4-n-butyl-amidinobenzoyl-β-m-chlorophenyl-α,α-dimethyl-β-alanyl)-4-piperidineacetic acid (3.5 mg, 6.0%).

NMR: ¹H (400 MHz: CD₃OD: 25° C.) 0.98–1.30, m, 2H: 1.02, t, J=7.4 Hz, 3H: 1.30, s, 3H: 1.37, s, 3H: 1.46–1.54, m, 2H: 1.71–1.87, m, 4H: 1.96–2.07, m, 1H: 2.18–2.20, m, 2H: 2.82–3.03, br-s, 2H: 3.45, t, J=7.2 Hz, 2H: 4.51, br-d, J=13.6 Hz, 2H: 5.54, s. 1H: 7.29–7.40, m, 3H: 7.81, d, J=8.4 Hz, 2H: 7.95–7.98, m, 2H; MS: [M+H]⁺ calculated: 555.274, found: 555.4

A spectrum of analytical HPLC using Wakosil-II 5C18HG (φ 4.6×250 mm) column at a flow rate of 1.0 ml/min at room temperature by elution in a gradient of 20–50% acetonitrile (60 min) in 0.1% TFA had a single peak at a retention time of 39.11 minutes.

EXAMPLE 19

Synthesis of N-(N-4-amidinobenzoyl-β-phenyl-α,α-dimethyl-β-alanyl)-4-piperidineacetic acid ethyl ester

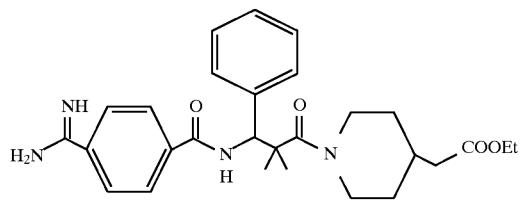

(1) N-4-Cyanobenzoyl-β-phenyl-α,α-dimethyl-β-alanyl-4-piperidineacetic acid ethyl ester The same procedure as in Example 2-(6-2) was performed with N-4-cyanobenzoyl-β-phenyl-α,α-dimethyl-β-alanine (1.0 g, 3.10 mmol) using ethyl 4-piperidine acetate (1.59 g, 9.31 mmol) to yield an oil of N-4-cyanobenzoyl-β-phenyl- α,α-dimethyl-β-alanyl-4-piperidineacetic acid ethyl ester (0.96 g, 65.1%).

NMR: ¹H (270 MHz: CDCl₃: 25° C.) 0.96–1.28, m, 2H: 1.25, t, J=7.3 Hz, 3H: 1.34, s, 3H: 1.51, s, 3H: 1.64–1.81, m, 2H: 1.87–2.10, m, 1H: 2.20, d, J=7.3 Hz, 2H: 2.60–2.88, m, 2H: 4.12, q, J=7.3 Hz, 2H: 4.19–4.42, m, 2H: 5.06, d, J=8.8 Hz, 1H: 7.21–7.34, m, 3H: 7.39–7.46, m, 2H: 7.71, d, J=8.8 Hz, 2H: 7.92, d, J=8.8 Hz, 2H: 8.99, d, J=8.8 Hz, 1H ¹³C (67.5 MHz: CDCl₃: 25° C.) 14.2, 25.3, 26.6, 31.8, 32.1, 32.9, 40.7, 46.8, 60.4, 63.6, 114.8, 118.1, 127.6, 127.7, 128.2, 129.0, 132.3, 138.5, 139.4, 164.3, 172.1, 175.7 MS: [M+Na]⁺ calculated: 476.255, found: 476.3

(2) Synthesis of the titled compound

The same procedure as in Example 2-(6-3) was performed with N-4-cyanobenzoyl-β-phenyl-α,α-dimethyl-β-alanyl-4-piperidineacetic acid ethyl ester (360 mg, 0.76 mmol) to yield an oil of N-4-amidinobenzoyl-β-phenyl-α,α-dimethyl-β-alanyl-4-piperidineacetic acid ethyl ester. The oil was crystallized from ether (193 mg, 51.8%).

NMR: ¹H (400 MHz: CDCl₃: 25° C.) 0.97–1.24, m, 2H: 1.22, t, J=7.2 Hz, 3H: 1.27, s, 3H: 1.41, s, 3H: 1.73, br-d, J=13.2 Hz, 2H: 1.93–2.06, m, 1H: 2.10–2.22, m, 2H: 2.62–2.75, br-m, 1H: 2.77–2.93, br-s, 1H: 4.10, dd, J=7.6 Hz, 14.8 Hz, 2H: 4.21–4.45, br-m, 2H: 5.20, d, J=8.8 Hz, 7.21–7.34, m, 3H: 7.45, d, J=8.0 Hz, 2H: 7.614–7.696, m, 4H; MS: [M+H]⁺ calculated: 493.281, found: 493.3

EXAMPLE 20

Synthesis of N-(N-4-amidinobenzoyl-β-phenyl-α,α-dimethyl-β-alanyl)-4-piperidineacetic acid t-butyl ester

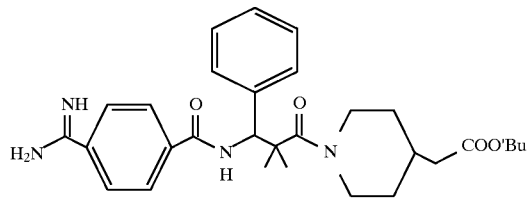

(1) N-4-Cyanobenzoyl-β-phenyl-α,α-dimethyl-β-alanyl-4-piperidineacetic acid t-butyl ester The same procedure as in Example 2-(6-2) was performed with N-4-cyanobenzoyl-β-phenyl-α,α-dimethyl-β-alanine (0.5 g, 1.55 mmol) using t-butyl 4-piperidine acetate (0.93 g, 4.66 mmol) to yield an oil of N-4-cyanobenzoyl-β-phenylα,α-dimethyl-β-alanyl-4-piperidineacetic acid t-butyl ester (470 mg, 60.2%).

NMR: ¹H (270 MHz: CDCl₃: 25° C.) 0.91–1.24, m, 2H: 1.34, s, 3H: 1.44, s, 9H: 1.51, s, 3H: 1.73, m, 2H: 1.85–2.06, m, 1H: 2.11, d, J=7.3 Hz, 2H: 2.59–2.88, m, 2H: 4.15–4.44, m, 2H: 5.05, d, J=8.8 Hz, 1H: 7.21–7.34, m, 3H: 7.39–7.48, m, 2H: 7.72, d, J=8.3 Hz, 2H: 7.92, d, J=8.3 Hz, 2H: 9.01, d, J=8.8 Hz, 1H ¹³C(67.5 MHz: CDCl₃: 25° C.) 25.3, 26.6, 28.1, 31.7, 32.1, 33.1, 41.9, 46.8, 63.6, 80.5, 114.8, 118.2, 127.6, 127.7, 128.2, 129.0, 132.3, 138.5, 139.4, 164.3, 171.5, 175.0; MS: [M+Na]⁺ calculated: 504.286, found: 504.4

(2) Synthesis of the titled compound

The same procedure as in Example 2-(6-3) was performed with N-4-cyanobenzoyl-β-phenylα,α-dimethyl-β-alanyl-4-piperidineacetic acid t-butyl ester (450 mg, 0.89 mmol) to yield an oil of N-4-amidinobenzoyl-β-phenylα,α-dimethyl-β-alanyl-4-piperidineacetic acid t-butyl ester (200 mg, 43.0%).

NMR: ¹H (400 MHz: CDCl₃: 25° C.) 0.97–1.19, m, 2H: 1.30, s, 3H: 1.40, s, 3H: 1.43, s, 9H: 1.66–1.75, br-m, 2H: 1.88–2.01, m, 1H: 2.10, d, J=7.2 Hz, 2H: 2.66, br-t, J=12.0 Hz, 1H: 2.74–2.90, br-s, 1H: 4.19–4.36, br-m, 2H: 5.13, d, J=8.8 Hz, 1H: 7.24, t, J=7.6 Hz, 1H: 7.31, t, J=7.4 Hz, 2H: 7.45, d, J=7.2 Hz, 2H: 7.67, d, J=8.8 Hz, 2H: 7.71, d, J=8.8 Hz, 2H ¹³C(100 MHz: CDCl₃: 25° C.) 22.81, 24.88, 26.12, 28.12, 31.74, 32.03, 33.09, 41.98, 46.94, 62.66, 80.58, 127.77, 127.88, 128.12, 128.30, 129.01, 130.55, 139.05, 165.35, 165.95, 171.64, 175.28; MS: [M+H]⁺ calculated: 521.313, found: 521.3

EXAMPLE 21

Synthesis of N-(N-4-amidinobenzoyl-N-methyl-β-phenyl-α,α-dimethyl-β-alanyl)-4-piperidineacetic acid

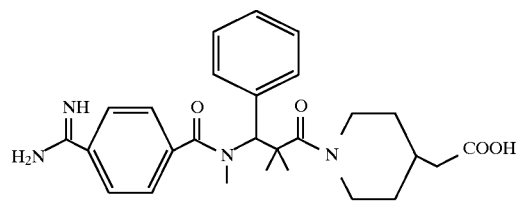

(1) N-Methyl-4-phenyl-3,3-dimethyl-2-azetidinone

Sodium hydride (60% oil) (0.48 g, 12 mmol) was added at 0° C. to a tetrahydrofuran (40 ml) solution of 4-phenyl-3,3-dimethyl-2-azetidinone (1.75 g, 10 mmol) as prepared in Example 2-(2) and the mixture was reacted at 0° C. for 15 minutes. To the reaction solution, methyl iodide (0.74 ml, 12 mol) was added dropwise and the temperature of the mixture was returned to room temperature. The reaction was performed for 2 hours and stopped by adding a saturated aqueous solution of ammonium chloride. The reaction mixture was extracted 2 times with ethyl acetate and washed 3 times with a saturated aqueous solution of NaCl. The organic layer was dried over anhydrous sodium sulfate and the solvent was distilled off. The obtained oil was applied to a silica gel column and eluted with a mixed solution (hexane:ethyl acetate=2:1). The desired fractions were collected and the solvents were distilled off to yield N-methyl-4-phenyl-3,3-dimethyl-2-azetidinone (1.89 g, quant.).

NMR: ¹H (270 MHz: CDCl₃: 25° C.) 0.76, s, 3H: 1.43, s, 3H: 2.86, s, 3H: 4.31, s, 1H: 7.14–7.23, m, 2H: 7.28–7.50, m, 3H; MS: [M+Na]⁺ calculated: 212.105, found: 211.8

(2) N-4-Cyanobenzoyl-N-methyl-β-phenylα,α-dimethyl-β-alanine

The same procedure as in Example 2-(3) was performed with N-methyl-4-phenyl-3,3-dimethyl-2-azetidinone (2.43 g, 12.8 mmol) to yield a powder of N-methyl-β-phenylα,α-dimethyl-β-alanine hydrochloride (3.00 g, 96.2%).

NMR: ¹H (270 MHz: D₂O: 25° C.) 1.10, s, 3H: 1.25, s, 3H: 2.47, s, 3H: 4.31, s, 1H: 7,30–7.38, m, 2H; MS: [M+H]⁺ calculated: 208.134, found: 208.0

The same procedure as in Example 2-(6-1) was performed with the obtained N-methyl-β-phenylα,α-dimethyl-β-alanine hydrochloride (1.13 g, 5 mmol) to yield a crystal of N-4-cyanobenzoyl-N-methyl-β-phenylα,α-dimethyl-β-alanine (1.02 g, 60.6%).

NMR: ¹H (270 MHz: CD₃OD: 25° C.) 1.43, s, 3H: 1.48, s, 3H: 2.76, s, 3H: 5.27, s, 1H: 7.15–7.55, m, 5H: 7.60, d, J=7.8 Hz, 2H: 8.31, d, J=7.8 Hz, 2H; MS: [M+Na]⁺ calculated: 359.137, found: 358.9

(3) N-(N-4-Cyanobenzoyl-N-methyl-β-phenylα,α-dimethyl-β-alanyl)-4-piperidineacetic acid benzyl ester The same procedure as in Example 2-(6-2) was performed with N-4-cyanobenzoyl-N-methyl-β-phenylα,α-dimethyl- β-alanine (0.67 g, 2.0 mmol) to yield a crystal of N-(N-4-cyanobenzoyl-N-methyl-β-phenyl-α,α-dimethyl-β-alanyl)-4-piperidineacetic acid benzyl ester (1.13 g, quant.).

NMR: $^1$H (270 MHz: CDCl$_3$: 25° C.) 1.53, s, 3H: 1.57, s, 3H: 1.53–1.82, m, 4H: 1.94, br-s, 1H: 2.13, d, J=6.8 Hz, 2H: 2.53–2.90, m, 2H: 2.67, s, 3H: 4.48, br-t, J=13.6 Hz, 2H: 5.08, s, 2H: 5.06–5.20, m, 1H: 7.24–7.50, m, 10H: 7.53, d, J=7.8 Hz, 2H: 7.74, d, J=7.8 Hz, 2H; MS: [M+Na]$^+$ calculated: 574.268, found: 574.2

(4) N-(N-4-Amidinobenzoyl-N-methyl-β-phenylα,α-dimethyl-β-alanyl)-4-piperidineacetic acid benzyl ester The same procedure as in Example 2-(6-3) was performed with N-(N-4-cyanobenzoyl-N-methyl-β-phenylα,α-dimethyl-β-alanyl)-4-piperidineacetic acid benzyl ester (417 mg, 0.75 mmol) to yield an oil of N-(N-4-amidinobenzoyl-N-methyl-β-phenylα,α-dimethyl-β-alanyl)-4-piperidineacetic acid benzyl ester (158 mg, 37.0%).

NMR: $^1$H (270 MHz: CDCl$_3$: 25° C.) 1.35–1.78, m, 4H: 1.46, s, 3H: 1.51, s, 3H: 1.80–2.05, br-m, 1H: 2.11, d, J=6.4 Hz, 2H: 2.48–2.95, m, 2H: 2.58, s, 3H: 4.41, br-t, J=13.5 Hz, 2H: 5.06, s, 2H: 5.08, s, 1H: 7.12–7.45, m, 10H: 7.43, d, J=8.3 Hz, 2H: 7.98, d, J=8.3 Hz, 2H; MS: [M+H]$^+$ calculated: 569.313, found: 569.2

(5) Synthesis of the titled compound

The same procedure as in Example 2-(6-4) was performed with N-(N-4-amidinobenzoyl-N-methyl-β-phenylα,α-dimethyl-β-alanyl)-4-piperidineacetic acid benzyl ester (105 mg, 0.185 mmol) to yield N-(N-4-amidinobenzoyl-N-methyl-β-phenylα,α-dimethyl-β-alanyl)-4-piperidineacetic acid (39.6 mg, 44.7%).

NMR: $^1$H (400 MHz: CD$_3$OD: 25° C.) 1.28–1.60, m, 2H: 1.55, s, 3H: 1.57, s, 3H: 1.64–1.75, m, 2H: 1.85–2.00, m, 1H: 2.06, m, 2H: 2.71, s, 2H: 2.60–3.05, m, 2H: 4.49, br-t, J=13.5 Hz, 2H: 5.06, m, 1H: 7.28–7.50, m, 5H: 7.67, d, J=7.6 Hz, 2H: 7.90, d, J=7.6 Hz, 2H: $^{13}$C(100 MHz: CD3OD: 25° C.) 26.75, 27.32, 33.69, 34.89, 38.00, 42.28, 47.46, 48.08, 62.77, 129.20, 129.99, 130.44, 130.53, 131.34, 131.67, 138.85, 144.05, 162.98, 168.82, 174.89, 176.70; MS: [M+H]$^+$ calculated: 479.266, found: 479.3

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 38.94 minutes.

EXAMPLE 22

Synthesis of N-(N-4-amidinobenzoyl-β-methyl-α,α-dimethyl-β-alanyl)-4-piperidineacetic acid

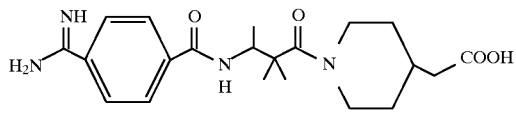

(1) 4-Methyl-3,3-dimethyl-2-azetidinone

Chlorosulfonyl isocyanate (hereinafter abbreviated to "CSI") (7 ml, 71 mmol) was added dropwise to 2-methyl-2-butene (20 ml, 188 mmol) at −78° C. in a pressure vessel under sealed conditions and reaction was performed at room temperature for 6 hours. The resulting reaction mixture was added to a 2N aqueous solution of sodium thiosulfate under cooling with ice. To the mixture, a 4N aqueous solution of sodium hydroxide was added under vigorous stirring to maintain the pH of the water bath in the range of 9–10. After the separation of the obtained mixture, the aqueous layer was extracted 2 times with diethyl ether. The collected organic layer was washed with a saturated aqueous solution of NaCl and dried over magnesium sulfate. The magnesium sulfate was removed by filtration and the solvent was distilled off in vacuo to yield the desired 4-m ethyl-3,3-dimethyl-2-azetidinone (7.8 g, 68 mmol, 96%).

NMR: $^1$H (270 MHz: CDCl$_3$: 25° C.) 1.07, d, J=7.4 Hz, 3H: 1.20, s, 3H: 1.32, s, 3H: 2.77, q, J=7.4 Hz, 1H: $^{13}$C(67.5 MHz: CDCl3: 25° C.) 9.26, 22.35, 27.91, 53.51, 54.59, 171.58; MS: [M+H]$^+$ calculated: 114.084, found: 114.1

(2) N-4-Cyanobenzoyl-β-methylα,α-dimethyl-β-alanyl-4-piperidineacetic acid methyl ester 6N HCl (100 ml) was added to 4-methyl-3,3-dimethyl-2-azetidinone (1.7 g, 10 mmol) and the mixture was stirred at room temperature for 24 hours. The reaction solution was washed with chloroform and the solvent was distilled off under vacuum to yield β-methylα,α-dimethyl-β-alanine hydrochloride. The obtained amino acid was dissolved in DMF (100 ml). To the resulting solution, triethylamine (Et$_3$N) (15 ml) and 4-cyanobenzoyl-N-hydroxysuccinimide ester (4-cyanobenzoyl-OSu) (2.5 g, 10.1 mmol) were added under cooling with ice and the mixture was stirred at room temperature overnight. After the solvent was distilled off, the residue was dissolved in a 1N aqueous solution of sodium carbonate and washed with ether. The aqueous layer was adjusted to pH 3 with citric acid under cooling with ice and extracted with ethyl acetate. The ethyl acetate layer was washed with a saturated aqueous solution of NaCl and dried over anhydrous sodium sulfate. The solvent was distilled off to yield crude N-4-cyanobenzoyl-β-methyl-α,α-dimethyl-β-alanine.

The unpurified crude N-4-cyanobenzoyl-β-methyl-α,α-dimethyl-β-alanine (2.6 g, 10 mmol) was dissolved in methylene chloride (30 ml). To the resulting solution, BOP reagent (4.5 g, 10 mmol) and triethylamine (Et$_3$N) (6.5 ml, 50 mmol) were added under cooling with ice and the mixture was stirred for 30 minutes. To the reaction solution was added methyl 4-piperidineacetate (3.2 g, 20 mmol) and the mixture was stirred overnight. After the solvent was distilled off, the residue was dissolved in ethyl acetate, washed sequentially with a 5% aqueous solution of citric acid, a 5% aqueous solution of sodium bicarbonate and a saturated aqueous solution of NaCl 3 times each and dried over anhydrous sodium sulfate.

The solvent was distilled off and the residue was applied to a silica gel column and eluted with a mixed solution (hexane:ethyl acetate=3:1). The desired fractions were collected and the solvents were distilled off to yield an oil of N-4-cyanobenzoyl-β-methyl-α,α-dimethyl-β-alanyl-4-piperidineacetic acid methyl ester (2.1 q, 5.2 mmol, yield: 52% based on the amino acid).

NMR: $^1$H (400 MHz: CD$_3$OD: 25° C.) 0.65–0.95, m, 2H: 0.81–0.85, m, 3H: 1.06–1.10, m, 3H: 1.23–1.26, m, 3H: 1.30–1.52, m, 2H: 1.63–1.74, br-s, 1H: 1.87–1.95, m, 2H: 2.27–2.36, m, 1H: 2.76–2.85, m, 1H: 3.17–3.20, m, 1H: 3.29–3.30, m, 3H: 3.81–3.94, m, 0.8H: 4.20–4.28, m, 1.2H: 7.47–7.58, m, 4H; MS: [M+H]$^+$ calculated: 400.215, found: 400.4

(3) Synthesis of the titled compound

The same procedure as in Example 9-(4) was performed with N-4-cyanobenzoyl-β-methyl-α,α-dimethyl-β-alanyl-4-piperidineacetic acid methyl ester (165 mg, 0.41 mmol) to yield N-(N-4-amidinobenzoyl-β-methyl-α,α-dimethyl-β-alanyl)-4-piperidineacetic acid (68 mg, 0.16 mmol, 40%).

NMR: $^1$H (400 MHz: CD$_3$OD: 25° C.) 1.00–1.25, m, 2H: 1.18–1.22, m, 3H: 1.41–1.46, m, 3H: 1.60–1.63, m, 3H: 1.68–1.95, m, 2H: 2.00–2.14, m, 1H: 2.19–2.29, m, 2H: 2.64–2.70, m, 1H: 3.09–3.20, m, 1H: 3.29–3.31, m, 3H: 3.46–3.52, m, 1H: 4.23–4.30, m, 1H: 4.55–4.65, m, 1H:

7.81–7.99, m, 4H: $^{13}$C(100 MHz: CD$_3$OD: 25° C.) 14.50, 14.73, 15.14, 25.69, 25.79, 2565.39, 26.78, 33.56, 33.73, 34.37, 34.86, 34.99, 35.12, 42.17, 42.24, 43.29, 43.39, 43.96, 44.09, 58.09, 58.31, 129.53, 129.66, 129.71, 130.17, 132.96, 134.54, 142.81, 168.62, 168.70, 168.84, 176.75, 176.9; MS: [M+H]$^+$ calculated: 403.227, found: 403.1

EXAMPLE 23

Synthesis of N-(N-4-amidinobenzoyl-β-phenylα,α-dimethyl-β-alanyl)-4-piperazineacetic acid

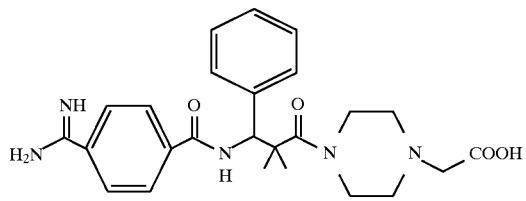

(1) N-4-Cyanobenzoyl-β-phenylα,α-dimethyl-β-alanyl-4-piperazineacetic acid benzyl ester The same procedure as in Example 2-(6-2) was performed with N-4-cyanobenzoyl-β-phenyl-α,α-dimethyl-β-alanine (0.4 g, 1.24 mmol) and piperazineacetic acid benzyl ester (0.87 g, 3.72 mmol) to yield an oil of N-4-cyanobenzoyl-β-phenyl-α,α-dimethyl-β-alanyl-4-piperazineacetic acid benzyl ester (0.48 g, 70.0%).

MS: [M+Na]$^+$ calculated: 561.266, found: 561.3

(2) Synthesis of the titled compound

The same procedure as in Example 2-(6-3) was performed with N-4-cyanobenzoyl-β-phenyl-α,α-dimethyl-β-alanyl-4-piperazineacetic acid benzyl ester (200 mg, 0.4 mmol) to yield an oil of N-4-amidinobenzoyl-β-phenyl-α,α-dimethyl-β-alanyl-4-piperazineacetic acid benzyl ester (80 mg, 36.0%).

MS: [M+H]$^+$ calculated: 556.292, found: 556.3

The same procedure as in Example 2-(6-4) was performed with the obtained N-4-amidinobenzoyl-β-phenyl-α,α-dimethyl-β-alanyl-4-piperazineacetic acid benzyl ester (70 mg, 0.13 mmol) to yield N-(N-4-amidinobenzoyl-β-phenyl-α,α-dimethyl-β-alanyl)-4-piperazineacetic acid (32 mg, 53.2%).

NMR: $^1$H (400 MHz: CD$_3$OD: 25° C.) 1.32, s, 3H: 1.33, s, 3H: 3.24–3.37, m, 2H: 3.35–3.48, m, 2H: 3.97–4.07, m, 4H: 5.66, s, 1H: 7.28–7.38, m, 3H: 7.49–7.50, m, 2H: 7.88–7.90, m, 2H: 7.93–7.96, m, 2H; MS: [M+H]$^+$ calculated: 466.245, found: 466.3

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 30.5 minutes.

EXAMPLE 24

Synthesis of N-(N-4-amidinobenzoyl-β-i-butylα,α-dimethyl-β-alanyl)-4-piperidineacetic acid

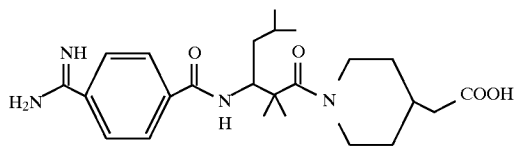

The same procedure as in Example 3 was performed with isovaleric aldehyde to yield N-(N-4-amidinobenzoyl-β-i-butyl-α,α-dimethyl-β-alanyl)-4-piperidineacetic acid (34.2 mg).

NMR: $^1$H (400 MHz: CD$_3$OD: 25° C.) 0.92, d, J=7.2 Hz, 3H: 0.94, d, J=6.0 Hz, 3H: 1.11–1.35, m, 3H: 1.52–1.63, m, 1H: 1.69, ddd, J=3.2 Hz, 11.2 Hz, 14.4 Hz, 1H: 1.84, br-d, J=12.8 Hz, 2H: 1.97–2.11, m, 1H: 2.25, d, J=7.2 Hz, 2H: 2.80–3.05, br-s, 2H: 4.48–4.61, m, 2H: 4.70, br-t, J=8.8 Hz, 1H: 7.88, dt, J=8.8 Hz, 2.0 Hz, 2H: 7.98, dt, J=8.8 Hz, 2.0 Hz, 2H; MS: [M+H]$^+$ calculated : 444.274, found : 445.3

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 33.22 minutes.

Example 25

Synthesis of N-(N-4-amidinobenzoyl-β-p-chlorophenyl-α,α-dimethyl-β-alanyl)-4-piperidineacetic acid

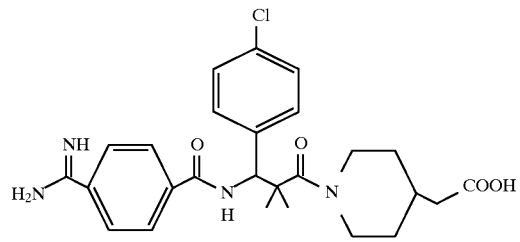

The same procedure as in Example 3 was performed with p-chlorobenzaldehyde to yield N-(N-4-amidinobenzoyl-β-p-chlorophenyl-α,α-dimethyl-β-alanyl)-4-piperidineacetic acid (6.4 mg).

NMR: $^1$H (400 MHz: CD$_3$OD: 25° C.) 1.09, q, J=12.4 Hz, 1H: 1.22, q, J=12.4 Hz, 1H: 1.29, s, 3H: 1.35, s, 3H: 1.81, br-d, J=12.0 Hz, 2H: 1.94–2.07, m, 1H: 2.14–2.25, m, 2H: 2.75–3.00, m, 2H: 4.51, br-d, J=12.0 Hz, 2H: 5.56, s, 1H: 7.33, d, J=8.4 Hz, 2H: 7.44, d, J=8.4 Hz, 2H: 7.89, d, J=8.8 Hz, 2H: 7.96, d, J=8.8 Hz, 2H $^{13}$C (100 MHz: CD$_3$OD: 25° C.) 25.17, 25.73, 33.92, 33.98, 35.02, 42.25, 47.71, 61.58, 130.0, 130.2, 132.3, 133.2, 135.4, 139.6, 141.7, 169.0, 176.6, 176.8; MS: [M+H]$^+$ calculated : 499.211, found : 499.4

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 36.96 minutes.

EXAMPLE 26

Synthesis of N-(N-4-amidinobenzoyl-β-o-methoxyphenyl-α,α-dimethyl-β-alanyl)-4-piperidineacetic acid

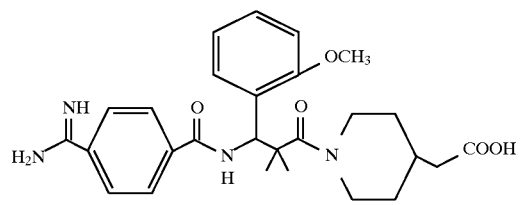

The same procedure as in Example 3 was performed with o-methoxybenzaldehyde to yield N-(N-4-amidinobenzoyl- β-o-methoxyphenyl-α,α-dimethyl-β-alanyl)-4-piperidineacetic acid (19.3mg).

NMR: $^1$H (400 MHz: CD$_3$OD: 25° C.) 1.04–1.17, m, 1H: 1.23, s, 3H: 1.30, s, 3H: 1.27–1.46, m, 1H: 1.81, br-d, d=12.8 Hz, 2H: 1.98–2.06, m, 1H: 2.15–2.26, m, 2H: 2.55–3.15, m, 2H: 3.92, s, 3H: 4.62, br-t, J=12.0 Hz, 2H: 6.28–6.30, m, 1H: 6.95, dt, J=0.8 Hz, 7.2 Hz, 1H: 7.04, d, J=7.04 Hz, 1H: 7.29, ddd, J=1.2 Hz, 7.28 Hz, 7.28 Hz, 1H: 7.42, dd, J=1.6 Hz, 8.0 Hz, 1H: 7.85–7.92, m, 4H; MS: [M+H]$^+$ calculated : 495.261, found : 495.2

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 38.27 minutes.

Example 27

Synthesis of N-(N-4-amidinobenzoyl-β-p-hydroxyphenyl-α,α-dimethyl-β-alanyl)-4-piperidineacetic acid

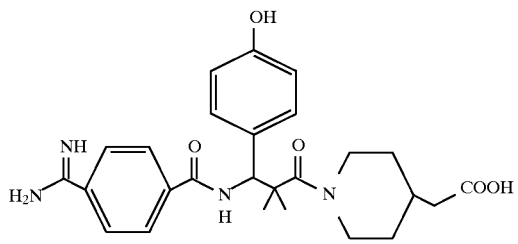

The same procedure as in Example 3 was performed with p-benzyloxybenzaldehyde to yield N-(N-4-amidinobenzoyl-β-p-hydroxyphenyl-α,α-dimethyl-β-alanyl)-4-piperidineacetic acid (25.0 mg).

NMR: $^1$H (400 MHz: CD$_3$OD: 25° C.) 1.08, dq, J=1.6 Hz, 10.4 Hz, 1H: 1.22, dq, J=1.4 Hz, 10.4 Hz, 1H: 1.29, s, 3H: 1.33, s, 3H: 1.79, br-d, J=13.2 Hz, 2H: 1.94–2.07, m, 1H: 2.13–2.24, m, 2H: 2.55–3.00, m, 2H: 4.44–4.53, m, 2H: 5.48, s, 1H: 6.74, d, J=6.8 Hz, 2H: 7.25, d, J=8.8 Hz, 2H: 7.87, d, J=8.8 Hz, 2H: 7.95, d, J=8.8 Hz, 2H; MS: [M+H]$^+$ calculated: 481.245, found 481.1

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 26.27 minutes.

EXAMPLE 28

Synthesis of N-(N-4-amidinobenzoyl-β-m-hydroxyphenyl-α,α-dimethyl-β-alanyl)-4-piperidineacetic acid

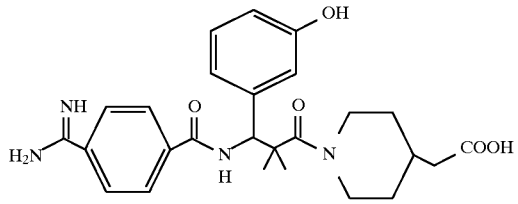

The same procedure as in Example 3 was performed with m-benzyloxybenzaldehyde to yield N-(N-4-amidinobenzoyl-β-m-hydroxyphenyl-α,α-dimethyl-β-alanyl)-4-piperidineacetic acid (17.7 mg).

NMR: $^1$H (400 MHz: CD$_3$OD: 25° C.) 1.05, dq, J=1.6 Hz, 8.8 Hz, 1H: 1.23, dq, J=1.6 Hz, 12.4 Hz, 1H: 1.32, s, 3H: 1.36, s, 3H: 1.79, br-t, J=11.0 Hz, 2H: 1.92–2.07, m, 1H: 2.13–2.24, m, 2H: 2.77–2.98, m, 2H: 4.48, br-d, J=13.2 Hz, 2H: 5.46, s, 1H: 6.71, dd, J=1.2 Hz, 9.6 Hz, 1H: 6.85, t, J=1.2 Hz, 1H: 6.89, br-d, J=7.6 Hz, 1H: 7.14, t, J=7.6 Hz, 1H: 7.88, d, J=8.8 Hz, 2H: 7.96, d, J=8.8 Hz, 2H $^{13}$C(100 MHz: CD$_3$OD: 25° C.) 25.55, 26.34, 33.91, 35.06, 42.27, 47.72, 62.11, 116.41, 117.48, 121.7, 130.1, 130.9, 133.2, 141.8, 142.2, 159.2, 168.9, 176.8, 177.1; MS; [M+H]$^+$ calculated : 481.245, found : 481.2

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 28.35 minutes.

EXAMPLE 29

Synthesis of N-(N-4-amidinobenzoyl-β-1-propenyl-α,α-dimethyl-β-alanyl )-4-piperidineacetic acid

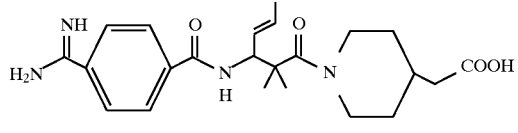

The same procedure as in Example 9 was performed with crotonaldehyde to yield N-(N-4-amidinobenzoyl-β-1-propenyl-α,α-dimethyl-β-alanyl)-4-piperidineacetic acid (22.3 mg).

NMR: $^1$H (400 MHz: CD$_3$OD: 25° C.) 1.13–1.27, m, 2H: 1.32, s, 6H: 1.70, d, J=5.2 Hz, 3H: 1.82, br-d, J=12.4 Hz, 2H: 1.96–2.09, m, 1H: 2.24, d, J=6.8 Hz, 2H: 2.60–3.04, m, 2H: 4.47, br-d, J=13.2 Hz, 2H: 4.87, br-d, J=7.2 Hz, 1H: 5.64, ddd, J=1.6 Hz, 7.2 Hz, 15.2 Hz, 1H: 5.73, dq, J=5.2 Hz, 15.2 Hz, 1H: 7.87, d, J=8.8 Hz, 2H: 7.97, d, J=8.8 Hz, 2H; MS: [M+H]$^+$ calculated : 429.250, found : 429.3

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 30.28 minutes.

EXAMPLE 30

Synthesis of N-(N-4-amidinobenzoyl-β-3,3,3-trifluoropropyl-α,α-dimethyl-β-alanyl)-4-piperidineacetic acid

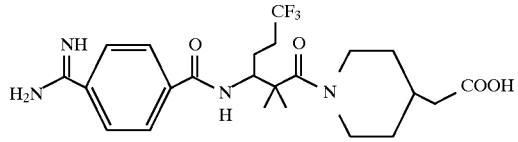

The same procedure as in Example 9 was performed with 4,4,4-trifluorobutylaldehyde to yield N-(N-4-amidinobenzoyl-β-3,3,3-trifluoropropyl-α,α-dimethyl-β-alanyl)-4-piperidineacetic acid (25.2 mg).

NMR: $^1$H (400 MHz: CD$_3$OD: 25° C.) 1.13–1.25, m, 2H: 1.33, s, 3H: 1.35, m, 3H: 1.73–1.94, m, 4H: 1.98–2.21, m,

1H: 2.12–2.24, m, 2H: 2.24, d, J=6.8 Hz, 2H: 2.75–3.10, m, 2H: 4.49, br-d, J=13.6 Hz, 2H: 4.55, dd, J=2.4 Hz, 10.8 Hz, 1H: 7.89, dt, J=8.4 Hz, 2.0 Hz, 2H: 7.99, dt, J=8.4 Hz, 2.0 Hz, 2H; MS: [M+H]+ calculated : 485.238, found : 485.2

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 33.82 minutes.

EXAMPLE 31

Synthesis of N-(((N-4-amidinobenzoyl)-1-amino)-1-pentyl-1-cyclohexane-carbonyl)-4-piperidineacetic acid

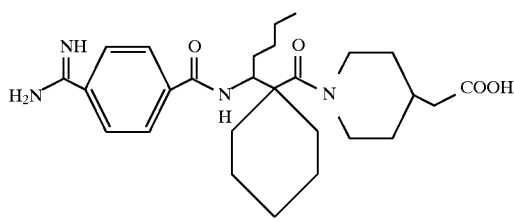

The same procedure as in Example 3 was performed with methyl hexahydrobenzoate and n-butyraldehyde to yield N-(((N-4-amidinobenzoyl)-1-amino)-1-pentyl-1-cyclohexanecarbonyl)-4-piperidineacetic acid (11.0 mg).

NMR: $^1$H (400 MHz: CD$_3$OD: 25° C.) 0.88, t, J=6.8 Hz, 3H: 1.13–1.51, m, 11H: 1.57–1.71, m, 5H: 1.85, br-t, J=14.8 Hz, 2H: 2.02–2.33, m, 1H: 2.20–2.26, m, 3H: 2.34, br-d, J=12.0 Hz, 1H: 2.75–3.15, m, 2H: 4.56–4.74, m, 3H: 7.89, d, J=8.8 Hz, 2H: 8.01, d, J=8.8 Hz, 2H; MS: [M+H]+ calculated : 485.313, found : 485.1

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 40.80 minutes.

EXAMPLE 32

Synthesis of N-(N-4-amidinobenzoyl-β-p-N,N-dimethylaminophenyl-α,α-dimethyl-β-alanyl)-4-piperidineacetic acid

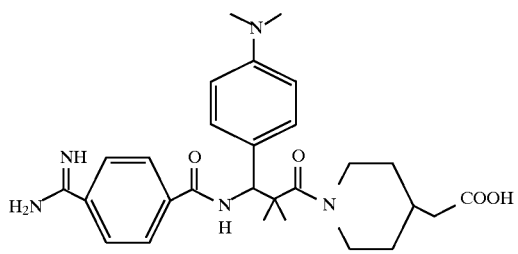

The same procedure as in Example 3 was performed with p-N,N-dimethylaminobenzaldehyde to yield N-(N-4-amidinobenzoyl-β-p-N,N-dimethylaminophenyl-α,α-dimethyl-β-alanyl)-4-piperidineacetic acid (107.0 mg).

NMR: $^1$H (400 MHz: CD$_3$OD: 25° C.) 1.07, dq, J=1.6 Hz, 8.8 Hz, 1H: 1.23, dq, J=1.6 Hz, 12.4 Hz, 1H: 1.30, s, 3H: 1.35, s, 3H: 1.76–1.84, m, 2H: 1.97–2.07, m, 1H: 2.18–2.21, m, 2H: 2.82–2.96, m, 2H: 3.10, s, 6H: 4.50, br-d, J=12.8 Hz, 2H: 5.53, s, 1H: 7.17, d, J=8.8 Hz, 2H: 7.49, d, J=8.8 Hz, 2H: 7.89, d, J=8.8 Hz, 2H: 7.96, d, J=8.8 Hz, 2H $^{13}$C(100 MHz: CD$_3$OD: 25° C.) 25.28, 25.84, 33.90, 33.91, 35.02, 42.27, 44.64, 47.68, 61.76, 118.0, 130.1, 132.0, 141.7, 148.6, 169.0, 176.7, 189.2; MS: [M+H]+ calculated : 508.292, found : 508.2

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 19.28 minutes.

EXAMPLE 33

Synthesis of N-(N-4-amidinobenzoyl-β-m-trifluoromethylphenyl-α,α-dimethyl-β-alanyl)-4-piperidineacetic acid

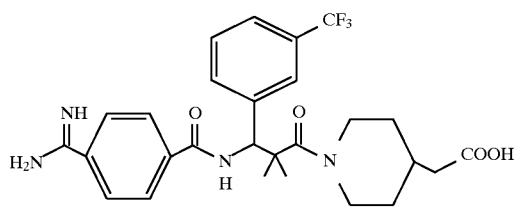

The same procedure as in Example 3 was performed with m-trifluoromethylbenzaldehyde to yield N-(N-4-amidinobenzoyl-β-m-trifluoromethylphenyl-α,α-dimethyl-β-alanyl)-4-piperidine acetic acid (119.3 mg).

NMR: $^1$H (400 MHz: CD$_3$OD: 25° C.) 1.11, q, J=11.6 Hz, 1H: 1.21, q, J=12.8 Hz, 1H: 1.30, s, 3H: 1.37, s, 3H: 1.82, br-d, J=12.8 Hz, 2H: 1.97–2.07, m, 1H: 2.15–2.26, m, 2H: 2.83–2.98, m, 2H: 4.47–4.56, m, 2H: 5.66, s, 1H: 7.54, t, J=7.6 Hz, 1H: 7.60, d, J=7.6 Hz, 1H: 7.74, d, J=8.8 Hz, 1H: 7.81, br-s, 1H: 7.89, d, J=8.8 Hz, 2H: 7.97, d, J=7.97 Hz, 2H; $^{13}$C(100 MHz: CD$_3$OD: 25° C.) 25.18, 25.63, 33.94, 35.02, 42.25, 47.72, 61.93, 126.3, 127.2, 130.2, 130.7, 132.5, 133.3, 134.6, 141.5, 142.3, 162.8, 163.1, 168.8, 169.1, 176.6, 176.7; MS: [M+H]+ calculated : 533.237, found : 533.2

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 45.09 minutes.

EXAMPLE 34

Synthesis of N-(N-4-amidinobenzoyl-β-p-n-butylphenyl-α,α-dimethyl-β-alanyl)-4-piperidineacetic acid

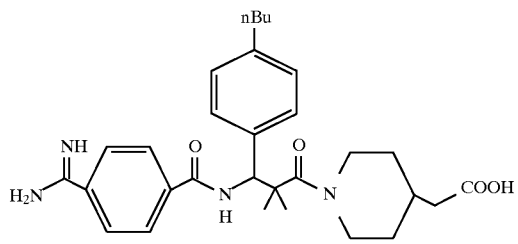

The same procedure as in Example 3 was performed with p-n-butylbenzaldehyde to yield N-(N-4-amidinobenzoyl-β- p-n-butylphenyl-α,α-dimethyl-β-alanyl)-4-piperidineacetic acid (138.2 mg).

NMR: $^1$H (400 MHz: CD$_3$OD: 25° C.) 0.92, t, J=7.2 Hz, 3H: 1.07, q, J=11.6 Hz, 1H: 1.23, q, J=12.0 Hz, 1H: 1.30, s, 3H: 1.34, s, 3H: 1.28–1.40, m, 2H: 1.54–1.63, m, 2H: 1.75–1.81, m, 2H: 1.94–2.08, m, 1H: 2.14–2.25, m, 2H: 2.60, t, J=7.6 Hz, 2H: 2.74–2.97, m, 2H: 4.50, br-d, J=6.5 Hz, 2H: 5.54, s, 1H: 7.15, d, J=8.4 Hz, 2H: 7.33, d, J=8.4 Hz, 2H: 7.88, d, J=8.8 Hz, 2H: 7.96, d, J=8.8 Hz, 2H $^{13}$C(100 MHz: CD$_3$OD: 25° C.) 15.02, 24.12, 25.50, 26.06, 33.91, 35.02, 35.65, 36.98, 42.27, 47.70, 61.76, 130.0, 130.1, 130.4, 133.1, 137.9, 141.9, 144.4, 168.8, 168.9, 176.7, 177.0; MS: [M+H]$^+$ calculated : 521.313, found : 521.2

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 54.72 minutes.

EXAMPLE 35

Synthesis of N-(N-4-amidino-2-fluorobenzoyl-β-n-butyl-α,α-dimethyl-β-alanyl)-4-piperidineacetic acid

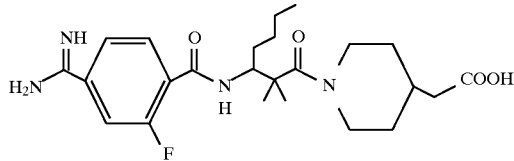

(1) N-Boc-β-n-butyl-α,α-dimethyl-β-alanine

β-n-butyl-α,α-dimethyl-β-alanine hydrochloride (3.65 g, 17.40 mmol) was dissolved into 10% aqueous sodium carbonate (18.4 ml). To the resulting solution was added dioxane solution (50 ml) of di-t-butylcarbonate (4.6 g, 20.87 mmol) under cooling with ice and stirred at room temperature overnight. The solvent was distilled off and the resulting residue was dissolved into water, washed with ether and adjusted to pH 3 with citric acid under cooling with ice, followed by the several times of ethyl acetate extraction. The combined organic layer was washed with brine, dried over anhydrous sodium sulfate. The solvent were removed in vacuo, and recrystallized from ether-hexane mixed solvent to give crystal of N-Boc-β-n-butyl-α,α-dimethyl-β-alanine (3.16 g, 66.4%).

NMR: $^1$H (270 MHz: CD$_3$OD: 25° C.) 0.84–0.93, m, 3H: 1.06, s, 3H: 1.14, s, 3H: 1.22–1.46, m, 6H: 1.44, s, 9H: 3.71–3.82, m, 1H; MS: [M+Na]$^+$ calculated : 296.184, found : 296.2

(2) N-Boc-β-n-butyl-α,α-dimethyl-β-alanyl-piperidineacetic acid methyl ester

To a solution of N-Boc-β-n-butyl-α,α-dimethyl-β-alanine (1.68 g, 6.13 mmol) in dichloromethane (30 ml) was added HATU reagent (2.8 g, 7.37 mmol) and di-i-propylethylamine (6.58 ml, 36.8 mmol) under cooling with ice. After being stirred for 30 min, to the reaction mixture was added 4-piperidineacetic acid methyl ester (1.45 g, 9.19 mmol) and stirred overnight at room temperature. After the solvent was distilled off, the resulting residue was dissolved into ethyl acetate and washed with 5% aqueous citric acid, 5% aqueous sodium bicarbonate, and brine for three times respectively. The organic layer was dried over anhydrous sodium sulfate. After the solvent was distilled off, the residue was subjected to the silica gel column chromatography (2.2×20 cm) and eluted with hexane:ethyl acetate=2:1 to give powder of N-Boc-β-n-butyl-α,α-dimethyl-β-alanyl-piperidineacetic acid methyl ester (1.70 g, 67.2%).

NMR: $^1$H (270 MHz: CD$_3$OD: 25° C.) 0.84–0.93, m, 3H: 1.10, s, 3H: 1.21, s, 3H: 1.06–1.42, m, 8H: 1.44, s, 9H: 1.73–1.86, m, 2H: 1.95–2.12, m, 1H: 2.28, d, J=6.8 Hz, 2H: 2.74–3.02, m, 2H: 3.65, s, 3H: 3.88–4.01, m, 1H: 4.42–4.57, m, 2H: 6.55, d, J=9.8 Hz, 1H; MS: [M+Na]$^+$ calculated: 435.284, found: 435.1

(3) N-(N-2-fluoro-4-cyanobenzoyl-β-n-butyl-α,α-dimethyl-β-alanyl)-4-piperidineacetic acid methyl ester To the N-Boc-β-n-butyl-α,α-dimethyl-β-alanyl-piperidineacetic acid methyl ester (0.77 g, 1.86 mmol) was added anisole (0.7 ml) and TFA (20 ml). The reaction mixture was stirred for 1 h under cooling with ice. After TFA was removed in vacuo at room temperature, the resulting residue was washed with hexane for 3 times and dissolved into DMF (20 ml) under cooling with ice. After being neutralized by triethylamine, 2-fluoro-4-cyanobenzoic acid (0.40 g, 2.42 mmol), HOBT (0.33 g, 2.42 mmol) and WSDC (0.56 g, 2.91 mmol) were added and stirred overnight. After the solvent was distilled off, the resulting residue was dissolved into ethyl acetate and washed with 5% aqueous citric acid, 5% aqueous sodium bicarbonate, and brine for three times respectively. The organic layer was dried over anhydrous sodium sulfate. After the solvent was distilled off, the residue was subjected to the silica gel column chromatography (1.8×20 cm) and eluted with hexane:ethyl acetate= 3:1 to give a powder of N-(N-2-fluoro-4-cyanobenzoyl-β-n-butyl-α,α-dimethyl-β-alanyl)-4-piperidineacetic acid methyl ester (366 mg, 42.8%).

NMR: $^1$H (270 MHz: CDCl$_3$: 25° C.) 0.87, m, 3H: 1.08–1.42, m, 6H: 1.34, s, 3H: 1.40, s, 3H: 1.59–1.75, m, 2H: 1.73–1.86, m, 2H: 1.96–2.15, m, 1H: 2.27, d, J=6.8 Hz, 2H: 2.81, m, 2H: 3.68, s, 3H: 4.12, m, 1H: 4.40, br-d, J=13.2 Hz, 2H: 7.44, dd, J=1.5 Hz, 10.7 Hz, 1H: 7.55, dd, J=1.5 Hz, 8.3 Hz, 1H: 7.81, br-t, J=9.3 Hz, 1H: 8.12, t, J=7.8 Hz, 1H $^{13}$C(67.5 MHz: CDCl3: 25° C.) 14.0, 22.5, 24.2, 24.4, 29.4, 30.8, 32.0, 32.2, 33.1, 40.6, 46.4, 51.5, 59.9, 115.8, 115.9, 116.8, 116.9, 119.8, 120.3, 126.6, 126.8, 128.3, 128.4, 132.89, 132.94, 157.8, 161.5, 161.7, 161.8, 172.6, 174.9; MS: [M+Na]$^+$ calculated: 482.243, found: 482.1

(4) Synthesis of the titled compound

The same procedure as example 9-(4) was performed with N-(N-2-fluoro-4-cyanobenzoyl-β-n-butyl-α,α-dimethyl-β-alanyl)-4-piperidineacetic acid methyl ester (0.20 g, 0.44 mmol) to yield N-(N-4-amidino-2-fluorobenzoyl-β-n-butylα,α-dimethyl-β-alanyl)-4-piperidineacetic acid (20.1 mg, 9.9%).

NMR: $^1$H (400 MHz: CD$_3$OD: 25° C.) 0.91, br-t, J=6.4 Hz, 3H: 1.15–1.65, m, 8H: 1.25, s, 3H: 1.34, s, 3H: 1.80–1.88, m, 2H: 2.00–2.13, m, 1H: 2.25, d, J=7.2 Hz, 2H: 2.75–3.14, m, 2H: 4.47–4.58, m, 3H: 7.70, d, J=7.2 Hz, 2H: 7.81, t, J=7.2 Hz, 1H; MS: [M+H]$^+$ calculated: 463.272, found: 463.6

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 35.10 minutes.

EXAMPLE 36

Synthesis of N-(N-4-amidino-2-chlorobenzoyl-β-phenyl-α,α-dimethyl-β-alanyl)-4-piperidineacetic acid

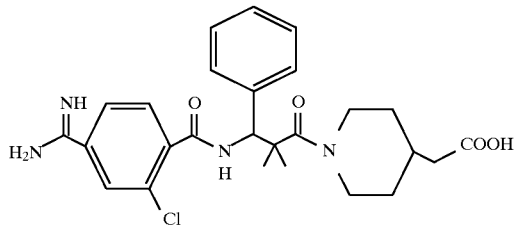

The same procedure as example 35-(1,2,3) was performed with β-phenyl-α,α-dimethyl-β-alanine hydrochloride to yield N-(N-2-chloro-4-cyanobenzoyl-β-phenyl-α,α-dimethyl-β-alanyl)-4-piperidineacetic acid benzylester. And then the same procedure as example 3 was performed with above compound to yield N-(N-4-amidino-2-chlorobenzoyl-β-phenyl-α,α-dimethyl-β-alanyl)-4-piperidineacetic acid (5.1 mg).

NMR: $^1$H (400 MHz: CD$_3$OD: 25° C.) 1.18–1.41, m, 4H: 1.27, s, 3H: 1.30, s, 3H: 1.86, br-d, J=11.2 Hz, 2H: 1.99–2.14, m, 1H: 2.25, d, J=7.2 Hz, 2H: 2.87–3.14, m, 2H: 4.57, br-d, J=12.4 Hz, 2H: 5.78, s, 1H: 7.28–7.37, m, 3H: 7.39–7.45, m, 2H: 7.58, d, J=8.0 Hz, 1H: 7.78, dd, J=1.2 Hz, 7.78 Hz, 1H: 7.93, d, J=2.0 Hz, 1H; MS: [M+H]$^+$ calculated: 499.211, found: 499.4

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 36.92 minutes.

EXAMPLE 37

Synthesis of N-((N-4-(N-1-acetoxyethyloxycarbonyl)amidinobenzoyl)-β-n-butyl-α,α-dimethyl-β-alanyl)-4-piperidineacetic acid

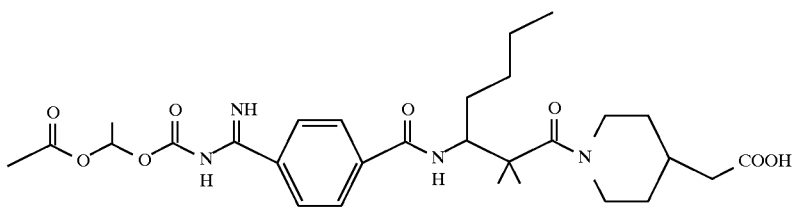

(1) α-acetoxyethyl-p-nitrophenyl carbonate

The same procedure as described in J. Alexander's paper (J. Med. Chem. 31, 318–322(1988)) was performed with p-nitrophenol and α-chloroethyl chloroformate to give α-acetoxyethyl-p-nitrophenyl carbonate (51.0%) as an oil in two steps.

NMR: $^1$H (270 MHz: CDCl$_3$: 25° C.) 1.62, d, J=5.8 Hz, 3H: 2.13, s, 3H: 6.84, q, J=5.8 Hz, 1H: 7.41, d, J=9.27 Hz, 2H: 8.28, d, J=9.27 Hz, 2H (2) N-((N-4-(N-1-acetoxyethyloxycarbonyl)amidinobenzoyl)-β-n-butyl-α,α-dimethyl-β-alanyl)-4-piperidineacetic acid benzyl ester N-(N-4-amidinobenzoyl-β-n-butyl-α,α-dimethyl-β-alanyl)-4-piperidineacetic acid benzyl ester from example 6-(3) (150 mg, 0.28 mmol) was added dehydrated THF (20 ml) and triethylamine (2 ml). To the resulting mixture was added dehydrated THF solution (5 ml) of α-acetoxyethyl-p-nitrophenyl carbonate (82.9 mg, 0.31 mmol) and the reaction mixture was stirred overnight. After the solvent was distilled off, the residue was dissolved into ethyl acetate and washed with 5% aqueous citric acid, 5% aqueous sodium bicarbonate, and brine for three times respectively. The organic layer was dried over anhydrous sodium sulfate. After the solvent was distilled off, the residue was subjected to the silica gel column chromatography (2.2×20 cm) and eluted with chloroform:methanol=50:1 to yield N-((N-4-(N-1-acetoxyethyloxycarbonyl)amidinobenzoyl)-β-n-butyl-α,α-dimethyl-β-alanyl)-4-piperidineacetic acid benzyl ester (92.8 mg, 52.8%) as an oil.

NMR: $^1$H (270 MHz: CDCl$_3$: 25° C.) 0.86, br-t, J=6.4 Hz, 3H: 1.16–1.43, m, 6H: 1.32, s, 3H: 1.40, s, 3H: 1.55, d, J=5.4 Hz, 3H: 1.70, br-s, 2H: 1.79, br-d, J=12.2 Hz, 2H: 2.04–2.10, m, 1H: 2.08, s, 3H: 2.31, d, J=7.3 Hz, 2H: 2.80, br-s, 2H: 4.03, m, 1H: 4.37, br-d, J=12.2 Hz, 2H: 5.12, s, 2H: 6.97, q, J=5.4 Hz, 1H: 7.32–7.39, m, 5H: 7.65, br-d, J=9.8 Hz, 1H: 7.82, d, J=8.8 Hz, 2H: 7.93, d, J=8.8 Hz, 2H; MS: [M+Na]$^+$ calculated: 687.336, found: 687.3

(3) Synthesis of the titled compound

The same procedure as example 2-(6-4) was performed with N-((N-4-(N-1-acetoxyethyloxycarbonyl)amidinobenzoyl)-β-n-butyl-α,α-dimethyl-β-alanyl)-4-piperidineacetic acid benzyl ester (78.0 mg, 0.12 mmol) to give N-((N-4-(1-acetoxyethyloxycarbonyl)amidinobenzoyl)-β-n-butyl-α,α-dimethyl-β-alanyl)-4-piperidineacetic acid (27 mg, 39.5%)

NMR: $^1$H (270 MHz: CD$_3$OD: 25° C) 0.87, t, J=6.8 Hz, 3H: 1.10–1.45, m, 6H: 1.24, s, 3H: 1.29, s, 3H: 1.45–1.71, br, 2H: 1.53, d, J=5.4 Hz, 3H: 1.75–1.91, br, 2H: 1.99–2.09, br, 1H: 2.06, s, 3H: 2.24, d, J=6.8 Hz, 2H: 2.80–3.05, br, 2H: 4.50–4.62, m, 3H: 6.88, q, J=5.4 Hz, 1H: 7.88, d, 8.3 Hz, 2H: 7.95, d, 8.3 Hz, 2H; MS: [M+H]$^+$ calculated: 575.308, found: 575.3

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 22.83 minutes.

EXAMPLE 38

Synthesis of N-((N-4-(N-1-acetoxyethyloxycarbonyl)amidinobenzoyl)-β-n-butyl-α,α-dimethyl-β-alanyl)-4-piperidineacetic acid ethyl ester

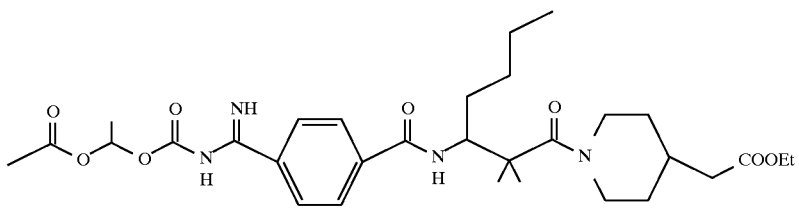

The same procedure as example 37-(2) was performed with N-(N-4-amidinobenzoyl-β-n-butyl-α,α-dimethyl-β-alanyl)-4-piperidineacetic acid ethyl ester (200 mg, 0.42 mmol) to give crude product (243 mg) as an oil. The afforded product was recrystallized from ether-hexane mixed solution to yeild N-((N-4-(N-1-acetoxyethyloxycarbonyl)amidinobenzoyl)-β-n-butyl-α,α-dimethyl-β-alanyl)-4-piperidineacetic acid ethyl ester (163 mg, 63.9%).

NMR: $^1$H (270 MHz: CDCl$_3$: 25° C.) 0.85, br-t, J=6.0 Hz, 3H: 1.16–1.41, m, 6H: 1.25, t, J=6.8, 3H: 1.33, s, 3H: 1.41, s, 3H: 1.57, d, J=5.4 Hz, 3H: 1.68, br-s, 2H: 1.79, br-d, J=12.2 Hz, 2H: 2.04–2.10, m, 1H: 2.08, s, 3H: 2.25, d, J=7.3 Hz, 2H: 2.80, br-s, 2H: 4.05–4.15, m, 1H: 4.13, q, J=6.8 Hz, 2H: 4.37, br-d, J=12.2 Hz, 6.98, q, J=5.4 Hz, 1H: 7.54, br-d, J=9.8 Hz, 1H: 7.83, d, J=8.3 Hz, 2H: 7.95, d, J=8.3 Hz, 2H; MS: [M+Na]$^+$ calculated: 625.322, found: 625.2

EXAMPLE 39

Synthesis of N-(N-4-amidinobenzoyl-β-m-hydroxyphenethyl-α,α-dimethyl-β-alanyl)-4-piperidineacetic acid

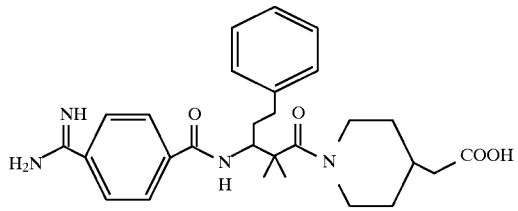

The same procedure as in Example 3 was performed with m-benzyloxycinnamaldehyde to yield N-(N-4-amidinobenzoyl-β-m-hydroxyphenethyl-α,α-dimethyl-β-alanyl)-4-piperidineacetic acid (94.3 mg).

NMR: $^1$H (270 MHz: CD$_3$OD: 25° C.) 0.77–0.98, br, 1H: 0.98–1.17, m, 1H: 1.20, s, 3H: 1.24, s, 3H: 1.57–1.75, m, 3H: 1.81–2.08, m, 2H: 2.20, d, J=6.8 Hz, 2H: 2.33–2.58, m, 2H: 2.62–2.94, m, 2H: 4.38, br-t, J=12.2 Hz, 2H: 4,59, br-t, J=9.3 Hz, 1H: 6.57–6.68, m, 3H: 7.08, t, J=6.8 Hz, 1H: 7.92, d, J=8.8 Hz, 2H: 8.05, d, J=8.8 Hz, 2H; [M+H]$^+$ calculated: 509.276, found: 509.3

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 29.06 minutes.

EXAMPLE 40

Synthesis of N-(N-4-amidinobenzoyl-β-ethynyl-α,α-dimethyl-β-alanyl)-4-piperidineacetic acid

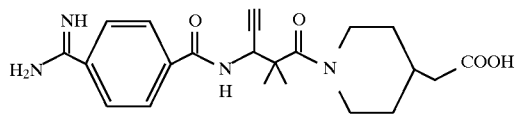

The same procedure as in Example 3 was performed with 4-ethynyl-3,3-dimethyl-2-azetidinone to yield N-(N-4-amidinobenzoyl-β-ethynyl-α,α-dimethyl-β-alanyl)-4-piperidineacetic acid (12.0 mg).

NMR: $^1$H (270 MHz: CD$_3$OD: 25° C.) 1.22, br-q, J=14.7 Hz, 2H: 1.43, s, 3H: 1.46, s, 3H: 1.78–1.90, m, 2H: 1.92–2.15, m, 1H: 2.25, d, J=7.3 Hz, 2H: 2.77, d, J=2.4 Hz, 1H: 2.85, br-t, J=12.2 Hz, 1H: 2.99, br-t, J=11.0 Hz, 1H: 4.43, d, J=13.2 Hz, 2H: 5.34, d, J=2.4 Hz, 1H: 7.88, d, J=8.3 Hz, 2H: 7.98, d, J=8.3 Hz, 2H; MS: [M+H]$^+$ calculated: 413.219, found: 413.3

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 24.16 minutes.

EXAMPLE 41

Synthesis of N-(N-4-amidino-2-fluorobenzoyl-β-ethyl-α,α-dimethyl-β-alanyl)-4-piperidineacetic acid

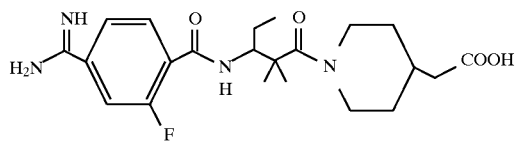

The same procedure as in Example 35 was performed with β-ethyl-α,α-dimethyl-β-alanine hydrochloride to yield N-(N-4-amidino-2-fluorobenzoyl-β-ethyl-α,α-dimethyl-β-alanyl)-4-piperidineacetic acid (6.7 mg).

NMR: $^1$H (270 MHz: CD$_3$OD: 25° C.) 0.97, t, J=7.3 Hz, 3H: 1.10–1.28, m, 2H: 1.25, s, 3H: 1.34, s, 3H: 1.56, m, 2H: 1.84, br-t, J=8.9 Hz, 2H: 1.95–2.15, m, 1H: 2.26, d, J=7.3 Hz, 2H: 2.75–3.08, m, 2H: 4.44, m, 1H: 4.53, br-d, J=13.7 Hz, 2H: 7.68, s, 1H: 7.70, d, J=7.3 Hz, 1H: 7.82, t, J=7.3 Hz, 1H; MS: [M+H]$^+$ calculated: 435.241, found: 435.2

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 26.01 minutes.

EXAMPLE 42

Synthesis of N-(N-4-amidino-2-fluorobenzoyl-β-methyl-α,α-dimethyl-β-alanyl)-4-piperidineacetic acid

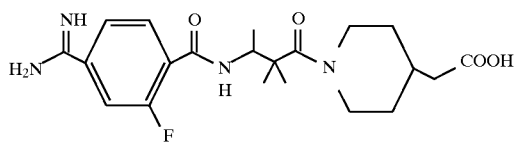

The same procedure as in Example 35 was performed with β-methyl-α,α-dimethyl-β-alanine hydrochloride to yield N-(N-4-amidino-2-fluorobenzoyl-β-methyl-α,α-dimethyl-β-alanyl)-4-piperidineacetic acid (25.0 mg).

NMR: $^1$H (270 MHz: CD$_3$OD: 25° C.) 1.05, d, J=7.5 Hz, 3H: 1.05–1.28, m, 2H: 1.27, s, 3H: 1.30, s, 3H: 1.81, m, 2H: 1.91–2.07, m, 1H: 2.26, d, J=7.4 Hz, 2H: 2.81–3.12, m, 2H: 4.41, m, 1H: 4.57, br-d, J=13.3 Hz, 2H: 7.62, s, 1H: 7.69, d, J=7.2 Hz, 1H: 7.79, t, J=7.3 Hz, 1H; MS: [M+H]$^+$ calculated: 421.225, found: 421.3

A spectrum of analytical HPLC using Wakosil-II5C18HG (φ 4.6×250 mm) column at a flow rate of 1.0 ml/min at room temperature by elution in a gradient of 10–40% acetonitrile (60 min) in 0.1% TFA had a single peak at a retention time of 21.77 minutes.

EXAMPLE 43

Ethyl N-(N-(4-(4-morpholinoimidoyl)benzoyl)-β-ethyl-α,α-dimethyl-β-alanyl)-4-piperidineacetate

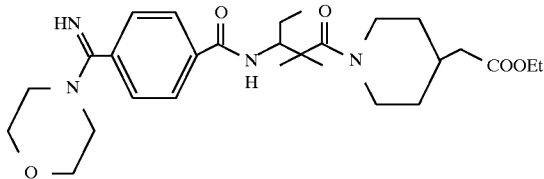

β-Ethyl-α,α-dimethyl-β-alanine hydrochloride (2.0 g, 11.07 mmol) was dissolved in a 10% aqueous solution of sodium carbonate (11.7 ml). To the resulting solution was added a dioxane solution (40 ml) of di-t-butyldicarbonate (2.9 g, 13.21 mmol) under cooling with ice and the mixture was stirred at room temperature overnight. The solvent was distilled off and the resulting residue was dissolved in water and washed with ether. The aqueous layer was adjusted to pH 3 with citric acid under cooling with ice, followed by ethyl acetate extraction. The collected ethyl acetate layer was washed with saturated saline and dried over anhydrous sodium sulfate. The solvent was distilled off to yield a crystal of N-Boc-β-ethyl-α,α-dimethyl-β-alanine (2.7 g, quant.) from a mixed solution of ether-hexane.

The obtained crystal (1.2 g, 4.89 mmol) was dissolved in methylene chloride (50 ml). To the resulting solution were added HATU reagent (2.8 g, 7.37 mmol) and diisopropylethylamine (5.2 ml, 29.35 mmol) under cooling with ice and the mixture was stirred for 30 minutes. To the mixture was added 4-piperidineacetic acid ethyl ester (1.26 g, 7.34 mmol) and the resulting mixture was stirred overnight. After the solvent was distilled off, the residue was dissolved in ethyl acetate, washed sequentially with a 5% aqueous solution of citric acid, a 5% aqueous solution of sodium hydrogencarbonate and saturated saline 3 times each, and dried over anhydrous sodium sulfate. After the solvent was distilled off, the residue was applied to a silica gel column (2.2×15 cm) and eluted with a mixed solution (hexane:ethyl acetate=5:1). The desired fractions were collected and the solvents were distilled off to yield a powder of N-(N-Boc-βethyl-α,α-dimethyl-β-alanyl)-4-piperidineacetic acid ethyl ester (1.77 g, 90.8%). MS: [M+H]$^+$ calculated: 399.286, found: 399.5

To the obtained N-(N-Boc-βethyl-α,α-dimethyl-β-alanyl)-4-piperidineacetic acid ethyl ester (0.38 g, 0.95 mmol) were added anisole (0.3 ml) and TFA (10 ml) and the mixture was stirred for 1 hour under cooling with ice. After the TFA was distilled off at room temperature, the residue was washed with hexane 3 times and dissolved in DMF (20 ml) under cooling with ice. After the resulting solution was neutralized with triethylamine, 4-(4-morpholinoimidoyl)benzoic acid (0.25 g, 1.05 mmol), HOBT (0.14 g, 1.05 mmol) and WSDC (0.22 g, 1.14 mmol) were added thereto and the mixture was stirred overnight. After the solvent was distilled off, the residue was dissolved in ethyl acetate, washed sequentially with a 5% aqueous solution of citric acid, a 5% aqueous solution of sodium hydrogencarbonate and saturated saline 3 times each, and dried over anhydrous sodium sulfate. After the solvent was distilled off, the residue was applied to a silica gel column (2.1 φ×20 cm) and eluted with a mixed solution (chloroform:ethanol=30:1). The desired fractions were collected and the solvents were distilled off to yield a powder of the titled compound (108 mg, 22%).

NMR: $^1$H (270 MHz: CDCl$_3$: 25° C.) 0.92, t, J=7.3 Hz, 3H: 1.11–1.24, m, 2H: 1.26, t, J=6.8 Hz, 3H: 1.31, s, 3H: 1.38, s, 3H: 1.62–1.88, m, 4H: 1.95–2.15, m, 1H: 2.25, d, J=7.3 Hz, 2H: 2.68–2.95, m, 2H: 3.33–3.45, m, 2H: 3.64–3.75, m, 2H: 3.83–4.08, m, 5H: 4.13, q, J=7.3 Hz, 2H: 4.40, br-d, J=12.7 Hz, 2H: 7.53, d, J=7.8 Hz, 2H: 7.90, d, J=7.8 Hz, 2H $^{13}$C (67.5 MHz: CDCl$_3$: 25° C.) 11.62, 14.22, 23.80, 24.13, 24.27, 31.96, 32.20, 33.10, 40.80, 44.99, 45.37, 46.49, 47.34, 50.12, 60.39, 61.03, 65.79, 66.32, 128.00, 128.37, 130.76, 138.85, 164.55, 166.19, 172.19, 175.14; MS: [M+H]$^+$ calculated: 515.323, found: 515.5; HRMS: C$_{28}$H$_{43}$N$_4$O$_5$ [M+H]$^+$ calculated: 515.3233, found: 515.3257

EXAMPLE 44

N-(N-(4-(4-Morpholinoimidoyl)benzoyl)-β-ethyl-α,α-dimethyl-β-alanyl)-4-piperidineacetic acid

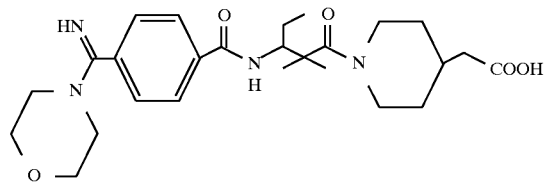

Ethyl N-(N-(4-(4-morpholinoimidoyl)benzoyl)-β-ethyl-α,α-dimethyl-β-alanyl)-4-piperidineacetate (28 mg, 54.4 mmol) as prepared in Example 43 was dissolved in ethanol (10 ml). To the resulting solution was added a 4N aqueous solution of NaOH (3 ml) under cooling with ice and the mixture was stirred for 3 hours. The mixture was neutralized with acetic acid under cooling with ice. After the ethanol was distilled off, the residue was dissolved in water and purified with a high performance liquid chromatography (HPLC) [column: ODS 5C$_{18}$ (μ bondasphere, φ 19×150 mm), mobile phase: (A) 0.1% TFA, (B) 100% CH$_3$CN/0.1% TFA, gradient: (A):(B)=76:24–74:26, 6 minutes, flow rate: 17 ml/min]. The desired fractions were collected and lyophilized to yield the titled compound (20.3 mg, 77%).

NMR: $^1$H (400 MHz: CD$_3$OD: 25° C.) 0.93, t, J=7.2 Hz, 3H: 1.13–1.35, m, 2H: 1.27, s, 3H: 1.30, s, 3H: 1.51–1.68, m, 2H: 1.84, br-t, J=13.6 Hz, 2H: 1.98–2.12, m, 1H: 2.25, d, J=6.8 Hz, 2H: 2.60–3.10, m, 2H: 3.45, t, J=4.4 Hz, 2H: 3.73, t, J=4.8 Hz, 2H: 3.81, t, J=4.4 Hz, 2H: 3.92, t, J=4.4 Hz, 2H: 4.46, dd, J=10.4 Hz, 4.0 Hz, 1H: 4.54, br-d, J=13.6 Hz, 2H: 7.72, d, J=8.4 Hz, 2H: 8.02, d, J=8.4 Hz, 2H $^{13}$C(100 MHz: CD$_3$OD: 25° C.) 12.73, 24.16, 24.60, 25.00, 34.02, 34.16, 35.17, 42.34, 48.00, 48.89, 52.20, 59.24, 67.12, 68.13, 130.29, 130.52, 133.58, 140.66, 166.97, 170.37, 176.81, 177.10; MS: [M+H]$^+$ calculated: 487.292, found: 487.4; HRMS: C$_{26}$H$_{39}$N$_4$O$_5$ [M+H]$^+$ calculated: 487.2920, found: 487.2897; HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 18.63 minutes.

EXAMPLE 45

Ethyl-N-(N-(4-(4-morpholinoimidoyl)-2-fluorobenzoyl)-β-ethyl-α,α-dimethyl-β-alanyl)-4-piperidineacetate

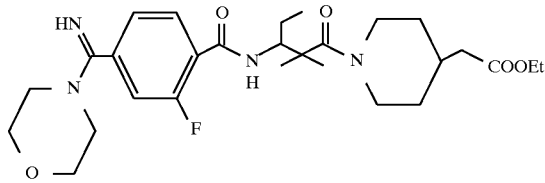

To N-Boc-β-ethyl-α,α-dimethyl-β-alanyl)-4-piperidineacetic acid ethyl ester (1.0 g, 2.51 mmol) as prepared in Example 43 were added anisole (1.0 ml) and TFA (30 ml) and the mixture was stirred for 1 hour under cooling with ice. After the TFA was distilled off at room temperature, the residue was washed with hexane 3 times and dissolved in DMF (50 ml) under cooling with ice. After the resulting solution was neutralized with triethylamine, 2-fluoro-4-cyanobenzoic acid (0.46 g, 2.76 mmol), HOBT (0.37 g, 2.76 mmol) and WSDC (0.63 g, 3.26 mmol) were added thereto and the mixture was stirred overnight. After the solvent was distilled off, the residue was dissolved in ethyl acetate, washed sequentially with a 5% aqueous solution of citric acid, a 5% aqueous solution of sodium hydrogencarbonate and saturated saline 3 times each, and dried over anhydrous sodium sulfate. After the solvent was distilled off, the residue was applied to a silica gel column (2.2×15 cm) and eluted with a mixed solution (hexane:ethyl acetate=3:1). The desired fractions were collected and the solvents were distilled off to yield a powder of N-(N-2-fluoro-4-cyanobenzoyl-β-ethyl-α,α-dimethyl-β-alanyl-4-piperidineacetic acid ethyl ester (855 mg, 76.5%).

MS: [M+Na]$^+$ calculated: 446.246, found: 446.5

The obtained ethyl-N-(N-4-cyano-2-fluorobenzoyl)-β-ethyl-α,α-dimethyl-β-alanyl)-4-piperidineacetate (4.1 g, 9.8 mmol) was dissolved in pyridine (200 ml). To the resulting solution was added triethylamine (50 ml) and the mixture was saturated with hydrogen sulfide gas. The reaction vessel was sealed and the reaction mixture was stirred at room temperature overnight. The pyridine was distilled off and the volatile products were removed by two cycles of toluene azeotropy. The residue was dissolved in acetone (200 ml) and methyl iodide (20 ml) was added thereto, followed by refluxing for 30 minutes. The solvent was distilled off and the residue was dissolved in methanol (200 ml). To the resulting solution was added morpholine (20 ml) and the mixture was refluxed for 2 hours. After the solvent was distilled off, the residue was dissolved in chloroform, washed with saturated saline and dried over anhydrous sodium sulfate. After the solvent was distilled off, the residue was applied to a silica gel column (1.5×14 cm) and eluted with a mixed solution (chloroform:methanol=30:1). The desired fractions were collected and the solvent was distilled off to yield a powder of the titled compound (1.4 g, 28%).

NMR: $^1$H (270 MHz: CDCl$_3$: 25° C.) 0.93, m, 3H: 1.12–1.41, m, 8H: 1.26, t, J=7.0 Hz, 3H: 1.57–1.89, m, 4H: 1.92–2.16, m, 1H: 2.24, d, J=6.8 Hz, 2H: 2.82, m, 2H: 3.41, br-s, 2H: 3.70, br-s, 2H: 3.85–3.97, m, 4H: 4.03–4.19, m, 1H: 4.13, q, J=7.3 Hz, 2H: 4.27–4.47, m, 2H: 7.32–7.43, m, 2H: 7.68–7.82, m, 1H: 8.00, t, J=7.6 Hz, 1H $^{13}$C(67.5 MHz: CDCl$_3$: 25° C.) 11.56, 14.22, 23.83, 23.93, 24.09, 31.97, 32.15, 32.96, 33.10, 40.60, 40.82, 40.07, 45.07(br), 46.46, 47.24, 50.11, 60.42, 60.72, 65.59, 66.20, 77.21, 116.41, 11.80, 124.22, 126.39, 126.58, 132.05, 132.18, 132.65, 157.86, 161.59, 162.74, 163.06, 172.26, 174.81; MS: [M+H]$^+$ calculated: 533.314, found: 533.4; HRMS: C$_{28}$H$_{42}$FN$_4$O$_5$ [M+H]$^+$ calculated: 533.3139, found: 533.3136

EXAMPLE 46

N-(N-(4-(4-morpholinoimidoyl)-2-fluorobenzoyl)-β-ethyl-α,α-dimethyl-β-alanyl)-4-piperidineacetic acid

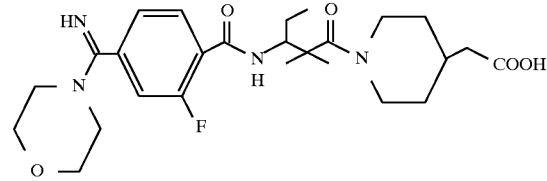

The same procedure as in Example 44 was performed with the compound of Example 45, i.e. ethyl-N-(N-(4-(4-morpholinoimidoyl)-2-fluorobenzoyl)-β-ethyl-α,α-dimethyl-β-alanyl)-4-piperidineacetate (200 mg, 0.38 mmol) to yield the titled compound (160 mg, 84%).

NMR: $^1$H (400 MHz: CD$_3$OD: 25° C.) 0.97, t, J=7.6 Hz, 3H: 1.12–1.25, m, 2H: 1.26, s, 3H: 1.34, s, 3H: 1.50–1.63, m, 2H: 1.78–1.91, m, 2H: 2.06, br-s, 1H: 2.26, d, J=7.2 Hz, 2H: 2.78–3.08, m, 2H: 3.39–3.50, m, 2H: 3.65–3.76, m, 2H: 3.76–3.84, m, 2H: 3.86–3.95, m, 2H: 4.37–4.45, m, 1H: 4.52, br-d, J=12.4 Hz, 2H: 7.53, d, J=7.6 Hz, 1H: 7.58, d, J=10.4 Hz: 7.85, t, J=7.6 Hz, 1H: $^{13}$C(100 MHz: CD$_3$OD: 25° C.) 12.68, 24.14, 24.71, 25.28, 34.04, 34.13, 35.15, 42.34, 47.30, 47.75, 48.92, 49.29, 52.20, 59.93, 67.05, 68.03, 118.47, 118.73, 126.45, 129.77, 129.92, 133.45, 134.51, 134.58, 160.35, 162.86, 165.60, 167.01, 176.77, 177.05; MS: [M+H]$^+$ calculated: 505.283, found: 505.5; HRMS: C$_{26}$H$_{36}$FN$_4$O$_5$ [M+H]$^+$ calculated: 505.2826, found: 505.2827; HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 19.46 minutes.

EXAMPLE 47

Ethyl-N-(N-(4-(N,N-diethylaminoimidoyl)-2-fluorobenzoyl)-β-ethyl-α,α-dimethyl-β-alanyl)-4-piperidineacetate

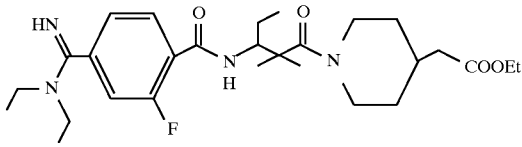

The same procedure as in Example 45 was performed with ethyl-N-(N-(4-cyano-2-fluorobenzoyl)-β-ethyl-α,α-dimethyl-β-alanyl)-4-piperidineacetate (1.4 g, 3.1 mmol) by using diethylamine (3.2 ml) as an amine to yield the titled compound (224 mg, 15%).

NMR: $^1$H (270 MHz: CDCl$_3$: 25° C.) 0.94, t, J=7.4 Hz, 3H: 1.17, t, J=7.0 Hz, 3H: 1.26, t, J=7.0 Hz, 3H: 1.12–1.39, m, 11H: 1.55–1.76, m, 2H: 1.80, br-d, J=11.9 Hz, 1.96–2.15, m. 1H: 2.25, d, J=6.8 Hz, 2.72–2.91, m, 2H: 3.29, q, J=6.1 Hz, 2H: 3.74, q, J=6.8 Hz, 2H: 4.13, q, J=J=7.3 Hz, 2H: 4.39–4.18, m, 1H: 4.42, br-d, J=12.7 Hz, 2H: 7.27, br-t, J=8.6 Hz, 7.61, br-t, J=8.5 Hz, 1H: 7.98, t, J=7.6 Hz, 1H $^{13}$C(67.5 MHz: CDCl$_3$: 25° C.) 11.17, 11.48, 13.62, 14.18, 23.64, 23.83, 23.93, 31.97, 32.12, 33.10, 40.82, 43.55, 45.02, 45.37, 46.53, 46.85, 60.22, 60.35, 76.53, 77.00, 77.21, 77.47, 115.48, 115.87, 123.28, 123.33, 125.76, 125.96, 132.50, 132.97, 133.11, 157.80, 161.51, 162.84, 172.21, 174.70; MS: [M+H]$^+$ calculated: 519.335, found 519.5; HRMS: C$_{28}$H$_{44}$FN$_4$O$_4$ [M+H]$^+$ calculated: 519.3346, found: 519.3360

EXAMPLE 48

N-(N-(4-(N,N-diethylaminoimidoyl)-2-fluorobenzoyl)-β-ethyl-α,α-dimethyl-β-alanyl)-4-piperidineacetic acid

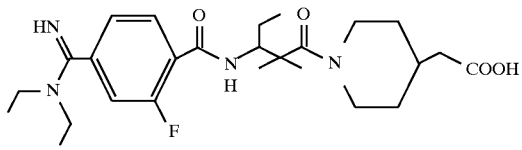

The same procedure as in Example 44 was performed with the compound of Example 47, i.e. ethyl-N-(N-(4-(N,N-diethylaminoimidoyl)-2-fluorobenzoyl)-β-ethyl-α,α-dimethyl-β-alanyl)-4-piperidineacetate (56 mg, 0.11 mmol) to yield the titled compound (29 mg, 54.7%).

NMR: $^1$H (400 MHz: CD$_3$OD: 25° C.) 0.97, t, J=7.2 Hz, 3H: 1.13–1.27, m, 2H: 1.19, t, J=7.2 Hz, 3H: 1.26, s, 3H: 1.34, s, 3H: 1.38, t, J=7.2 Hz, 3H: 1.50–1.63, m, 2H: 1.77–1.92, m, 2H: 1.98–2.13, m, 1H: 2.25, d, J=6.8 Hz, 2H: 2.60–3.05, m, 2H: 3.34, q, J=7.6 Hz, 2H: 3.69, q, J=7.6 Hz, 2H: 4.37–4.45, m, 1H: 4.52, br-d, J=12.8 Hz, 2H: 7.49, dd, J=7.6 Hz, 1.2 Hz, 1H: 7.57, d, J=10.4 Hz, 1H: 7.84, t, J=6.8 Hz, 1H $^{13}$C(100 MHz: CD$_3$OD: 25° C.) 12.16, 12.68, 14.52, 24.14, 24.73, 25.28, 34.05, 34.15, 35.19, 42.45, 45.45, 47.37, 47.77, 59.91, 117.74, 118.00, 125.70, 129.32, 129.46, 133.38, 135.35, 165.40, 167.08, 168.20, 176.88, 177.07; MS: [M+H]$^+$ calculated: 491.303, found: 491.4; HRMS: C$_{26}$H$_{40}$FN$_4$O$_4$ [M+H]$^+$ calculated: 491.3033, found: 491.3013; HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 21.19 minutes.

EXAMPLE 49

Ethyl-N-(N-(4-(1-piperidinoimidoyl)-2-fluorobenzoyl)-β-ethyl-α,α-dimethyl-β-alanyl)-4-piperidineacetate

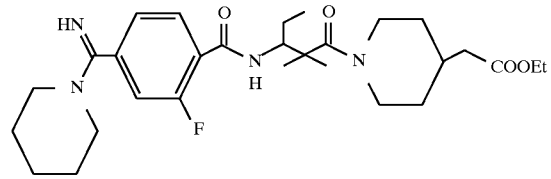

The same procedure as in Example 45 was performed with ethyl-N-(N-(4-cyano-2-fluorobenzoyl)-β-ethyl-α,α-dimethyl-β-alanyl)-4-piperidineacetate (1.4 g, 3.1 mmol) by using piperidine (3.1 ml) as an amine to yield the titled compound (487 mg, 30%).

NMR: $^1$H (270 MHz: CDCl$_3$: 25° C.) 0.95, t, J=7.3 Hz, 3H: 1.09–1.46, m, 2H: 1.26, t, J=7.2 Hz, 3H: 1.34, s, 3H: 1.39, s, 3H: 1.59–1.96, m, 8H: 1.96–2.19, m, 1H: 2.23–2.30, m, 2H: 2.74–2.92, m, 2H: 3.39, br-t, J=5.4 Hz, 2H: 3.79–3.86, m, 2H: 4.02–4.19, m, 1H: 4.14, q, J=7.0 Hz, 2H: 4.40, br-d, J=12.2 Hz, 2H: 7.22–7.37, m, 2H: 8.06, t, J=7.6 Hz, 1H $^{13}$C(67.5 MHz: CDCl$_3$: 25° C.) 11.56, 14.23, 20.80, 23.14, 23.83, 24.03, 24.15, 24.93, 26.24, 31.94, 32.17, 33.07, 40.79, 45.16, 45.40, 46.46, 48.73, 51.71, 60.48, 61.26, 77.20, 115.89, 116.29, 123.76, 126.31, 126.51, 132.79, 133.06, 133.11, 162.14, 162.64, 172.27, 174.78, 175.10; MS: [M+H]$^+$ calculated: 531.335, found: 531.3; HRMS: C$_{29}$H$_{44}$FN$_4$O$_4$ [M+H]$^+$ calculated: 531.3346, found: 531.3352

EXAMPLE 50

N-(N-(4-(1-piperidinoimidoyl)-2-fluorobenzoyl)-β-ethyl-α,α-dimethyl-β-alanyl)-4-piperidineacetic acid

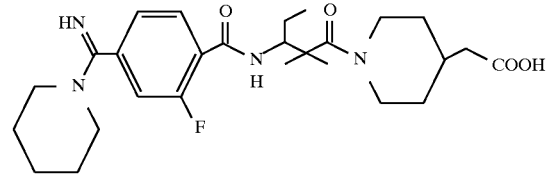

The same procedure as in Example 44 was performed with the compound of Example 49, i.e. ethyl-N-(N-(4-(1-piperidinoimidoyl)-2-fluorobenzoyl)-β-ethyl-α,α-dimethyl-β-alanyl)-4-piperidineacetate (100 mg, 0.188 mmol) to yield the titled compound (85.8 mg, 91%).

NMR: $^1$H (400 MHz: CD$_3$OD: 25° C.) 0.97, t, J=7.2 Hz, 3H: 1.13–1.25, m, 2H: 1.26, s, 3H: 1.34, s, 3H: 1.48–1.71, m, 4H: 1.72–1.94, m, 6H: 2.06, br-s, 1H: 2.26, d, J=6.4 Hz, 2H: 2.65–3.10, m, 2H: 3.40, br-s, 2H: 3.76, br-s, 2H: 4.37–4.46, m, 1H: 4.53, br-d, J=12 Hz, 2H: 7.50, d, J=7.6 Hz, 1H: 7.56, d, J=9.6 Hz, 1H: 7.84, t, J=6.8 Hz, 1H $^{13}$C(100 MHz: CD$_3$OD: 25° C.) 12.68, 24.03, 24.65, 25.08, 25.20, 26.83, 27.84, 34.02, 34.15, 35.15, 42.34, 47.31, 47.73, 53.44, 59.62, 118.11, 118.36, 126.08, 129.76, 133.30, 135.24, 135.32, 162.82, 164.54, 167.19, 176.81, 176.98; MS: [M+H]$^+$ calculated: 503.303, found: 503.3; HRMS: C$_{27}$H$_{40}$FN$_4$O$_4$ [M+H]$^+$ calculated: 503.3033, found: 503.3048; HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 22.14 minutes.

EXAMPLE 51

Ethyl-N-(N-(4-(1-pyrrolidinoimidoyl)-2-fluorobenzoyl)-β-ethyl-α,α-dimethyl-β-alanyl)-4-piperidineacetate

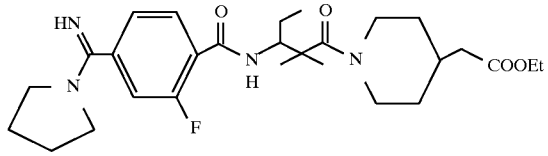

The same procedure as in Example 45 was performed with ethyl-N-(N-(4-cyano-2-fluorobenzoyl)-β-ethyl-α,α-dimethyl-β-alanyl)-4-piperidineacetate (1.4 g, 3.1 mmol) by using pyrrolidine (2.6 ml) as an amine to yield the titled compound (398 mg, 25%).

NMR: $^1$H (270 MHz: CDCl$_3$: 25° C.) 1.16–1.42, m, 2H: 1.26, t, J=7.3 Hz, 6H: 1.31, s, 3H: 1.37, s, 3H: 1.59–1.89, m, 4H: 1.91–2.30, m, 5H: 2.25, d, J=7.3 Hz, 2H: 2.71–2.91, m, 2H: 3.43, br-t, J=6.3 Hz, 2H: 3.76, br-s, 2H: 4.06–4.48, m, 1H: 4.13, q, J=6.9 Hz, 2H: 4.41, br-d, J=12.7 Hz, 2H: 7.28–7.43, m, 2H: 766, br-d, J=8.2 Hz, 1H: 8.00, br-t, J=8.2 Hz, 1H $^{13}$C(67.5 MHz: CDCl$_3$: 25° C.) 11.54, 14.20, 23.81, 23.86, 24.06, 24.85, 24.96, 25.51, 29.66, 31.99, 32.17, 32.29, 33.12, 40.83, 45.05, 45.37, 46.47, 49.13, 52.12, 60.39, 60.67, 77.20, 115.70, 116.10, 12.62, 125.94, 126.13, 132.60, 133.23, 133.35, 157.82, 160.89, 161.02, 161.53, 162.74, 172.24, 174.79; MS: [M+H]$^+$ calculated: 517.319, found: 517.4; HRMS: C$_{28}$H$_{42}$FN$_4$O$_4$ [M+H]$^+$ calculated: 517.3189, found: 517.3207

EXAMPLE 52

N-(N-(4-(1-pyrrolidinoimidoyl)-2-fluorobenzoyl)-β-ethyl-α,α-dimethyl-β-alanyl)-4-piperidineacetic acid

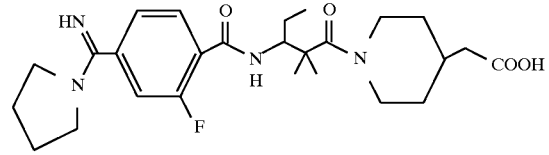

The same procedure as in Example 44 was performed with the compound of Example 51, i.e. ethyl-N-(N-(4-(1-pyrrolidinoimidoyl)-2-fluorobenzoyl)-β-ethyl-α,α-dimethyl-β-alanyl)-4-piperidineacetate (100 mg, 0.194 mmol) to yield the titled compound (36.4 mg, 38.5%).

NMR: $^1$H (400 MHz: CD$_3$OD: 25° C.) 0.97, t, J=7.2 Hz, 3H: 1.14–1.28, m, 2H: 1.26, s, 3H: 1.34, s, 3H: 1.50–1.62, m, 2H: 1.78–1.91, m, 2H: 1.94–2.13, m, 3H: 2.13–2.3, m, 2H: 2.26, d, J=7.2 Hz, 2H: 3.48, t, J=6.8 Hz, 2H: 3.63, t, J=7.2 Hz, 2H: 4.38–4.46, m, 1H: 4.53, br-d, J=12.8 Hz, 2H: 7.53, d, J=8.0 Hz, 1H: 7.57, d, J=10.4 Hz, 1H: 7.83, t, J=6.8 Hz, 1H $^{13}$C(100 MHz: CD$_3$OD: 25° C.) 12.68, 24.09, 24.69, 25.24, 26.68, 27.29, 34.05, 34.15, 35.17, 42.34, 47.39, 47.75, 50.93, 54.03, 59.77, 117.81, 118.07, 125.86, 129.50, 129.66, 133.25, 135.70, 135.79, 160.22, 163.28, 167.17, 167.21, 176.79, 177.03; MS: [M+H]$^+$ calculated: 489.288, found: 489.1; HRMS: C$_{26}$H$_{38}$FN$_4$O$_4$ [M+H]$^+$ calculated: 489.287, found: 489.2862; HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 20.70 minutes.

EXAMPLE 53

Ethyl-N-(N-(4-(1-4-piperidonoimidoyl)-2-fluorobenzoyl)-β-ethyl-α,α-dimethyl-β-alanyl)-4-piperidineacetate

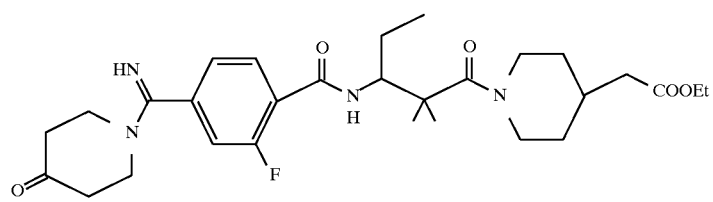

The same procedure as in Example 45 was performed with ethyl-N-(N-(4-cyano-2-fluorobenzoyl)-β-ethyl-α,α-dimethyl-β-alanyl)-4-piperidineacetate (1.4 g, 3.1 mmol) by using as an amine 4-piperidone monohydrate hydrochloride (4.8 g) dissolved in methanol and neutralized with triethylamine to yield the titled compound (183 mg, 11%).

NMR: $^1$H (270 MHz: CDCl$_3$: 25° C.) 0.93, t, J=7.0 Hz, 3H: 1.09–1.43, m, 2H: 1.26, t, J=7.0 Hz, 3H: 1.31, s, 3H: 1.36, s, 3H: 1.59–1.84, m, 2H: 1.80, br-d, J=10.8 Hz, 2H: 1.96–2.15, m, 1H: 2.25, d, J=6.8 Hz, 2H: 2.57, m, 2H: 2.82, br-s, 4H: 3.75, m, 2H: 4.02–4.19, m, 4H: 4.13, q, J=7.1 Hz, 2H: 4.37, br-d, J=12.2 Hz, 2H: 7.43, br-d, J=8.6 Hz, 2H: 7.70, br-t, J=8.2 Hz, 1H: 7.96, br-t, J=7.0 Hz, 1H $^{13}$C(67.5 MHz: CDCl$_3$: 25° C.) 11.53, 14.20, 23.77, 23.89, 24.09, 31.94, 32.14, 33.09, 38.08, 39.46, 40.80, 44.79, 45.00, 45.42, 46.41, 47.34, 60.39, 60.82, 77.20, 116.36, 116.76, 124.20, 126.54, 12.74, 132.24, 132.36, 157.72, 161.44, 162.81, 163.61, 172.21, 174.82; MS: [M+H]$^+$ calculated: 545.314, found: 545.3; HRMS: C$_{29}$H$_{42}$FN$_4$O$_5$ [M+H]$^+$ calculated: 545.3139, found: 545.3147

EXAMPLE 54

N-(N-(4-(1-4-piperidonoimidoyl)-2-fluorobenzoyl)-β-ethyl-α,α-dimethyl-β-alanyl)-4-piperidineacetic acid

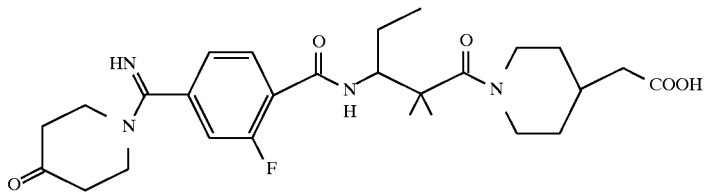

The same procedure as in Example 44 was performed with the compound of Example 53, i.e. ethyl-N-(N-(4-(1-4-piperidonoimidoyl)-2-fluorobenzoyl)-β-ethyl-α,α-dimethyl-β-alanyl)-4-piperidineacetate (30 mg, 0.06 mmol) to yield the titled compound (15 mg, 53%).

NMR: $^1$H (400 MHz: CD$_3$OD: 25° C.) 0.97, t, J=7.2 Hz, 3H: 1.13–1.28, m, 2H: 1.26, s, 3H: 1.34, s, 3H: 1.50–1.63, m, 2H: 1.75–1.90, m, 4H: 1.94–2.12, m, 3H: 2.25, d, J=6.8 Hz, 2H: 2.68–3.10, m, 2H: 3.40–3.50, m, 2H: 3.74–3.85, m, 2H: 4.36–4.45, m, 1H: 4.52, br-d, J=12.8 Hz, 2H: 7.52, d, J=8.0 Hz, 1H: 7.58, d, J=9.6 Hz, 1H: 7.84, t, J=7.2 Hz, 1H; $^{13}$C(100 MHz: CD$_3$OD: 25° C.) 12.68, 24.12, 24.71, 25.26, 34.05, 34.15, 35.17, 36.27, 37.11, 42.39, 46.40, 47.35, 47.79, 59.88, 96.09, 118.22, 118.49, 126.21, 129.66, 129.83, 133.40, 135.13, 135.21, 160.33, 162.84, 165.05, 167.08, 176.85, 177.05; MS: [M+H]$^+$ calculated: 517.283, found: 517.2 and 535.3 (monohydrate); HRMS: C$_{27}$H$_{38}$FN$_4$O$_5$ [M+H]$^+$ calculated: 517.2826, found: 517.2823; HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 18.49 minutes.

EXAMPLE 55

Ethyl-N-(N-(4-(4-hydroxy-1-piperidinoimidoyl)-2-fluorobenzoyl)-β-ethyl-α,α-dimethyl-β-alanyl)-4-piperidineacetate

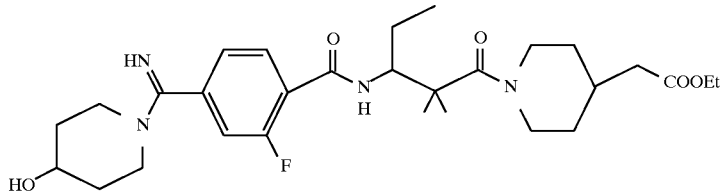

The same procedure as in Example 45 was performed with ethyl-N-(N-(4-cyano-2-fluorobenzoyl)-β-ethyl-α,α-dimethyl-β-alanyl)-4-piperidineacetate (1.4 g, 3.1 mmol) by using 4-hydroxypiperidine (3.1 g) as an amine to yield the titled compound (440 mg, 26%).

NMR: $^1$H (270 MHz: CDCl$_3$: 25° C.) 0.92, t, J=7.3 Hz, 3H: 1.09–1.39, m, 2H: 1.25, t, J=7.0 Hz, 6H: 1.29, s, 3H: 1.35, s, 3H: 1.55–1.92, m, 7H: 1.92–2.13, m, 2H: 2.24, d, J=6.8 Hz, 2H: 2.74–2.93, m, 2H: 3.22–3.36, m, 1H: 3.53–3.68, m, 1H: 3.68–3.83, m, 1H: 3.94–4.19, m, 3H: 4.12, q, J=7.2 Hz, 2H: 4.37, br-d, J=11.6 Hz, 2H: 7.29–7.39, m, 2H: 7.72, br-t, J=8.1 Hz, 1H: 7.94, t, J=7.6 Hz, 1H $^{13}$C(67.5 MHz: CDCl$_3$: 25° C.) 11.50, 14.18, 23.77, 23.98, 31.94, 32.09, 32.46, 33.07, 33.39, 40.79, 43.83, 45.03, 45.45, 46.47, 47.30, 60.42, 60.64, 63.91, 77.20, 113.76, 116.09, 116.48, 118.07, 123.97, 126.14, 126.34, 132.41, 132.74, 132.88, 157.80, 160.29, 160.84, 161.53, 162.26, 163.03, 172.29, 174.90; MS: [M+H]$^+$ calculated: 547.330, found: 547.4; HRMS: C$_{29}$H$_{44}$FN$_4$O$_5$ [M+H]$^+$ calculated: 547.3295, found: 547.3309

EXAMPLE 56

N-(N-(4-(4-hydroxy-1-piperidinoimidoyl)-2-fluorobenzoyl)-β-ethyl-α,α-dimethyl-β-alanyl)-4-piperidineacetic acid

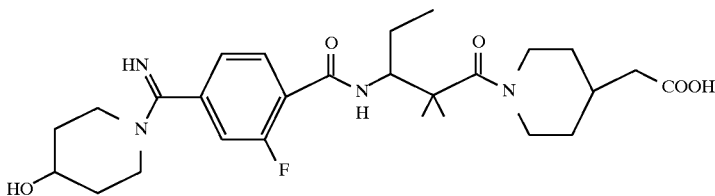

The same procedure as in Example 44 was performed with the compound of Example 55, i.e. ethyl-N-(N-(4-(4-hydroxy-1-piperidinoimidoyl)-2-fluorobenzoyl)-β-ethyl-α,α-dimethyl-β-alanyl)-4-piperidineacetate (200 mg, 0.37 mmol) to yield the titled compound (162 mg, 86%).

NMR: $^1$H (400 MHz: CD$_3$OD: 25° C.) 0.91–1.04, m, 3H: 1.12–1.28, m, 2H: 1.26, s, 3H: 1.34, s, 3H: 1.50–1.67, m, 3H: 1.74–1.95, m, 4H: 2.09, br-s, 2H: 2.26, br-d, J=6.4 Hz, 2H: 2.70–3.10, m, 2H: 3.30–3.38, br-s, 1H: 3.55–3.74, m, 2H: 3.90–4.08, m, 2H: 4.42, br-s, 1H: 4.53, br-d, J=12.0 Hz, 2H: 7.51, br-d, J=7.6 Hz, 1H: 7.57, br-d, J=10.0 Hz, 1H: 7.84, m, 1H; $^{13}$C(100 MHz: CD$_3$OD: 25° C.) 12.68, 24.03, 24.65, 25.20, 34.02, 34.15, 34.31, 35.15, 35.35, 42.32, 45.67, 47.37, 47.68, 59.66, 66.08, 118.14, 118.40, 126.12, 129.66, 129.83, 133.34, 135.13, 135.21, 160.30, 162.80, 164.81, 167.17, 176.79, 176.98; MS: [M+H]$^+$ calculated: 519.298, found: 519.3; HRMS: C$_{27}$H$_{40}$FN$_4$O$_5$ [M+H]$^+$ calculated: 519.2982, found: 519.2981; HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 18.62 minutes.

EXAMPLE 57

Ethyl-N-(N-(4-(3-thiazolidinoimidoyl)-2-fluorobenzoyl)-β-ethyl-α,α-dimethyl-β-alanyl)-4-piperidineacetate

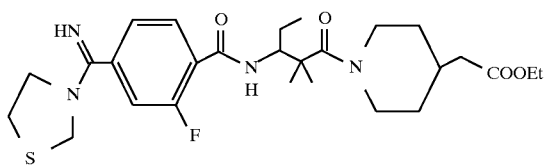

The same procedure as in Example 45 was performed with ethyl-N-(N-(4-cyano-2-fluorobenzoyl)-β-ethyl-α,α-dimethyl-β-alanyl)-4-piperidineacetate (1.48 g, 3.3 mmol) by using thiazolidine (2.5 ml) as an amine to yield the titled compound (314 mg, 23%).

NMR: $^1$H (400 MHz: CDCl$_3$: 25° C.) 0.92, t, J=7.2 Hz, 3H: 1.16, br-q, J=12.0 Hz, 2H: 1.24, t, J=7.2 Hz, 3H: 1.30, s, 3H: 1.35, s, 3H: 1.59–1.73, m, 2H: 1.78, br-d, J=12.0 Hz, 2H: 1.97–2.09, m, 1H: 2.23, d, J=6.8 Hz, 2H: 2.70–2.93, m, 2H: 3.05, t, J=6.4 Hz, 1H: 3.31, t, J=6.0 Hz, 1H: 3.72, t, J=5.6 Hz, 1H: 4.02–4.08, m, 2H: 4.12, q, J=6.8 Hz, 2H: 4.37, br-d, J=13.2 Hz, 2H: 4.41, s, 1H: 4.79, s, 1H: 7.34, t, J=8.4 Hz, 1H: 7.38, t, J=8.0 Hz, 1H: 7.98, q, J=8.0 Hz, 1H; $^{13}$C(100 MHz: CDCl$_3$: 25° C.) 11.65, 14.34, 23.99, 24.10, 24.23, 30.23, 30.54, 32.11, 32.29, 33.25, 40.95, 45.24, 45.55, 46.65, 51.06, 51.79, 54.42, 55.23, 60.51, 61.06, 61.14, 114.57, 115.85, 115.98, 116.13, 116.26, 117.44, 123.61, 123.70, 123.73, 126.83, 126.95, 132.79, 132.88, 133.03, 158.63, 160.73, 161.12, 161.32, 161.61, 162.71, 162.80, 172.31, 175.11; MS: [M+H]$^+$ calculated: 535.275, found: 535.4; HRMS: C$_{27}$H$_{40}$FN$_4$O$_4$S [M+H]$^+$ calculated: 535.2754, found: 535.2750

EXAMPLE 58

N-(N-(4-(3-thiazolidinoimidoyl)-2-fluorobenzoyl)-ethyl-α,α-dimethyl-β-alanyl)-4-piperidineacetic acid

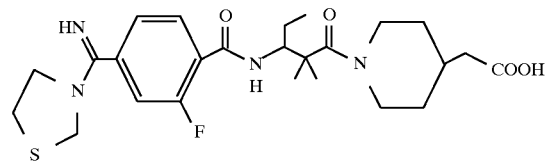

The same procedure as in Example 44 was performed with the compound of Example 57, i.e. ethyl-N-(N-(4-(3-thiazolidinoimidoyl)-2-fluorobenzoyl)-β-ethyl-α,α-dimethyl-β-alanyl)-4-piperidineacetate (150 mg, 0.28 mmol) to yield the titled compound (101 mg, 71%).

NMR: $^1$H(400 MHz: CD$_3$OD: 25° C.) 0.97, t, J=7.6 Hz, 3H: 1.12–1.28, m, 2H: 1.26, s, 3H: 1.34, s, 3H: 1.49–1.62, m, 2H: 1.84, br-t, J=11.2 Hz, 2H: 1.98–2.12, m, 1H: 2.26, d, J=7.6 Hz, 2H: 2.69–3.08, m, 2H: 3.13, t, J=6.4 Hz, 1H: 3.38, t, J=6.4 Hz, 1H: 3.79, t, J=6.0 Hz, 1H: 3.92, t, J=6.0 Hz, 1H: 4.42, dd, J=8.8 Hz, 4.8 Hz, 1H: 4.52, br-d, J=14.8 Hz, 2H: 4.56, s, 1H: 4.71, s, 1H: 7.57, ddd, J=7.6 Hz, 4.0 Hz, 1.6 Hz, 1H: 7.61, ddd, J=9.6 Hz, 4.0 Hz, 1.6 Hz, 1H: 7.85, t, J=7.6 Hz, 1H; $^{13}$C(100 MHz: CD$_3$OD: 25° C.) 12.68, 24.05, 24.65, 25.20, 31.81, 34.02, 35.15, 47.33, 47.77, 52.31, 53.68, 55.98, 57.24, 59.68, 117.14, 117.34, 117.85, 117.98, 118.11, 118.23, 125.82, 125.95, 129.90, 130.07, 133.36, 135.11, 135.21, 135.72, 160.21, 162.71, 162.99, 163.44, 163.73, 167.10, 076.79, 176.98; MS: [M+H]$^+$ calculated: 507.244, found: 507.2; HRMS: C$_{25}$H$_{36}$FN$_4$O$_4$S [M+H]$^+$ calculated: 507.2441, found: 507.2426; HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 20.97 minutes.

EXAMPLE 59

Ethyl-N-(N-(4-(1-hexamethyleneiminoimidoyl)-2-fluorobenzoyl)-β-ethyl-α,α-dimethyl-β-alanyl)-4-piperidineacetate

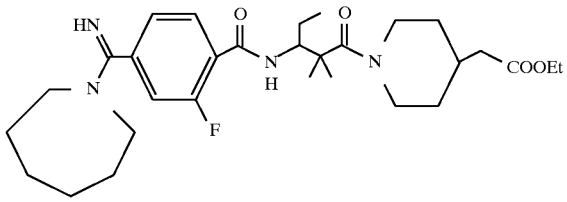

The same procedure as in Example 45 was performed with ethyl-N-(N-(4-cyano-2-fluorobenzoyl)-β-ethyl-α,α-dimethyl-β-alanyl)-4-piperidineacetate (1.48 g, 3.3 mmol) by using hexamethyleneimine (3.7 ml) as an amine to yield the titled compound (469 mg, 26%).

NMR: $^1$H (270 MHz: CDCl$_3$: 25° C.) 0.95, t, J=9.7 Hz, 3H: 1.18, br-q, J=12.4 Hz, 2H: 1.26, t, J=6.8 Hz, 3H: 1.31, s, 3H: 1.36, s, 3H: 1.52–1.87, m, 10H: 1.87–2.16, m, 3H: 2.25, d, J=6.8 Hz, 2H: 2.65–3.00, m, 2H: 3.41, br-t, J=5.4 Hz, 2H: 3.74–3.86, m, 2H: 4.13, q, J=7.3 Hz, 2H: 4.06–4.22, m, 1H: 4.42, br-d, J=13.2 Hz, 2H: 7.20–7.37, m, 2H: 7.98, t, J=7.8 Hz, 1H $^{13}$C(67.5 MHz: CDCl$_3$: 25° C.) 11.51, 14.20, 23.70, 23.84, 23.96, 25.17, 26.33, 27.40, 28.84, 32.00, 32.15, 33.13, 40.83, 45.04, 45.39, 46.56, 50.46, 51.88, 60.28, 60.36, 77.20, 115.61, 116.01, 123.45, 123.50, 125.82, 126.02, 132.56, 133.11, 133.23, 157.82, 160.55, 161.10, 161.54, 162.87, 163.13, 172.22, 174.75; MS: [M+H]$^+$ calculated: 545.350, found: 545.3; HRMS: C$_{30}$H$_{46}$FN$_4$O$_4$ [M+H]$^+$ calculated: 545.3502, found: 545.3512

EXAMPLE 60

N-(N-(4-(1-hexamethyleneiminoimidoyl)-2-fluorobenzoyl)-β-ethyl-α,α-dimethyl-β-alanyl)-4-piperidineacetic acid

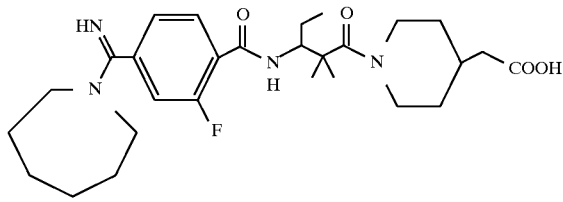

The same procedure as in Example 44 was performed with the compound of Example 59, i.e. ethyl-N-(N-(4-(1-hexamethyleneiminoimidoy 1)-2-fluorobenzoyl)-β-ethyl-α,α-dimethyl-β-alanyl)-4-piperidineacetate (150 mg, 0.28 mmol) to yield the titled compound (103 mg, 72%).

NMR: $^1$H (400 MHz: CD$_3$OD: 25° C.) 0.97, t, J=7.6 Hz, 3H: 1.13–1.28, m, 2H: 1.26, s, 3H: 1.34, s, 3H: 1.48–1.60, m, 2H: 1.60–1.72, m, 4H: 1.72–1.79, m, 2H: 1.85, br-t, J=11.6 Hz, 2H: 1.91–2.01, m, 2H: 2.01–2.13, m, 1H: 2.26, d, J=7.6 Hz, 2H: 2.74–3.09, m, 2H: 3.47, t, J=5.6 Hz, 2H: 3.74, t, J=6.0 Hz, 2H: 4.42, t, J=5.6 Hz, 1H: 4.52, br-d, J=13.2 Hz, 2H: 7.49, dd, J=8.0 Hz, 1.6 Hz, 1H: 7.55, dd, J=10.4 Hz, 1.6 Hz, 1H: 7.84, t, J=6.8 Hz, 1H $^{13}$C(100 MHz: CD$_3$OD: 25° C.) 12.68, 24.03, 24.65, 25.22, 27.14, 28.04, 29.28, 30.38, 34.04, 34.15, 35.15, 42.34, 47.35, 47.70, 52.05, 54.04, 59.62, 117.63, 117.81, 118.07, 125.79, 129.26, 129.41, 133.30, 135.52, 135.61, 165.60, 167.21, 176.81, 176.99; MS: [M+H]$^+$ calculated: 517.319, found: 517.4; HRMS: C$_{28}$H$_{42}$FN$_4$O$_4$ [M+H]$^+$ calculated: 517.3189, found: 517.3177; HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 23.23 minutes.

EXAMPLE 61

Ethyl-N-(N-(4-(N-thiomorpholinoimidoyl)-2-fluorobenzoyl)-β-ethyl-α,α-dimethyl-β-alanyl)-4-piperidineacetate

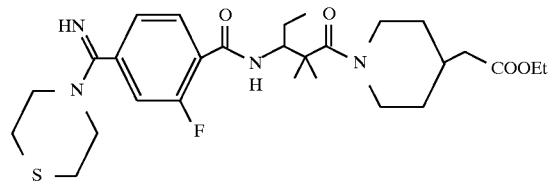

The same procedure as in Example 45 was performed with ethyl-N-(N-(4-cyano-2-fluorobenzoyl)-β-ethyl-α,α-dimethyl-β-alanyl)-4-piperidineacetate (1.48 g, 3.3 mmol) by using thiomorpholine (3.3 ml) as an amine to yield the titled compound (275 mg, 15%).

NMR: $^1$H (270 MHz: CDCl$_3$: 25° C.) 0.94, t, J=7.6 Hz, 3H: 1.18, br-q, J=13.2 Hz, 2H: 1.26, t, J=6.8 Hz, 3H: 1.31, s, 3H: 1.37, s, 3H: 1.55–1.89, m, 4H: 1.95–2.15, m, 1H: 2.25, d, J=6.8 Hz, 2H: 2.58–2.70, m, 2H: 2.72–3.00, m, 4H: 3.60–3.73, m, 2H: 3.85–4.26, m, 3H: 4.13, q, J=6.8 Hz, 2H: 4.40, br-d, J=12.4 Hz, 2H: 7.25–7.39, m, 2H: 8.00, t, J=8.9 Hz, 1H $^{13}$C(67.5 MHz: CDCl$_3$: 25° C.) 11.54, 14.22, 23.84, 24.06, 26.68, 27.97, 31.97, 32.15, 33.12, 40.82, 45.04, 45.39, 46.47, 50.05, 52.83, 60.41, 60.68, 77.20, 114.07, 116.10, 116.50, 118.39, 123.85, 123.89, 126.39, 126.58, 132.34, 132.48, 132.74, 157.92, 160.80, 161.35, 161.64, 162.71, 163.16, 172.24, 174.81; MS: [M+H]$^+$ calculated: 549.291, found: 549.4; HRMS: C$_{28}$H$_{42}$FN$_4$O$_4$S [M+H]$^+$ calculated: 549.2910, found: 549.2931

EXAMPLE 62

N-(N-(4-(N-thiomorpholinoimidoyl)-2-fluorobenzoyl)-β-ethyl-α,α-dimethyl-β-alanyl)-4-piperidineacetic acid

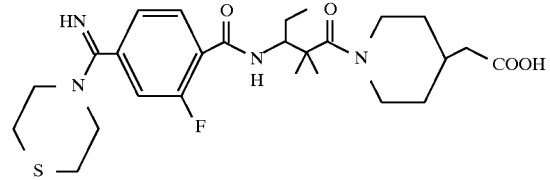

The same procedure as in Example 44 was performed with the compound of Example 61, i.e. ethyl-N-(N-(4-(N- thiomorpholinoimidoyl)-2-fluorobenzoyl)-β-ethyl-α,α-dimethyl-β-alanyl)-4-piperidineacetate (50 mg, 0.091 mmol) to yield the titled compound (40 mg, 84%).

NMR: $^1$H (400 MHz: CD$_3$OD: 25° C.) 0.97, t, J=7.2 Hz, 3H: 1.16–1.27, m, 2H: 1.26, s, 3H: 1.34, s, 3H: 1.53–1.61, m, 2H: 1.85, br-t, J=11.8 Hz, 2H: 2.01–2.13, m, 1H: 2.26, d, J=7.2 Hz, 2H: 2.71–2.74, m, 2H: 2.94–2.96, m, 2H: 2.80–3.02, m, 2H: 3.68–3.71, m, 2H: 4.05–4.08, m, 2H: 4.41, dd, J=4.8 Hz, 8.8 Hz, 2H: 4.52, br-d, J=13.2 Hz, 2H: 7.53, dd, J=1.2 Hz, 7.6 Hz, 1H: 7.59, dd, J=1.6 Hz, 10.4 Hz, 1H: 7.85, t, J=7.2 Hz, 1H $^{13}$C(100 MHz: CD$_3$OD: 25° C.) 12.68, 24.05, 24.65, 25.22, 28.00, 29.28, 34.02, 24.13, 35.15, 42.32, 47.37, 47.70, 51.74, 55.09, 59.71, 118.23, 118.49, 126.71, 129.70, 129.85, 133.45, 134.84, 134.93, 160.35, 162.86, 165.49, 167.08, 176.79, 176.99; MS: [M+H]$^+$ calculated: 521.260, found: 521.3; HRMS: C$_{26}$H$_{38}$FN$_4$O$_4$S [M+H]$^+$ calculated: 521.2597, found: 521.2598; HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 21.49 minutes.

EXAMPLE 63

Ethyl-N-(N-(4-(4-methyl-1-piperazinoimidoyl)-2-fluorobenzoyl)-β-ethyl-α,α-dimethyl-β-alanyl)-4-piperidineacetate

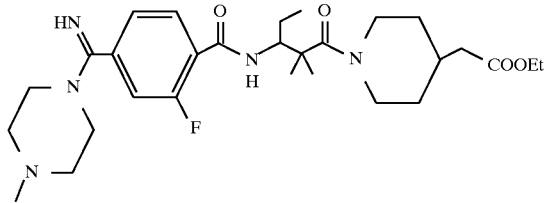

The same procedure as in Example 45 was performed with ethyl-N-(N-(4-cyano-2-fluorobenzoyl)-βethyl-α,α-dimethyl-β-alanyl)-4-piperidineacetate (1.48 g, 3.3 mmol) by using 1-methylpiperazine (3.7 ml) as an amine to yield the titled compound (514 mg, 28%).

NMR: $^1$H (270 MHz: CDCl$_3$: 25° C.) 0.90, t, J=7.3 Hz, 3H: 1.03–1.40, m, 2H: 1.25, t, J=7.3 Hz, 3H: 1.28, s, 3H: 1.32, s, 3H: 1.48–1.92, m, 4H: 2.03, br-s, 1H: 2.23, d, J=6.5 Hz, 2H: 2.65–3.00, m, 2H: 2.88, s, 3H: 3.42, br-s, 2H: 3.61, br-s, 2H: 3.78, br-s, 2H: 3.95–4.17, m, 1H: 4.11, q, J=6.8 Hz, 2H: 4.19–4.50, m, 4H: 7.44, m, 2H: 7.86, m, 1H $^{13}$C (67.5 MHz: CDCl$_3$: 25° C.) 11.42, 14.15, 23.75, 23.92, 31.86, 32.02, 33.03, 40.76, 42.87, 43.83, 45.00, 45.48, 46.39, 46.82, 51.28, 51.87, 60.42, 60.70, 77.20, 113.90, 116.65, 117.03, 118.18, 124.38, 126.83, 127.03, 131.38, 131.50, 132.22, 157.66, 160.44, 160.98, 161.39, 161.51, 162.05, 162.98, 164.10, 172.27, 174.88; MS: [M+H]$^+$ calculated: 546.346, found: 546.4; HRMS: C$_{29}$H$_{45}$FN$_5$O$_4$ [M+H]$^+$ calculated: 546.3455, found: 546.3443

EXAMPLE 64

N-(N-(4-(4-methyl-1-piperazinoimidoyl)-2-fluorobenzoyl)-β-ethyl-α,α-dimethyl-β-alanyl)-4-piperidineacetic acid

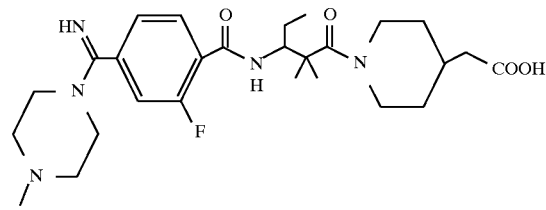

The same procedure as in Example 44 was performed with the compound of Example 63, i.e. ethyl-N-(N-(4-(4-methyl-1-piperazinoimidoyl)-2-fluorobenzoyl)-β-ethyl-α,α-dimethyl-β-alanyl)-4-piperidineacetate (60 mg, 0.11 mmol) to yield the titled compound (43 mg, 7%).

NMR: $^1$H (400 MHz: CD$_3$OD: 25° C.) 0.97, t, J=7.6 Hz, 3H: 1.14–1.27, m, 2H: 1.26, s, 3H: 1.34, s, 3H: 1.50–1.63, m, 2H: 1.84, br-t, J=10.0 Hz, 2H: 2.01–2.13, m, 1H: 2.25, d, J=6.8 Hz, 2H: 2.78–3.02, m, 2H: 2.93, s, 3H: 3.36, br-s, 2H: 3.54, br-s, 2H: 3.74, br-s, 2H: 4.09, br-s, 2H: 4.40, dd, J=4.4 Hz, 10.0 Hz, 1H: 4.51, br-d, J=13.6 Hz, 2H: 7.56, dd, J=1.2 Hz, 7.6 Hz, 1H: 7.61, dd, J=1.2 Hz, 10.0 Hz, 1H: 7.88, t, J=7.2 Hz, 1H $^{13}$C(100 MHz: CD$_3$OD: 25° C.) 12.68, 24.12, 24.67, 25.18, 34.02, 34.11, 35.13, 42.32, 44.59, 45.87, 47.73, 53.53, 54.39, 59.87, 118.58, 118.86, 126.56, 130.34, 133.60, 133.94, 162.84, 163.79, 166.61, 166.90, 176.79, 176.99, 186.89; MS: [M+H]$^+$ calculated: 518.314, found: 518.4; HRMS: C$_{27}$H$_{41}$FN$_5$O$_4$ [M+H]$^+$ calculated: 518.3142, found: 518.3125; HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 16.69 minutes.

EXAMPLE 65

Ethyl-N-(N-(4-(4-phenyl-1-piperazinoimidoyl)-2-fluorobenzoyl)-β-ethyl-α,α-dimethyl-β-alanyl)-4-piperidineacetate

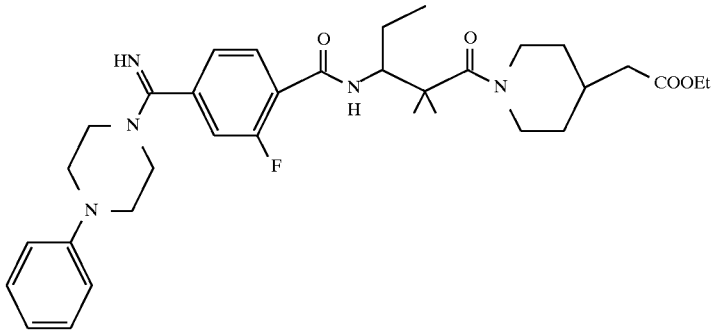

The same procedure as in Example 45 was performed with ethyl-N-(N-(4-cyano-2-fluorobenzoyl)-β-ethyl-α,α-dimethyl-β-alanyl)-4-piperidineacetate (1.48 g, 3.3 mmol) by using 1-phenylpiperazine (5.0 g) as an amine to yield the titled compound (237 mg, 12%).

NMR: $^1$H (270 MHz: CDCl$_3$: 25° C.) 0.94, t, J=7.3 Hz, 3H: 1.09–1.22, m, 2H: 1.26, t, J=7.0 Hz, 3H: 1.31, s, 3H: 1.36, s, 3H: 1.57–1.22, m, 2H: 1.79, br-d, J=11.3 Hz, 2H: 1.95–2.12, m, 1H: 2.24, d, J=7.0 Hz, 2H: 2.71–2.91, m, 2H: 3.21, br-s, 2H: 3.43, br-s, 2H: 3.57, br-s, 2H: 4.04–4.20, m, 3H: 4.13, q, J=7.1 Hz, 2H: 4.40, br-d, J=13.5 Hz, 2H: 6.90–6.98, m, 3H: 7.26–6.99, m, 4H: 8.00, t, J=7.3 Hz, 1H $^{13}$C(67.5 MHz: CDCl$_3$: 25° C.) 11.60, 14.30, 23.83, 24.00, 24.13, 31.99, 32.21, 33.14, 40.87, 45.29, 45.62, 46.56, 46.91, 49.00, 49.81, 50.02, 60.57, 61.19, 116.42, 116.80, 117.41, 122.54, 124.24, 126.62, 126.82, 129.66, 132.12, 132.25, 132.84, 148.84, 157.99, 160.42, 160.97, 161.72, 162.94, 163.11, 172.37, 175.17; MS: [M+H]$^+$ calculated: 608.361, found: 608.4

EXAMPLE 66

N-(N-(4-(4-phenyl-1-piperazinoimidoyl)-2-fluorobenzoyl)-β-ethyl-α,α-dimethyl-β-alanyl)-4-piperidineacetic acid The same procedure as in Example 44 was performed with the compound of Example 65, i.e. ethyl-N-(N-(4-(4-phenyl-1-piperazinoimidoyl)-2-fluorobenzoyl)-β-ethyl-α,α-dimethyl-β-alanyl)-4-piperidineacetate (50 mg, 0.082 mmol) to yield the titled compound (41 mg, 86%).

NMR: $^1$H (400 MHz: CD$_3$OD: 25° C.) 0.98, t, J=6.8 Hz, 3H: 1.14–1.31, m, 2H: 1.27, s, 3H: 1.35, s, 3H: 1.52–1.64, m, 2H: 1.79–1.92, m, 2H: 2.06, br-s, 1H: 2.26, d, J=6.4 Hz, 2H: 2.60–3.10, m, 2H: 3.48, br-s, 2H: 3.62, br-s, 2H: 3.96, br-s, 2H: 4.37–4.46, m, 1H: 4.52, br-d, J=12.8 Hz, 2H: 6.89, t, J=7.2 Hz, 1H: 6.99, d, J=7.6 Hz, 2H: 7.27, t, J=7.6 Hz, 2H: 7.56, d, J=7.6 Hz, 1H: 7.62, d, J=9.6 Hz, 1H: 7.87, t, J=7.6 Hz, 1H $^{13}$C(100 MHz: CD$_3$OD: 25° C.) 12.68, 24.18, 24.73, 25.28, 34.05, 34.13, 35.15, 42.34, 47.33, 47.73, 51.89, 60.02, 111.32, 118.49, 118.62, 118.75, 122.79, 126.46, 129.76, 131.09, 133.47, 134.73, 134.82, 152.38, 157.85, 160.39, 162.89, 165.42, 166.97, 176.77, 177.07; MS: [M+H]$^+$ calculated: 580.330, found: 580.3; HRMS: $C_{32}H_{43}FN_5O_4$ [M+H]$^+$ calculated: 580.3298, found: 580.3310; HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 26.52 minutes.

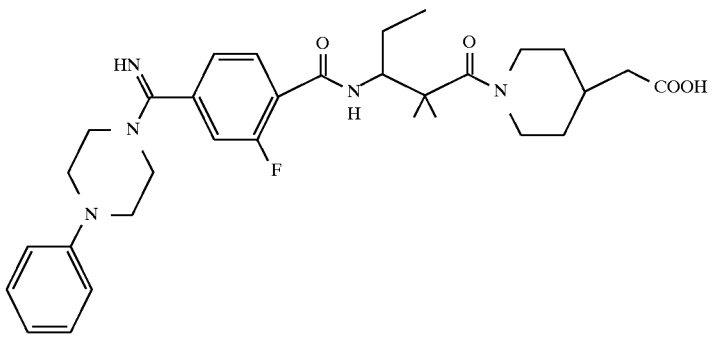

EXAMPLE 67

Ethyl-N-(N-(4-(4-(4-fluorophenyl)-1-piperazinoimidoyl)-2-fluorobenzoyl)-β-ethyl-α,α-dimethyl-β-alanyl)-4-piperidineacetate

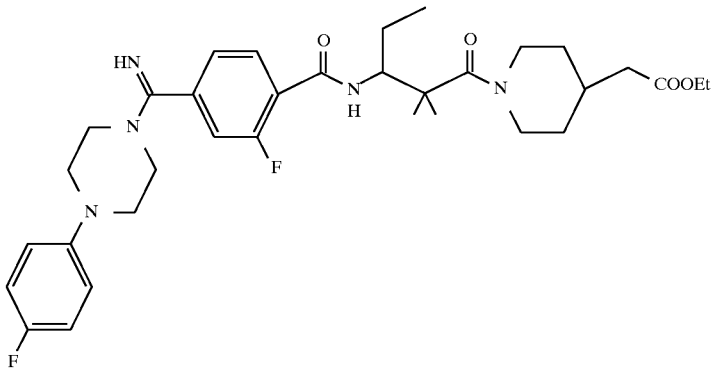

The same procedure as in Example 45 was performed with ethyl-N-(N-(4-cyano-2-fluorobenzoyl)-β-ethyl-α,α-dimethyl-β-alanyl)-4-piperidineacetate (1.48 g, 3.3 mmol) by using 1-(4-fluorophenyl) piperazine (5.9 g) as an amine to yield the titled compound (396 mg, 19%).

NMR: $^1$H (400 MHz: CDCl$_3$: 25° C.) 0.92, t, J=7.2 Hz, 3H: 1.16, br-q, J=12.0 Hz, 2H: 1.24, t, J=7.0 Hz, 3H: 1.30, s, 3H: 1.35, s, 3H: 1.60–1.72, m, 2H: 1.78, br-d, 11.6 Hz, 2H: 1.97–2.08, m, 1H: 2.23, d, J=6.8 Hz, 2H: 2.82, br-s, 2H: 3.15, m, 2H: 3.37, m, 2H: 3.59, m, 2H: 4.02–4.14, m, 3H: 4.11, q, J=7.2 Hz, 2H: 4.35, br-d, J=12.4 Hz, 2H: 6.92, dd, J=4.4 Hz, 9.6 Hz, 2H: 6.99, t, J=8.4 Hz, 2H: 7.33, dd, J=10.8 Hz, 14.0 Hz, 2H: 7.96, t, J=7.2 Hz, 1H $^{13}$C(67.5 MHz: CDCl$_3$: 25° C.) 11.60, 14.28, 23.83, 24.00, 24.14, 31.99, 32.21, 33.14, 40.86, 45.20, 45.56, 46.53, 46.98, 49.81, 49.96, 50.80, 60.57, 61.19, 115.99, 116.32, 116.42, 116.81, 119.36, 119.49, 124.25, 126.59, 126.79, 132.14, 132.26, 132.80, 145.74, 145.77, 156.79, 157.96, 160.35, 160.97, 161.69, 162.94, 163.11, 172.36, 175.14; MS: [M+H]$^+$ calculated: 626.352, found: 626.4

EXAMPLE 68

N-(N-(4-(4-(4-fluorophenyl)-1-piperazinoimidoyl)-2-fluorobenzoyl)-β-ethyl-α,α-dimethyl-β-alanyl)-4-piperidineacetic acid

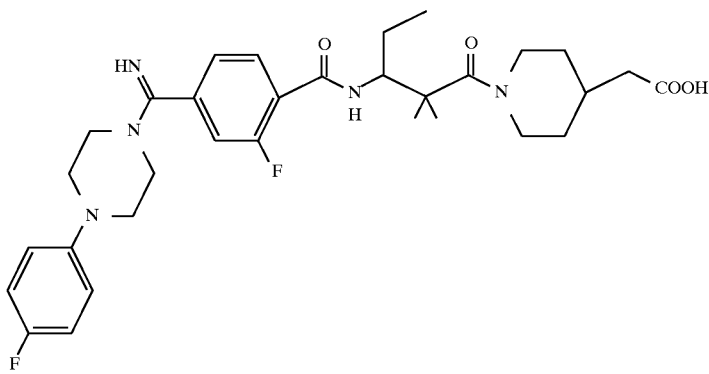

The same procedure as in Example 44 was performed with the compound of Example 67, i.e. ethyl-N-(N-(4-(4-(4-fluorophenyl)-1-piperazinoimidoyl)-2-fluorobenzoyl)-β-ethyl-α,α-dimethyl-β-alanyl)-4-piperidineacetate (80 mg, 0.13 mmol) to yield the titled compound (55 mg, 72%).

NMR: $^1$H (400 MHz: CD$_3$OD: 25° C.) 0.98, t, J=7.6 Hz, 3H: 1.15–1.28, m, 2H: 1.26, s, 3H: 1.35, s, 3H: 1.51–1.62, m, 2H: 1.84, br-t, J=11.2 Hz, 2H: 1.98–2.15, m, 1H: 2.25, d, J=7.2 Hz, 2H: 2.75–3.07, m, 2H: 3.20, t, J=4.8 Hz, 2H: 3.40, t, J=4.8 Hz, 2H: 3.61, t, J=4.4 Hz, 2H: 3.95, t, J=4.8 Hz, 2H: 4.41, dd, J=5.2 Hz, 9.6 Hz, 1H: 4.52, br-d, J=13.2 Hz, 2H: 7.01, d, J=6.8 Hz, 4H: 7.56, dd, J=1.2 Hz, 7.6 Hz, 1H: 7.61, d, J=10.4 Hz, 1H: 7.87, t, J=6.8 Hz, 1H $^{13}$C(100 MHz: CD$_3$OD: 25° C.) 12.68, 24.09, 24.67, 25.20, 34.04, 34.13, 35.15, 42.32, 47.31, 47.73, 50.86, 51.89, 51.96, 59.77, 117.27, 117.48, 118.49, 118.75, 120.67, 120.76, 126.46, 129.77, 129.92, 133.41, 134.71, 134.80, 149.14, 165.40, 167.06, 176.79, 176.98; MS: [M+H]$^+$ calculated: 598.320, found: 598.1, HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 27.32 minutes.

EXAMPLE 69

Benzyl-N-(N-(4-(4-morpholinoimidoyl)benzoyl-β-phenyl-α,α-dimethyl-β-alanyl)-4-piperidineacetate

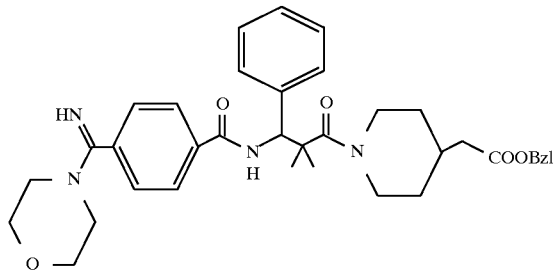

The same procedure as in Example 43 was performed with N-(N-β-ethyl-α,α-dimethyl-β-alanyl)-4-piperidineacetic acid benzyl ester (0.5 g, 0.98 mmol) obtained by a condensation reaction of N-Boc-β-ethyl-α,α-dimethyl-β-alanine with 4-piperidineacetic acid benzyl ester to thereby yield the titled compound (270 mg, 44%).

NMR: $^1$H (270 MHz: CDCl$_3$: 25° C.) 0.73–1.38, m, 2H: 1.30, s, 3H: 1.45, s, 3H: 1.63–1.82, m, 2H: 1.92–2.12, m, 1H: 2.25, d, J=7.6 Hz, 2H: 2.32–2.88, m, 2H: 3.28–3.42, m, 2H: 3.58–3.73, m, 2H: 3.81–4.05, m, 4H: 4.16–4.45, m, 2H: 5.05–5.16, m, 1H: 5.10, s, 2H: 7.20–7.49, m, 12H: 7.79–7.91, m, 2H: $^{13}$C(67.5 MHz: CDCl$_3$: 25° C.) 24.93, 26.21, 29.68, 31.74, 32.04, 32.09, 32.95, 32.99, 40.62, 45.42, 45.65, 46.93, 47.42, 50.14, 62.84, 65.74, 66.30, 77.20, 127.10, 127.67, 128.22, 128.31, 128.57, 128.95, 129.76, 130.83, 135.77, 135.93, 138.49, 139.19, 161.57, 164.42, 164.83, 171.93, 175.42; MS: [M+H]$^+$ calculated: 625.338, found: 625.4

EXAMPLE 70

N-(N-(4-(4-morpholinoimidoyl)benzoyl-β-phenyl-α,α-dimethyl-β-alanyl)-4-piperidineacetic acid

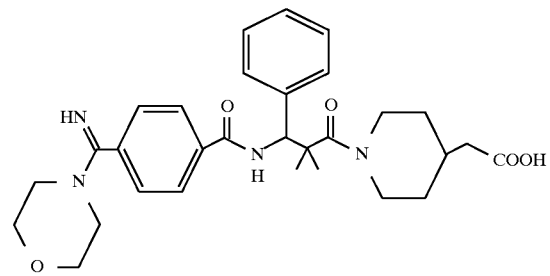

The compound of Example 69, i.e. benzyl-N-(N-(4-(4-morpholinoimidoyl)benzoyl-β-phenyl-α,α-dimethyl-β-alanyl)-4-piperidineacetate (54 mg, 0.086 mmol) was dissolved in a 80% aqueous methanol solution (10 ml) containing 2% acetic acid. To the resulting solution was added 5% palladium carbon (10 mg) and the mixture was stirred overnight under a hydrogen atmosphere. After the solvent was distilled off, the residue was dissolved in a 1N aqueous solution of acetic acid and purified by HPLC in the same manner as in Example 44 to yield the titled compound (32 mg, 69%).

NMR: $^1$H (400 MHz: CD$_3$OD: 25° C.) 1.07, dq, J=1.4 Hz, 9.2 Hz, 1H: 1.22, dq, J=1.3 Hz, 9.2 Hz, 1H: 1.30, s, 3H: 1.35, s, 3H: 1.74–1.85, m, 2H: 1.93–2.08, m, 1H: 2.13–2.24, m, 2H: 2.80–2.97, m, 2H: 3.44, t, J=4.4 Hz, 2H: 3.73, t, J=4.8 Hz, 2H: 3.80, t, J=3.6 Hz, 2H: 3.92, dd, J=3.6 Hz, 5.6 Hz, 2H: 4.50, br-t, J=9.2 Hz, 2H: 5.57, s, 1H: 7.26–7.35, m, 4H: 7.43, br-d, J=8.8 Hz, 1H: 7.72, d, J=8.0 Hz, 2H: 7.98, dt, J=8.4 Hz, 2.0 Hz, 2H $^{13}$C(100 MHz: CD$_3$OD: 25° C.) 25.29, 25.99, 33.89, 33.94, 35.02, 42.28, 47.61, 47.75, 47.92, 48.67, 52.18, 61.98, 67.10, 68.11, 129.57, 129.96, 130.36, 130.35, 133.65, 140.56, 140.66, 144.75, 163.30, 164.47, 166.92, 169.00, 176.79, 176.92; MS: [M+H]$^+$ calculated: 535.292, found: 535.3; HRMS: C$_{30}$H$_{39}$N$_4$O$_5$ [M+H]$^+$ calculated: 535.2920, found: 535.2935; HPLC analysis A spectrum of analytical HPLC using Wakosil-II5C18HG (φ 4.6×250 mm) column at a flow rate of 1.0 ml/min at room temperature by elution in a gradient of 10–55% acetonitrile (30 min) in 0.1% TFA had a single peak at a retention time of 23.61 minutes.

EXAMPLE 71

Methyl-N-(N-(4-(1-pyrrolidinoimidoyl)-2-fluorobenzoyl)-β-ethyl-α,α-dimethyl-β-alanyl)-4-piperidineacetate

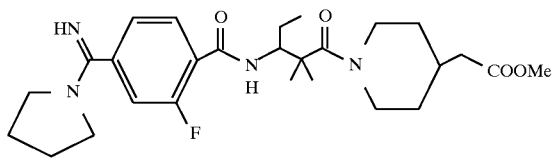

N-Boc-β-ethyl-α,α-dimethyl-β-alanine was condensed with 4-piperidineacetic acid methyl ester in the same manner as in Example 43 to yield N-(N-β-ethyl-α,α-dimethyl-β-alanyl)-4-piperidineacetic acid methyl ester. From the resulting compound, methyl-N-(N-(4-cyano-2-fluorobenzoyl)-β-ethyl-α,α-dimethyl-β-alanyl)-4-piperidineacetate was derived in the same manner as in Example 45. The same procedure as in Example 45 was performed with this compound (1.0 g, 2.3 mmol) by using pyrrolidine (1.9 ml) as an amine to yield the titled compound (248 mg, 21%).

NMR: $^1$H (400 MHz: CDCl$_3$: 25° C.) 0.92, t, J=7.4 Hz, 3H: 1.15, q, J=12.6 Hz, 2H: 1.29, s, 3H: 1.34, s, 3H: 1.61–1.69, m, 2H: 1.77, br-d, J=12 Hz, 2H: 1.96, br-t, J=6.6 Hz, 2H: 1.98–2.07, m, 1H: 2.13, br-t, J=6.4 Hz, 2H: 2.24, d, J=7.2 Hz, 2H: 2.81, br-s, 2H: 3.41, t, J=6.6 Hz, 2H: 3.65, s, 3H: 3.73, m, 2H: 4.08, br-t, J=8.8 Hz, 1H: 4.38, br-d, J=12.8 Hz, 2H: 7.31, br-d, J=10.8 Hz, 1H: 7.36, br-d, J=8.0 Hz, 1H: 7.98, t, J=7.6 Hz, 1H $^{13}$C(100 MHz: CDCl$_3$: 25° C.) 11.65, 23.96, 24.05, 24.16, 24.96, 25.60, 32.11, 32.29, 33.23, 40.67, 45.19, 45.50, 46.67, 49.28, 51.59, 52.27, 60.81, 115.87, 115.87, 116.13, 123.66, 123.70, 126.26, 126.39, 132.77, 133.35, 133.45, 158.59, 161.10, 162.85, 172.73, 175.00; MS: [M+H]$^+$ calculated: 503.303, found: 503.4

EXAMPLE 72

N-(N-4-amidino-2-fluorobenzoyl-β-ethyl-α,α-dimethy-β-alanyl)-4-piperidineacetic acid ethyl ester

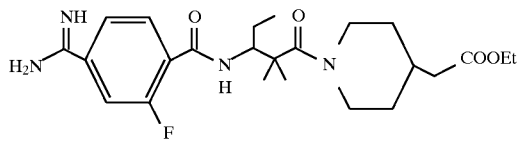

The same procedure as in Example 45 was performed with ethyl-N-(N-(4-cyano-2-fluorobenzoyl)-β-ethyl-α,α-dimethyl-β-alanyl)-4-piperidineacetate (0.42 mg, 0.94 mmol) by using ammonium acetate (500 mg) as an amine to yield the titled compound (200 mg, 48%).

MS: [M+H]$^+$ calculated: 463.272, found: 463.4

Comparative Example 1

Synthesis of N-(N-4-amidinobenzoyl-β-alanyl)-4-piperidineacetic acid

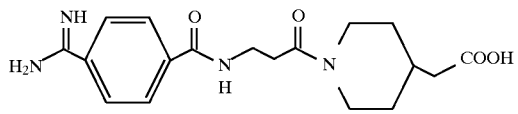

(1) Synthesis of the titled compound by a solid phase method
The same procedure as in Example 2-(5) was performed with Fmoc-β-alanine to yield a powder of N-(N-4-amidinobenzoyl-β-alanyl)-4-piperidineacetic acid (56.0 mg).

NMR: $^1$H (400 MHz: CD$_3$OD: 25° C.) 1.12, dq, J=4.4 Hz, 12.8 Hz, 1H: 1.20, dq, J=4.0 Hz, 12.4 Hz, 1H: 1.80, br-t, J=16.0 Hz, 2H: 1.94–2.05, m, 1H: 2.21, d, J=6.8 Hz, 2H: 2.65, dt, J=2.4 Hz, 12.4 Hz, 1H: 2.68–2.80, m, 2H: 3.10, dt, J=2.8 Hz, 13.2 Hz, 1H: 3.66, t, J=14.0 Hz, 2H: 3.97, br-d, J=13.6 Hz, 1H: 4.51, br-d, J=13.6 Hz, 1H: 7.88, dt, J=2.0 Hz, 8.4 Hz, 2H: 8.00, dt, J=2.0 Hz, 8.4 Hz, 2H $^{13}$C(100 MHz: CD$_3$OD: 25° C.) 33.45, 34.20, 34.33, 35.01, 38.44, 42.47, 43.80, 47.73, 129.92, 130.07, 133.16, 141.39, 168.80, 169.15, 172.29, 177.01; MS: [M+Na]$^+$ calculated: 36.19, found: 361.6

A spectrum of analytical HPLC using CrestPak C18T-5 (φ 4.6×250 mm) column at a flow rate of 1.0 ml/min by elution in a gradient of 0–40% acetonitrile (40 min) in 0.1% TFA had a single peak at a retention time of 19.60 minutes.

Comparative Example 2

Synthesis of N-(N-4-amidinobenzoyl-β-methyl-β-alanyl)-4-piperidineacetic acid

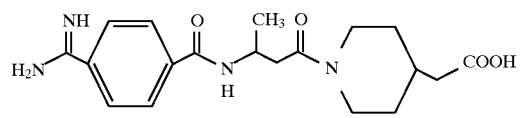

(1) N-Fmoc-DL-2-Amino-n-butyric acid
2-Amino-butyric acid (5 g) was protected with Fmoc by the same procedure as in Example 2-(3) to yield a crystal of N-Fmoc-DL-2-amino-n-butyric acid (12.1 g, 76.7%).

NMR: $^1$H (270 MHz: CDCl$_3$: 45° C.) 1.24, m, 3H: 2.53, br-s, 2H: 4.11, m, 1H: 4.20, t, 1H (J=6.8 Hz): 4.41, d, 2H (J=6.8 Hz): 7.29, t, 2H (J=7.3 Hz): 7.36, t, 2H (J=7.3 Hz): 7.57, d, 2H (J=7.3 Hz): 7.73, d, 2H (J=7.3 Hz): $^{13}$C (67.5 MHz: CDCl$_3$) 20.4, 40.3, 44.0, 47.4, 66.9, 120.0, 125.0, 127.1, 127.8, 141.4, 144.0; MS: [M+Na]$^+$ calculated: 348.13, found: 348.2

(2) Synthesis of the titled compound by a solid phase method
The same procedure as in Example 2-(5) was performed with N-Fmoc-DL-2-amino-n-butyric acid to yield a powder of N-(N-4-amidinobenzoyl-β-methyl-β-alanyl)-4-piperidineacetic acid (38.0 mg).

NMR: $^1$H (400 MHz: CD$_3$OD: 27° C.) 1.03–1.28, m, 2H: 1.32, m, 3H: 1.72–1.89, m, 2H: 1.98, br-s, 1H: 2.23, br-s, 2H: 2.62, br-s, 2H: 2.78, br-s, 1H: 3.14, br-s, 1H: 4.03–4.08, m, 1H: 4.49, br-s, 2H: 7.88, 8.00, br-sX 2, 2H X 2; MS: [M+H]$^+$ calculated: 375.203, found: 375

A spectrum of analytical HPLC using CrestPak C18T-5 (φ 4.6×250 mm) column at a flow rate of 1.0 ml/min by elution in a gradient of 10–40% acetonitrile (30 min) in 0.1% TFA had a single peak at a retention time of 12.07 minutes.

Comparative Example 3

Synthesis of N-(N-4-amidinobenzoyl-β-phenyl-β-alanyl)-4-piperidineacetic acid

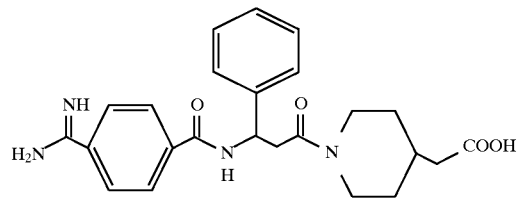

(1) N-Fmoc-DL-β-Phenyl-β-alanine
DL-3-Amino-3-phenyl-propionic acid (2 g) was protected with Fmoc by the same procedure as in Example 2-(3) to yield a crystal of N-Fmoc-DL-β-phenyl-β-alanine (3.2 g, 68.2%).

NMR: ¹H (270 MHz: CDCl₃: 45° C.) 2.81, m, 2H: 4.19, t, 1H (J=7.3 Hz): 4.34, d, 2H (J=7.3 Hz): 5.13, dd, 1H (J=6.8, 14.7 Hz): 7.14–7.56, m, 9H: 7.56, br-s, 2H: 7.74, d, 2H (J=7.3 Hz); MS: [M+Na]⁺ calculated: 410.147, found: 410.1

(2) Synthesis of the titled compound by a solid phase method

The same procedure as in Example 2-(5) was performed with N-Fmoc-DL-β-phenyl-β-alanine to yield a powder of N-(N-4-amidinobenzoyl-β-phenyl-β-alanyl)-4-piperidineacetic acid (19.1 mg).

NMR: ¹H (270 MHz: CD₃OD: 27° C.) 0.81–1.08, m, 2H: 1.70, br-d, J=12, 2H: 1.85–2.05, m, 1H: 2.12–2.17, m, 2H: 2.57, br-t, J=12 Hz, 1H: 2.91–3.18, m, 3.91, br-d, J=13 Hz, 1H: 4.46, br-d, J=13 Hz, 1H: 5.54–5.59, m, 1H: 7.24–7.43, m, 5H: 7.86–7.90, m, 2H: 8.00–8.05, m, 2H; MS: [M+H]⁺ calculated: 437.219, found: 437

A spectrum of analytical HPLC using CrestPak C18T-5 (φ 4.6×250 mm) column at a flow rate of 1.0 ml/min by elution in a gradient of 10–40% acetonitrile (30 min) in 0.1% TFA had a single peak at a retention time of 22.47 minutes.

Comparative Example 4

Synthesis of N-(N-4-amidinobenzoyl-α-ethyl-β-alanyl)-4-piperidineacetic acid

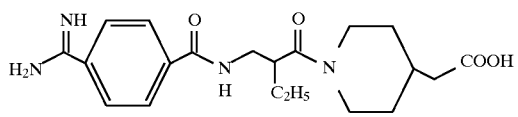

(1) N-t-Butyloxycarbonyl(Boc)-α-ethyl-β-alanine t-butyl ester t-Butyloxycarbonyl-β-alanine t-butyl ester (2.26 g) was added dropwise to a solution of lithium diisopropylamide (LDA) (6.9 ml, 13.8 mmol) in tetrahydrofuran (10 ml) at −78° C. and hexamethylphosphoroamide (HMPA) (2 ml) was added thereto. The temperature of the reaction solution was elevated gradually to −20° C. over 1 hour and lowered again to −78° C. To the reaction solution, ethyl bromide (0.76 ml) was added dropwise. The temperature of the solution was elevated to 0° C. over 2 hours and the reaction was stopped by adding a saturated aqueous solution of ammonium chloride. After the solvent was distilled off, the residue was dissolved in ethyl acetate and washed sequentially with a 5% aqueous solution of sodium hydrogencarbonate, a 5% aqueous solution of citric acid and a saturated aqueous solution of NaCl 3 times each. The ethyl acetate layer was dried over anhydrous sodium sulfate and the solvent was then distilled off to yield an oil. The obtained oil was applied to a silica gel column (2.5×40 cm) and eluted with a mixed solution (hexane:ethyl acetate=40:1). The desired fractions were collected and the solvents were distilled off to yield an oil of N-t-butyloxycarbonyl-α-ethyl-β-alanine-t-butyl ester (0.98 g, 38.9%).

NMR: ¹H (270 MHz: CDCl₃: 27° C.) 0.94, t, 3H (J=7.4 Hz): 1.44, br-s, 9H: 1.46, s, 9H: 1.46–1.67, m, 2H: 2.37–2.47, m, 1H, 3.16–3.36, m, 2H: 4.84, br-s, 1H; MS: [M+Na]⁺ calculated: 296.194, found: 296.1

(2) N-Fmoc-α-ethyl-β-alanine

Anisole (0.5 ml) and trifluoroacetic acid (10 ml) were added to N-t-butyloxycarbonyl-α-ethyl-β-alanine-t-butyl ester (0.98 g) and the mixture was stirred at room temperature for 12 hours. After trifluoroacetic acid was distilled off, the residue was dissolved in water (5 ml) and neutralized with a 10% aqueous solution of sodium carbonate. The product was protected with Fmoc by the same procedure as in Example 2-(3). A crystal of N-Fmoc-α-ethyl-β-alanine (437 mg, 36%) was obtained upon recrystallization from hexane.

NMR: ¹H (270 MHz: CDCl₃: 45° C.) 0.98, t, 3H (J=7.3 Hz): 1.44–1.81, m, 2H: 2.32–2.58, m, 1H: 3.19–3.50, m, 2H: 4.21, t, 1H (J=6.8 Hz): 4.36, d, 2H (J=6.8 Hz): 5.53, br-s, 1H: 7.31, t, 2H (J=7.3 Hz): 7.38, t, 2H (J=7.3 Hz): 7.9, d, 2H (J=7.3 Hz): 7.75, d, 2H (J=7.3 Hz): ¹³C(67.5 MHz: CDCl₃) 11.3, 22.5, 41.5, 46.6, 47.1, 66.4, 119.6, 124.9, 126.8, 127.4, 141.0, 143.8, 156.2, 176.4; MS: [M+Na]⁺ calculated: 362.145, found: 362.1

(3) Synthesis of the titled compound by a solid phase method

The same procedure as in Example 2-(5) was performed with N-Fmoc-α-ethyl-β-alanine to yield a powder of N-(N-4-amidinobenzoyl-α-ethyl-β-alanyl)-4-piperidineacetic acid (33.2 mg).

NMR: ¹H (400 MHz: CD₃OD: 27° C.) 0.92, m, 4H: 1.13, m, 1H: 1.57–1.81, m, 5H: 1.97, s, 2H: 2.24, br-s, 1H: 3.09, m, 1H: 3.23, m, 1H: 3.50, m, 2H: 4.12, br-s, 1H: 4.56, br-s, 1H: 7.88–8.02, m, 4H; MS: [M+H]⁺ calculated: 389.219, found: 389.3

A spectrum of analytical HPLC using CrestPak C18T-5 (φ 4.6×250 mm) column at a flow rate of 1.0 ml/min by elution in a gradient of 10–40% acetonitrile (30 min) in 0.1% TFA had a single peak at a retention time of 15.75 minutes.

Comparative Example 5

Synthesis of N-(N-4-amidinobenzoyl-β-phenyl-α-ethyl-β-alanyl)-4-piperidineacetic acid

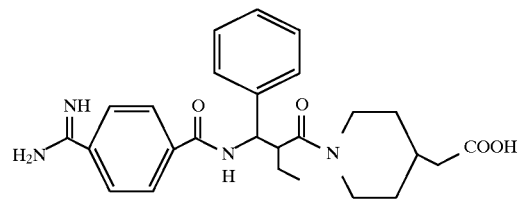

(1) 4-Phenyl-3-ethyl-2-azetidinone

The same procedure as in Example 2-(2) was performed with ethyl n-butyrate (6.6 ml, 50 mmol) and benzaldehyde (5.0 ml, 50 mmol) to yield 4-phenyl-3-ethyl-2-azetidinone (1.56 g, 18.9%).

NMR: ¹H (270 MHz: CDCl₃: 27° C.) 0.77, dd, 3H (J=6.9, 6.9 Hz): 1.13, ddq, 1H (J=6.3, 6.3, 13.0 Hz): 1.41, ddq, 1H (J=6.3, 6.3, 13.0 Hz): 3.32–3.43, m, 1: 4.88, d, 1H (J=5.5 Hz): 6.28, br-s, 1H: 7.25–7.43, m, 5H (2) N-Fmoc-β-Phenyl-α-ethyl-β-alanine 6N HCl (100 ml) was added to 4-phenyl-3-ethyl-2-azetidinone (1.56 g, 9.45 mmol) and the mixture was stirred at room temperature for 24 hours. The reaction mixture was washed with chloroform. The solvent was distilled off and dried. The residue was protected with Fmoc by the same procedure as in Example 2-(3) to yield an oil. The oil was applied to a silica gel column (φ 2.5×40 cm) and eluted with a mixed solution (chloroform:methanol=50:1). The desired fractions were collected and the solvents were distilled off to yield N-Fmoc-β-phenyl-α-ethyl-β-alanine (1.69 g, 44.2%).

NMR: ¹H (270 MHz: CDCl₃: 27° C.) 0.82–1.01, m, 3H: 1.57–1.82, m, 2H: 4.13–4.22, m, 1H: 4.26–4.47, m, 2H:

4.75–4.92, m, 2H: 7.01–7.44, m, 9H: 7.45–7.67, m, 2H: 7.73–7.84, m, 2H; MS: [M+Na]⁺ calculated: 438.186, found: 438.2

(3) Synthesis of the titled compound by a solid phase method

The same procedure as in Example 2-(5) was performed with N-Fmoc-β-phenyl-α-ethyl-β-alanine to yield a powder of N-(N-4-amidinobenzoyl-β-phenyl-α-ethyl-β-alanyl)-4-piperidineacetic acid (25.8 mg).

NMR: ¹H (270 MHz: CD₃OD: 27° C.) –0.02, br-ddd, J=3.4 Hz, 15 Hz, 22 Hz, 0.8H: 0.45, br-ddd, J=3.4 Hz, 15 Hz, 23 Hz, 0.8H: 0.84–0.93, m, 4H: 1.07, m, 0.4H: 1.41–1.98, m, 6H: 2.17–2.50, m, 2.2H: 2.94, br-t, J=12 Hz, 0.8H: 3.34–3.43, m, 1H: 3.92, br-d, J=12 Hz, 1H: 4.33, br-d, J=15 Hz, 0.3H: 4.44, br-d, J=14 Hz, 0.7H: 5.27, d, J=11 Hz, 0.3H: 5.32, d, J=11 Hz, 0.7H: 7.24–7.42, m, 5H: 7.89, d, J=8.6 Hz, 2H: 8.02, dd, J=1.5 Hz, 8.0 Hz, 2H; MS: [M+H]⁺ calculated: 465.250, found: 465.3

A spectrum of analytical HPLC using CrestPak C18T-5 (ϕ 4.6×250 mm) column at a flow rate of 1.0 ml/min by elution in a gradient of 10–40% acetonitrile (60 min) in 0.1% TFA had a single peak at a retention time of 29.12 minutes.

Comparative Example 6

Synthesis of N-(N-4-amidinobenzoyl-β-trans-styryl-α-ethyl-β-alanyl)-4-piperidineacetic acid

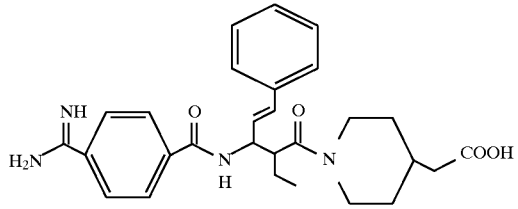

(1) 4-trans-Styryl-3-ethyl-2-azetidinone

The same procedure as in Comparative Example 5-(1) was performed with ethyl n-butyrate (6.6 ml, 50 mmol) and cinnamaldehyde (50 ml, 6.6 mmol) to yield 4-trans-styryl-3-ethyl-2-azetidinone (1.74 g, 17.3%).

NMR: ¹H (270 MHz: CD₃OD: 27° C.) 1.01, dd, J=8.3 Hz, 8.3 Hz, 3H: 1.52–1.72, m, 1H: 1.79, dqq, J=17 Hz, 8.3 Hz, 8.3 Hz, 1H: 3.26–3.39, m, 1H: 4.39, dd, J=6.4 Hz, 6.4 Hz, 1H: 5.95, br-s, 1H: 6.23, dd, J=6.4 Hz, 16 Hz, 1H: 6.64, d, J=16 Hz, 1H: 7.25–7.45, m, 5H; MS: [M+H]⁺ calculated: 202.123, found: 202.0

(2) N-Fmoc-β-trans-Styryl-α-ethyl-β-alanine 4-trans-Styryl-3-ethyl-2-azetidinone (1.74 g, 9.66 mmol) was protected with Fmoc by the same procedure as in Example 2-(3) to yield N-Fmoc-β-trans-styryl-α-ethyl-β-alanine (0.79 g, 21.9%).

NMR: ¹H (270 MHz: CD₃OD: 27° C.) 0.85–1.05, m, 3H: 1.44–1.83, m, 2H: 2.46–2.61, m, 1H: 4.25, br-t, J=6.5 Hz, 1H: 4.36–4.58, m, 3H: 6.18, dd, J=7.5 Hz, 16 Hz, 1H: 6.57, d, J=16 Hz, 1H: 7.16–7.45, m, 9H: 7.62, d, J=6.5 Hz, 2H: 7.77, d, J=6.5 Hz, 2H; MS: [M+Na]⁺ calculated: 464.194, found: 464.2

(3) Synthesis of the titled compound by a solid phase method

The same procedure as in Example 2-(5) was performed with N-Fmoc-β-trans-styryl-α-ethyl-β-alanine to yield a powder of N-(N-4-amidinobenzoyl-β-trans-styryl-α-ethyl-β-alanyl)-4-piperidineacetic acid (7.6 mg).

NMR: ¹H (270 MHz: CD₃OD: 27° C.) 0.65–1.22, m, 5H: 1.55–1.98, m, 6.5H: 2.23, d, J=6.7 Hz, 0.5H: 2.53–2.62, m, 2H: 3.04–3.16, m, 2H: 4.21, br-d, J=14 Hz, 1H: 4.56, br-t, J=13 Hz, 1H: 6.28, dd, J=16 Hz, 8.4 Hz, 1H: 6.54, d, J=16 Hz, 1H: 7.22–7.42, m, 5H: 7.88–8.08, m, 4H; MS: [M+H]⁺ calculated: 491.266, found: 491.6

A spectrum of analytical HPLC using CrestPak C18T-5 (ϕ 4.6×250 mm) column at a flow rate of 1.0 ml/min by elution in a gradient of 10–40% acetonitrile (60 min) in 0.1% TFA had a single peak at a retention time of 40.65 minutes.

Comparative Example 7

Synthesis of N-(N-4-amidinobenzoyl-α-isopropyl-β-alanyl)-4-piperidineacetic acid

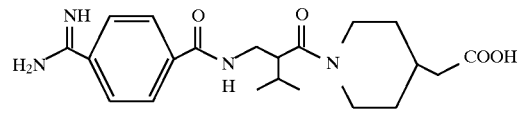

(1) N-t-Butyloxycarbonyl-α-isopropyl-β-alanine t-butyl ester

N-t-Butyloxycarbonyl-β-alanine t-butyl ester (2.0 g) was isopropylated by the same procedure as in Comparative Example 4-(1) using isopropyl iodide (1.8 ml) to yield an oil of N-t-butyloxycarbonyl-α-isopropyl-β-alanine t-butyl ester (990 mg, 42%).

NMR: ¹H (270 MHz: CDCl₃) 0.91, d, J=6.21 Hz, 6H: 1.42, m, 18H: 1.91, dt, J=6.83 Hz, 6.84 Hz, 1H: 2.28, m, 1H: 3.12–3.35, m, 2H: 4.83, m, 1H: ¹³C(67.5 MHz: CDCl₃) 19.97, 20.32, 28.12, 28.40, 28.75, 40.01, 52.90, 79.09, 80.69, 155.85, 175.05

(2) N-Fmoc-α-isopropyl-β-alanine

Dioxane containing 4N HCl was added to N-t-butyloxycarbonyl-α-isopropyl-β-alanine t-butyl ester (0.93 g) and the mixture was stirred at room temperature for 12 hours. After the solvents were distilled off, the residue was dissolved in water (25 ml) and neutralized with a 10% aqueous solution of sodium carbonate. The product was protected with Fmoc by the same procedure as in Example 2-(3). A crystal of N-Fmoc-α-isopropyl-β-alanine (790 mg, 65%) was obtained upon recrystallization from hexane.

NMR: ¹H (270 MHz: CDCl₃: 60° C.) 0.94, br-s, 6H: 1.85–2.24, m, 3H: 3.31, br-s, 2H: 4.15, m, 1H: 4.46, m, 1H: 5.8–6.4, br-s, 1H: 7.24–7.40, m, 4H: 7.53, m, 2H: 7.72, m, 2H: ¹³C(67.5 MHz: CDCl₃) 14.10, 19.82, 20.03, 20.47, 20.95, 28.77, 40.52, 47.43, 52.13, 61.07, 67.58, 120.13, 124.93, 127.25, 127.92, 141.57, 143.77; MS: [M+Na]⁺ calculated: 376.163, found: 376.2

(3) Synthesis of the titled compound by a solid phase method

The same procedure as in Example 2-(5) was performed with N-Fmoc-α-isopropyl-β-alanine to yield a powder of N-(N-4-amidinobenzoyl-α-isopropyl-β-alanyl)-4-piperidineacetic acid (18.0 mg).

NMR: ¹H (270 MHz: CDCl₃OD: 27° C.) 0.76–1.19, m, 2H: 0.92, d, J=6.4 Hz, 2H: 0.97, d, J=7.6 Hz, 1.2H: 1.06, d, J=6.8 Hz, 2.8H: 1.54–1.98, m, 5H: 2.60, dt, J=13 Hz, 2.8 Hz, 1H: 2.89–2.23, m, 2H: 3.41–3.51, m, 1H: 3.67–3.76, m, 1H: 4.09, br-d, J=14 Hz, 1H: 4.50–4.65, m, 1H: 7.86–8.04, m, 4H; MS: [M+H]⁺ calculated: 403.234, found: 403.3

A spectrum of analytical HPLC using CrestPak C18T-5 (ϕ 4.6×250 mm) column at a flow rate of 1.0 ml/min by elution in a gradient of 10–40% acetonitrile (30 min) in 0.1% TFA had a single peak at a retention time of 15.68 minutes.

Comparative Example 8

Synthesis of N-(N-4-amidinobenzoyl-β-phenyl-α-isopropyl-β-alanyl)-4-piperidineacetic acid

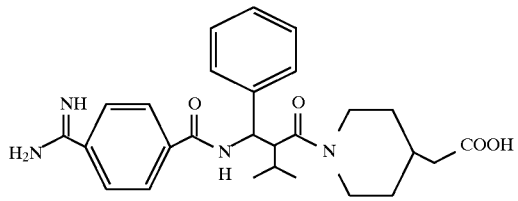

(1) 4-Phenyl-3-isopropyl-2-azetidinone

The same procedure as in Comparative Example 5-(1) was performed with ethyl isovalerate (7.5 ml, 50 mmol) and benzaldehyde (5 ml, 50 mm 1) to yield a crystal of 4-phenyl-3-isopropyl-2-azetidinone (2.13 g, 22.5%).

NMR: $^1$H (270 MHz: CDCl$_3$: 27° C.) 1.45, d, J=6.4 Hz, 3H: 1.07, d, J=6.4 Hz, 3H: 1.63–1.79, m, 1H: 3.15, ddd, J=5.0 Hz, 11.2 Hz, 1.6 Hz, 1H: 4.84, d, J=5.0 Hz, 1H: 6.1, br-s, 1H: 7.29–7.42, m, 5H (2) N-Fmoc-β-Phenyl-α-isopropyl-β-alanine 4-Phenyl-3-isopropyl-2-azetidinone (2.13 g, 11.25 mmol) was protected with Fmoc by the same procedure as in Example 2-(3) to yield a crystal of N-Fmoc-β-phenyl-α-isopropyl-β-alanine (1.48 g, 32.0%).

NMR: $^1$H (270 MHz: CDCl$_3$: 27° C.) 0.76–1.09, m, 6H: 2.03–2.25, m, 1H: 2.55–2.85, m, 1H: 0.73, t, J=4.9 Hz, 1H: 4.27–4.51, m, 2H: 5.07, m, 1H: 7.19–7.33, m, 9H: 7.38, t, J=5.3 Hz, 1H: 7.52, d, J=2.4 Hz, 1H: 7.75, d, J=7.3 Hz, 2H; MS: [M+Na]$^+$ calculated: 452.202, found: 452.3

(3) Synthesis of the titled compound by a solid phase method

The same procedure as in Example 2-(5) was performed with N-Fmoc-β-phenyl-α-isopropyl-β-alanine to yield a powder of N-(N-4-amidinobenzoyl-β-phenyl-α-isopropyl-β-alanyl)-4-piperidineacetic acid (10 mg).

NMR: $^1$H (270 MHz: CD$_3$OD: 27° C.) 0.08, br-t, J=9.6 Hz, 1H: 0.39, br-t, J=12.7 Hz, 1H: 0.96–1.13, m, 6H: 1.47, br-t, J=12 Hz, 1H: 1.55–1.95, m, 3H: 2.18–2.60, m, 3H: 2.89–2.98, m, 1H: 3.54, br-dt, J=11, 4.3 Hz, 1H: 3.94, br-d, J=16 Hz, 0.9H: 4.19, br-d, J=15 Hz, 0.4H: 4.40, br-d, J=13 Hz, 0.7H: 5.45–5.56, m, 1H: 7.26–7.44, m, 5H: 7.86–8.02, m, 4H; MS: [M+H]$^+$ calculated: 479.266, found: 479.4

A spectrum of analytical HPLC using CrestPak C18T-5 (φ 4.6×250 mm) column at a flow rate of 1.0 ml/min by elution in a gradient of 10–40% acetonitrile (60 min) in 0.1% TFA had a single peak at a retention time of 31.41 minutes.

Comparative Example 9

Synthesis of N-(N-4-amidinobenzoyl-β-trans-styryl-α-isopropyl-β-alanyl)-4-piperidineacetic acid

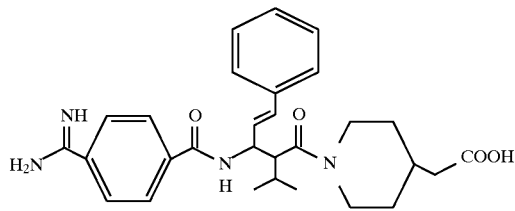

(1) 4-trans-Styryl-3-isopropyl-2-azetidinone

The same procedure as in Comparative Example 5-(1) was performed with ethyl isovalerate (7.5 ml, 50 mmol) and cinnamaldehyde (6.6 ml, 50 mol) to yield 4-trans-styryl-3-isopropyl-2-azetidinone (8.7 g, 83.1%).

NMR: $^1$H (270 MHz: CDCl$_3$: 27° C.) 0.91, d, 3H (J=7.4 Hz): 1.18, d, 3H (J=6.4 Hz: 1.95–2.14, m, 1H: 3.06, dd, 1H (J=5.6, 13.0 Hz): 4.37, dd, 1H (J=6.0, 8.4 Hz): 5.89, br-s, 1H: 6.28, dd, 1H (J=7.7, 14.0 Hz): 6.67, d, 1H (J=15.0 Hz): 7.23–7.45, m, 5H; MS: [M+H]$^+$ calculated: 216.139, found: 216.1

(2) N-Fmoc-β-trans-Styryl-α-isopropyl-β-alanine 4-trans-Styryl-3-isopropyl-2-azetidinone (6.28 g, 30 mmol) was protected with Fmoc by the same procedure as in Example 2-(3) to yield N-Fmoc-β-trans-styryl-α-isopropyl-β-alanine (1.51 g, 21.5%).

NMR: $^1$H (270 MHz: CDCl$_3$: 27° C.) 0.95–1.25, m, 6H: 1.90–2.85, m, 2H: 4.10–5.10, m, 2H: 6.13–6.60, m, 4H: 7.22–7.39, m, 9H: 7.59, d, J=6.8 Hz, 2H: 7.6, d, J=7.3 Hz, 2H; MS: [M+Na]$^+$ calculated: 478.200, found: 478.2

(3) Synthesis of the titled compound by a solid phase method

The same procedure as in Example 2-(5) was performed with N-Fmoc-β-trans-styryl-α-isopropyl-β-alanine to yield a powder of N-(N-4-amidinobenzoyl-β-trans-styryl-α-isopropyl-β-alanyl)-4-piperidineacetic acid (9.0 mg).

NMR: $^1$H (270 MHz: CD$_3$OD: 27° C.) 0.65–1.10, m, 7.5H: 1.58–2.13, m, 7H: 2.21–2.24, m, 0.5H: 2.51–2.60, m, 1H: 2.94–3.13, m, 0.5H: 3.40, dd, J=6.5 Hz, 9.7 Hz, 0.5H: 4.11–4.20, m, 1H: 4.59, br-d, J=13 Hz, 1H: 5.06, dd, J=8.4 Hz, 16 Hz, 1H: 6.35–6.65, m, 2H: 7.21–7.45, m, 5H: 7.87–8.09, m, 4H; MS: [M+H]$^+$ calculated: 505.281, found: 505.3

A spectrum of analytical HPLC using CrestPak C18T-5 (φ 4.6×250 mm) column at a flow rate of 1.0 ml/min by elution in a gradient of 10–40% acetonitrile (30 min) in 0.1% TFA had a single peak at a retention time of 31.37 minutes.

Comparative Example 10

Synthesis of N-(N-4-amidinobenzoyl-β-phenyl-α-methyl-β-alanyl)-4-piperidineacetic acid

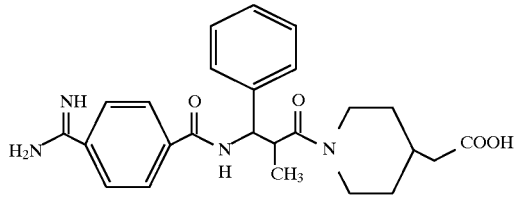

(1) 4-Phenyl-3-methyl-2-azetidinone

The same procedure as in Example 2-(2) was performed with ethyl propionate (5.73 ml, 50 mmol) and benzaldehyde (8.0 ml, 50 mmol) to yield 4-phenyl-3-methyl-2-azetidinone (1.19 g, 15.0%).

NMR: $^1$H (270 MHz: CDCl$_3$: 25° C.) 0.82, d, J=7.32 Hz, 3H: 3.52–3.64, m, 1H: 4.88, d, J=5.86 Hz, 1H: 6.27, br-s, 1H(NH): 7.26–7.44, m, 5H; MS: [M+H]$^+$ calculated: 162.092, found: 162.0

(2) N-4-Cyanobenzoyl-β-phenyl-α-methyl-β-alanine

The same procedure as in Example 2-(3) was performed with 4-phenyl-3-methyl-2-azetidinone (1.19 g, 7.37 mmol) to yield a powder of β-phenyl-α-methyl-β-alanine hydrochloride (1.32 g, 83.2%).

NMR:$^1$H (270 MHz: CD$_3$OD: 25° C.) 1.26, d, J=7.32 Hz, 3H: 3.06–3.18, m, 1H: 4.49, d, J=7.81 Hz, 1H: 7.43, s, 5H; MS: [M+H]$^+$ calculated: 180.102, found: 179.9

The same procedure as in Example 2-(6-1) was performed with the obtained β-phenyl-α-methyl-β-alanine hydrochloride (1.0 g, 4.63 mmol) to yield a crystal of N-4-cyanobenzoyl-β-phenyl-α-methyl-β-alanine (1.43 g, quant.).

NMR: $^1$H (270 MHz: CD$_3$OD: 25° C.) 1.30, d, J=6.8 Hz, 3H: 3.10–3.19, dq, J=7.8 Hz, 6.8 Hz, 1H: 5.37, d, J=7.8 Hz, 1H: 7.16–7.48, m, 5H: 7.81, d, J=8.3 Hz, 2H: 7.91, d, J=8.3 Hz, 2H $^{13}$C(67.5 MHz: CD$_3$OD: 25° C.) 13.83, 44.13, 55.73, 114.39, 117.69, 126.95, 127.38, 127.70, 128.13, 132.01, 134.04, 138.20, 139.24, 165.58, 176.11; MS: [M+Na]$^+$ calculated: 331.106, found: 330.9

(3) N-4-Cyanobenzoyl-β-phenyl-α-methyl-β-alanyl-4-piperidineacetic acid benzyl ester The same procedure as in Example 2-(6-2) was performed with N-4-cyanobenzoyl-β-phenyl-α-methyl-β-alanine (0.5 g, 1.62 mmol) to yield an oil of N-4-cyanobenzoyl-β-phenyl-α-methyl-β-alanyl-4-piperidineacetic acid benzyl ester (0.75 g, 88.4%).

NMR: $^1$H (270 MHz: CDCl$_3$: 25° C.) 0.27–0.51, m, 0.5H: 0.51–0.74, m, 0.5H: 0.99–1.35, m, 1H: 1.22, d, J=6.5 Hz, 3H: 1.41–1.78, m, 2H: 1.78–2.00, m, 1H: 2.00–2.18, m, 1.3H: 2.18–2.50, m, 1.7H: 2.68, br-t, J=12.1Hz, 0.5H: 2.93, br-t, J=11.9 Hz, 0.5H: 3.40–3.51, m, 1H: 3.82, br-d, J=10.26 Hz, 1H: 4.31–4.51, m, 1H: 5.09, s, 2H: 5.34, br-t, J=8.37 Hz, 1H: 7.17–7.45, m, 10H: 7.70, d, J=8.1 Hz, 2H: 7.98, d, J=8.1 Hz, 2H: 8.14–8.29, m, 1H; MS: [M+Na]$^+$ calculated: 546.237, found: 546.2

(4) Synthesis of the titled compound

The same procedure as in Example 2-(6-3) was performed with N-4-cyanobenzoyl-β-phenyl-α-methyl-β-alanyl-4-piperidineacetic acid benzyl ester (500 mg, 0.95 mmol) to yield an oil of N-4-amidinobenzoyl-β-phenyl-α-methyl-β-alanyl-4-piperidineacetic acid benzyl ester (185 mg, 35.8%). The same procedure as in Example 2-(6-4) was performed with N-4-amidinobenzoyl-β-phenyl-α-methyl-β-alanyl-4-piperidineacetic acid benzyl ester to yield N-(N-4-amidinobenzoyl-β-phenyl-α-methyl-β-alanyl)-4-piperidineacetic acid (111 mg, 95.1%).

NMR: $^1$H (270 MHz: CD$_3$OD: 25° C.) −0.03–0.06, m, 0.5H: 0.40–0.59, m, 0.5H: 0.96–1.22, m, 1H: 1.25–1.29, m, 3H: 1.39–1.87, m, 3H: 1.87–2.01, m, 1.5H: 2.18–2.21, m, 0.5H: 2.22–2.62, m, 1.5H: 2.94, br-t, J=11.1 Hz, 0.5H: 3.46–3.65, m, 1H: 3.86, br-d, J=13.8 Hz, 1H: 4.26, br-d, J=13.2 Hz, 0.3H: 4.37, br-d, J=13.2 Hz, 0.7H: 5.34, d, J=10.8 Hz, 1H: 7.23–7.43, m, 5H: 7.84–7.91, m, 2H: 7.96–8.05, m, 2H $^{13}$C(67.5 MHz: CD$_3$OD: 25° C.) 16.92, 16.98, 33.18, 33.28, 33.71, 34.28, 34.69, 41.92, 42.34, 42.91, 43.64, 44.19, 47.57, 47.97, 59.35, 59.55, 129.16, 129.55, 130.07, 130.11, 130.23, 130.51, 133.15, 141.63, 143.15, 143.76, 168.75, 169.04, 174.91, 175.05, 176.65, 176.78; MS: [M+H]$^+$ calculated: 451.234, found: 451.2

A spectrum of analytical HPLC using Wakosil-II 5C18HG (φ 4.6×250 mm) column at a flow rate of 1.0 ml/min at room temperature by elution in a gradient of 10–40% acetonitrile (60 min) in 0.1% TFA had a single peak at a retention time of 26.83 minutes.

Experimental Example 1

Platelet Aggregation-Inhibiting Ability of the Compounds of the Present Invention (Measurement of in vitro Human Platelet Aggregation using PRP)

Healthy male volunteers who had not taken any medicines for at least two weeks were selected as subjects. Blood was collected from the forearm vein of each subject on an empty stomach using a #19 needle and a plastic syringe preliminarily charged with ¹/₁₀ volume of a 3.8% sodium citrate solution. Immediately after the blood collection, the syringe was shaken gently to mix the blood with the sodium citrate solution. The mixed blood was centrifuged (1100 rpm, 250 g) at room temperature for 15 minutes and the rotation was stopped without applying the brake. Then, the supernatant was collected with a Komagome type pipette to obtain platelet-rich plasma (PRP). The PRP was stored at room temperature. The blood remaining after centrifuging was further centrifuged (3500 rpm, 1500 g) at room temperature for 15 minutes and the rotation was stopped without applying the brake. The supernatant was collected to obtain platelet-poor plasma (PPP). After the preparation of the PRP, the number of platelets was counted and only samples containing more than 2×10$^8$ of platelets per milliliter were subjected to the following experiments.

Platelet aggregation was measured using an 8-channel platelet aggregation measuring instrument (Hematracer, Nikoh Bioscience, Tokyo, Japan) on the basis of the change in light transmittance through the PRP. First, the PPP and PRP (each 200 μl) were placed in glass cuvettes and incubated at 37° C. Thereafter, the transmittance was measured. The transmittance of the PPP was determined as 100% and that of the PRP as 0%. Then, 10 μl of physiological saline or a sample-containing physiological saline was added to the PRP and incubated at 37° C. for one minute. A collagen solution (10 μl) at a concentration of 100 μg/ml was added (final concentration: 5 μg/ml) to induce aggregation and thereafter the transmittance was measured over 7 minutes. After aggregation with collagen and ADP was confirmed, only those samples in which the maximum aggregation with collagen was at least 70% were subjected to the experiment.

The sample was dissolved in physiological saline to give a concentration of $2.2 \times 10^{-2}$ M and a 2-fold dilution series was prepared for use in the experiments. The samples insoluble in the physiological saline were dissolved in physiological saline containing 10% DMSO (dimethyl sulfoxide).

The results were calculated as follows:

$$\text{Percent aggregation inhibition} = \left[ 1 - \frac{\text{Maximum percent aggregation upon the addition of sample}}{\text{Maximum percent aggregation upon the addition of physiological saline}} \right] \times 100$$

A graph was constructed by plotting the percent aggregation inhibition against the sample concentration and the concentration at which the aggregation was inhibited by 50% ($IC_{50}$) was calculated from the graph. $IC_{50}$ of each sample is shown in Tables 2 and 3.

TABLE 2

Platelet Aggregation-Inhibiting Activity of the Compounds of the Present Invention

| Compound | Activity ($IC_{50}$, μM) |
|---|---|
| The Compound Prepared in Example 1 | 0.57 |
| The Compound Prepared in Example 2 | 0.19 |
| The Compound Prepared in Example 3 | 0.084 |
| The Compound Prepared in Example 4 | 0.089 |
| The Compound Prepared in Example 5 | 0.19 |
| The Compound Prepared in Example 6 | 0.084 |
| The Compound Prepared in Example 7 | 0.17 |
| The Compound Prepared in Example 8 | 0.25 |
| The Compound Prepared in Example 9 | 0.18 |
| The Compound Prepared in Example 10 | 0.23 |
| The Compound Prepared in Example 11 | 0.16 |
| The Compound Prepared in Example 12 | 0.17 |
| The Compound Prepared in Example 13 | 0.27 |
| The Compound Prepared in Example 14 | 0.46 |
| The Compound Prepared in Example 15 | 0.18 |
| The Compound Prepared in Example 16 | 0.33 |
| The Compound Prepared in Example 17 | 0.18 |
| The Compound Prepared in Example 18 | 1.00 |
| The Compound Prepared in Example 21 | 0.33 |
| The Compound Prepared in Example 22 | 0.52 |
| The Compound Prepared in Example 23 | 0.62 |
| The Compound Prepared in Example 24 | 0.080 |
| The Compound Prepared in Example 25 | 0.48 |
| The Compound Prepared in Example 26 | 0.34 |
| The Compound Prepared in Example 27 | 0.20 |
| The Compound Prepared in Example 28 | 0.076 |
| The Compound Prepared in Example 29 | 0.10 |
| The Compound Prepared in Example 30 | 0.093 |
| The Compound Prepared in Example 31 | 0.16 |
| The Compound Prepared in Example 32 | 0.47 |
| The Compound Prepared in Example 33 | 0.41 |
| The Compound Prepared in Example 34 | 0.15 |
| The Compound Prepared in Example 35 | 0.073 |
| The Compound Prepared in Example 36 | 0.36 |
| The Compound Prepared in Example 39 | 0.19 |
| The Compound Prepared in Example 40 | 0.15 |
| The Compound Prepared in Example 41 | 0.061 |
| The Compound Prepared in Example 42 | 0.075 |
| The Compound Prepared in Comparative Example 1 | 2.5 |
| The Compound Prepared in Comparative Example 2 | 50.0 |
| The Compound Prepared in Comparative Example 3 | 5.2 |
| The Compound Prepared in Comparative Example 4 | 0.89 |
| The Compound Prepared in Comparative Example 5 | 16.0 |
| The Compound Prepared in Comparative Example 6 | 85.0 |
| The Compound Prepared in Comparative Example 7 | 17.0 |
| The Compound Prepared in Comparative Example 8 | 82.0 |
| The Compound Prepared in Comparative Example 9 | 90.0 |
| The Compound Prepared in Comparative Example 10 | 16.0 |

Table 2 shows that the 2-dimethyl-substituted compound prepared in Example 1 and the α-dialkyl-substituted compounds prepared in Examples 2–18 and 21–36 as substituted at the β position have higher platelet-aggregation inhibiting activity than the compounds prepared in the comparative examples which are unsubstituted, β-monoalkyl-substituted or β-monoalkyl-substituted compounds. Moreover, it is clear that the α-monoalkyl-substituted compounds prepared in Comparative Examples 5–6 and 8–10 as substituted at the β position are much lower in platelet-aggregation inhibiting activity.

The compounds prepared in Examples 19, 20, 37 and 38 are prodrugs.

TABLE 3

Platelet Aggregation-Inhibiting Activity of the Compounds of the Present Invention

| Compound | Activity ($IC_{50}$, μM) |
|---|---|
| The Compound Prepared in Example 44 | 0.22 |
| The Compound Prepared in Example 46 | 0.15 |
| The Compound Prepared in Example 50 | 0.22 |
| The Compound Prepared in Example 52 | 0.087 |
| The Compound Prepared in Example 54 | 0.12 |
| The Compound Prepared in Example 56 | 0.052 |
| The Compound Prepared in Example 58 | 0.043 |
| The Compound Prepared in Example 60 | 0.23 |
| The Compound Prepared in Example 62 | 0.12 |
| The Compound Prepared in Example 64 | 0.069 |
| The Compound Prepared in Example 66 | 0.057 |
| The Compound Prepared in Example 68 | 0.087 |
| The Compound Prepared in Example 70 | 0.24 |

Table 3 shows that the compounds of the present invention have high platelet-aggregation inhibiting activity.

The compounds prepared in Examples 43, 45, 47, 49, 51, 53, 55, 57, 59, 61, 63, 65, 67, 69 and 71 are prodrugs.

Experimental Example 2

Stability of the compounds in mouse liver homogenate

Stability of the compounds of the present invention in mouse liver homogenate was examined according to the following method. Male ICR mice weighing about 30 grams were used in this experiment. Liver was excised and homogenized in ice-cold phosphate-buffered saline (PBS) for 5 min. The homogenate was then sonicated for another 5 min on ice and this fraction was used as liver homogenate.

Test and reference compounds were dissolved in PBS so as to be 5 mM. This compound solution (0.3 ml) was added to 2.7 ml of the liver homogenate mentioned above on ice and then this mixed solution was incubated at 37° C. After 30, 60 and 120 min, 400 μl of the mixed solution was sampled and 100 μl of acetonitrile was added and the mixed solution was stirred vigorously. After centrifugation at 12000 rpm for 10 min to remove insoluble fraction, the concentration of each compound in the supernatant was determined by reversed phase HPLC using C18 analytical column (Wakopack, Wako Pure Chem. Co. Ltd., Tokyo Japan).

FIG. 1 shows the results of this experiment in which the abscissa represents incubation time of the sample and the ordinate represents the relative concentration of the sample at each time point. Concentration of the sample at time zero (without incubation at 37° C.) was defined as 100% and those at each time point were represented by relative values. As shown in this figure, RGDS (arginine-glycine-asparatic acid-serine), which was a reference compound of this experiment, was degraded very rapidly and after 30 min only a trace amount was observed. On the other hand, compound of Example 2 and compound of Example 3 were not degraded at all during the incubation period of 120 min.

These results indicate that compounds of the present invention are very stable and difficult to degrade despite the fact that they contain two peptide bonds in the molecule. This stability will result from the structural characteristics of the compounds of the present invention; they a have non-natural β-alanine structure with side chains at both α and β-position in the middle of the molecule and these side chains will contribute to the spatial hindrance in the vicinity of the peptide bonds, both of which will result in lower accessibility and reactivity of proteases or peptidases. This high stability of the compounds of the present invention in vitro suggest that they will be also stable and maintain their pharmacological effects in vivo for at least several hours.

Experimental Example 3

Time Course of the Concentration in Plasma after Oral Administration (Oral Administration Test)

Male SD rats which had been starved from the previous day were used in this experiment. Two test substances, the compounds of Examples 46 and 72 were dissolved in distilled water and administered into the stomach of rats with an oral probe. Each compound was administered in an amount of 10 mg per kg of body weight. Blood samples were collected 30, 60 and 120 minutes after the administration. The concentration of each compound which was in an active state (i.e., free carboxylic acid) in plasma was determined by HPLC.

Figure 2:
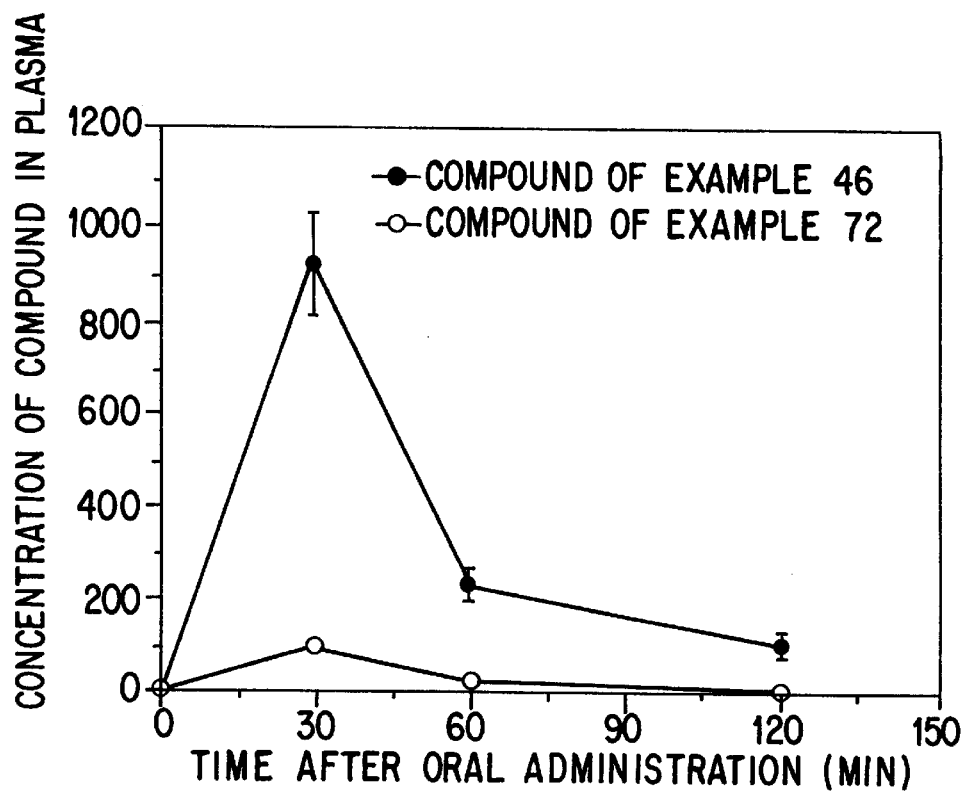
FIG. 2 shows time course of concentration of the compound on example 46 in blood after oral administration.

The results are shown in FIG. 2. In this Figure, the horizontal axis represents time after the oral administration and the vertical axis represents the concentration of the active form of each compound in plasma. Each point represents the mean value for three rats and the standard error. The compound of Example 46 within the scope of the invention revealed a significantly higher concentration in plasma than the compound of Example 72 at every point of determination. When the peak values at 30 minutes after the oral administration are compared, the difference was about 10 times as great. This shows that the compound of Example 46 (i.e. a compound of the invention) clearly has a higher bioavailability than the compound of Example 72.

Experimental Example 4

Acute Toxicity Test

The compounds of the present invention were intravenously injected into mice in an amount of 100 mg/kg but no toxicity was observed.

Formulation Example 1

Each of the compounds prepared in Examples 1–72 (100 mg) was dissolved in 100 ml of physiological saline. Under aseptic conditions, the obtained solution was charged in a 2.5 ml volume ampule and the ampule was sealed to prepare an injection preparation.

Formulation Example 2

A mixture (1 ml) of ethanol and water was added to a mixture consisting of one of the compounds prepared in Examples 1–72 (500 mg), crystalline cellulose (50 mg) and lactose (450 mg) and the two mixtures were blended intimately. The blend was granulated by a conventional method to prepare granules.

What is claimed is:

1. A compound of the following general formula (I) or a pharmaceutically acceptable salt thereof:

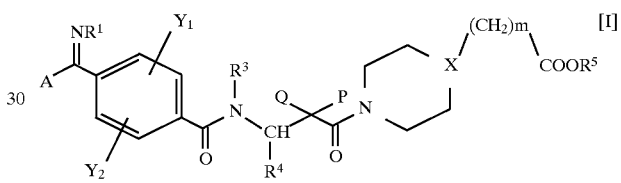

wherein A is an amino;

R$^1$ hydrogen, a lower alkyl or a physiologically cleavable amino-protecting group;

R$^3$ hydrogen, lower alkyl, lower alkenly, lower alkynl, ar (lower) alkyl or aryl;

R$^4$ hydrogen, a lower alkyl, lower alkenyl, lower alkynyl, hydroxy (lower) alkyl, nitrooxy (lower) alkyl, nitrosooxy (lower) alkyl, amino (lower alkyl or heterocycle-substituted lower alkyl; ar (lower) alkyl, ar (lower) alkenyl or ar (lower) alkynyl, the aryl portions of which are optionally substituted with a lower alkyl, halogen, nitro, amino, carboxyl, hydroxy (lower) alkyl, hydroxyl or protected hydroxyl; aryl or a heterocyclic group either of which is optionally substituted with a lower alkyl, halogen, nitro, amino, carboxyl, hydroxy (lower) alkyl, hydroxyl or protected hydroxyl; a cycloalkyl with a 3–8 membered ring, the ring portion of which is optionally substituted with lower alkyl, halogen, nitro, amino carboxyl, hydroxy (lower) alkyl, hydroxyl or protected hydroxyl; a lower alkyl, a lower alkynyl or a lower alkenyl which is substituted with a 3–8 membered cycloalkyl; or a lower alkyloxy;

P and Q are each independently lower alkyl, or when combined together, form a cycloalkyl with the adjacent carbon atom;

R$^5$ is hydrogen or a physiologically cleavable carboxyl-protecting group;

X is CH;

Y$_1$ and Y$_2$ are independently hydrogen, a lower alkyl, halogen, hydroxy, a lower alkoxy, a lower acyloxy, an acyl, caboxyl, a lower alkoxycarbonyl, nitro or trifluoromethyl; and m is an integer of 0 to 2.

2. The compound or its pharmaceutically acceptable salt of claim 1, wherein P and Q are both methyl.

3. The compound or its pharmaceutically acceptable salt of claim 1, wherein P and Q are both methyl and m is 1.

4. The compound or its pharmaceutically acceptable salt of claim 1, wherein A is primary or secondary amine.

5. The compound or its pharmaceutically acceptable salt of claim 1, wherein A is a tertiary amine and $R^1$ is hydrogen.

6. The compound or its pharmaceutically acceptable salt of claim 5, wherein A is a cyclic tertiary amine.

7. The compound or its pharmaceutically acceptable salt of claim 5, wherein A is a tertiary amine represented by the following general formula (IIa), (III) or (IV)

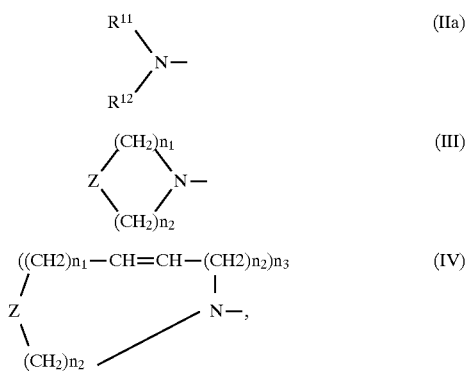

wherein $R^{11}$ and $R^{12}$ are each independently a lower alkyl, lower alkenyl, lower alkynyl, ar (lower) alkyl or aryl;

Z is oxygen; sulfur;

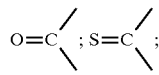

carbon substituted with hydrogen, a lower alkyl, lower alkenyl, lower alkynyl, ar (lower) alkyl, hydroxyl or substituted hydroxyl, amino or substituted amino, nitro, nitrooxy, nitrosooxy, halogen, thiol or substituted thiol, or aryl; or nitrogen substituted with hydrogen, a lower alkyl, lower alkenyl, lower alkynyl, ar (lower)alkyl, hydroxyl or substituted hydroxyl, amino or substituted amino, nitro, nitroso or aryl;

$n_1$, $n_2$ and $n_4$ are each independently an integer of 0 to 6 and $n_3$ is an integer of 0 to 3.

8. A pharmaceutical composition comprising the compound or its salt of claim 1 and a pharmaceutically acceptable carrier.

9. The pharmaceutical composition of claim 8, which is used for inhibiting platelet aggregation.

10. The pharmaceutical composition of claim 8, which is used for inhibiting blood coagulation in extracorporeal circulation.

11. The pharmaceutical composition of claim 8, which is used for inhibiting the reocclusion of coronary arteries.

12. A method for inhibiting platelet aggregation, which comprises administering a platelet aggregation inhibiting amount of the compound or its salt of claim 1 to a patent in need thereof.

13. A method of inhibiting blood coagulation in extracorporeal circulation, which comprises administering a blood coagulation inhibiting amount of the compound or its salt of claim 1 to a patient in need thereof.

14. A method for inhibiting the reocclusion of coronary arteries, which comprises administering a reocclusion inhibiting amount of the compound or its salt of claim 1 to a patient in need thereof.

* * * * *

UNITED STATES PATENT AND TRADEMARK OFFICE
CERTIFICATE OF CORRECTION

PATENT NO. : 5,866,592
DATED : February 22, 1999
INVENTOR(S) : Yoshiio HAYASHI, et al.

Page 1 of 4

It is certified that error appears in the above-identified patent and that said Letters Patent is hereby corrected as shown below:

Column 2, line 54, delete "been".

Column 2, line 57, after "residues" at end of line, change the comma to a period.

Column 2, line 58, change "these" to –These–.

Column 6, line 2, change "behzyl" to –benzyl–.

Column 6, line 46, change "tatrahy-" to –tetrahy–.

Column 19, line 8, change "hundreds" to –hundred–.

Column 20, line 14, change "enhanced" to –greater–.

Column 20, line 20, change "antiboitics" to –antibiotics–.

Column 22, line 40, change "HCI" to –HC1–.

Column 26, line 23, change "reulting" to –resulting–.

Column 26, line 26, change "res idue" to –residue–.

Column 49, line 46, change "phenyla" to –phenyl-α–.

Column 49, line 61, change "phenyla" to –phenyl-α–.

Column 49, line 63, change "phenyla" to –phenyl-α–.

Column 50, line 46, change "phenyla" to –phenyl-α–.

UNITED STATES PATENT AND TRADEMARK OFFICE
CERTIFICATE OF CORRECTION

PATENT NO. : 5,866,592
DATED : February 22, 1999
INVENTOR(S) : Yoshiio HAYASHI, et al.

It is certified that error appears in the above-identified patent and that said Letters Patent is hereby corrected as shown below:

Column 50, line 50, change "phenylα" to --phenyl-α--.

Column 50, line 56, change "phenylα" to --phenyl-α--.

Column 50, line 58, change "phenylα" to --phenyl-α--.
Column 50, line 64, change "phenylα" to --phenyl-α--.

Column 50, line 67, change "phenylα" to --phenyl-α--.

Column 51, line 10, change "phenylα" to --phenyl-α--.

Column 51, line 13, change "phenylα" to --phenyl-α--.

Column 51, line 16, change "phenylα" to --phenyl-α--.

Column 51, line 26, change "phenylα" to --phenyl-α--.

Column 51, line 28, change "phenylα" to --phenyl-α--.

Column 52, line 9, change "methylα" to --methyl-α--.

Column 52, line 15, change "methylα" to --methyl-α--.

Column 53, line 8, change "phenylα" to --phenyl-α--.

Column 53, line 20, change "phenylα" to --phenyl-α--.

Column 59, line 42, change "were" to --was--.

UNITED STATES PATENT AND TRADEMARK OFFICE
CERTIFICATE OF CORRECTION

PATENT NO. : 5,866,592
DATED : February 22, 1999
INVENTOR(S) : Yoshiio HAYASHI, et al.

It is certified that error appears in the above-identified patent and that said Letters Patent is hereby corrected as shown below:

Column 60, line 53, change "butylα" to -butyl-α.

Column 63, line 17, change "yeild" to -yield-.

Column 66, line 7, change "βethyl" to -β-ethyl-.

Column 66, line 10, change "βethyl" to -β-ethyl-.

Column 77, line 56, change "hexamethyleneiminoimidoy l" to -hexamethyleneiminoimidoyl-.

Column 79, line 44, change "βethyl" to -β-ethyl-.

Column 80, line 33, change "7%" to -76%-.

Column 87, line 27, change "dimethy-β-alanyl" to -dimethyl-β-alanyl-.

Column 88, line 4, change "36.19" to -361.19-.

Column 93, line 25, change "mm l" to -mmol-.

Column 98, line 21, change "β-monoalkyl" to -α-monoalkyl-.

Column 100, line 34, change "amino" to -amine-.

Column 100, line 37, change "alkenly" to -alkenyl-.

UNITED STATES PATENT AND TRADEMARK OFFICE
CERTIFICATE OF CORRECTION

PATENT NO. : 5,866,592
DATED : February 22, 1999
INVENTOR(S) : Yoshiio HAYASHI, et al.

It is certified that error appears in the above-identified patent and that said Letters Patent is hereby corrected as shown below:

Column 100, line 42, change "(lower" (second occurrence) to -(lower)-

Column 100, line 65, change "caboxyl" to -carboxyl-.

Column 101, line 15, change "(IV)" to -(IV);-.

Column 102, line 27, change "patent" to -patient-.

Signed and Sealed this

Eighth Day of May, 2001

Attest:

NICHOLAS P. GODICI

Attesting Officer

Acting Director of the United States Patent and Trademark Office